US010993938B2

(12) United States Patent
Shao et al.

(10) Patent No.: US 10,993,938 B2
(45) Date of Patent: May 4, 2021

(54) LACTAM COMPOUND, PREPARATION METHOD AND USE THEREOF

(71) Applicant: OCEAN UNIVERSITY OF CHINA, Shandong (CN)

(72) Inventors: Changlun Shao, Shandong (CN); Changyun Wang, Shandong (CN); Xiaofeng Mou, Shandong (CN); Rufang Xu, Shandong (CN)

(73) Assignee: OCEAN UNIVERSITY OF CHINA, Qingdao (CN)

( * ) Notice: Subject to any disclaimer, the term of this patent is extended or adjusted under 35 U.S.C. 154(b) by 0 days.

(21) Appl. No.: 16/585,444

(22) Filed: Sep. 27, 2019

(65) Prior Publication Data
US 2020/0030312 A1 Jan. 30, 2020

Related U.S. Application Data

(63) Continuation-in-part of application No. PCT/CN2018/080727, filed on Mar. 27, 2018.

(30) Foreign Application Priority Data

Mar. 28, 2017 (CN) .......................... 201710191282.1

(51) Int. Cl.
| *A61K 31/4704* | (2006.01) |
| *A61P 31/12* | (2006.01) |
| *A61K 31/13* | (2006.01) |
| *A61K 31/4709* | (2006.01) |
| *A61K 31/522* | (2006.01) |
| *A61K 31/7056* | (2006.01) |
| *A61K 31/7072* | (2006.01) |
| *A61K 38/21* | (2006.01) |
| *C07D 215/22* | (2006.01) |
| *C07D 401/06* | (2006.01) |
| *C07D 405/06* | (2006.01) |
| *C07D 409/06* | (2006.01) |
| *C07D 413/12* | (2006.01) |
| *C07H 19/04* | (2006.01) |

(52) U.S. Cl.
CPC .......... *A61K 31/4704* (2013.01); *A61K 31/13* (2013.01); *A61K 31/4709* (2013.01); *A61K 31/522* (2013.01); *A61K 31/7056* (2013.01); *A61K 31/7072* (2013.01); *A61K 38/21* (2013.01); *A61P 31/12* (2018.01); *C07D 215/22* (2013.01); *C07D 401/06* (2013.01); *C07D 405/06* (2013.01); *C07D 409/06* (2013.01); *C07D 413/12* (2013.01); *C07H 19/04* (2013.01)

(58) Field of Classification Search
CPC .................................................. A61K 31/4704
USPC ........................................................ 546/158
See application file for complete search history.

(56) References Cited

FOREIGN PATENT DOCUMENTS

| CN | 104945319 A | 9/2015 |
| CN | 104945320 A | 9/2015 |
| WO | 2009060015 A1 | 5/2009 |
| WO | 2018177296 | 10/2018 |

OTHER PUBLICATIONS

Li et al.: "A Concise Synthesis of (±)-Yaequinolone A2": Chinese Journal of Chemistry, 2009, 27(7): 1379-1381.
An et al.: "4-Phenyl-3,4-dihydroquinolone Derivatives from Aspergillus Nidulans MA-143, an Endophytic Fungus Isolated from the Mangrove Plant *Rhizophora stylosa*": Journal of Natural Products, 2013, 76: 1896-1901.
Written Opinion in corresponding PCT application PCT/CN2018/080727 dated Jul. 4, 2018.
International Search Report in corresponding PCT Application No. PCT/CN2018/080727, dated Jul. 4, 2018.

*Primary Examiner* — Nizal S Chandrakumar
(74) *Attorney, Agent, or Firm* — Leason Ellis LLP

(57) ABSTRACT

Provided is a lactam compound, a tautomer, a stereoisomer, a racemate, a nonequal mixture of enantiomers, a geometric isomer, a solvate, a pharmaceutically acceptable salt thereof, or a solvate of the salt of the compound, and a pharmaceutical composition containing the compound. Also provided are the use of such compounds and their pharmaceutical compositions as drugs, especially as antiviral drugs.

5 Claims, No Drawings

LACTAM COMPOUND, PREPARATION METHOD AND USE THEREOF

CROSS-REFERENCE TO RELATED APPLICATIONS

The present application is a continuation-in-part application based on International Patent Application No. PCT/CN2018/080727, which claims priority to Chinese Patent Application No. 201710191282.1, and titled "Lactam compound, and preparation method therefor and use thereof", all of which are incorporated herein by reference in their entireties.

TECHNICAL FIELD

The invention relates to the field of medicine, and specifically to a class of lactam derivatives, their combinations and their uses as drugs, especially as drugs with antiviral functions.

BACKGROUND ART

Viruses can be easily divided into two categories, enveloped virus and non-enveloped virus, depending on whether their outer shell contains a lipid rich membrane or not. The non-enveloped virus enters the infected cells mainly through swallowing through clathrin. The invasion of enveloped virus is mainly the fusion process between the capsid and the host cell membrane. At present, the research and development of antiviral agents are mainly based on two aspects: one is the level of virus infection, the other is the level of host cell defense. Most antiviral drugs now on the market are based on the virus itself, which means the receptor is virus itself. Interferon (IFN), the first generation of antiviral drugs to be developed, is named for its ability to "interfere" with virus replication. In recent years, more and more antiviral drugs have been developed and widely used in clinical treatment. For example, after interferon, ribavirin, acyclovir, valacyclovir, zidovudine, telbivudine and other nucleoside drugs which can interfere with virus transcription or replication developed rapidly, which occupy 50% antiviral drug market.

Although many antiviral drugs have been used effectively in clinic, drug-resistant viruses have emerged in recent years. The cause of drug resistance is mainly caused by the mutation of virus gene, which makes the antiviral drugs lose their target. For example, herpes simplex virus mutated in the thymidine kinase gene, acyclovir and ganciclovir cannot convert into active components in cells, thus becoming resistant to these drugs. Mutations in the M2 protein gene of influenza A virus make it resistant to amantadine or rimantadine. The variation of HIV reverse transcriptase or protease gene is also the main cause of drug resistance. Mutations in the unstructured 5 A and envelope gene 2-glycoprotein of HCV make it resistant to interferon. In conclusion, the development of new antiviral drugs is urgent.

SUMMARY OF THE INVENTION

The technical problem to be solved by the present disclosure is to overcome the defects of the existing technical solutions for treating tumors and provide a new effective choice for the treatment of tumors.

A compound having a structure of formula I or II, a tautomer, a stereoisomer, a racemate, a unequal mixture of enantiomers, a geometric isomer, a solvate, a pharmaceutically acceptable salt thereof, or a solvate of the salt of the compound,

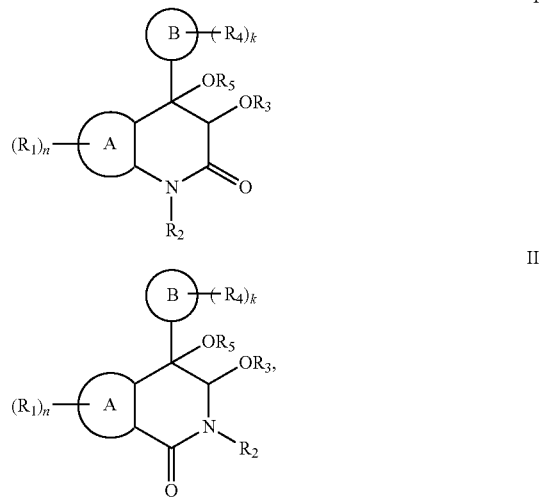

wherein A and B are each independently selected from five-membered or six-membered aromatic ring, eterocyclic ring, carbon ring, or carbon heterocyclic ring; n is 1, 2, 3, or 4; k is 1, 2, 3, 4 or 5;

$R_1$ and $R_4$ are each independently selected from hydrogen, halogen, hydroxy, amino, nitro, cyano, alkyl, halogenated alkyl, alkoxy, alkylamino, alkanoyl, hydroxyalkoxy, hydroxyalkylamino, hydroxyalkanoyl, haloalkoxy, haloalkylamino, haloalkanoyl, aminoalkoxy, cycloalkyl, cycloalkyloxy, cycloalkylamino, cycloalkanoyl, alkenyl, alkenylalkoxy, alkenylalkylamino, alkenylalkanoyl, alkynyl, alkynylalkoxy, alkynylalkylamino, alkynylalkanoyl, aryl, aryloxy, aroyl, arylamino, arylalkoxy, arylalkylamino, heteroaryl, heteroaryloxy, heteroaroyl, heteroarylamino, heteroarylalkoxy, heteroarylalkylamino, heteroarylalkanoyl, heterocycloalkyl, heterocyclyloxy, heterocyclylamino, heterocyclylanoyl, heterocyclylalkoxy, heterocyclylalkylamino, heterocyclylalkanoyl, azidoalkoxy, fused bicyclyl, fused heterobicyclyl, fused bicyclyl aliphatic, fused heterobicyclyl aliphatic, fused bicycloxy, fused heterobicycloxy, fused bicyclylamino, fused heterobicyclylamino, fused bicyclylalkoxy, fused heterobicyclylalkoxy, fused bicyclylalkylamino, fused heterobicyclylalkylamino, fused bicycloxyalkoxy, fused heterobicycloxyalkoxy, fused bicyclylaminoalkoxy, fused heterobicyclylaminoalkoxy, fused bicyclyl-C(═O)—, fused bicyclyl-C(═O)O—, fused heterobicyclyl-C(═O)—, fused heterobicyclyl-C(═O)O—, fused bicyclylamino-C(═O)—, fused heterobicyclylamino-C(═O)—, fused bicyclyl-C(═O)N($R_6$)—, fused heterobicyclyl-C(═O)N($R_6$)—, spiro bicyclyl, spiro heterobicyclyl, spiro bicyclyl aliphatic, spiro heterobicyclyl aliphatic, spiro bicycloxy, spiro heterobicycloxy, spiro bicyclylamino, spiro heterobicyclylamino, spiro bicyclylalkoxy, spiro heterobicyclylalkoxy, spiro bicyclylalkylamino, spiro heterobicyclylalkylamino, spiro bicycloxyalkoxy, spiro heterobicycloxyalkoxy, spiro bicyclylaminoalkoxy, spiro heterobicyclylaminoalkoxy, spiro bicyclyl-C(═O)—, spiro bicyclyl-C(═O)O—, spiro heterobicyclyl-C(═O)—, spiro heterobicyclyl-C(═O)O—, spiro bicyclylamino-C(═O)—, spiro heterobicyclylamino-C(═O)—, spiro bicyclyl-C(═O)N($R_6$)—, spiro heterobicyclyl-C(═O)N($R_6$)—, $R_7R_6N-$, $-C(=O)NR_6R_7$, $-OC(=O)NR_6R_7$, $-OC(=O)OR_6$, $-N(R_6)C(=O)NR_6R_7$, $-N(R_6)C(=O)OR_7$, $-N(R_6)C(=O)-R_7$, $R_6R_7N-S(=O)_t-$, $R_6S(=O)_t-$, $R_6S(=O)_tN(R_7)-$, $R_7R_6N$-alkyl, $R_6S(=O)_t$-alkyl, $R_7R_6N-C(=O)$-alkyl, $R_7R_6N$-alkoxy, $R_6S(=O)_t$-alkoxy, $R_6R_7N-C(=O)$-alkoxy, aryl-$(CH_2)_p$-G-$(CH_2)_m-$, heteroaryl-$(CH_2)_p$-G-$(CH_2)_m-$, heterocyclyl-$(CH_2)_p$-G-$(CH_2)_m-$, or cycloalkyl-$(CH_2)_p$-G-$(CH_2)_m-$, wherein G is selected from O, S, $NR_7$, $S(=O)$, $S(=O)_2$, $C(=O)$, $-C(=O)N(R_7)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein each of the aryl-$(CH_2)_p$-G-$(CH_2)_m-$, heteroaryl-$(CH_2)_p$-G-$(CH_2)_m-$, heterocyclyl-$(CH_2)_p$-G-$(CH_2)_m-$, and cycloalkyl-$(CH_2)_p$-G-$(CH_2)_m-$ is optionally substituted by one or more substituents selected from F, Cl, Br, I, alkyl, alkenyl, alkynyl, alkoxy or cyano;

$R_2$, $R_3$ and $R_5$ are each independently selected from hydrogen, alkyl, halogenated alkyl, alkanoyl, hydroxyalkanoyl, haloalkanoyl, cycloalkyl, cycloalkanoyl, alkenyl, alkenylalkanoyl, alkynyl, alkynylalkanoyl, aryl, aroyl, heteroaryl, heteroaroyl, heteroarylalkanoyl, heterocycloalkyl, heterocyclic acyl, heterocyclylalkanoyl, azide alkyl, fused bicyclyl, fused heterobicyclyl, fused bicyclyl-$C(=O)-$, fused heterobicyclyl-$C(=O)-$, fused bicyclylamino-$C(=O)-$, fused heterobicyclylamino-$C(=O)-$, spiro bicyclyl, spiro heterobicyclyl, spiro bicyclyl aliphatic, spiro heterobicyclyl aliphatic, spiro bicyclyl-$C(=O)-$, spiro heterobicyclyl-$C(=O)-$, spiro bicyclylamino-$C(=O)-$, spiro heterobicyclylamino-$C(=O)-$, $-C(=O)NR_6R_7$, $R_6R_7N-S(=O)_t-$, $R_6S(=O)_t-$, $R_7R_6N-C(=O)$-alkyl, $R_6S(=O)_t$-alkyl, $R_6R_7N-C(=O)$-alkyl, aryl-$(CH_2)_p$-G-$(CH_2)_m-$, heteroaryl-$(CH_2)_p$-G-$(CH_2)_m-$, heterocyclyl-$(CH_2)_p$-G-$(CH_2)_m-$, or cycloalkyl-$(CH_2)_p$-G-$(CH_2)_m-$, wherein G is selected from O, S, $NR_8$, $S(=O)$, $S(=O)_2$, $C(=O)$, $-C(=O)N(R_6)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein each of the aryl-$(CH_2)_p$-G-$(CH_2)_m-$, heteroaryl-$(CH_2)_p$-G-$(CH_2)_m-$, heterocyclyl-$(CH_2)_p$-G-$(CH_2)_m-$, or cycloalkyl-$(CH_2)_p$-G-$(CH_2)_m-$ is optionally substituted by one or more substituents selected from F, Cl, Br, I, alkyl, alkenyl, alkynyl, alkoxy or cyano, aryl, heteroaryl, cycloalkyl, heterocyclyl;

$R_8$ is selected from hydrogen, $R_6R_7NC(=O)-$, $R_6OC(=O)-$, $R_6C(=O)-$, $R_6R_7NS(=O)-$, $R_6OS(=O)-$, $R_6S(=O)-$, $R_6R_7NS(=O)_2-$, $R_6OS(=O)_2-$, $R_6S(=O)_2-$, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or carbocyclyl;

$R_6$ and $R_7$ are each independently selected from hydrogen, aliphatic, haloaliphatic, hydroxyaliphatic, aminoaliphatic, alkoxyaliphatic, alkylaminoaliphatic, alkylthioaliphatic, arylaliphatic, heteroarylaliphatic, heterocyclylaliphatic, cycloalkylaliphatic, aryloxyaliphatic, heterocyclyloxyaliphatic, cycloalkyloxyaliphatic, arylaminoaliphatic, heterocyclylaminoaliphatic, cycloalkylaminoaliphatic, aryl, heteroaryl, heterocyclyl or cycloalkyl; with the proviso that where $R_6$ and $R_7$ are bonded to a same nitrogen atom, $R_6$ and $R_7$ together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from N, O, S, or Se, and the number of the hetero atoms is 1-5;

$R_1$, $R_2$, $R_3$, $R_4$, $R_5$, $R_6$, $R_7$, $R_8$ are optionally substituted by one or more substituents selected from deuterium, halogen, hydroxyl, hydroxymethyl, carboxyl, acetylamino, alkyl, alkoxy, alkylamino, cycloalkyl, alkenyl, alkynyl, trifluoromethyl, trifluoroacetyl, thiol, halogen, nitro, amino, azido ($-N_3$), guanidyl, cyano, tert-butoxycarbonyl (-Boc), carbonyl ($-C=O$), oxo ($=O$), thio ($=S$), sulfonyl, aryl, heteroaryl, heterocyclyl.

In some implementations, The compound, the tautomer, the stereoisomer, the racemate, the nonequal mixture of enantiomers, the geometric isomer, the solvate, the pharmaceutically acceptable salt thereof, or the solvate of the salt of the compound in this invention, having a structure of formula III or IV,

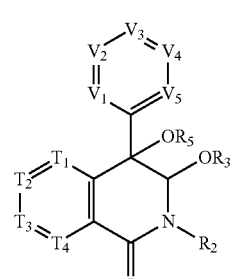

III

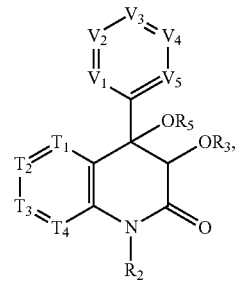

IV wherein $T_1$, $T_2$, $T_3$, $T_4$ are each independently selected from N or $CR_1$, and no more than three N atoms are among them; $V_1$, $V_2$, $V_3$, $V_4$, are each independently selected from N or $CR_4$, and no more than three N atoms are among them;

wherein $R_1$ and $R_4$ are each independently selected from H, F, Cl, Br, I, hydroxy, amino, nitro, cyano, carboxyl, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclylanoyl, C4-C12 heterocyclyl C1-C6 alkoxy, C4-C12 heterocyclyl C1-C6 alkylamino, C4-C12 heterocyclyl C1-C6 alkanoyl, $R_7R_6N-$, $-C(=O)NR_6R_7$, $-OC(=O)NR_6R_7$, $-OC(=O)OR_6$, $-N(R_6)C(=O)NR_6R_7$, $-N(R_6)C(=O)OR_7$, $-N(R_6)C(=O)-R_7$, $R_6R_7N-S(=O)_t-$, $R_6S(=O)_t-$, $R_6S(=O)_t-NR_7-$, $R_7R_6N-$C1-C6 alkyl, $R_6S(=O)_t-$C1-C6 alkyl, $R_6R_7N-C(=O)-$C1-C6 alkyl, $R_7R_6N-$C1-C6 alkoxy, $R_6S(=O)_t-$C1-C6 alkoxy, $R_6R_7N-C(=O)-$C1-C6 alkoxy, C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, or C3-C10 cycloalkyl-$(CH_2)_p$-G-$(CH_2)_m-$, wherein G is selected from O, S, $NR_8$, $S(=O)$, $S(=O)_2$, $C(=O)$, $-C(=O)N(R_6)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein the C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, and C3-C10 cycloalkyl-$(CH_2)_p$-G-$(CH_2)_m-$ are each optionally substituted by one or more substituents selected from F, Cl, Br, I, alkyl, alkenyl, alkynyl, alkoxy or cyano;

$R_2$, $R_3$ and $R_5$ are each independently selected from hydrogen, C1-C20 alkyl, C1-C20 haloalkyl, C1-C20 alkanoyl, hydroxy-substituted C1-C20 alkanoyl, C1-C20 haloalkanoyl, C3-C10 cycloalkyl, C3-C10 cycloalkanoyl, C2-C8 alkenyl, C2-C8 alkenyl alkyl, C2-C8 alkynyl, C2-C8 alkynyl alkyl, C6-C10 aryl, C6-C10 aroyl, C5-C12 heteroaryl, C5-C12 heteroaroyl, C4-C12 heterocyclyl C1-C6 alkanoyl, C5-C12 fused bicyclyl, C5-C12 fused heterobicyclyl, $-C(=O)NR_6R_7$, $R_6R_7N-S(=O)_t-$, $R_6S(=O)_t-$, $R_7R_6N-$C1-C6 alkyl, $R_6S(=O)_t-$C1-C6 alkyl, $R_6R_7N-C(=O)-$C1-C6 alkyl, C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, or C3-C10 cycloalkyl-$(CH_2)_p$-G-$(CH_2)_m-$, wherein G is selected from O, S, $NR_8$, $S(=O)$, $S(=O)_2$, $C(=O)$, $-C(=O)N(R_6)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein the C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, and C3-C10 cycloalkyl-$(CH_2)_p$-G-$(CH_2)_m-$ are each optionally substituted by one or more substituents selected from F, Cl, Br, I, cyano, alkyl, alkenyl, alkynyl, alkox, aryl, heteroaryl, cycloalkyl, heterocyclyl;

$R_8$ is selected from H, $R_6R_7NC(=O)-$, $R_6OC(=O)-$, $R_6C(=O)-$, $R_6R_7NS(=O)-$, $R_6OS(=O)-$, $R_6S(=O)-$, $R_6R_7NS(=O)_2-$, $R_6OS(=O)_2-$, $R_6S(=O)_2-$, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl or C3-C10 cycloalkyl;

$R_6$ and $R_7$ are each independently selected from H, D, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl or C3-C10 cycloalkyl; with the proviso that where $R_6$ and $R_7$ are bonded to a same nitrogen atom, $R_6$ and $R_7$, together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from N, O, S, or Se, and the number of the hetero atoms is 1-5;

wherein $R_1$, $R_2$, $R_3$, $R_4$, $R_5$, $R_6$, $R_7$, $R_8$ are optionally substituted by one or more substituents selected from deuterium, halogen, hydroxyl, hydroxymethyl, carboxyl, acetylamino, alkyl, alkoxy, alkylamino, cycloalkyl, alkenyl, alkynyl, trifluoromethyl, trifluoroacetyl, thiol, nitro, amino, azido ($-N_3$), guanidyl, cyano, tert-butoxycarbonyl (-Boc), carbonyl ($-C=O$), oxo ($=O$), thio ($=S$), sulfonyl, aryl, heteroaryl, heterocyclyl; and in formula IV, when $V_1$, $V_2$, $V_3$, $V_4$, $V_5$, $T_3$, $T_4$ are CH, $T_1$ is C—OH, or C—OAc, or C—OMe, or C—OBn, or C-OEt, or C—OPr, or C—OCH$_2$C≡CH, or C—OCOCH$_2$Cl, or C—OCOPr, $R_3$ is CH$_3$, $R_2$, and $R_5$ are H, $T_2$ is CR$_1$, $R_1$ is not

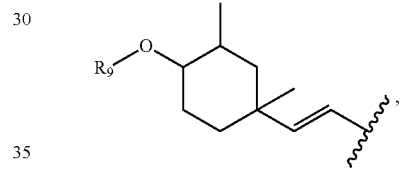

wherein $R_9$ is selected from amino acid residue with carboxyl end which is free of hydroxyl; and in formula IV, when $V_1$, $V_2$, $V_4$, $V_5$, $T_3$, $T_4$ are CH, $V_3$, is COCH$_3$, $T_1$ is C—OH, or CH, $R_2$ is H, $R_3$ is CH$_3$, or H, $R_5$ is H, $R_1$ is no H or

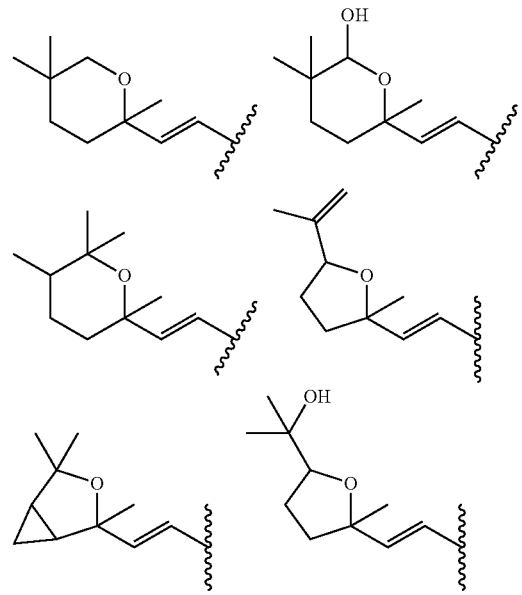

-continued

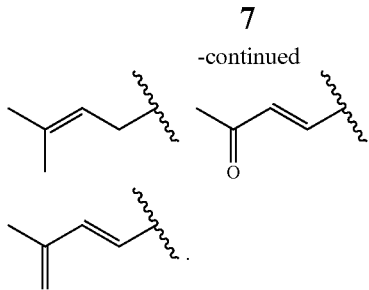

In some implementations, the compound, the tautomer, the stereoisomer, the racemate, the nonequal mixture of enantiomers, the geometric isomer, the solvate, the pharmaceutically acceptable salt thereof, or the solvate of the salt of the compound in this invention, having a structure of formula V or VI,

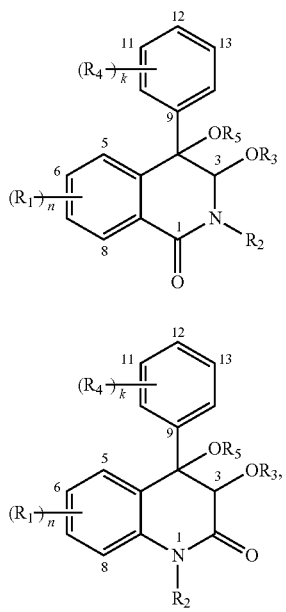

n=1, 2, 3, or 4; k=1, 2, 3, 4, or 5, wherein $R_1$ and $R_4$ are each independently selected from H, F, Cl, Br, I, hydroxy, amino, nitro, cyano, caiboxyl, C1-C20 alkyl, C1-C20 haloalkyl, C1-C20 alkoxy, C1-C20 alkylamino, C1-C20 alkanoyl, hydroxy-substituted C1-C20 alkoxy, hydroxy-substituted C1-C20 alkylamino, hydroxy-substituted C1-C20 alkanoyl, C1-C20 haloalkoxy, C1-C20 haloalkylamino, C1-C20 haloalkanoyl, C1-C20 aminoalkoxy, C3-C10 cycloalkyl, C3-C10 cycloalkyloxy, C3-C10 cycloalkylamino, C3-C10 cycloalkanoyl, C2-C8 alkenyl, C2-C8 alkynyl, C6-C10 aryl, C6-C10 aryloxy, C6-C10 aroyl, C6-C10 arylamino, C6-C10 aryl C1-C6 alkoxy, C6-C10 arylalkylamino, C5-C12 heteroaryl, C5-C12 heteroaryloxy, C5-C12 heteroaroyl, C5-C12 heteroarylamino, C5-C12 heteroaryl C1-C6 alkoxy, C5-C12 heteroaryl C1-C6 alkylamino, C4-C12 heterocyclyl C1-C6 alkanoyl, C4-C12 heterocycloalkyl, C4-C12 heterocyclyloxy, C4-C12 heterocyclylamino, C4-C12 heterocyclanoyl, C4-C12 heterocyclyl C1-C6 alkoxy, C4-C12 heterocyclyl C1-C6 alkylamino, C4-C12 heterocyclyl C1-C6 alkanoyl, $R_7R_6N-$, $-C(=O)NR_6R_7$, $-OC(=O)NR_6R_7$, $-OC(=O)OR_6$, $-N(R_6)C(=O)NR_6R_7$, $-N(R_6)C(=O)OR_7$, $-N(R_6)C(=O)-R_7$, $R_6R_7N-S(=O)_t-$, $R_6S(=O)_t-$, $R_6S(=O)_t-NR_7-$, $R_7R_6N-C1-C6$ alkyl, $R_6S(=O)_t-C1-C6$ alkyl, $R_6R_7N-C(=O)-C1-C6$ alkyl, $R_7R_6N-C1-C6$ alkoxy, $R_6S(=O)_t-C1-C6$ alkoxy, $R_6R_7N-C(=O)-C1-C6$ alkoxy, C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, or C3-C10 cycloalkyl-$(CH_2)_p$-G-$(CH_2)_m-$, wherein G is selected from O, S, $NR_8$, S(=O), S(=O)$_2$, C(=O), $-C(=O)N(R_6)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein the C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, and C3-C10 cycloalkyl-$(CH_2)_p$-G-$(CH_2)_m-$ are each optionally substituted by one or more substituents selected from F, Cl, Br, I, alkyl, alkenyl, alkynyl, alkoxy or cyano;

$R_2$, $R_3$ and $R_5$ are each independently selected from hydrogen, C1-C20 alkyl, C1-C20 haloalkyl, C1-C20 alkanoyl, hydroxy-substituted C1-C20 alkanoyl, C1-C20 haloalkanoyl, C3-C10 cycloalkyl, C3-C10 cycloalkanoyl, C2-C8 alkenyl, C2-C8 alkenyl alkyl, C2-C8 alkynyl, C2-C8 alkynyl alkyl, C6-C10 aryl, C6-C10 aroyl, C5-C12 heteroaryl, C5-C12 heteroaroyl, C4-C12 heterocyclyl C1-C6 alkanoyl, C5-C12 fused bicyclyl, C5-C12 fused heterobicyclyl, $-C(=O)NR_6R_7$, $R_6R_7N-S(=O)_t-$, $R_6S(=O)_t-$, $R_7R_6N-C1-C6$ alkyl, $R_6S(=O)_t-C1-C6$ alkyl, $R_6R_7N-C(=O)-C1-C6$ alkyl, C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, or C3-C10 cycloalkyl-$(CH_2)_p$-G-$(CH_2)_m-$, wherein G is selected from O, S, $NR_8$, S(=O), S(=O)$_2$, C(=O), $-C(=O)N(R_6)-$, $-OC(=O)N(R_6)-$, $-OC(=O)-$, $-N(R_6)C(=O)N(R_6)-$, $-(R_6)N-S(=O)_t-$, $-OS(=O)_t-$, or $-OS(=O)_tN(R_6)-$, wherein each t is 1 or 2, p and m are each independently 0, 1, 2, 3 or 4, wherein the C6-C10 aryl-$(CH_2)_p$-G-$(CH_2)_m-$, C5-C12 heteroaryl-$(CH_2)_p$-G-$(CH_2)_m-$, C4-C12 heterocyclyl-$(CH_2)_p$-G-$(CH_2)_m-$, and C3-C10 cycloalkyl-$(CH_2)_p$-G-$(CH_2)_m-$ are each optionally substituted by one or more substituents selected from F, Cl, Br, I, cyano, alkyl, alkenyl, alkynyl, alkox, aryl, heteroaryl, cycloalkyl, heterocyclyl;

$R_8$ is selected from H, $R_6R_7NC(=O)-$, $R_6OC(=O)-$, $R_6C(=O)-$, $R_6R_7NS(=O)-$, $R_6OS(=O)-$, $R_6S(=O)-$, $R_6R_7NS(=O)_2-$, $R_6OS(=O)_2-$, $R_6S(=O)_2-$, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl or C3-C10 cycloalkyl;

$R_6$ and $R_7$ are each independently selected from H, D, C1-C3 aliphatic, C1-C3 haloaliphatic, C1-C3 hydroxyaliphatic, C1-C3 aminoaliphatic, C1-C3 alkoxy C1-C3 aliphatic, C1-C3 alkylamino C1-C3 aliphatic, C1-C3 alkylthio C1-C3 aliphatic, C6-C10 aryl C1-C3 aliphatic, C5-C9 heteroaryl C1-C3 aliphatic, C4-C10 heterocyclyl C1-C3 aliphatic, C3-C10 cycloalkyl C1-C3 aliphatic, C6-C10 aryloxy C1-C3 aliphatic, C4-C10 heterocyclyloxy C1-C3 aliphatic, C3-C10 cycloalkyloxy C1-C3 aliphatic, C6-C10 arylamino C1-C3 aliphatic, C4-C10 heterocyclylamino C1-C3 aliphatic, C3-C10 cycloalkylamino C1-C3 aliphatic, C6-C10 aryl, C5-C10 heteroaryl, C4-C10 heterocyclyl or C3-C10 cycloalkyl; with the proviso that where $R_6$ and $R_7$ are bonded to a same nitrogen atom, $R_6$ and $R_7$, together with the nitrogen atom they are attached to, optionally form a substituted or unsubstituted 3-8 membered ring, a substituted or unsubstituted fused bicyclic ring or a substituted or unsubstituted spiro bicyclic ring, wherein hetero atoms in the heterocyclyl, heteroaryl, fused heterobicyclyl or spiro heterocyclyl are independently selected from N, O, S, or Se, and the number of the hetero atoms is 1-5;

wherein $R_1$, $R_2$, $R_3$, $R_4$, $R_5$, $R_6$, $R_7$, $R_8$ are optionally substituted by one or more substituents selected from deuterium, halogen, hydroxyl, hydroxymethyl, carboxyl, acetylamino, alkyl, alkoxy, alkylamino, cycloalkyl, alkenyl, alkynyl, trifluoromethyl, trifluoroacetyl, thiol, nitro, amino, azido (—$N_3$), guanidyl, cyano, tert-butoxycarbonyl (-Boc), carbonyl (—C=O), oxo (=O), thio (=S), sulfonyl, aryl, heteroaryl, heterocyclyl; and in formula IV, when $V_1$, $V_2$, $V_3$, $V_4$, $V_5$, $T_3$, $T_4$ are CH, $T_1$ is C—OH, or C—OAc, or C—OMe, or C—OBn, or C—OEt, or C—OPr, or C—OCH$_2$C≡CH, or C—OCOCH$_2$Cl, or C—OCOPr, $R_3$ is CH$_3$, $R_2$, and $R_5$ are H, $T_2$ is CR$_1$, $R_1$ is not

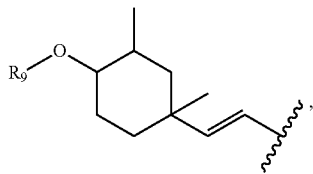

wherein $R_9$ is selected from amino acid residue with carboxyl end which is free of hydroxyl; and in formula IV, when $V_1$, $V_2$, $V_4$, $V_5$, $T_3$, $T_4$ are CH, $V_3$ is COCH$_3$, $T_1$ is C—OH, or CH, $R_2$ is H, $R_3$ is CH$_3$, or H, $R_5$ is H, $R_1$ is no H or

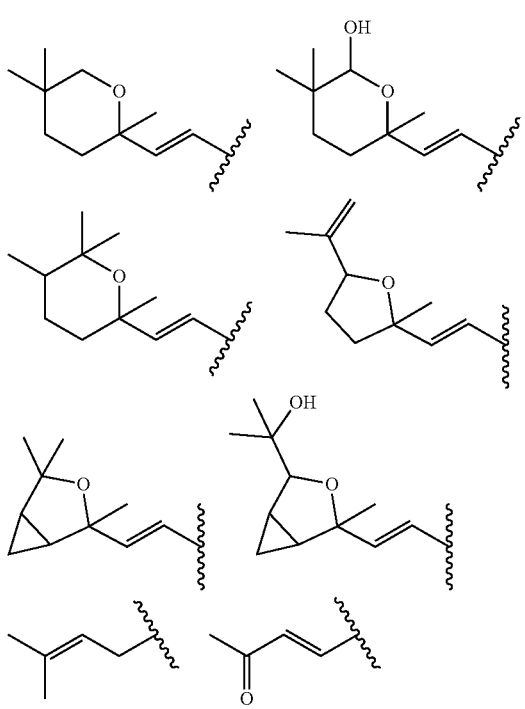

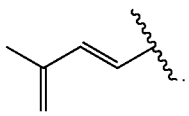

The compound, the tautomer, the stereoisomer, the racemate, the nonequal mixture of enantiomers, the geometric isomer, the solvate, the pharmaceutically acceptable salt thereof, or the solvate of the salt of the compound in this invention, wherein $R_1$ and $R_4$ are each independently selected from H, D, F, Cl, Br, I, hydroxy, amino, nitro, cyano, methyl, ethyl, propyl, isopropyl, butyl, tert-butyl, $C_5H_{11}$, $C_6H_{13}$, $C_8H_{17}$, trifluoromethyl, hydroxymethyl, aminomethyl, methoxy, ethoxy, tert-butoxy, methylamino, ethylamino, isopropylamino, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, prenyl or monoterpene or sesquiterpene derived from isoprene unit, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, thienyl, thiazolyl, piperidinyl, piperazinyl, indolyl, carbazolyl, benzofuranyl, tetrahydrofuranyl, tetrahydropyranyl, pyrimidine, purine, —N(CH$_3$)$_2$, —C(C=O)NH—C1-C4 alkyl, —OC(C=O)—NH—C1-C4 alkyl, —OC(O=O)O—C1-C4 alkyl, —NHC(=O)NH—C1-C4 alkyl, —NHC(=O)O—C1-C4 alkyl, —NHC(=O)—C1-C4 alkyl, C1-C4 alkyl-NH—S(=O)$_2$—, C1-C4 alkyl-S(=O)$_2$—, C1-C4 alkyl-S(=O)$_2$NH—, phenyl-(CH$_2$)$_p$-G-(CH$_2$)$_m$—, fluorophenyl-(CH$_2$)$_p$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, or cyclohexyl-(CH$_2$)$_p$-G-(CH$_2$)$_m$—, wherein G is selected from O, S, S(=O), S(=O)$_2$, C(=O), p and m are each independently 0, 1, 2 or 3, wherein the C6-C10 aryl-(CH$_2$)$_p$-G-(CH$_2$)$_m$— is optionally substituted by one or more substituents selected from F, Cl, Br, I, methyl, ethyl, propyl, ethynyl, propynyl, butynyl, methoxy, ethoxy or cyano, wherein $R_1$, $R_2$, $R_3$, $R_4$ are each optionally substituted by one or more substituents selected from F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl;

$R_2$, $R_3$, and $R_5$ are selected from H, methyl, ethyl, propyl, isopropyl, butyl, tert-butyl, $C_5H_{11}$, $C_6H_{13}$, $C_8H_{17}$, trifluoromethyl, hydroxymethyl, aminomethyl, 3-hydroxy-propyl, acetyl, trifluoroacetyl, cyanoacetyl, methylaminoacetyl, propionyl, isopropionyl, 2-hydroxypropanoyl, 2-aminopropanoyl, 2-chloropropanoyl, 2-bromopropanoyl, pentanoyl, hexanoyl, heptanoyl, methacryloyl, phenyl, benzoyl, p-nitrophenyl, p-methylbenzoyl, m-fluorobenzoyl, p-aminobenzoyl, p-methoxybenzoyl, 2,4-dimethylbenzoyl, m-azidobenzoyl, benzyl, p-chlorobenzyl, vinyl, propenyl, allyl, n-butenyl, isobutenyl, n-pentenyl, isopentenyl, cyclopropyl, cyclopropanoyl, cyclopentanoyl, cyclohexanoyl, 3-pyridinecarbonyl, naphthyl, phenethylimidazolyl, pyridyl, pyrrolyl, oxazolyl, isoxazolyl, triazolyl, tetrazolyl, furyl, pyranyl, thienyl, thiazolyl, piperidinyl, piperazinyl, indolyl, carbazolyl, benzofuranyl, tetrahydrofuranyl, tetrahydropyranyl, pyrimidine, purine, pentose, hexose, —(C=O)NH—C1-C4 alkyl, C1-C4 alkyl-NH—S(=O)$_2$—, C1-C4 alkyl-S(=O)$_2$—, phenyl-(CH$_2$)$_p$-G-(CH$_2$)$_m$—, fluorophenyl-(CH$_2$)$_p$-G-(CH$_2$)$_m$—, thiazolyl-(CH$_2$)$_p$-G-(CH$_2$)$_m$—, pyridyl-(CH$_2$)$_p$-G-(CH$_2$)$_m$—, phenylethyl, or cyclohexyl-(CH$_2$)$_p$-G-(CH$_2$)$_m$—, wherein G is selected from O, S, S(=O), S(=O)$_2$, C(=O), p and m are each independently 0, 1, 2 or 3, wherein the C6-C10 aryl-(CH$_2$)$_p$-G-(CH$_2$)$_m$— is optionally substituted by one or more substituents selected from F, Cl, Br, I, methyl, ethyl, propyl, ethynyl, propynyl, butynyl, methoxy, ethoxy or cyano, wherein R$_2$, R$_3$, and R$_5$ are optionally substituted by one or more substituents selected from D, F, Cl, Br, I, hydroxy, hydroxymethyl, carboxy, acetylamino, C1-C6 alkyl, C1-C6 alkoxy, C1-C6 alkylamino, trifluoromethyl, trifluoroacetyl, thiol, nitro, amino, azido (—N3), guanidyl, cyano, tert-butoxycarbonyl (-Boc), carbonyl (—C=O), oxo (=O), thio (=S), sulfonyl and phenyl.

The compound, the tautomer, the stereoisomer, the racemate, the nonequal mixture of enantiomers, the geometric isomer, the solvate, the pharmaceutically acceptable salt thereof, or the solvate of the salt of the compound according to claim 1, having one of the following structures,

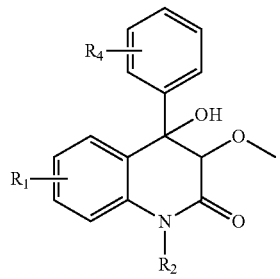

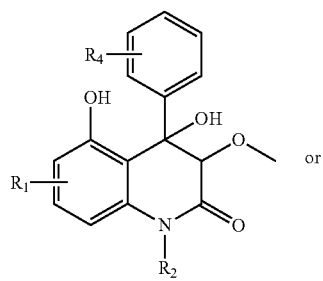

or

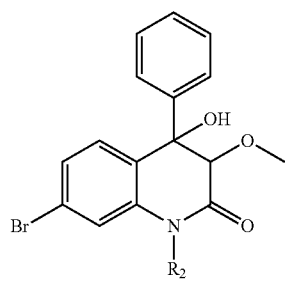

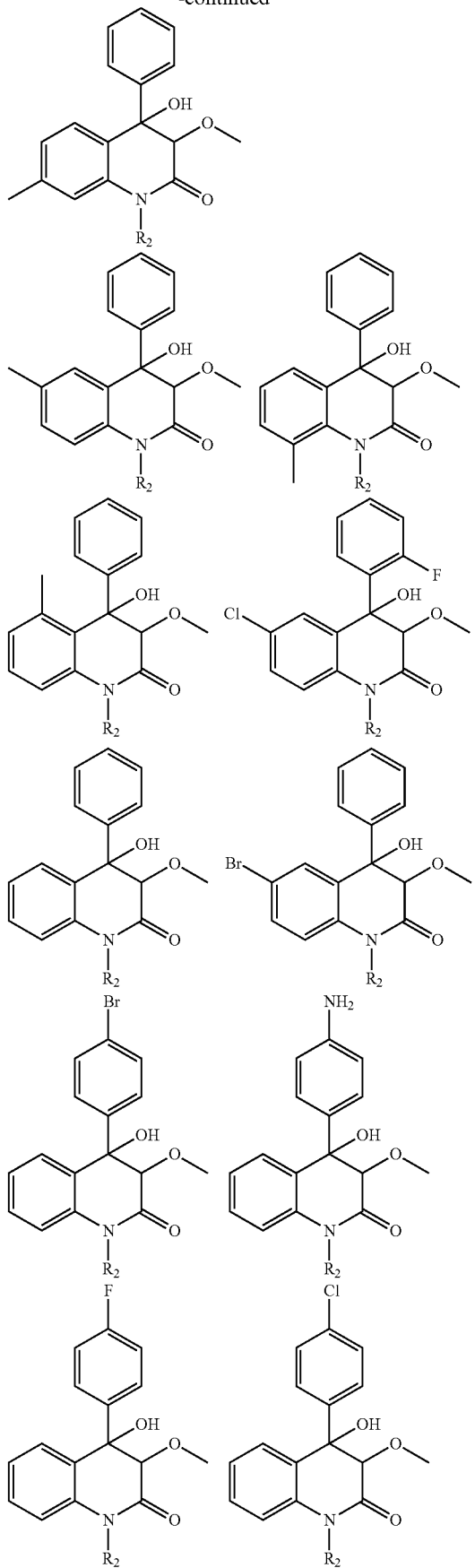

-continued
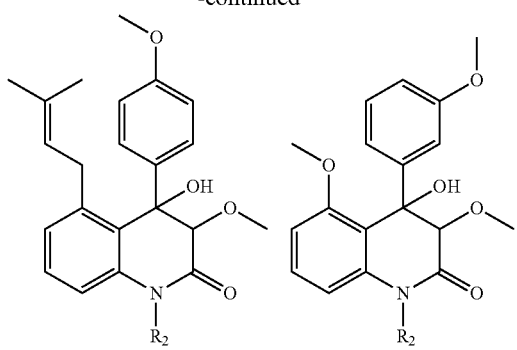
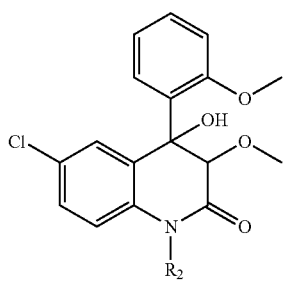
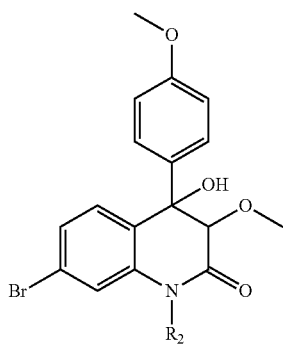
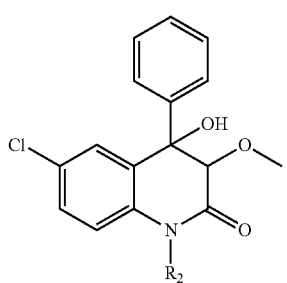
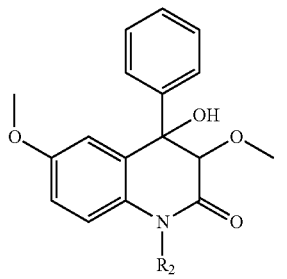
-continued
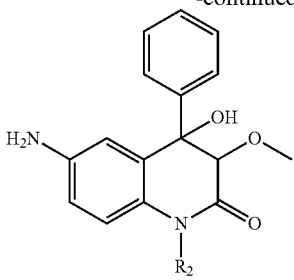
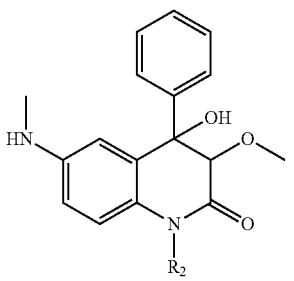
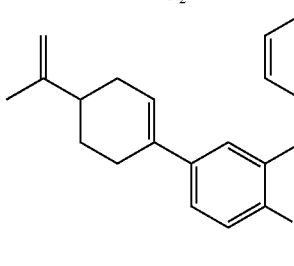
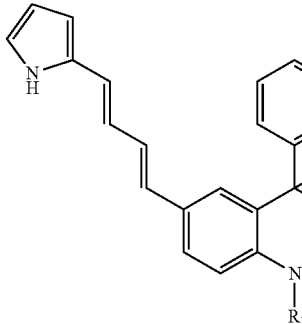
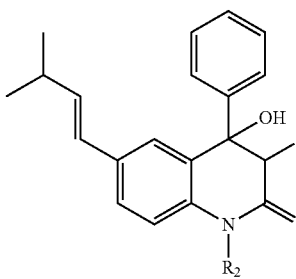

15
-continued
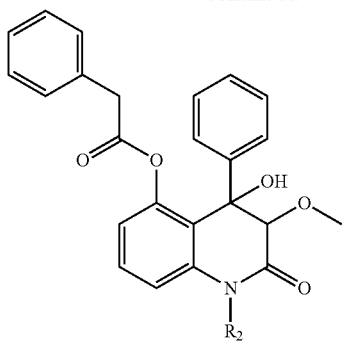
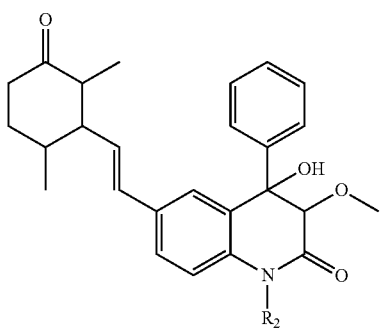
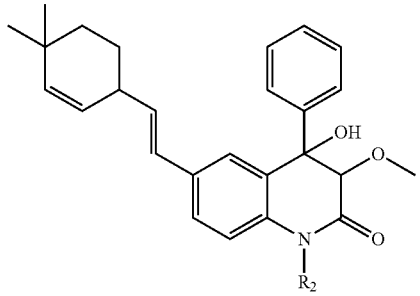
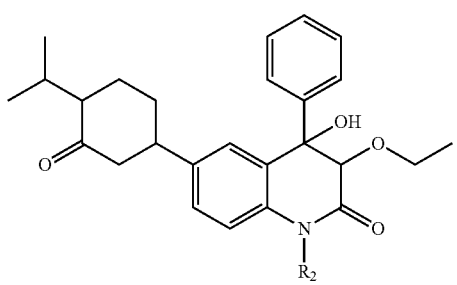
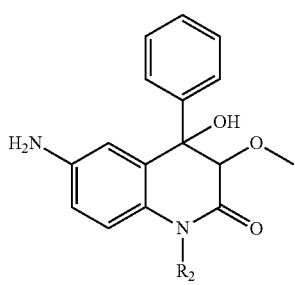
16
-continued
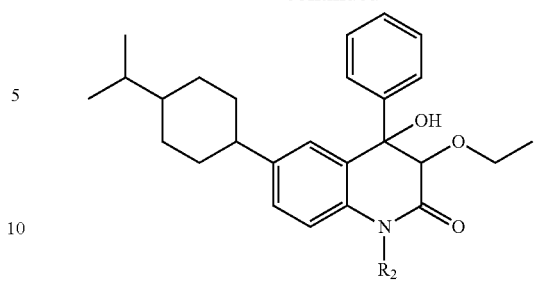
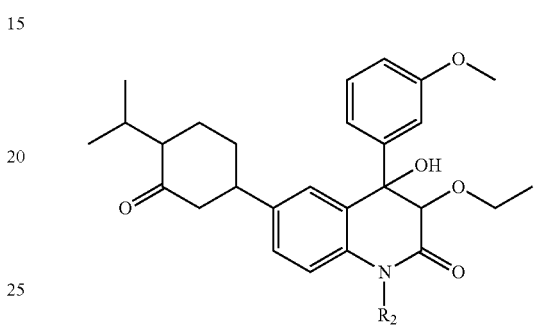
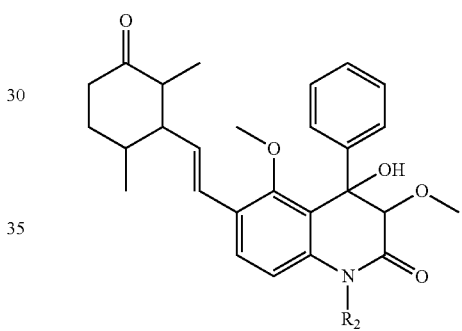
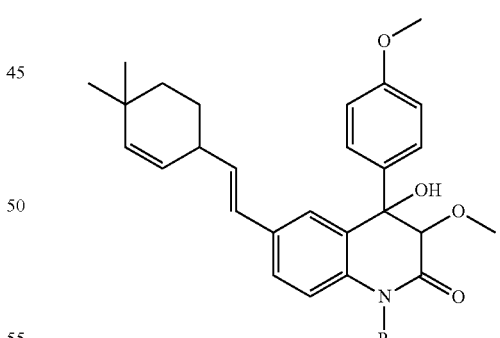
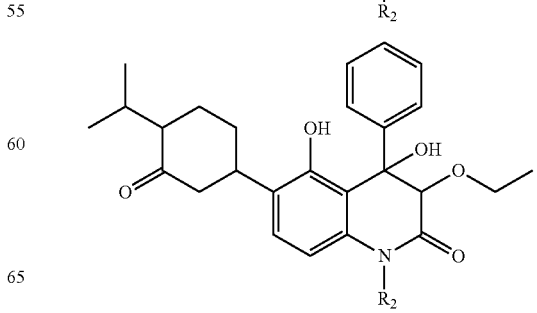

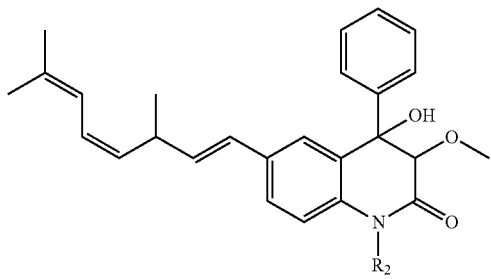
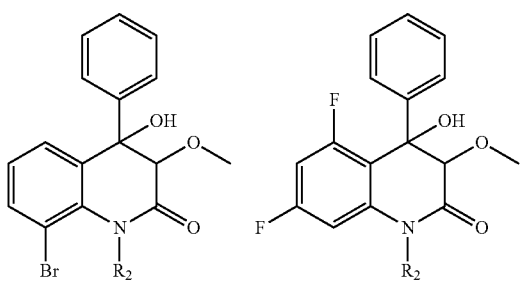
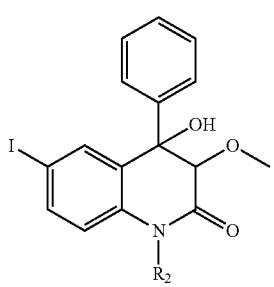
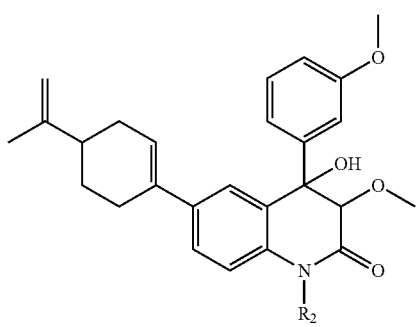
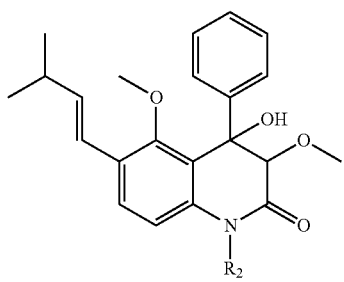
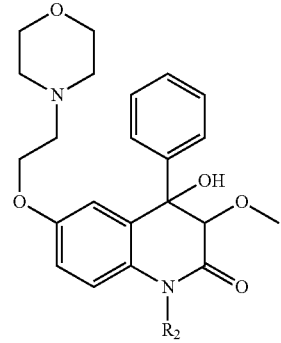
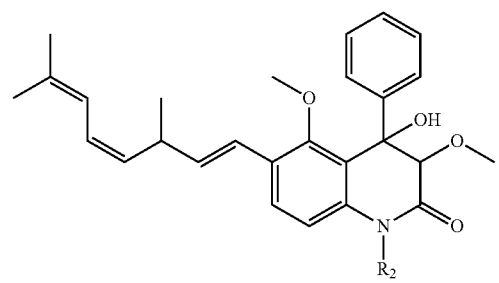
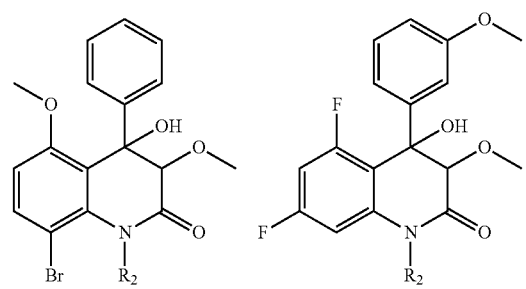
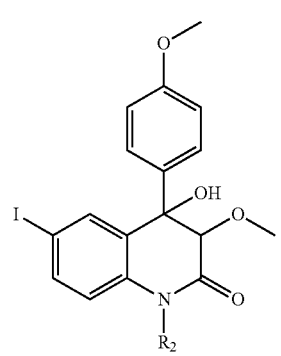

-continued

Wherein R₂ is selected from following substituents:

—C₂H₅  n-C₃H₇-  n-C₄H₉  n-C₅H₁₁-  —CH(CH₃)₂
—H₂CHC=CH₂  —H₂CCCH  CH₂CH₂CH(CH₃)₂
—H₂CHC=C(CH₃)₂  —CH₂OH  —C₂H₄OH
—C₂H₄N(CH₃)₂  —CH₂NH₂  C₂H₄NH₂
—C₂H₄N(C₂H₅)₂  —C₃H₆OH  —CH₂N(CH₃)₂

H  CH₃

-continued
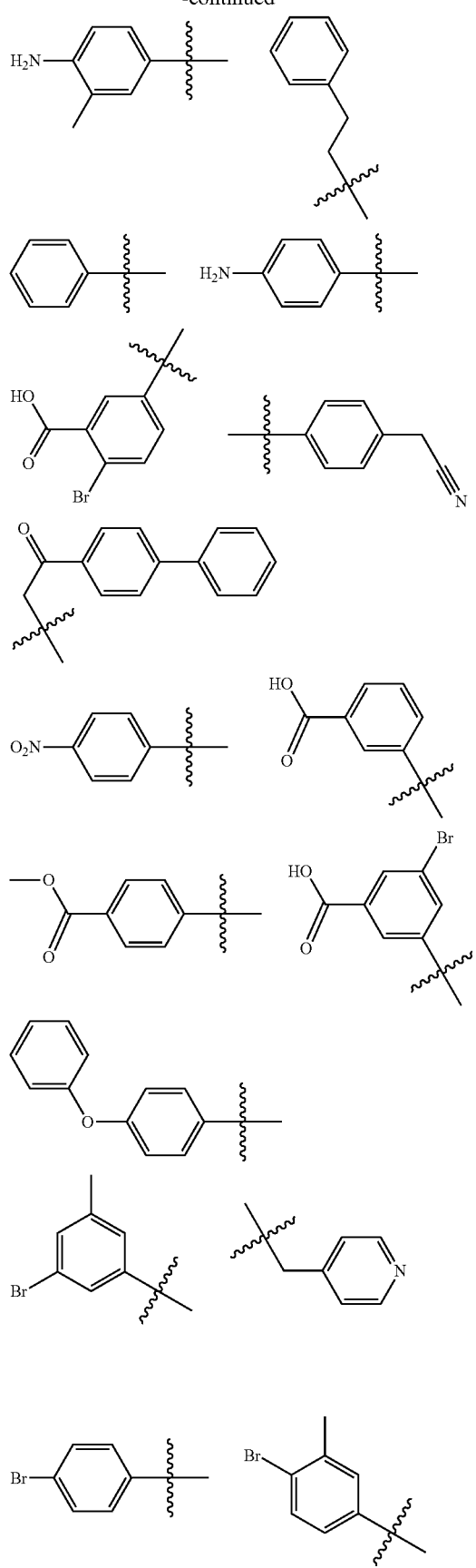
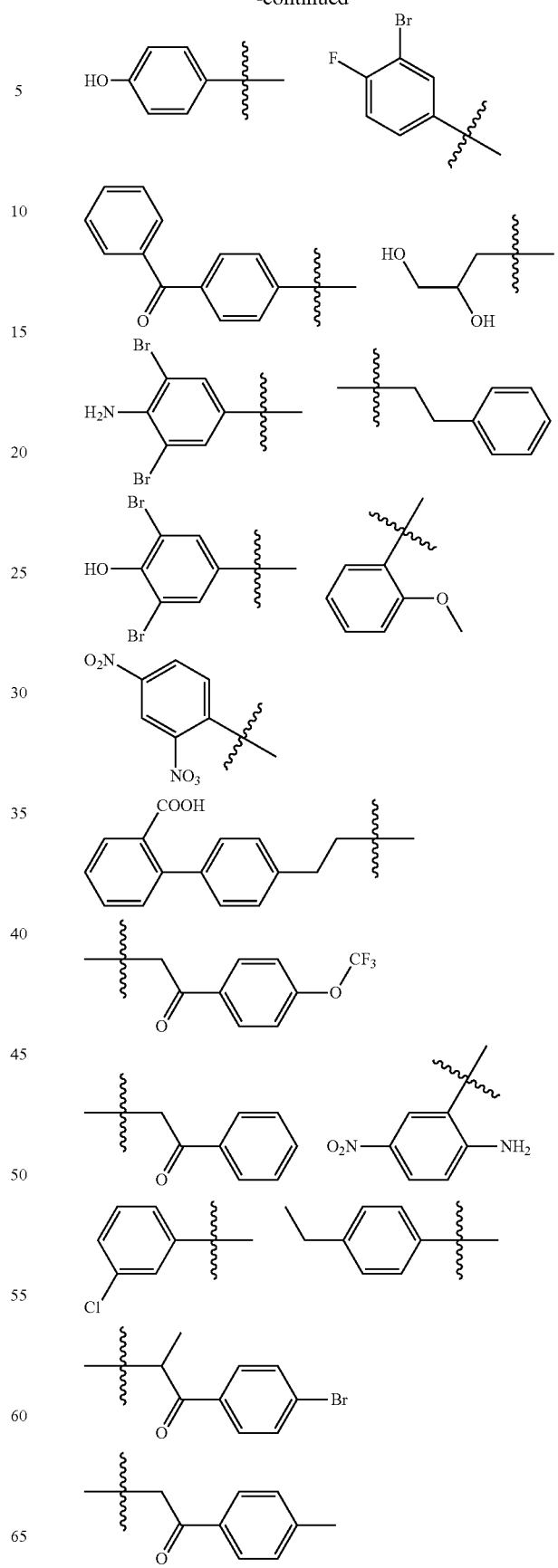

-continued
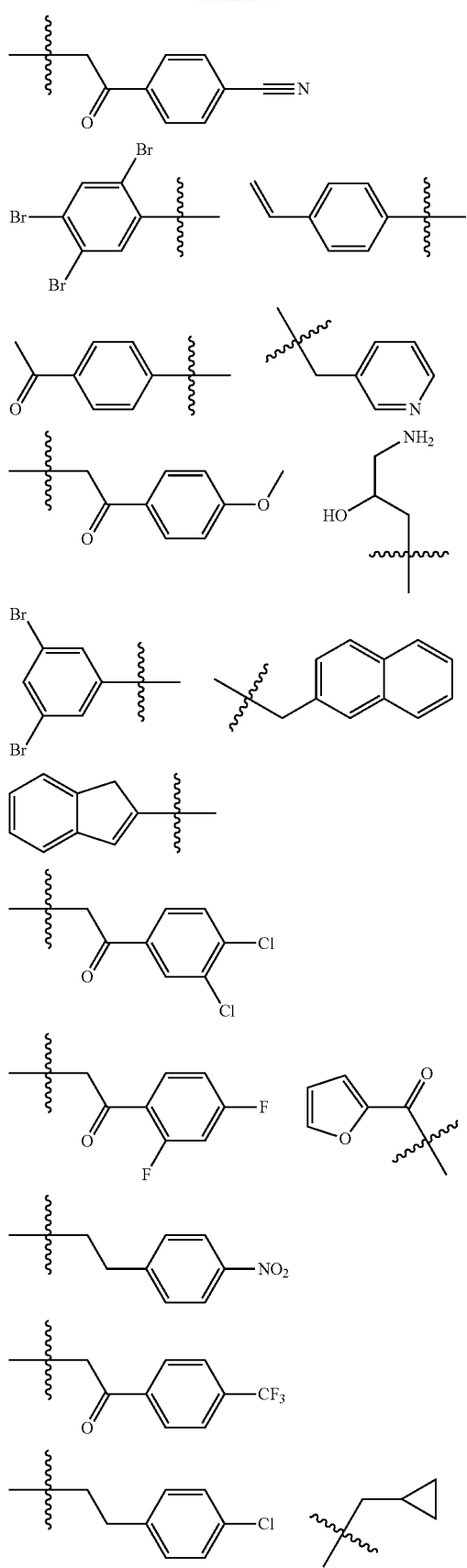
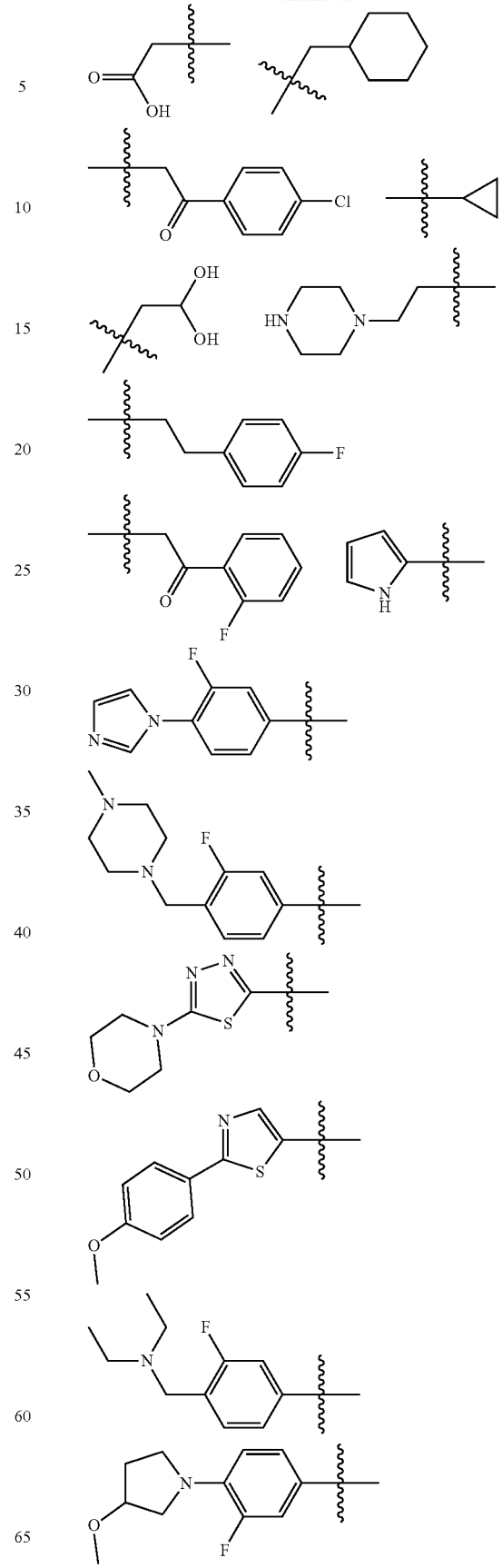

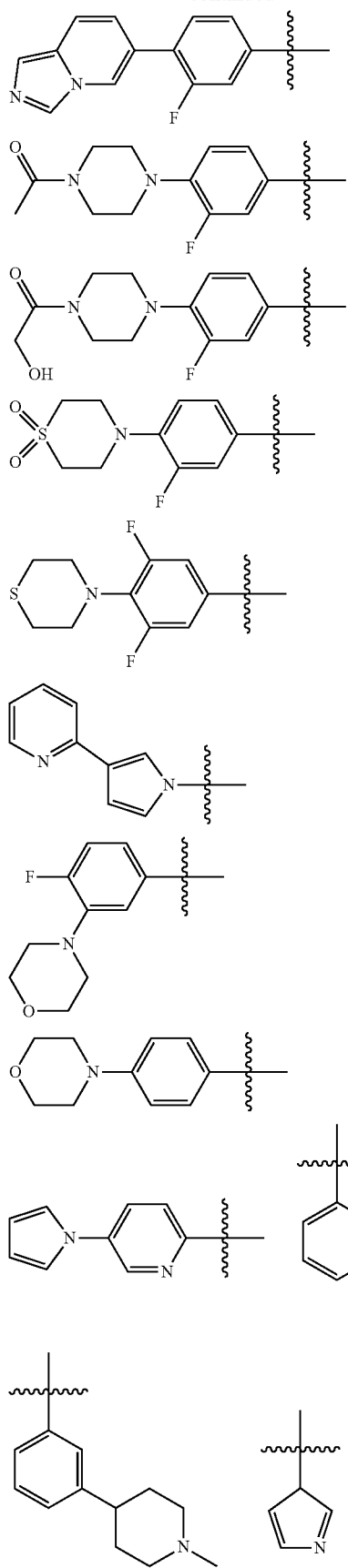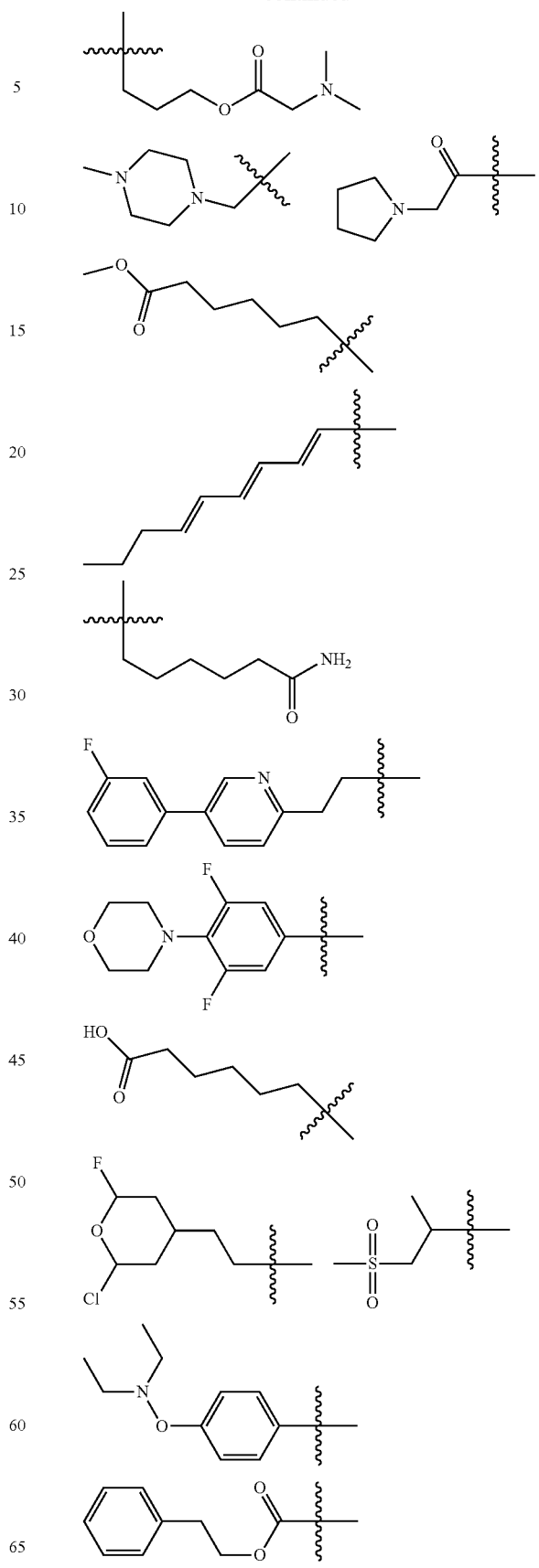

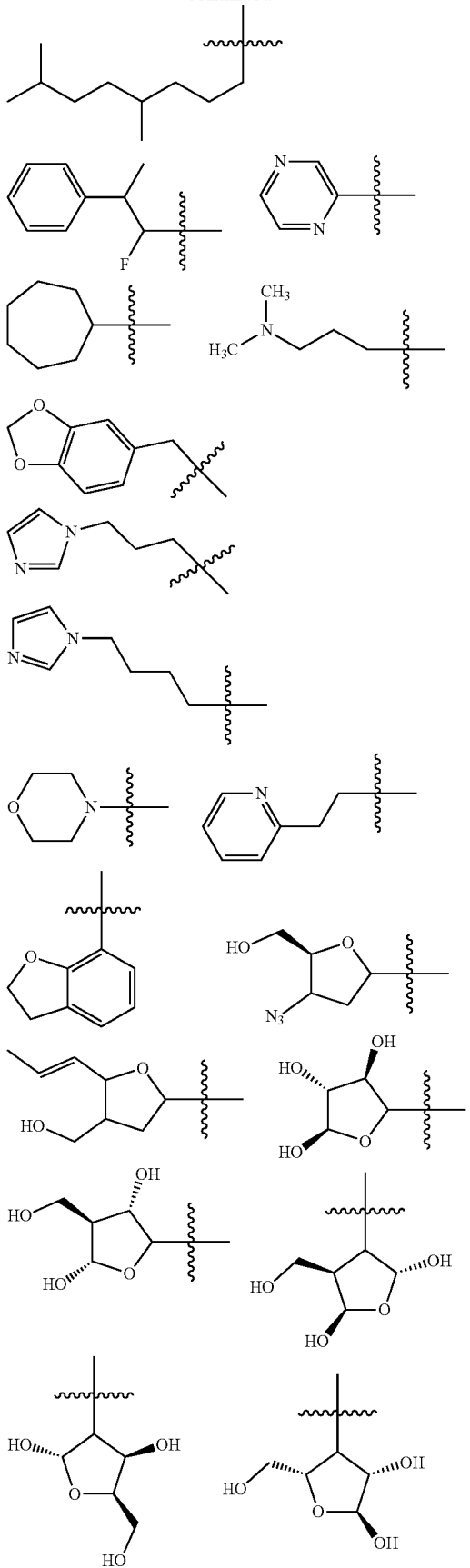

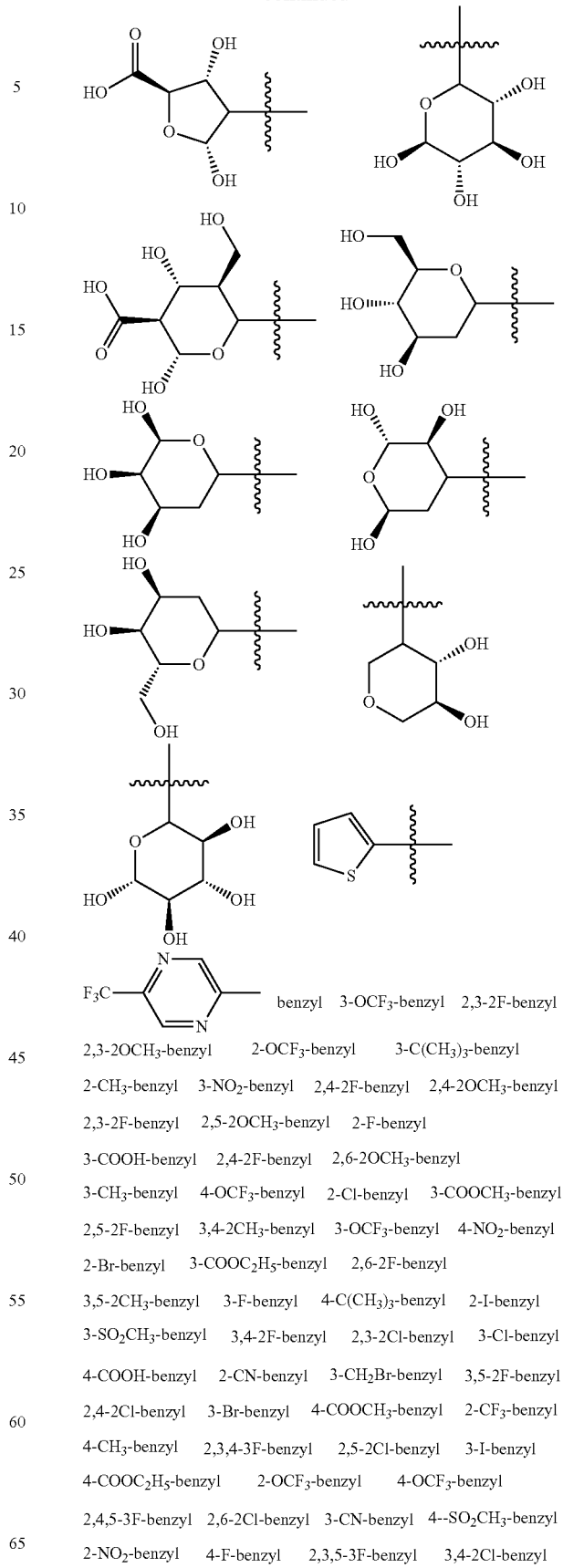

benzyl 3-OCF$_3$-benzyl 2,3-2F-benzyl
2,3-2OCH$_3$-benzyl 2-OCF$_3$-benzyl 3-C(CH$_3$)$_3$-benzyl
2-CH$_3$-benzyl 3-NO$_2$-benzyl 2,4-2F-benzyl 2,4-2OCH$_3$-benzyl
2,3-2F-benzyl 2,5-2OCH$_3$-benzyl 2-F-benzyl
3-COOH-benzyl 2,4-2F-benzyl 2,6-2OCH$_3$-benzyl
3-CH$_3$-benzyl 4-OCF$_3$-benzyl 2-Cl-benzyl 3-COOCH$_3$-benzyl
2,5-2F-benzyl 3,4-2CH$_3$-benzyl 3-OCF$_3$-benzyl 4-NO$_2$-benzyl
2-Br-benzyl 3-COOC$_2$H$_5$-benzyl 2,6-2F-benzyl
3,5-2CH$_3$-benzyl 3-F-benzyl 4-C(CH$_3$)$_3$-benzyl 2-I-benzyl
3-SO$_2$CH$_3$-benzyl 3,4-2F-benzyl 2,3-2Cl-benzyl 3-Cl-benzyl
4-COOH-benzyl 2-CN-benzyl 3-CH$_2$Br-benzyl 3,5-2F-benzyl
2,4-2Cl-benzyl 3-Br-benzyl 4-COOCH$_3$-benzyl 2-CF$_3$-benzyl
4-CH$_3$-benzyl 2,3,4-3F-benzyl 2,5-2Cl-benzyl 3-I-benzyl
4-COOC$_2$H$_5$-benzyl 2-OCF$_3$-benzyl 4-OCF$_3$-benzyl
2,4,5-3F-benzyl 2,6-2Cl-benzyl 3-CN-benzyl 4--SO$_2$CH$_3$-benzyl
2-NO$_2$-benzyl 4-F-benzyl 2,3,5-3F-benzyl 3,4-2Cl-benzyl -continued 3-CF$_3$-benzyl  4-CH$_2$Br-benzyl  2-C(CH$_3$)$_3$-benzyl  4-Cl-benzyl 2,3,6-3F-benzyl  3,5-2Cl-benzyl  2,3,5,6-4F-benzyl 2-F-3-Cl-benzyl  2-COOH-benzyl  4-Br-benzyl  2,4,6-3F-benzyl 2-F-3-Cl-benzyl  2,3,4,5,6-5F-benzyl  2-Cl-4-F-benzyl 2-COOCH$_3$-benzyl  4-I-benzyl  2,3,4,5-4F-benzyl 2-F-3-Br-benzyl  2,3-2CF$_3$-benzyl  3-F-4-OCH$_3$-benzyl 2-COOC$_2$H$_5$-benzyl  4-CN-benzyl  3,4,5-3F-benzyl 3-CF$_3$-5-CF$_3$-benzyl  2,4-2CF$_3$-benzyl  3-Cl-5-F-benzyl 2-SO$_2$CH$_3$-benzyl  4-CF$_3$-benzyl  2,4,5,6-4F-benzyl 3-Cl-4-F-benzyl  2,5-2CF$_3$-benzyl  2-Br-5-F-benzyl 2,6-2CF$_3$-benzyl  2-CN-5-F-benzyl  3,4-2CF$_3$-benzyl 2-Cl-5-CF$_3$-benzyl  3,5-2CF$_3$-benzyl;

wherein R$_1$ and R$_4$ are selected from following substitutions:

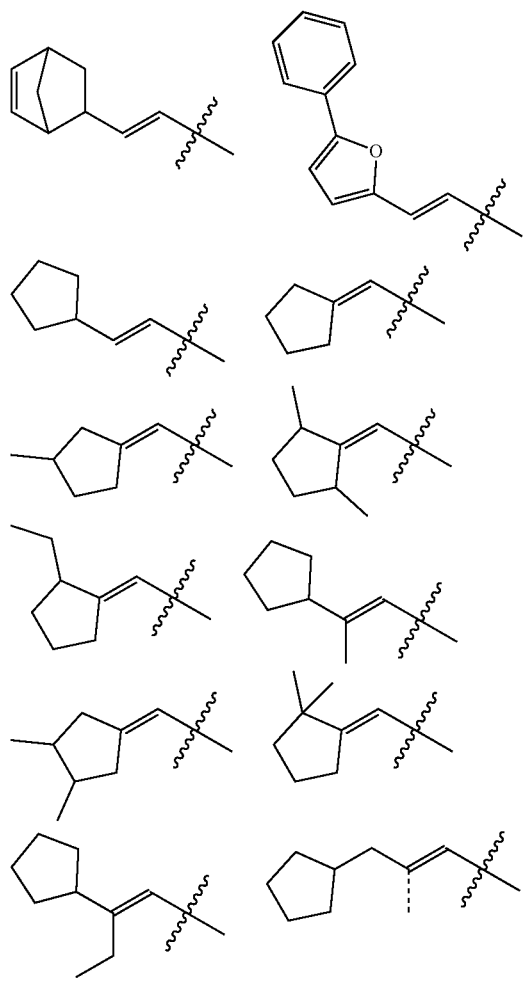

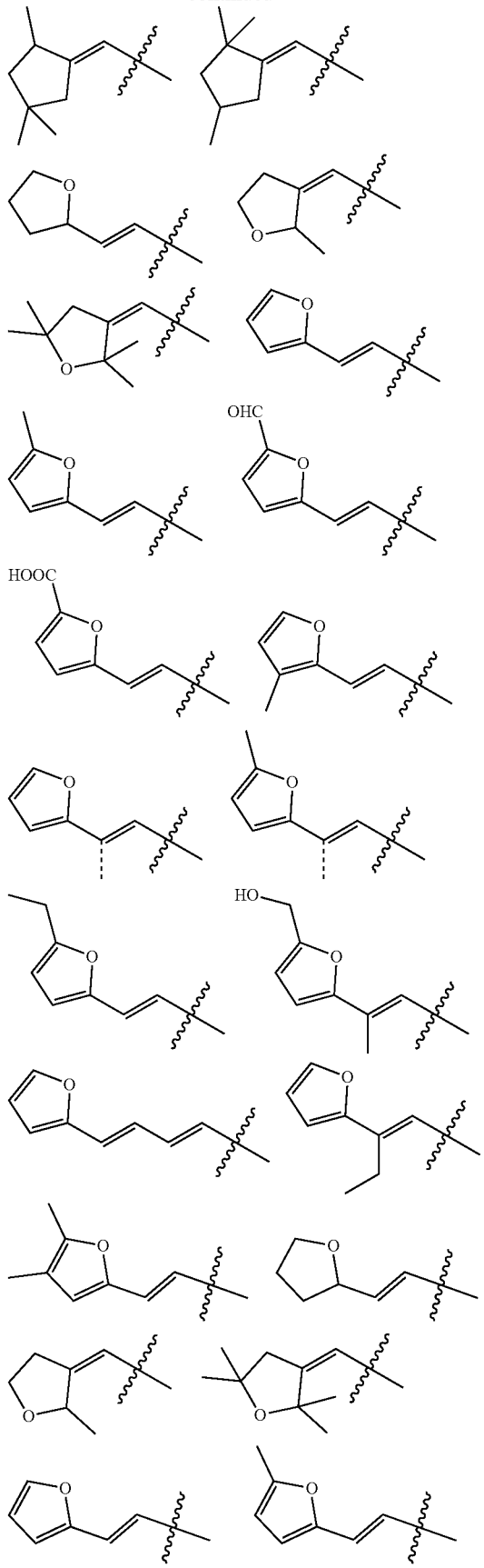

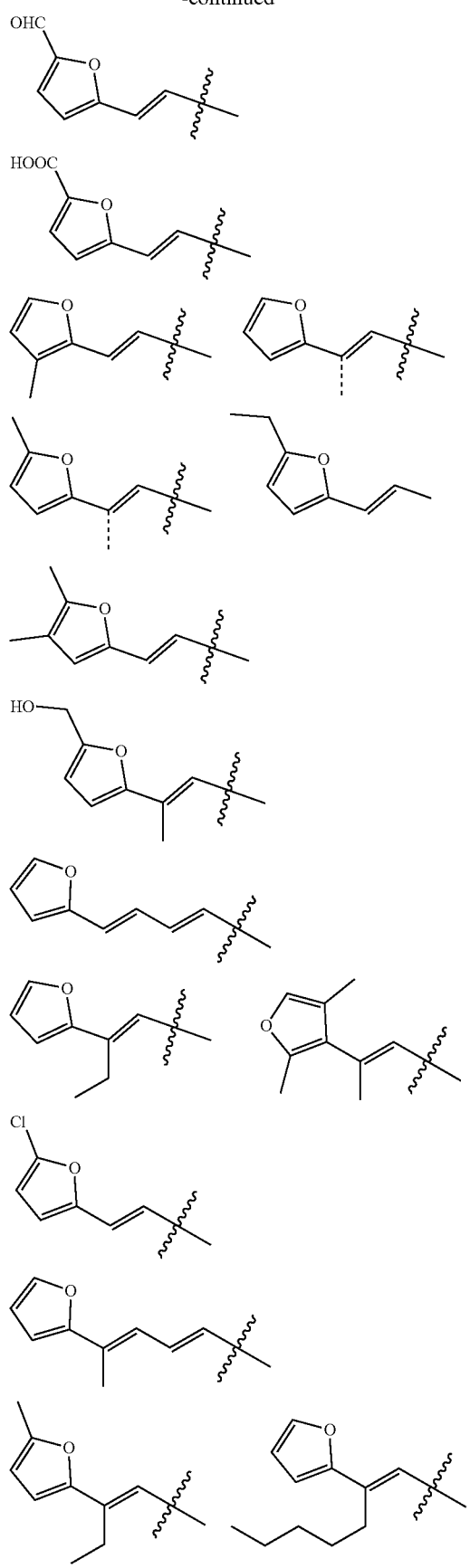
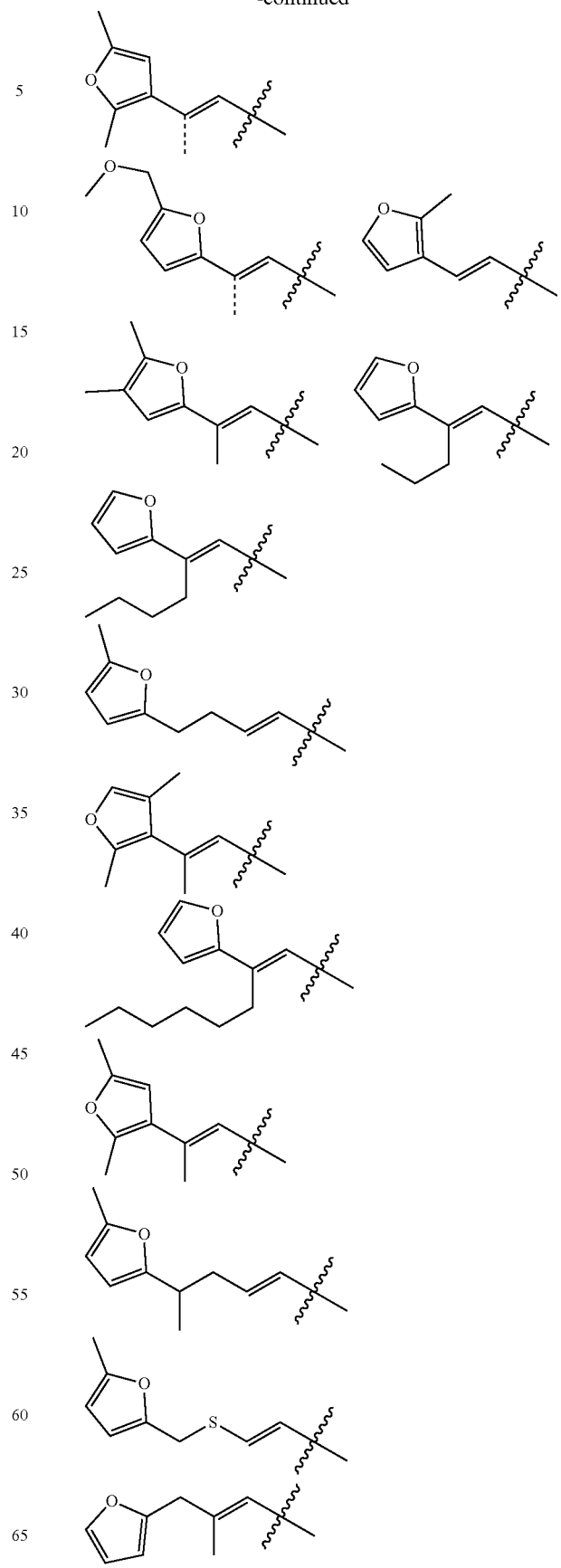

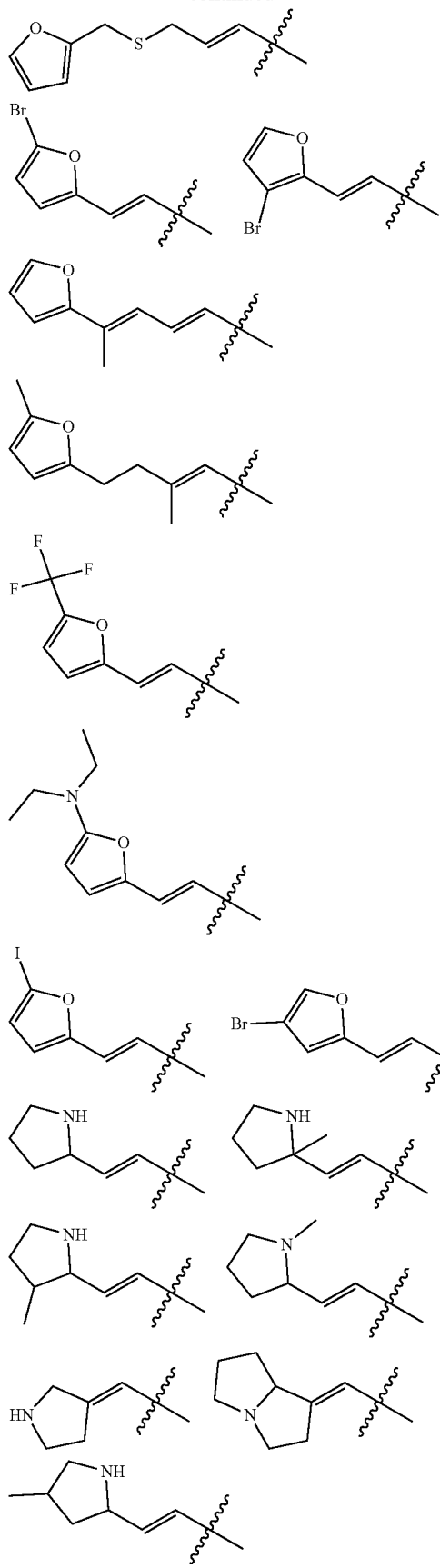
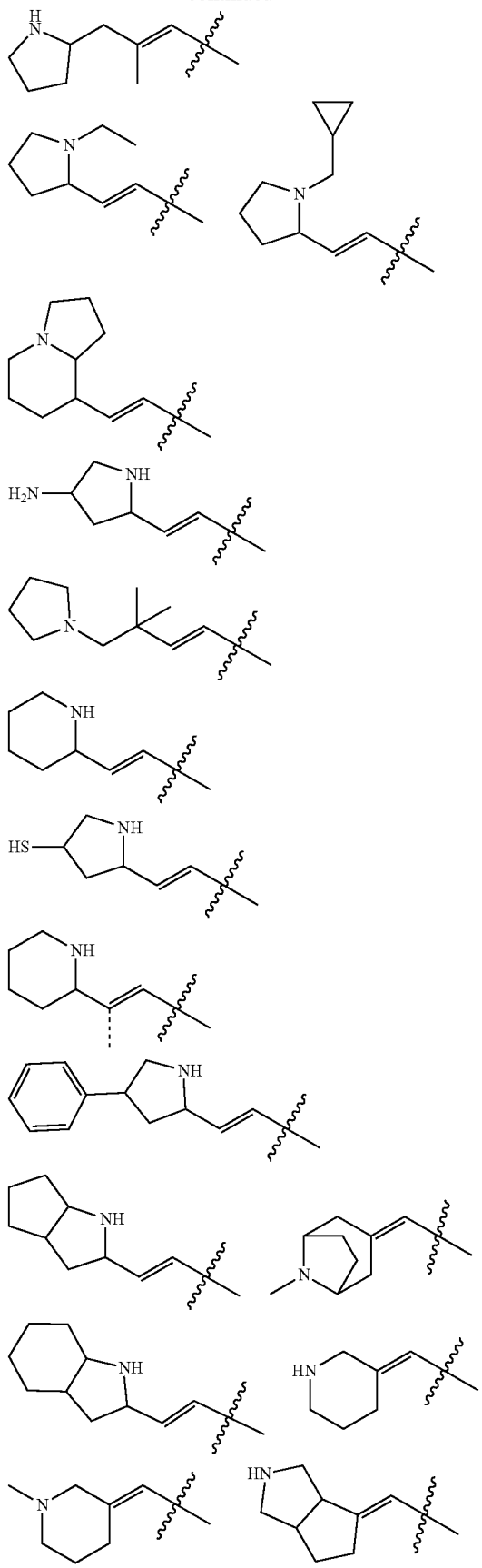

-continued
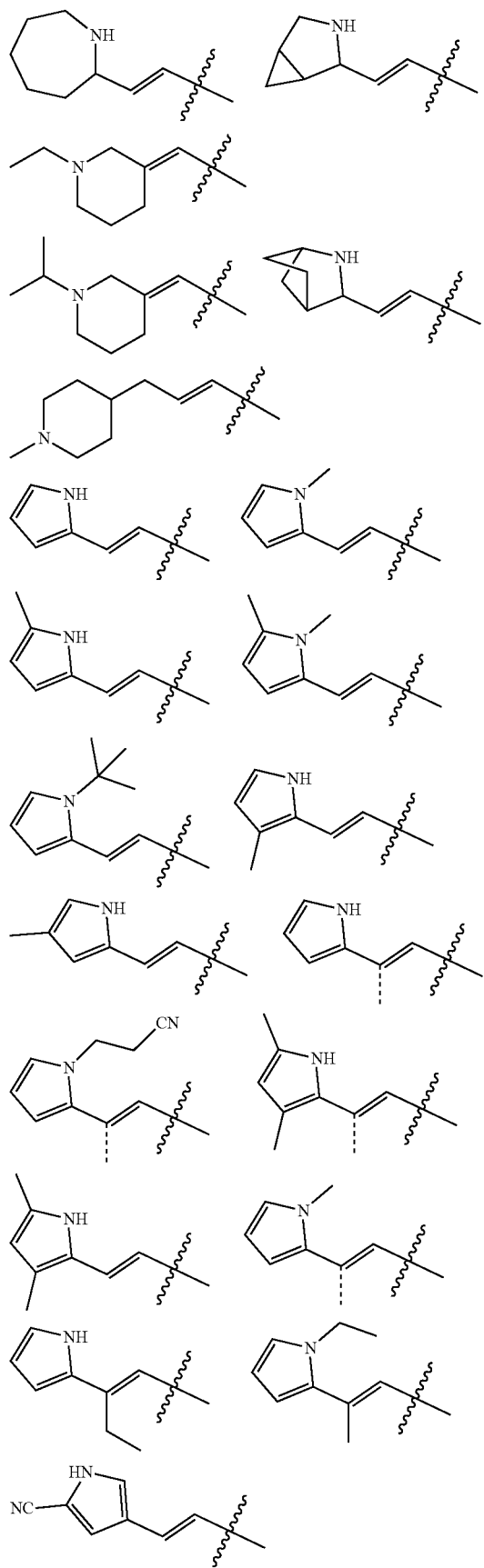
-continued
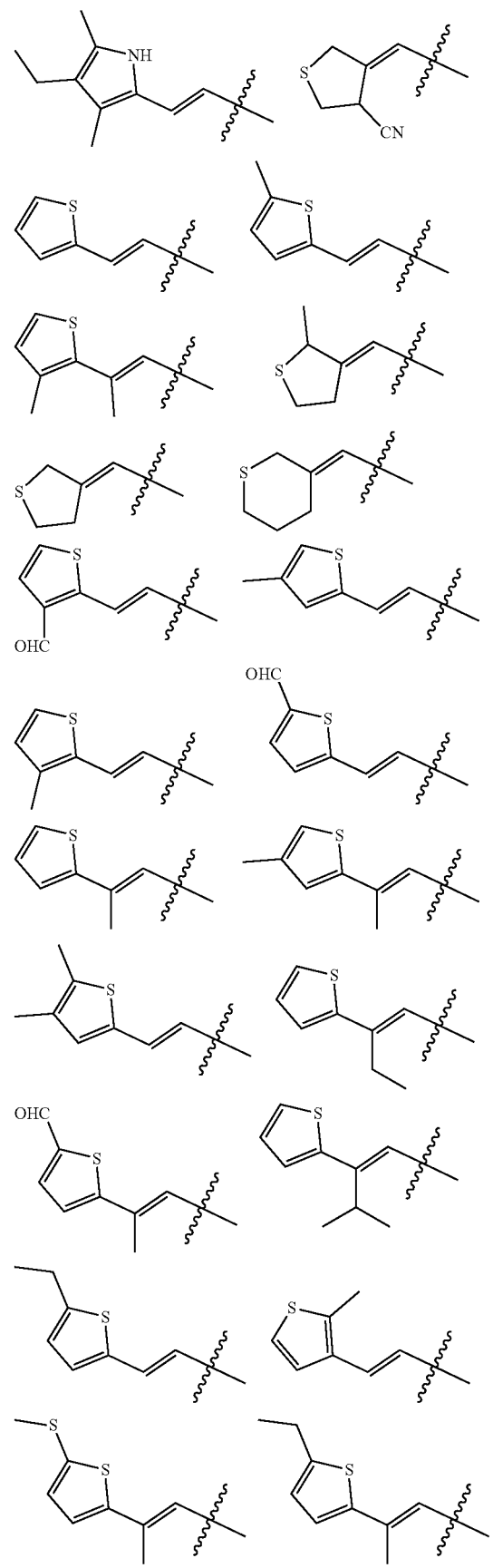

-continued
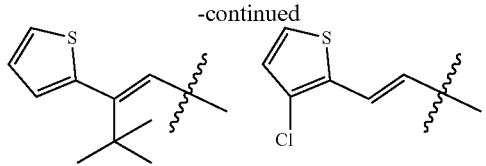
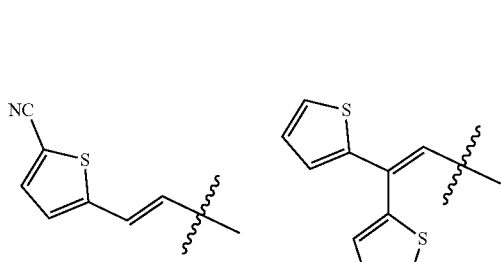
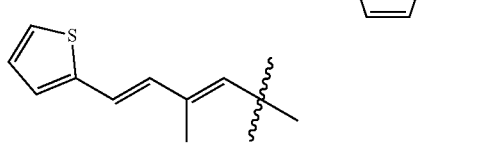
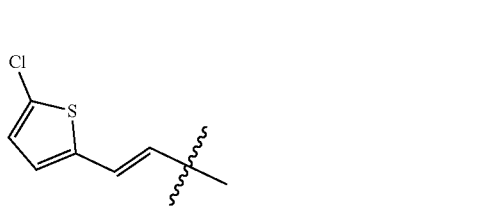
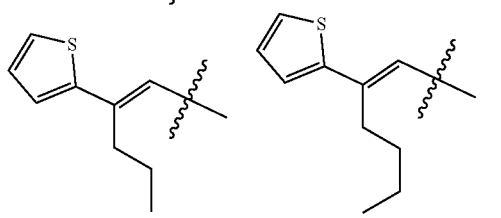
-continued
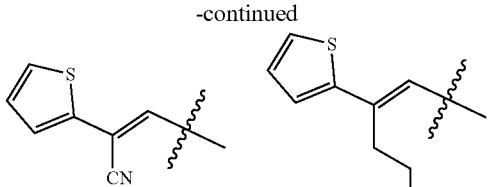
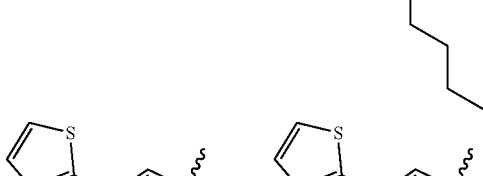
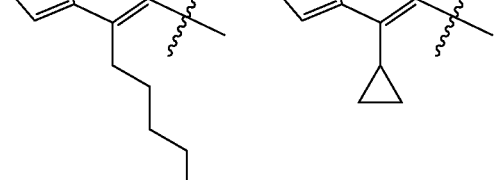
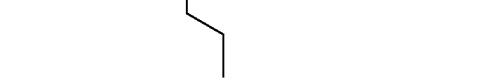
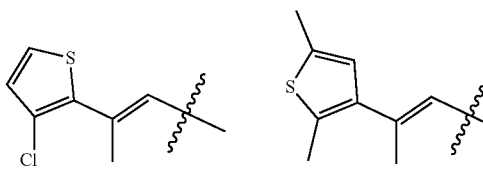
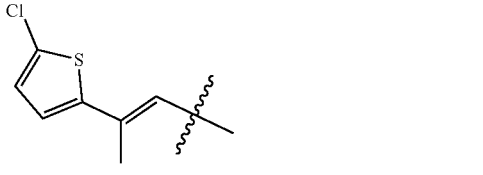
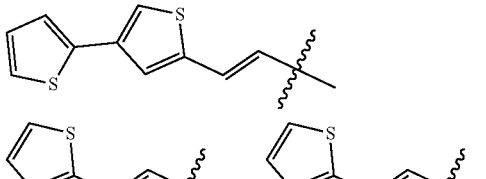
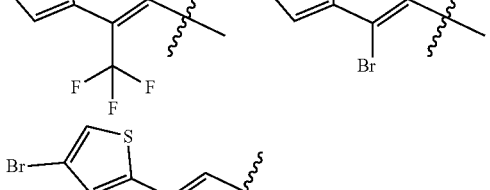
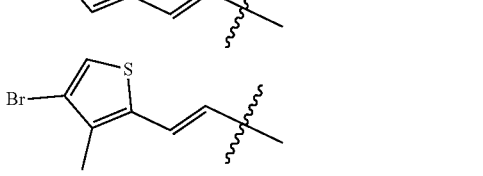
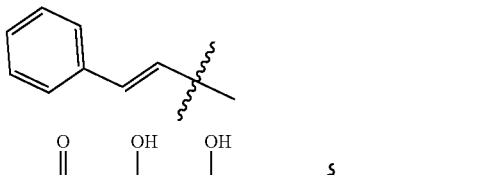
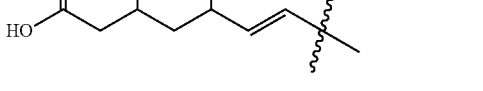

-continued

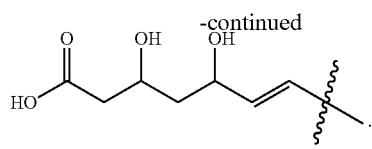

Some compounds of the present invention may be described but not limited to the specific compounds listed in Tables 1-4.

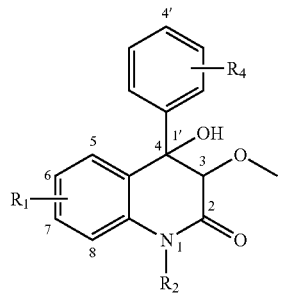

TABLE 1

| | R₁ | R₂ | R₄ |
|---|---|---|---|
| 1. | H | 4-Br-benzyl | H |
| 2. | H | 3-OCH₃-benzyl | H |
| 3. | H | 3-NO₂-benzyl | H |
| 4. | H | 3-Cl-benzyl | H |
| 5. | H | 3-CH₃-benzyl | H |
| 6. | H | 4-CH₃-benzyl | H |
| 7. | H | 3-F-benzyl | H |
| 8. | H | 4-F-benzyl | H |
| 9. | H | benzyl | |
| 10. | H | 2-Cl-5-CF₃-benzyl | H |
| 11 | H | 2-F-4-Br-benzyl | H |
| 12. | H | 3,4-2F-benzyl | H |
| 13. | H | 4-OCF₃-benzyl | H |
| 14. | H | 3,5-2F-benzyl | H |
| 15. | H | 2-Br-benzyl | H |
| 16. | H | 1,5-2Cl-benzyl | H |
| 17. | H | 2-F-4-Cl-benzyl | H |
| 18. | H | 2-F-benzyl | H |
| 19. | H | 2-Cl-benzyl | H |
| 20. | H | 2,5-2F-benzyl | H |
| 21. | H | 2-CH₃-benzyl | H |
| 22. | H | 2,4,5-3F-benzyl | H |
| 23. | H | 2,6-2F-benzyl | H |
| 24. | 6-Cl | 3-Cl-benzyl | H |
| 25. | 6-Cl | 3-F-benzyl | H |
| 26. | 6-Cl | 4-Cl-benzyl | H |
| 27. | 6-Cl | 4-F-benzyl | H |
| 28. | 6-Cl | 4-Br-benzyl | H |
| 29. | 6-Cl | benzyl | H |
| 30. | 6-Cl | 4-CH₃-benzyl | H |
| 31. | 6-Cl | 2-F-4-Br-benzyl | H |
| 32. | 6-Cl | 3,4,-2F-benzyl | H |
| 33. | 6-Cl | 2-Cl-5-CF₃-benzyl | H |
| 34. | 6-Cl | 3-CF₃-benzyl | H |
| 35. | 6-Cl | 2,6,-2Cl-benzyl | H |
| 36. | 6-Cl | 2-F-4-Cl-benzyl | H |
| 37. | 6-Cl | 2-CN-benzyl | H |
| 38. | 6-Cl | 3,5-2CF₃-benzyl | H |
| 39. | 6-Cl | 3,4-2Cl-benzyl | H |
| 40. | H | 2-I-benzyl | 4'-Cl |
| 41. | H | 2-Cl-benzyl | 4'-Cl |
| 42. | H | 2-Br-benzyl | 4'-F |
| 43. | H | 2-I-benzyl | 4'-F |
| 44. | H | 2-F-benzyl | 4'-F |
| 45. | H | 2-Cl-benzyl | 4'-F |
| 46. | H | 4-Br-benzyl | 4'-F |
| 47. | H | 3-Cl-benzyl | 4'-F |
| 48. | H | 2-Br-benzyl | 4'-Br |
| 49. | H | 2-I-benzyl | 4'-Br |
| 50. | H | 4-F-benzyl | 4'-Br |
| 51. | H | 4-Cl-benzyl | 4'-Br |
| 52. | H | 3-I-benzyl | 4'-Br |
| 53. | H | ![methyl ester group] | H |
| 54. | H | —H₂CHC=C(CH₃)₂ | H |
| 55. | H | ![dimethylaminomethyl group] | H |
| 56. | H | —C₂H₄N(C₂H₅)₂ | H |
| 57. | H | ![epoxide group] | H |
| 58. | H | ![4-acetamidophenyl group] | H |
| 59. | H | ![2-fluorophenyl group] | H |
| 60. | H | ![2-hydroxynaphthyl group] | H |
| 61. | H | ![4-trifluoromethylphenyl group] | H |
| 62. | H | ![2-ethylphenyl group] | H |
| 63. | H | ![3-methoxycarbonylphenyl group] | H |

TABLE 1-continued
| | R₁ | R₂ | R₄ |
|---|---|---|---|
| 64. | H | 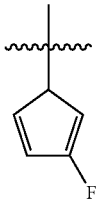 [SMILES: *C1C=CC(F)=C1] | H |
| 65. | H | 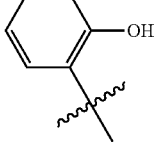 | H |
| 66. | H | 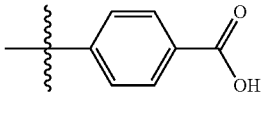 [SMILES: *c1ccc(C(=O)O)cc1] | H |
| 67. | H | 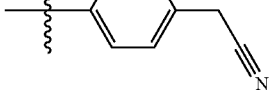 | H |
| 68. | H | 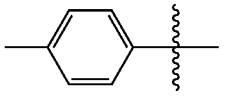 [SMILES: *c1ccc(C)cc1] | H |
| 69. | H | 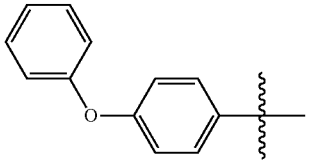 [SMILES: *c1ccc(Oc2ccccc2)cc1] | H |
| 70. | H | 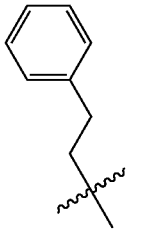 [SMILES: *CCc1ccccc1] | H |
| 71. | H | 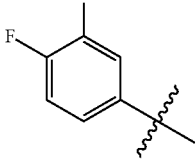 | H |
| 72. | H | 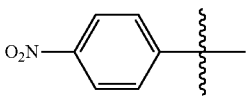 | H |
| 73. | H | 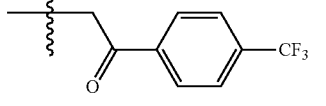 | H |
| 74. | H | 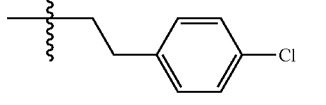 | H |
| 75. | H | 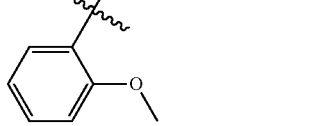 | H |
| 76. | H | 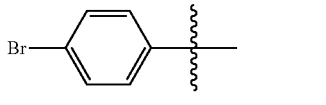 | H |
| 77. | H | 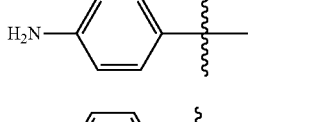 | H |
| 78. | H | 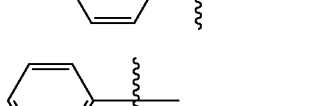 | H |
| 79. | H | 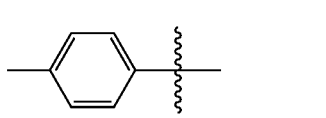 [SMILES: *c1ccc(C)cc1] | H |
| 80. | H | 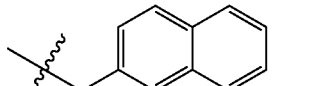 | H |
| 81. | H |  | H |
| 82. | H |  | H |
| 83. | 6-I | 4-Br-benzyl | H |
| 84. | 6-I | 3-OCH₃-benzyl | H |
| 85. | 6-I | 3-NO₂-benzyl | H |
| 86. | 6-I | 3-Cl-benzyl | H |
| 87. | 6-I | 3-CH₃-benzyl | H |
| 88. | 6-I | 4-CH₃-benzyl | H |
| 89. | 6-I | 3-F-benzyl | H |
| 90. | 6-I | 4-F-benzyl | H |
| 91. | 6-I | benzyl | H |
| 92. | 6-I | 2-Cl-5-CF₃-benzyl | H |
| 93. | 6-I | 2-F-4-Br-benzyl | H |
| 94. | 6-I | 3,4-2F-benzyl | H |
| 95. | 6-I | 4-OCF₃-benzyl | H |

TABLE 1-continued

| | R₁ | R₂ | R₄ |
|---|---|---|---|
| 96. | 6-I | 3,5-2F-benzyl | H |
| 97. | 6-I | 2-Br-benzyl | H |
| 98. | 6-I | 1,5-2Cl-benzyl | H |
| 99. | 6-I | 2-F-4-Cl-benzyl | H |
| 100. | 6-I | 2-F-benzyl | H |
| 101. | 6-I | 2-Cl-benzyl | H |
| 102. | 6-I | 2,5-2F-benzyl | H |
| 103. | 6-I | 2-CH₃-benzyl | H |
| 104. | 6-I | 2,4,5-3F-benzyl | H |
| 105. | 6-I | 2,6-2F-benzyl | H |
| 106. | 6-I | n-C₅H₁₁- | H |
| 107. | 6-I | —H₂CHC═CH₂ | H |
| 108. | 6-I | —CH₂OH | H |
| 109. | 6-I | —C₂H₄N(CH₃)₂ | H |
| 110. | 6-I | —C₃H₆OH | H |
| 111. | 6-I | (4-F-phenyl) | H |
| 112. | 6-I | (CH(NH₂)CH(OH)-) | H |
| 113. | 6-I | (CH(N(CH₃)₂)CH(OH)-) | H |
| 114. | 6-I | (CH(NHEt)CH(OH)-) | H |
| 115. | 6-I | CH₃ | H |
| 116. | 6-I | (4-Cl-phenyl) | H |
| 117. | 6-I | (3-OMe-phenyl) | H |
| 118. | 6-I | (4-OMe-phenyl) | H |
| 119. | 6-I | (3-COOH-4-OH-phenyl) | H |
| 120. | 6-I | (4-NH₂-3-Br-phenyl) | H |
| 121. | 6-I | (4-isopropyl-phenyl) | H |
| 122. | 6-I | (2,4-diNO₂-3-NH₂-phenyl) | H |
| 123. | 6-I | (3-I-phenyl) | H |
| 124. | 6-I | phenyl | H |
| 125. | 6-I | (2-Br-4-COOH-phenyl) | H |
| 126. | 6-I | (CH(NHEt)CH(OH)-) | H |
| 127. | 6-I | (3-Br-5-COOH-phenyl) | H |
| 128. | 6-I | (4-Cl-phenyl) | H |
| 129. | 6-I | (4-OH-phenyl) | H |

TABLE 1-continued

| | R₁ | R₂ | R₄ |
|---|---|---|---|
| 130. | 6-I | 4-OCH₃-phenyl | H |
| 131. | 6-I | 3,5-diBr-4-OH-phenyl | H |
| 132. | 6-I | 4-NH₂-3-Br-phenyl | H |
| 133. | 6-I | 2-NH₂-4-NO₂-phenyl | H |
| 134. | 6-I | 2-NH₂-3,5-diNO₂-phenyl | H |
| 135. | 6-I | 2,4,5-triBr-phenyl | H |
| 136. | 6-I | phenyl | H |
| 137. | 6-I | 3,5-diBr-phenyl | H |
| 138. | 6-I | 3-COOH-phenyl | H |
| 139. | 6-I | 4-NO₂-phenethyl | H |
| 140. | 6-I | 4-Br-phenyl | H |
| 141. | 6-I | 2-(4-Cl-phenyl)-2-oxoethyl | H |
| 142. | 6-I | 4-NH₂-3,5-diBr-phenyl | H |
| 143. | 5-Br | 4-Br-benzyl | H |
| 144. | 5-Br | 3-OCH₃-benzyl | H |
| 145. | 5-Br | 3-NO₂-benzyl | H |
| 146. | 5-Br | 3-Cl-benzyl | H |
| 147. | 5-Br | 3-CH₃-benzyl | H |
| 148. | 5-Br | 4-CH₃-benzyl | H |
| 149. | 5-Br | 3-F-benzyl | H |
| 150. | 5-Br | 4-F-benzyl | H |
| 151. | 5-Br | benzyl | H |
| 152. | 5-Br | 2-Cl-5-CF₃-benzyl | H |
| 153. | 5-Br | 2-F-4-Br-benzyl | H |
| 154. | 5-Br | 3,4-2F-benzyl | H |
| 155. | 5-Br | 4-OCF₃-benzyl | H |
| 156. | 5-Br | 3,5-2F-benzyl | H |
| 157. | 5-Br | 2-Br-benzyl | H |
| 158. | 5-Br | 1,5-2Cl-benzyl | H |
| 159. | 5-Br | 2-F-4-Cl-benzyl | H |
| 160. | 5-Br | 2-F-benzyl | H |
| 161. | 5-Br | 2-Cl-benzyl | H |
| 162. | 5-Br | 2,5-2F-benzyl | H |
| 163. | 5-Br | 2-CH₃-benzyl | H |
| 164. | 5-Br | 2,4,5-3F-benzyl | H |
| 165. | 5-Br | 2,6-2F-benzyl | H |
| 166. | 5-Br | 4-(cyanomethyl)phenyl | H |
| 167. | 5-Br | 4-(cyanomethyl)phenyl | H |
| 168. | 5-Br | 4-phenoxyphenyl | H |
| 169. | 5-Br | 4-phenoxyphenyl | H |

TABLE 1-continued

| | R₁ | R₂ | R₄ |
|---|---|---|---|
| 170. | 5-Br | 3-Br-4-F-phenyl | H |
| 171. | 5-Br | 3-Br-4-F-phenyl | H |
| 172. | 5-Br | 2-methoxyphenyl | H |
| 173. | 5-Br | 2-methoxyphenyl | H |
| 174. | 5-Br | 3-chlorophenyl | H |
| 175. | 5-Br | 3-chlorophenyl | H |
| 176. | 5-Br | 4-vinylphenyl | H |
| 177. | 5-Br | 4-vinylphenyl | H |
| 178. | 5-Br | 2-naphthylmethyl | H |
| 179. | 5-Br | 2-naphthylmethyl | H |
| 180. | 5-Br | -CH(CH₃)C(O)-(4-CF₃-phenyl) | H |
| 181. | 5-Br | -CH(CH₃)C(O)-(4-CF₃-phenyl) | H |
| 182. | 5-Br | cyclopropyl | H |
| 183. | 5-Br | cyclopropyl | H |
| 184. | 5-Br | 3-fluoro-4-(1H-imidazol-1-yl)phenyl | H |
| 185. | 5-Br | 3-fluoro-4-(1H-imidazol-1-yl)phenyl | H |
| 186. | 5-Br | 3-fluoro-4-(imidazo[1,5-a]pyridin-6-yl)phenyl | H |
| 187. | 5-Br | 3-fluoro-4-(imidazo[1,5-a]pyridin-6-yl)phenyl | H |
| 188. | 5-Br | —H₂CHC═C(CH₃)₂ | H |
| 189. | 5-Br | 4-(cyanomethyl)phenyl | H |
| 190. | 5-Br | —C₂H₄N(C₂H₅)₂ | |
| 191. | 5-Br | 4-phenoxyphenyl | H |

TABLE 1-continued

| | R₁ | R₂ | R₄ |
|---|---|---|---|
| 192. | 5-Br | 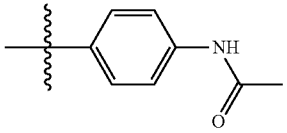 [SMILES: *c1ccc(NC(C)=O)cc1] | H |
| 193. | 5-Br | 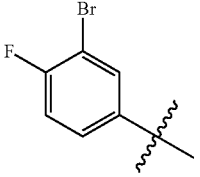 [SMILES: *c1ccc(F)c(Br)c1] | H |
| 194. | 5-Br | 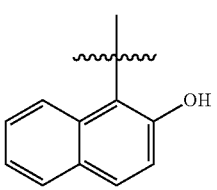 [SMILES: *c1c(O)ccc2ccccc12] | H |
| 195. | 5-Br | 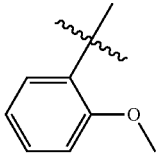 [SMILES: *c1ccccc1OC] | H |
| 196. | 5-Br | 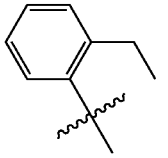 [SMILES: *c1ccccc1CC] | H |
| 197. | 5-Br | 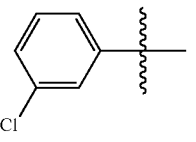 [SMILES: *c1cccc(Cl)c1] | H |
| 198. | 5-Br | 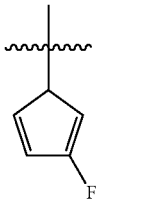 [SMILES: *C1C=CC(F)=C1] | H |
| 199. | 5-Br | 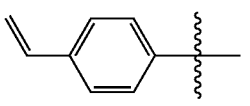 | H |
| 200. | 5-Br | 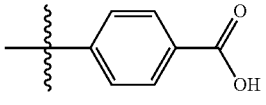 | H |
| 201. | 5-Br | 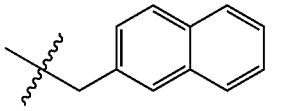 [SMILES: *Cc1ccc2ccccc2c1] | H |

TABLE 1-continued

| | R₁ | R₂ | R₄ |
|---|---|---|---|
| 202. | 5-Br | 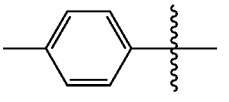 | H |
| 203. | 8-F | 4-Br-benzyl | H |
| 204. | 8-F | 3-OCH₃-benzyl | H |
| 205. | 8-F | 3-NO₂-benzyl | H |
| 206. | 8-F | 3-Cl-benzyl | H |
| 207. | 8-F | 3-CH₃-benzyl | H |
| 208. | 8-F | 4-CH₃-benzyl | H |
| 209. | 8-F | 3-F-benzyl | H |
| 210. | 8-F | 4-F-benzyl | H |
| 211. | 8-F | benzyl | H |
| 212. | 8-F | 2-Cl-5-CF₃-benzyl | H |
| 213. | 8-F | 2-F-4-Br-benzyl | H |
| 214. | 8-F | 3,4-2F-benzyl | H |
| 215. | 8-F | 4-OCF₃-benzyl | H |
| 216. | 8-F | 3,5-2F-benzyl | H |
| 217. | 8-F | 2-Br-benzyl | H |
| 218. | 8-F | 1,5-2Cl-benzyl | H |
| 219. | 8-F | 2-F-4-Cl-benzyl | H |
| 220. | 8-F | 2-F-benzyl | H |
| 221. | 8-F | 2-Cl-benzyl | H |
| 222. | 8-F | 2,5-2F-benzyl | H |
| 223. | 8-F | 2-CH₃-benzyl | H |
| 224. | 8-F | 2,4,5-3F-benzyl | H |
| 225. | 8-F | 2,6-2F-benzyl | H |
| 226. | 8-F | —CH(CH₃)₂ | H |
| 227. | 8-F | n-CH₅H₁₁- | H |
| 228. | 8-F | —C₂H₄OH | H |
| 229. | 8-F | —CH₂OH | H |
| 230. | 8-F | —CH₂N(CH₃)₂ | H |
| 231. | 8-F | —C₃H₆OH | H |
| 232. | 8-F | 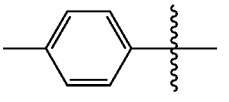 | H |
| 233. | 8-F | 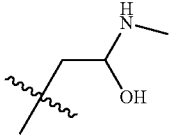 [SMILES: *CC(O)NC] | H |
| 234. | 8-F | H | H |
| 235. | 8-F | 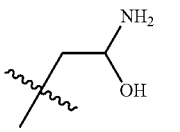 | H |
| 236. | 8-F | 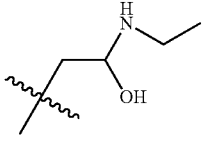 [SMILES: *CC(O)NCC] | H |
| 237. | 8-F | 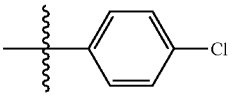 [SMILES: *c1ccc(Cl)cc1] | H |

TABLE 1-continued
| | R₁ | R₂ | R₄ |
|---|---|---|---|
| 238. | 8-F | 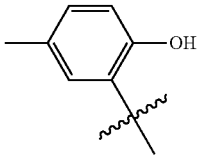 [SMILES: *c1cc(C)ccc1O] | H |
| 239. | 8-F | 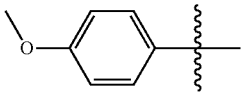 [SMILES: *c1ccc(OC)cc1] | H |
| 240. | 8-F | 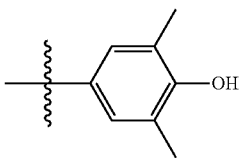 [SMILES: *c1cc(C)c(O)c(C)c1] | H |
| 241. | 8-F | 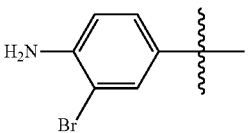 | H |
| 242. | 8-F | 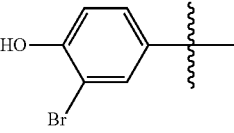 | H |
| 243. | 8-F | 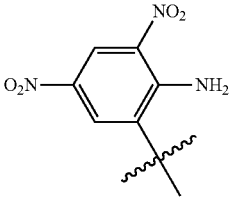 [SMILES: *c1cc([N+](=O)[O-])cc([N+](=O)[O-])c1N] | H |
| 244. | 8-F | 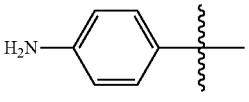 | H |
| 245. | 8-F | 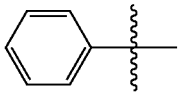 [SMILES: *c1ccccc1] | H |
| 246. | 8-F | 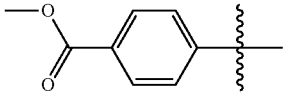 | H |
| 247. | 8-F | 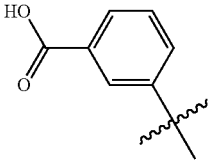 [SMILES: *c1cccc(C(=O)O)c1] | H |
| 248. | 8-F | 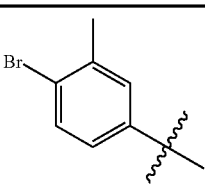 | H |
| 249. | 8-F | 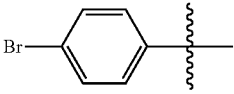 [SMILES: *c1ccc(Br)cc1] | H |
| 250. | 8-F | 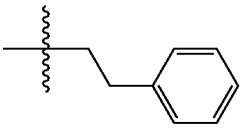 [SMILES: *CCc1ccccc1] | H |
| 251. | 8-F | 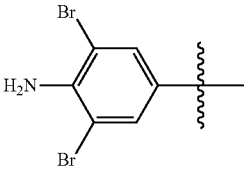 | H |
| 252. | 8-F | 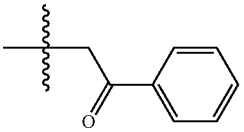 [SMILES: *CC(=O)c1ccccc1] | H |
| 253. | 8-F | 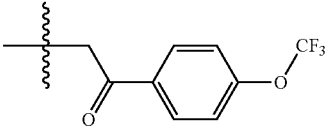 [SMILES: *CC(=O)c1ccc(OC(F)(F)F)cc1] | H |
| 254. | 8-F | 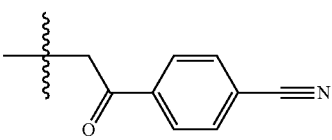 [SMILES: *CC(=O)c1ccc(C#N)cc1] | H |
| 255. | 8-F | 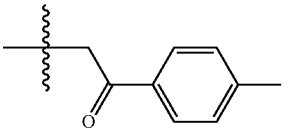 [SMILES: *CC(=O)c1ccc(C)cc1] | H |
| 256. | 8-F | 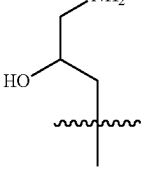 | H |
| 257. | 8-F | 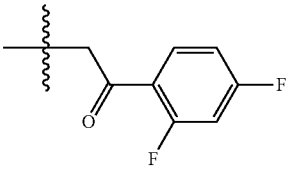 [SMILES: *CC(=O)c1ccc(F)cc1F] | H |

TABLE 1-continued

| | R₁ | R₂ | R₄ |
|---|---|---|---|
| 258. | 8-F | 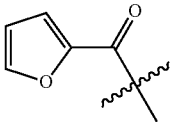 [SMILES: *C(=O)c1ccco1] | H |
| 259. | 8-F | 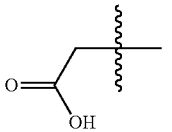 [SMILES: *CC(=O)O] | H |
| 260. | 8-F | 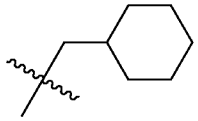 [SMILES: *CC1CCCCC1] | H |
| 261. | 8-F | 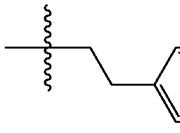 | H |
| 262. | 8-F | 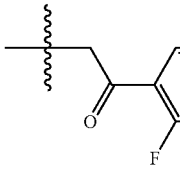 | H |
| 263. | 6-OH | 4-Br-benzyl | H |
| 264. | 6-OH | 3-OCH₃-benzyl | H |
| 265. | 6-OH | 3-NO₂-benzyl | H |
| 266. | 6-OH | 3-Cl-benzyl | H |
| 267. | 6-OH | 3-CH₃-benzyl | H |
| 268. | 6-OH | 4-CH₃-benzyl | H |
| 269. | 6-OH | 3-F-benzyl | H |
| 270. | 6-OH | 4-F-benzyl | H |
| 271. | 6-OH | benzyl | H |
| 272. | 6-OH | 2-Cl-5-CF₃-benzyl | H |
| 273. | 6-OH | 2-F-4-Br-benzyl | H |
| 274. | 6-OH | 3,4-2F-benzyl | H |
| 275. | 6-OH | 4-OCF₃-benzyl | H |
| 276. | 6-OH | 3,5-2F-benzyl | H |
| 277. | 6-OH | 2-Br-benzyl | H |
| 278. | 6-OH | 1,5-2Cl-benzyl | H |
| 279. | 6-OH | 2-F-4-Cl-benzyl | H |
| 280. | 6-OH | 2-F-benzyl | H |
| 281. | 6-OH | 2-Cl-benzyl | H |
| 282. | 6-OH | 2,5-2F-benzyl | H |
| 283. | 6-OH | 2-CH₃-benzyl | H |
| 284. | 6-OH | 2,4,5-3F-benzyl | H |
| 285. | 6-OH | 2,6-2F-benzyl | H |
| 286. | 6-OH | 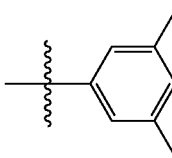 | H |
| 287. | 6-OH | CH₃ | H |
| 288. | 6-OH | 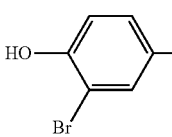 | H |
| 289. | 6-OH | 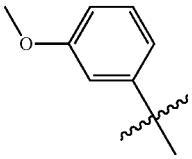 [SMILES: *c1cccc(OC)c1] | H |
| 290. | 6-OH | 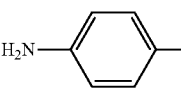 | H |
| 291. | 6-OH | 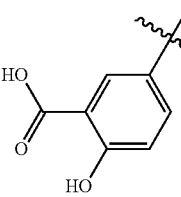 | H |
| 292. | 6-OH | 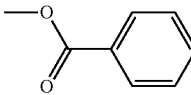 | H |
| 293. | 6-OH | 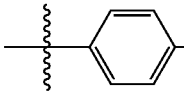 | H |
| 294. | 6-OH | 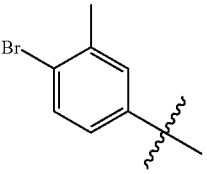 [SMILES: *c1ccc(Br)c(C)c1] | H |
| 295. | 6-OH | 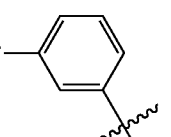 | H |
| 296. | 6-OH | 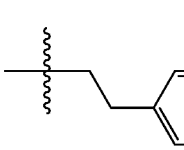 | H |
| 297. | 6-OH | 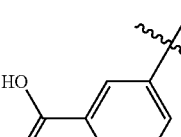 | H |
| 298. | 6-OH | 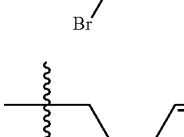 | H |

TABLE 1-continued
| | R₁ | R₂ | R₄ |
|---|---|---|---|
| 299. | 6-OH | 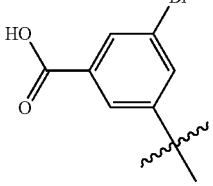 | H |
| 300. | 6-OH | 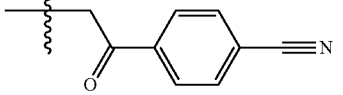 | H |
| 301. | 6-OH | 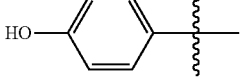 | H |
| 302. | 6-OH | 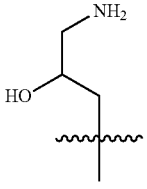 | H |
| 303. | 6-OH | 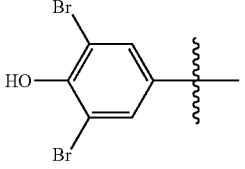 [SMILES: *c1cc(Br)c(O)c(Br)c1] | H |
| 304. | 6-OH | 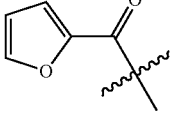 | H |
| 305. | 6-OH | 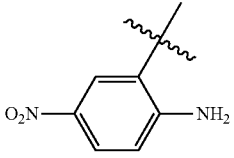 [SMILES: *c1cc([N+](=O)[O-])ccc1N] | H |
| 306. | 6-OH | 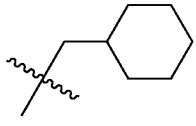 [SMILES: *CC1CCCCC1] | H |
| 307. | 6-OH | 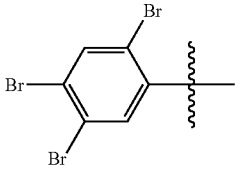 [SMILES: *c1cc(Br)c(Br)cc1Br] | H |
| 308. | 6-OH | 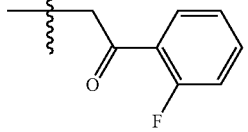 | H |
| 309. | 6-OH | 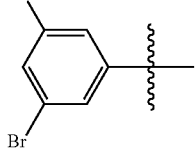 | H |
| 310. | 6-OH | 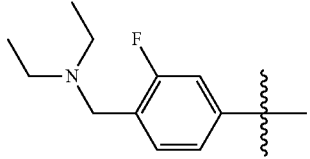 [SMILES: *c1ccc(CN(CC)CC)c(F)c1] | H |
| 311. | 6-OH | 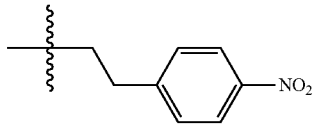 [SMILES: *CCc1ccc([N+](=O)[O-])cc1] | H |
| 312. | 6-OH | 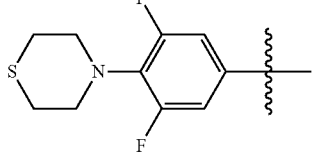 | H |
| 313. | 6-OH | 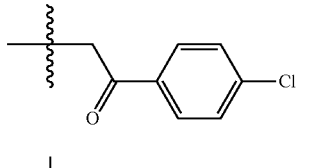 | H |
| 314. | 6-OH | 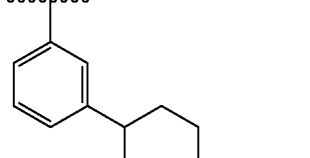 | H |
| 315. | 6-OH | 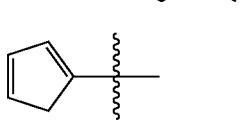 | H |
| 316. | 6-OH | 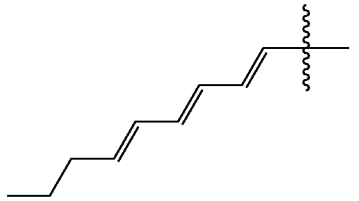 [SMILES: */C=C/C=C/C=C/CCC] | H |

TABLE 1-continued

| | R₁ | R₂ | R₄ |
|---|---|---|---|
| 317. | 6-OH | 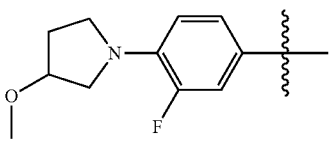 [SMILES: *c1ccc(N2CCC(OC)C2)c(F)c1] | H |
| 318. | 6-OH | 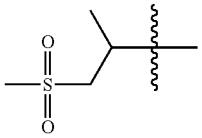 [SMILES: *C(C)CS(C)(=O)=O] | H |
| 319. | 6-OH | 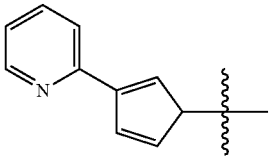 [SMILES: *C1C=CC(c2ccccn2)=C1] | H |
| 320. | 6-OH | 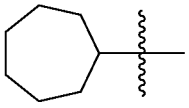 [SMILES: *C1CCCCCC1] | H |
| 321. | 6-OH | 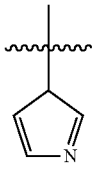 | H |
| 322. | 6-OH | 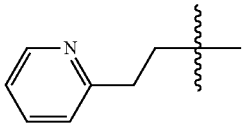 [SMILES: *CCc1ccccn1] | H |
| 323. | 6-OH | 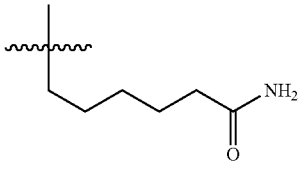 [SMILES: *CCCCCC(N)=O] | H |
| 324. | 6-OH | 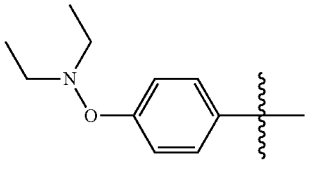 [SMILES: *c1ccc(ON(CC)CC)cc1] | H |
| 325. | 6-OCH₃ | 4-Br-benzyl | H |
| 326. | 6-OCH₃ | 3-OCH₃-benzyl | H |
| 327. | 6-OCH₃ | 3-NO₂-benzyl | H |
| 328. | 6-OCH₃ | 3-Cl-benzyl | H |
| 329. | 6-OCH₃ | 3-CH₃-benzyl | H |
| 330. | 6-OCH₃ | 4-CH₃-benzyl | H |
| 331. | 6-OCH₃ | 3-F-benzyl | H |
| 332. | 6-OCH₃ | 4-F-benzyl | H |
| 333. | 6-OCH₃ | benzyl | H |
| 334. | 6-OCH₃ | 2-Cl-5-CF₃-benzyl | H |
| 335. | 6-OCH₃ | 2-F-4-Br-benzyl | H |
| 336. | 6-OCH₃ | 3,4-2F-benzyl | H |
| 337. | 6-OCH₃ | 4-OCF₃-benzyl | H |
| 338. | 6-OCH₃ | 3,5-2F-benzyl | H |
| 339. | 6-OCH₃ | 2-Br-benzyl | H |
| 340. | 6-OCH₃ | 1,5-2Cl-benzyl | H |
| 341. | 6-OCH₃ | 2-F-4-Cl-benzyl | H |
| 342. | 6-OCH₃ | 2-F-benzyl | H |
| 343. | 6-OCH₃ | 2-Cl-benzyl | H |
| 344. | 6-OCH₃ | 2,5-2F-benzyl | H |
| 345. | 6-OCH₃ | 2-CH₃-benzyl | H |
| 346. | 6-OCH₃ | 2,4,5-3F-benzyl | H |
| 347. | 6-OCH₃ | 2,6-2F-benzyl | H |
| 348. | 6-OCH₃ | 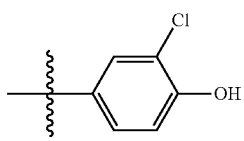 [SMILES: *c1ccc(O)c(Cl)c1] | H |
| 349. | 6-OCH₃ | 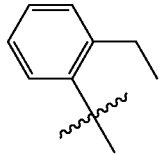 [SMILES: *c1ccccc1CC] | H |
| 350. | 6-OCH₃ | 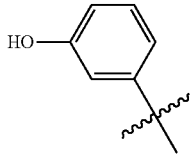 | H |
| 351. | 6-OCH₃ | 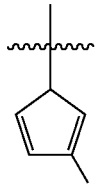 | H |
| 352. | 6-OCH₃ | 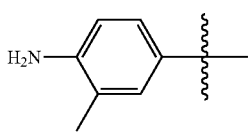 | H |
| 353. | 6-OCH₃ | 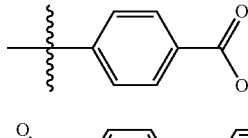 | H |
| 354. | 6-OCH₃ | 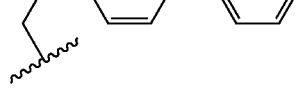 | H |
| 355. | 6-OCH₃ | 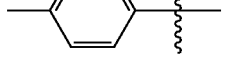 | H |
| 356. | 6-OCH₃ | 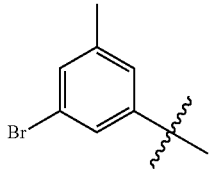 [SMILES: *c1cc(C)cc(Br)c1] | H |

TABLE 1-continued
| | R₁ | R₂ | R₄ |
|---|---|---|---|
| 357. | 6-OCH₃ | 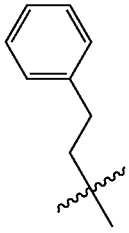 [SMILES: *CCc1ccccc1] | H |
| 358. | 6-OCH₃ | 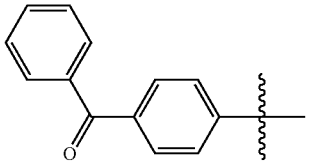 | H |
| 359. | 6-OCH₃ | 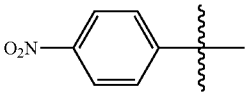 | H |
| 360. | 6-OCH₃ | 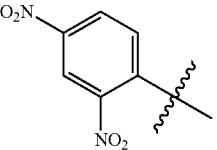 [SMILES: *c1ccc([N+](=O)[O-])cc1[N+](=O)[O-]] | H |
| 361. | 6-OCH₃ | 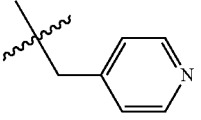 [SMILES: *Cc1ccncc1] | H |
| 362. | 6-OCH₃ | 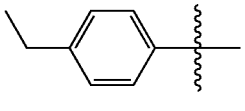 [SMILES: *c1ccc(CC)cc1] | H |
| 363. | 6-OCH₃ | 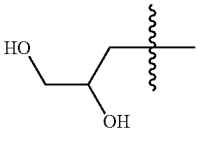 [SMILES: *CC(O)CO] | H |
| 364. | 6-OCH₃ | 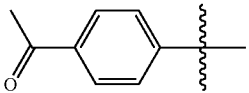 [SMILES: *c1ccc(C(C)=O)cc1] | H |
| 365. | 6-OCH₃ | 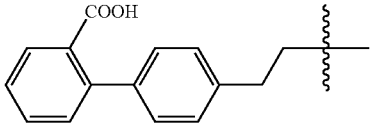 [SMILES: *CCc1ccc(-c2ccccc2C(=O)O)cc1] | H |
| 366. | 6-OCH₃ | 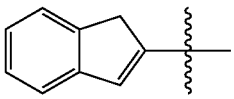 [SMILES: *C1=Cc2ccccc2C1] | H |
| 367. | 6-OCH₃ | 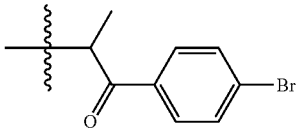 [SMILES: *C(C)C(=O)c1ccc(Br)cc1] | H |
| 368. | 6-OCH₃ | 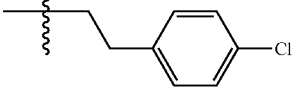 | H |
| 369. | 6-OCH₃ | 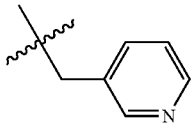 | H |
| 370. | 6-OCH₃ | 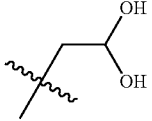 [SMILES: *CC(O)O] | H |
| 371. | 6-OCH₃ | 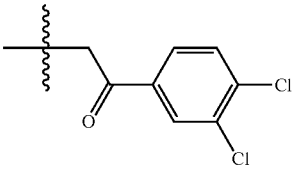 | H |
| 372. | 6-OCH₃ | 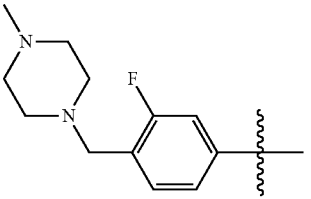 [SMILES: *c1ccc(CN2CCN(C)CC2)c(F)c1] | H |
| 373. | 6-OCH₃ | 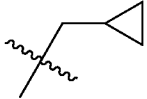 [SMILES: *CC1CC1] | H |
| 374. | 6-OCH₃ | 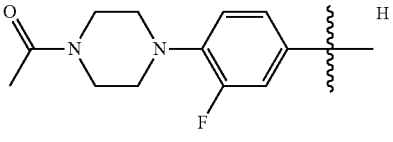 | H |
| 375. | 6-OCH₃ | 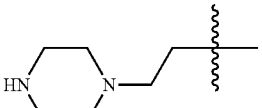 | H |
| 376. | 6-OCH₃ | 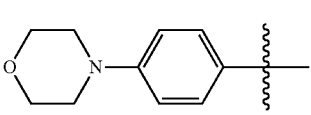 [SMILES: *c1ccc(N2CCOCC2)cc1] | H |
| 377. | 6-OCH₃ | 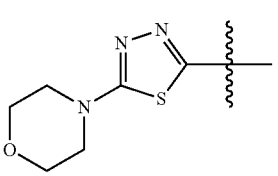 [SMILES: *c1nnc(N2CCOCC2)s1] | H |

TABLE 1-continued

| | R₁ | R₂ | R₄ |
|---|---|---|---|
| 378. | 6-OCH₃ | (1-methylpiperazin-4-yl)methyl | H |
| 379. | 6-OCH₃ | 4-(2-hydroxyacetyl)piperazin-1-yl on 3-fluorophenyl | H |
| 380. | 6-OCH₃ | 4-morpholino-3,5-difluorophenyl | H |
| 381. | 6-OCH₃ | 6-(pyrrol-1-yl)pyridin-3-yl | H |
| 382. | 6-OCH₃ | 2,5-dimethylheptyl chain | H |
| 383. | 6-OCH₃ | 1-(pyrrolidin-1-yl)propan-2-one-3-yl | H |
| 384. | 6-OCH₃ | 4-(imidazol-1-yl)butyl | H |
| 385. | 7-FCH₂ | 4-Br-benzyl | H |
| 386. | 7-FCH₂ | 3-OCH₃-benzyl | H |
| 387. | 7-FCH₂ | 3-NO₂-benzyl | H |
| 388. | 7-FCH₂ | 3-Cl-benzyl | H |
| 389. | 7-FCH₂ | 3-CH₃-benzyl | H |
| 390. | 7-FCH₂ | 4-CH₃-benzyl | H |
| 391. | 7-FCH₂ | 3-F-benzyl | H |
| 392. | 7-FCH₂ | 4-F-benzyl | H |
| 393. | 7-FCH₂ | benzyl | H |
| 394. | 7-FCH₂ | 2-Cl-5-CF₃-benzyl | H |
| 395. | 7-FCH₂ | 2-F-4-Br-benzyl | H |
| 396. | 7-FCH₂ | 3,4-2F-benzyl | H |
| 397. | 7-FCH₂ | 4-OCF₃-benzyl | H |
| 398. | 7-FCH₂ | 3,5-2F-benzyl | H |
| 399. | 7-FCH₂ | 2-Br-benzyl | H |
| 400. | 7-FCH₂ | 1,5-2Cl-benzyl | H |
| 401. | 7-FCH₂ | 2-F-4-Cl-benzyl | H |
| 402. | 7-FCH₂ | 2-F-benzyl | H |
| 403. | 7-FCH₂ | 2-Cl-benzyl | H |
| 404. | 7-FCH₂ | 2,5-2F-benzyl | H |
| 405. | 7-FCH₂ | 2-CH₃-benzyl | H |
| 406. | 7-FCH₂ | 2,4,5-3F-benzyl | H |
| 407. | 7-FCH₂ | 2,6-2F-benzyl | H |
| 408. | 7-FCH₂ | n-C₃H₇- | H |
| 409. | 7-FCH₂ | —C₂H₅ | H |
| 410. | 7-FCH₂ | CH₂CH₂CH(CH₃)₂ | H |
| 411. | 7-FCH₂ | —H₂CCCH | H |
| 412. | 7-FCH₂ | C₂H₄NH₂ | H |
| 413. | 7-FCH₂ | —CH₂NH₂ | H |
| 414. | 7-FCH₂ | methyl propanoate-2-yl | H |
| 415. | 7-FCH₂ | methyl butanoate-3-yl | H |
| 416. | 7-FCH₂ | H₂N-CH(CH₃)- | H |
| 417. | 7-FCH₂ | (CH₃)₂N-CH(CH₃)- | H |
| 418. | 7-FCH₂ | 3-Cl-phenyl | H |
| 419. | 7-FCH₂ | 2-(oxiran-2-yl)propan-2-yl | H |
| 420. | 7-FCH₂ | 4-(OCF₃)phenyl | H |
| 421. | 7-FCH₂ | 2-F-phenyl | H |
| 422. | 7-FCH₂ | 3-Cl-4-OH-phenyl | H |
| 423. | 7-FCH₂ | 4-CF₃-phenyl | H |
| 424. | 7-FCH₂ | 3-OH-phenyl (with methyl) | H |
| 425. | 7-FCH₂ | 3-(methoxycarbonyl)phenyl | H |

TABLE 1-continued
| | $R_1$ | $R_2$ | $R_4$ |
|---|---|---|---|
| 426. | 7-FCH$_2$ | 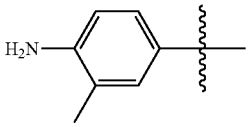 | H |
| 427. | 7-FCH$_2$ | 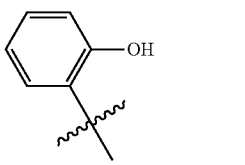 [SMILES: *c1ccccc1O] | H |
| 428. | 7-FCH$_2$ | 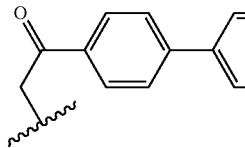 | H |
| 429. | 7-FCH$_2$ | 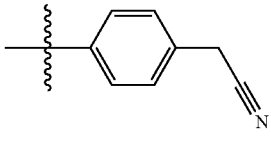 [SMILES: *c1ccc(CC#N)cc1] | H |
| 430. | 7-FCH$_2$ | 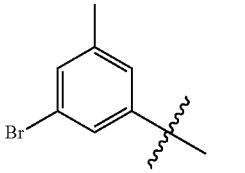 | H |
| 431. | 7-FCH$_2$ | 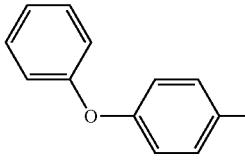 | H |
| 432. | 7-FCH$_2$ | 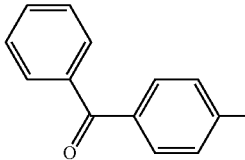 | H |
| 433. | 7-FCH$_2$ | 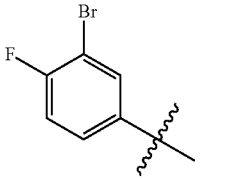 [SMILES: *c1ccc(F)c(Br)c1] | H |
| 434. | 7-FCH$_2$ | 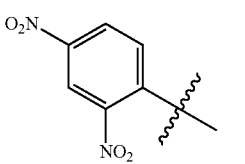 [SMILES: *c1ccc([N+](=O)[O-])cc1[N+](=O)[O-]] | H |
| 435. | 7-FCH$_2$ | 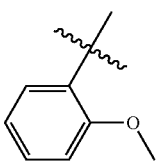 [SMILES: *c1ccccc1OC] | H |
| 436. | 7-FCH$_2$ | 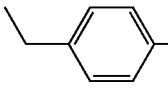 | H |
| 437. | 7-FCH$_2$ | 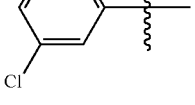 | H |
| 438. | 7-FCH$_2$ | 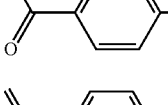 | H |
| 439. | 7-FCH$_2$ | 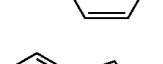 | H |
| 440. | 7-FCH$_2$ | 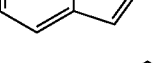 | H |
| 441. | 7-FCH$_2$ | 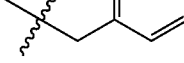 | H |
| 442. | 7-FCH$_2$ | 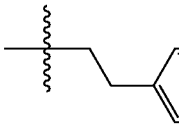 | H |
| 443. | 7-FCH$_2$ | 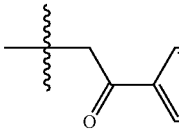 | H |
| 444. | 7-FCH$_2$ | 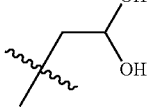 | H |
| 445. | 6-Cl | —C$_2$H$_4$OH | H |
| 446. | 6-Cl | 3-OCH$_3$-benzyl | H |
| 447. | 6-Cl | 3-NO$_2$-benzyl | H |
| 448. | 6-Cl | n-C$_5$H$_{11}$- | H |
| 449. | 6-Cl | 3-CH$_3$-benzyl | H |
| 450. | 6-Cl | —CH$_2$OH | H |
| 451. | 6-Cl | n-C$_3$H$_7$- | H |
| 452. | 6-Cl | —C$_3$H$_6$OH | H |
| 453. | 6-Cl | CH$_2$CH$_2$CH(CH$_3$)$_2$ | H |
| 454. | 6-Cl | —CH(CH$_3$)$_2$ | H |
| 455. | 6-Cl | C$_2$H$_4$NH$_2$ | H |
| 456. | 6-Cl | 3,4-2F-benzyl | H |
| 457. | 6-Cl | 4-OCF$_3$-benzyl | H |

TABLE 1-continued
| | R1 | R2 | R4 |
|---|---|---|---|
| 458. | 6-Cl | 3,5-2F-benzyl | H |
| 459. | 6-Cl | 2-Br-benzyl | H |
| 460. | 6-Cl | 1,5-2Cl-benzyl | H |
| 461. | 6-Cl | —C2H4N(CH3)2 | H |
| 462. | 6-Cl | 2-F-benzyl | H |
| 463. | 6-Cl | 2-Cl-benzyl | H |
| 464. | 6-Cl | 2,5-2F-benzyl | H |
| 465. | 6-Cl | 2-CH3-benzyl | H |
| 466. | 6-Cl | 2,4,5-3F-benzyl | H |
| 467. | 6-Cl | 2,6-2F-benzyl | H |
| 468. | 6-Cl | 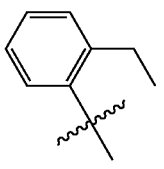 [SMILES: *c1ccccc1CC] | H |
| 469. | 6-Cl | 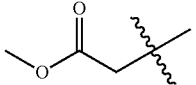 [SMILES: *CC(=O)OC] | H |
| 470. | 6-Cl | 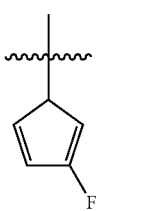 [SMILES: *C1C=CC(F)=C1] | H |
| 471. | 6-Cl | 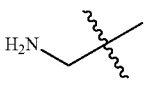 | H |
| 472. | 6-Cl | 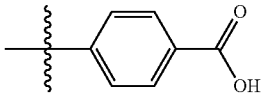 | H |
| 473. | 6-Cl | 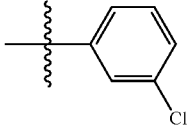 [SMILES: *c1cccc(Cl)c1] | H |
| 474. | 6-Cl | 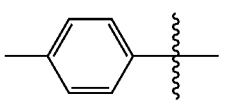 [SMILES: *c1ccc(C)cc1] | H |
| 475. | 6-Cl | 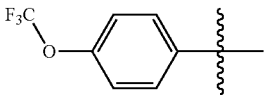 | H |
| 476. | 6-Cl | 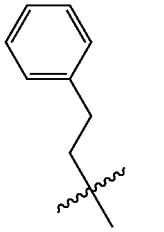 [SMILES: *CCc1ccccc1] | H |
TABLE 1-continued
| | R1 | R2 | R4 |
|---|---|---|---|
| 477. | 6-Cl | 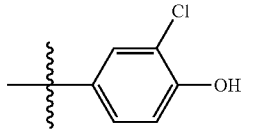 [SMILES: *c1ccc(O)c(Cl)c1] | H |
| 478. | 6-Cl | 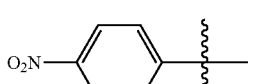 | H |
| 479. | 6-Cl | 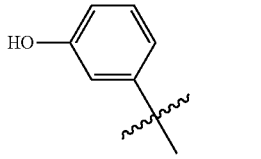 [SMILES: *c1cccc(O)c1] | H |
| 480. | 6-Cl | 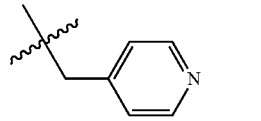 [SMILES: *Cc1ccncc1] | H |
| 481. | 6-Cl | 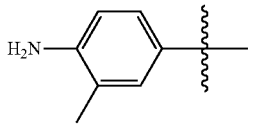 | H |
| 482. | 6-Cl | 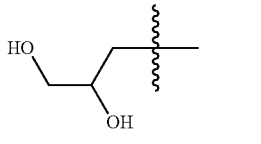 [SMILES: *CC(O)CO] | H |
| 483. | 6-Cl | 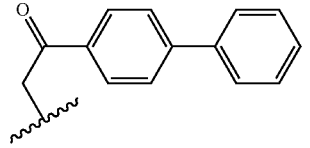 [SMILES: *CC(=O)c1ccc(-c2ccccc2)cc1] | H |
| 484. | 6-Cl | 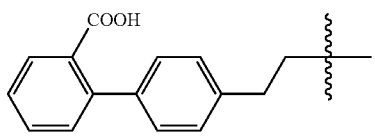 [SMILES: *CCc1ccc(-c2ccccc2C(=O)O)cc1] | H |
| 485. | 6-Cl | 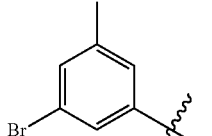 | H |
| 486. | 6-Cl | 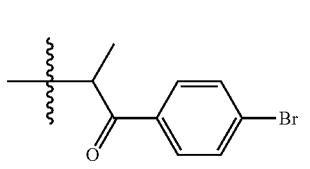 [SMILES: *C(C)C(=O)c1ccc(Br)cc1] | H |

TABLE 1-continued

| | R₁ | R₂ | R₄ |
|---|---|---|---|
| 487. | 6-Cl | 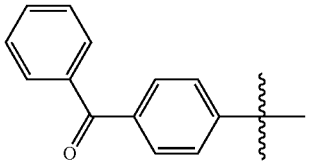 [SMILES: *c1ccc(C(=O)c2ccccc2)cc1] (4-benzoylphenyl) | H |
| 488. | 6-Cl | 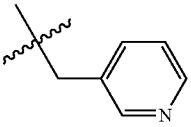 (pyridin-3-ylmethyl) | H |
| 489. | 6-Cl | 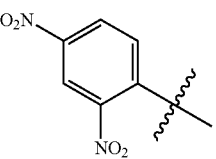 [SMILES: *c1ccc([N+](=O)[O-])cc1[N+](=O)[O-]] (2,4-dinitrophenyl) | H |
| 490. | 6-Cl | 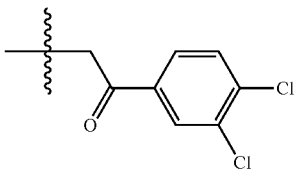 [SMILES: *CC(=O)c1ccc(Cl)c(Cl)c1] (3,4-dichlorophenacyl) | H |
| 491. | 6-Cl | 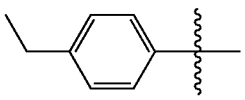 (4-ethylphenyl) | H |
| 492. | 6-Cl | 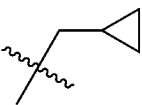 [SMILES: *CC1CC1] (cyclopropylmethyl) | H |
| 493. | H | 4-Br-benzyl | 4'-F |
| 494. | H | 3-OCH₃-benzyl | 4'-F |
| 495. | H | 3-NO₂-benzyl | 4'-F |
| 496. | H | 3-Cl-benzyl | 4'-F |
| 497. | H | 3-CH₃-benzyl | 4'-F |
| 498. | H | 4-CH₃-benzyl | 4'-F |
| 499. | H | 3-F-benzyl | 4'-F |
| 500. | H | 4-F-benzyl | 4'-F |
| 501. | H | benzyl | 4'-F |
| 502. | H | 2-Cl-5-CF₃-benzyl | 4'-F |
| 503. | H | 2-F-4-Br-benzyl | 4'-F |
| 504. | H | 3,4-2F-benzyl | 4'-F |
| 505. | H | 4-OCF₃-benzyl | 4'-F |
| 506. | H | 3,5-2F-benzyl | 4'-F |
| 507. | H | 2-Br-benzyl | 4'-F |
| 508. | H | 1,5-2Cl-benzyl | 4'-F |
| 509. | H | 2-F-4-Cl-benzyl | 4'-F |
| 510. | H | 2-F-benzyl | 4'-F |
| 511. | H | 2-Cl-benzyl | 4'-F |
| 512. | H | 2,5-2F-benzyl | 4'-F |
| 513. | H | 2-CH₃-benzyl | 4'-F |
| 514. | H | 2,4,5-3F-benzyl | 4'-F |
| 515. | H | 2,6-2F-benzyl | 4'-F |
| 516. | H | 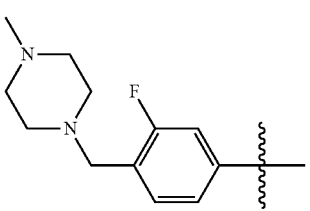 [SMILES: *c1ccc(CN2CCN(C)CC2)c(F)c1] | 4'-F |
| 517. | H | n-C₃H₇- | 4'-F |
| 518. | H | 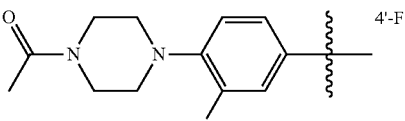 | 4'-F |
| 519. | H | CH₂CH₂CH(CH₃)₂ | 4'-F |
| 520. | H | 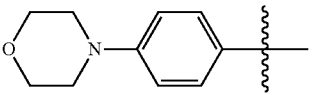 | 4'-F |
| 521. | H | C₂H₄NH₂ | 4'-F |
| 522. | H | 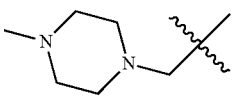 [SMILES: *CN1CCN(C)CC1] | 4'-F |
| 523. | H | 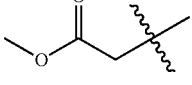 | 4'-F |
| 524. | H | 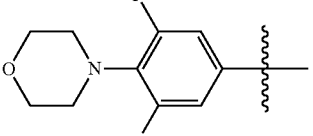 | 4'-F |
| 525. | H | 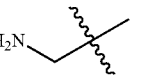 | 4'-F |
| 526. | H | 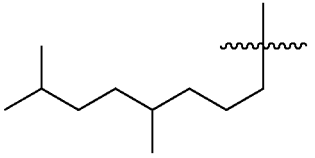 [SMILES: *CCCC(C)CCC(C)C] | 4'-F |
| 527. | H | 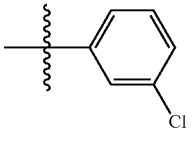 [SMILES: *c1cccc(Cl)c1] | 4'-F |
| 528. | H | 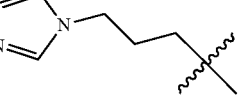 | 4'-F |
| 529. | H | 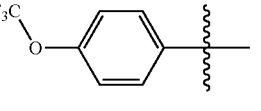 | 4'-F |
| 530. | H | 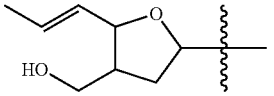 [SMILES: *C1CC(CO)C(/C=C/C)O1] | 4'-F |

TABLE 1-continued

| | R₁ | R₂ | R₄ |
|---|---|---|---|
| 531. | H | 3-Cl-4-OH-phenyl | 4'-F |
| 532. | H | -CH₂-C(O)-(3,4-diCl-phenyl) | 4'-F |
| 533. | H | 3-HO-phenyl | 4'-F |
| 534. | H | -CH₂-cyclopropyl | 4'-F |
| 535. | H | 4-H₂N-3-methyl-phenyl | 4'-F |
| 536. | H | -CH₂CH₂-(4-aminopiperazin-1-yl) | 4'-F |
| 537. | H | -CH₂-C(O)-(4-biphenyl) | 4'-F |
| 538. | H | 5-(morpholin-4-yl)-1,3,4-thiadiazol-2-yl | 4'-F |
| 539. | H | 3-Br-5-methyl-phenyl | 4'-F |
| 540. | H | 4-[4-(hydroxyacetyl)piperazin-1-yl]-2-F-phenyl | 4'-F |
| 541. | H | 4-benzoyl-phenyl | 4'-F |
| 542. | H | 5-(pyrrol-1-yl)pyridin-2-yl | 4'-F |
| 543. | H | 2,4-dinitro-phenyl | 4'-F |
| 544. | H | -CH₂-C(O)-(pyrrolidin-1-yl) | 4'-F |
| 545. | H | 4-ethyl-phenyl | 4'-F |
| 546. | H | -(CH₂)₅-C(O)OH | 4'-F |
| 547. | H | 4-acetyl-phenyl | 4'-F |
| 548. | H | -CH(F)-CH(phenyl)- | 4'-F |
| 549. | H | 1H-inden-2-yl | 4'-F |
| 550. | H | -(CH₂)₃-(imidazol-1-yl) | 4'-F |
| 551. | H | -CH₂CH₂-(4-Cl-phenyl) | 4'-F |

TABLE 1-continued

| | R₁ | R₂ | R₄ |
|---|---|---|---|
| 552. | H | 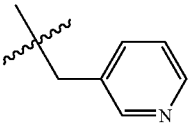 | 4'-F |
| 553. | H | 4-Br-benzyl | 4'-Cl |
| 554. | H | 3-OCH₃-benzyl | 4'-Cl |
| 555. | H | 3-NO₂-benzyl | 4'-Cl |
| 556. | H | 3-Cl-benzyl | 4'-Cl |
| 557. | H | 3-CH₃-benzyl | 4'-Cl |
| 558. | H | 4-CH₃-benzyl | 4'-Cl |
| 559. | H | 3-F-benzyl | 4'-Cl |
| 560. | H | 4-F-benzyl | 4'-Cl |
| 561. | H | benzyl | 4'-Cl |
| 562. | H | 2-Cl-5-CF₃-benzyl | 4'-Cl |
| 563. | H | 2-F-4-Br-benzyl | 4'-Cl |
| 564. | H | 3,4-2F-benzyl | 4'-Cl |
| 565. | H | 4-OCF₃-benzyl | 4'-Cl |
| 566. | H | 3,5-2F-benzyl | 4'-Cl |
| 567. | H | 2-Br-benzyl | 4'-Cl |
| 568. | H | 1,5-2Cl-benzyl | 4'-Cl |
| 569. | H | 2-F-4-Cl-benzyl | 4'-Cl |
| 570. | H | 2-F-benzyl | 4'-Cl |
| 571. | H | 2-Cl-benzyl | 4'-Cl |
| 572. | H | 2,5-2F-benzyl | 4'-Cl |
| 573. | H | 2-CH₃-benzyl | 4'-Cl |
| 574. | H | 2,4,5-3F-benzyl | 4'-Cl |
| 575. | H | 2,6-2F-benzyl | 4'-Cl |
| 576. | H | 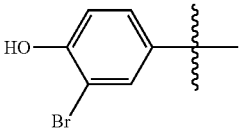 [SMILES: *c1ccc(O)c(Br)c1] | 4'-Cl |
| 577. | H | 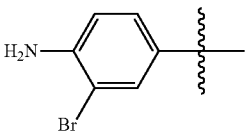 [SMILES: *c1ccc(N)c(Br)c1] | 4'-Cl |
| 578. | H | 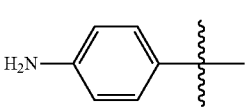 | 4'-Cl |
| 579. | H | 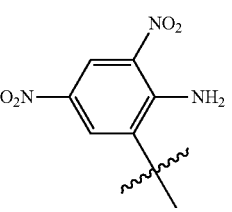 [SMILES: *c1cc([N+](=O)[O-])cc([N+](=O)[O-])c1N] | 4'-Cl |
| 580. | H | 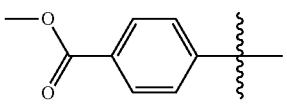 | 4'-Cl |
| 581. | H | 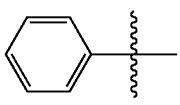 [SMILES: *c1ccccc1] | 4'-Cl |
| 582. | H | 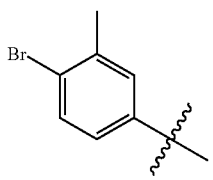 [SMILES: *c1ccc(Br)c(C)c1] | 4'-Cl |
| 583. | H | 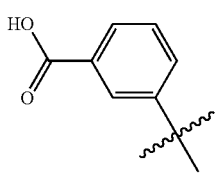 | 4'-Cl |
| 584. | H | 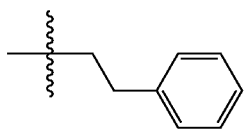 [SMILES: *CCc1ccccc1] | 4'-Cl |
| 585. | H | 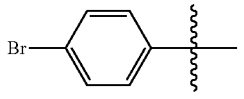 | 4'-Cl |
| 586. | H | 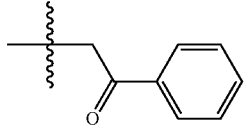 [SMILES: *CC(=O)c1ccccc1] | 4'-Cl |
| 587. | H | 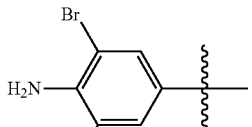 | 4'-Cl |
| 588. | H | 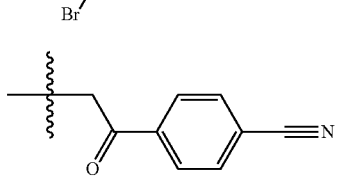 | 4'-Cl |
| 589. | H | 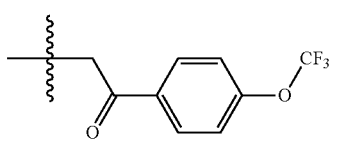 [SMILES: *CC(=O)c1ccc(OC(F)(F)F)cc1] | 4'-Cl |
| 590. | H | 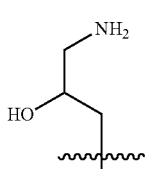 | 4'-Cl |
| 591. | H | 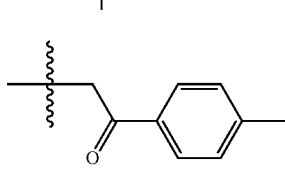 | 4'-Cl |

TABLE 1-continued

| | R₁ | R₂ | R₄ |
|---|---|---|---|
| 592. | H | (2-furyl-C(O)-C(CH₃)-) | 4'-Cl |
| 593. | H | (-C(CH₃)-CH₂-C(O)-4-methoxyphenyl) | 4'-Cl |
| 594. | H | (-C(CH₃)-CH₂-cyclohexyl) | 4'-Cl |
| 595. | H | (-C(CH₃)-CH₂-C(O)-2,4-difluorophenyl) | 4'-Cl |
| 596. | H | (-C(CH₃)-CH₂-C(O)-2-fluorophenyl) | 4'-Cl |
| 597. | H | (-C(CH₃)-CH₂-COOH) | 4'-Cl |
| 598. | H | (4-(diethylaminomethyl)-3-fluorophenyl-C(CH₃)-) | 4'-Cl |
| 599. | H | (-CH₂-CH₂-4-fluorophenyl) | 4'-Cl |
| 600. | H | (4-(thiomorpholin-4-yl)-3,5-difluorophenyl-C(CH₃)-) | 4'-Cl |
| 601. | H | (5-(2-(4-methoxyphenyl)thiazolyl)-C(CH₃)-) | 4'-Cl |
| 602. | H | (3-(1-methylpiperidin-4-yl)phenyl-C(CH₃)-) | 4'-Cl |
| 603. | H | (4-(1,1-dioxothiomorpholin-4-yl)-3-fluorophenyl-C(CH₃)-) | 4'-Cl |
| 604. | H | (polyene chain) | 4'-Cl |
| 605. | H | (3-(morpholin-4-yl)phenyl-C(CH₃)-) | 4'-Cl |
| 606. | H | (-C(CH₃)-CH(CH₃)-CH₂-S(O)₂-CH₃) | 4'-Cl |
| 607. | H | (methyl ester-alkyl chain-C(CH₃)-) | 4'-Cl |
| 608. | H | (cycloheptyl-C(CH₃)-) | 4'-Cl |

TABLE 1-continued

| | R₁ | R₂ | R₄ |
|---|---|---|---|
| 609. | H | 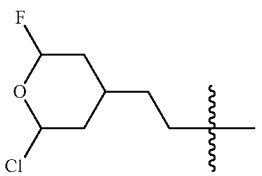 [SMILES: *CCC1CC(F)OC(Cl)C1] | 4'-Cl |
| 610. | H | 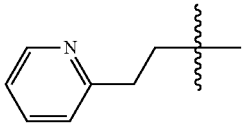 | 4'-Cl |
| 611. | H | 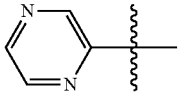 [SMILES: *c1cnccn1] | 4'-Cl |
| 612. | H | 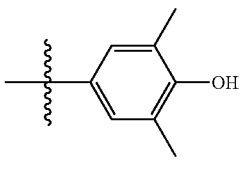 [SMILES: *c1cc(C)c(O)c(C)c1] | 4'-Cl |
| 613. | H | 4-Br-benzyl | 4'-Br |
| 614. | H | 3-OCH₃-benzyl | 4'-Br |
| 615. | H | 3-NO₂-benzyl | 4'-Br |
| 616. | H | 3-Cl-benzyl | 4'-Br |
| 617. | H | 3-CH₃-benzyl | 4'-Br |
| 618. | H | 4-CH₃-benzyl | 4'-Br |
| 619. | H | 3-F-benzyl | 4'-Br |
| 620. | H | 4-F-benzyl | 4'-Br |
| 621. | H | benzyl | 4'-Br |
| 622. | H | 2-Cl-5-CF₃-benzyl | 4'-Br |
| 623. | H | 2-F-4-Br-benzyl | 4'-Br |
| 624. | H | 3,4-2F-benzyl | 4'-Br |
| 625. | H | 4-OCF₃-benzyl | 4'-Br |
| 626. | H | 3,5-2F-benzyl | 4'-Br |
| 627. | H | 2-Br-benzyl | 4'-Br |
| 628. | H | 1,5-2Cl-benzyl | 4'-Br |
| 629. | H | 2-F-4-Cl-benzyl | 4'-Br |
| 630. | H | 2-F-benzyl | 4'-Br |
| 631. | H | 2-Cl-benzyl | 4'-Br |
| 632. | H | 2,5-2F-benzyl | 4'-Br |
| 633. | H | 2-CH₃-benzyl | 4'-Br |
| 634. | H | 2,4,5-3F-benzyl | 4'-Br |
| 635. | H | 2,6-2F-benzyl | 4'-Cl |
| 636. | H | 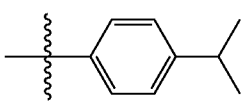 [SMILES: *c1ccc(C(C)C)cc1] | 4'-Br |
| 637. | H | 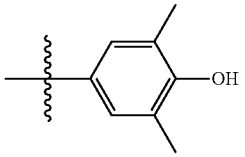 [SMILES: *c1cc(C)c(O)c(C)c1] | 4'-Br |
| 638. | H | 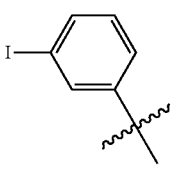 | 4'-Br |
| 639. | H | 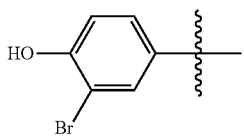 [SMILES: *c1ccc(O)c(Br)c1] | 4'-Br |
| 640. | H | 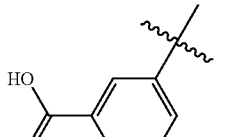 | 4'-Br |
| 641. | H | 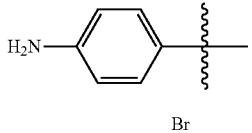 | 4'-Br |
| 642. | H | 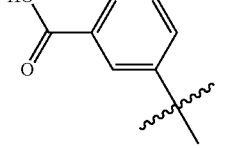 | 4'-Br |
| 643. | H | 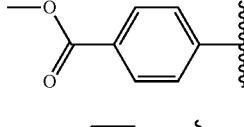 | 4'-Br |
| 644. | H | 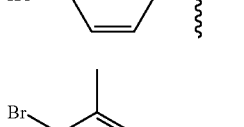 | 4'-Br |
| 645. | H | 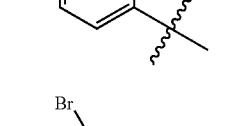 | 4'-Br |
| 646. | H | 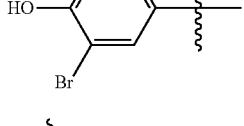 | 4'-Br |
| 647. | H | 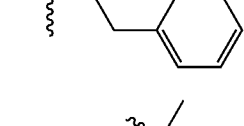 | 4'-Br |
| 648. | H | 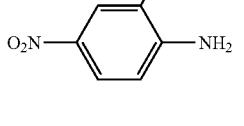 | 4'-Br |

TABLE 1-continued

| | R₁ | R₂ | R₄ |
|---|---|---|---|
| 649. | H | (CH₂-C(=O)-phenyl) | 4'-Br |
| 650. | H | (2,4,5-tribromophenyl) | 4'-Br |
| 651. | H | (CH₂-C(=O)-4-cyanophenyl) | 4'-Br |
| 652. | H | (3,5-dibromophenyl) | 4'-Br |
| 653. | H | (CH(CH₂NH₂)-CH(OH)-CH₂-) | 4'-Br |
| 654. | H | (CH₂-CH₂-4-nitrophenyl) | 4'-Br |
| 655. | H | (CH(CH₃)-C(=O)-2-furyl) | 4'-Br |
| 656. | H | (CH₂-C(=O)-4-chlorophenyl) | 4'-Br |
| 657. | H | (CH₂-cyclohexyl) | 4'-Br |
| 658. | H | (cyclopentadienyl-C(CH₃)-) | 4'-Br |
| 659. | H | (CH₂-C(=O)-2-fluorophenyl) | 4'-Br |
| 660. | H | (3-fluoro-4-(3-methoxypyrrolidin-1-yl)phenyl) | 4'-Br |
| 661. | H | (3-fluoro-4-((diethylamino)methyl)phenyl) | 4'-Br |
| 662. | H | (2-(pyridin-2-yl)cyclopentadienyl) | 4'-Br |
| 663. | H | (3,5-difluoro-4-(thiomorpholin-4-yl)phenyl) | 4'-Br |
| 664. | H | (3-pyrrolinyl) | 4'-Br |
| 665. | H | (3-(1-methylpiperidin-4-yl)phenyl) | 4'-Br |
| 666. | H | (-(CH₂)₅-C(=O)-NH₂) | 4'-Br |

TABLE 1-continued

| | R₁ | R₂ | R₄ |
|---|---|---|---|
| 667. | H | (2E,4E,6E)-nona-2,4,6-trienyl group | 4'-Br |
| 668. | H | 4-(N,N-diethylaminooxy)phenyl | 4'-Br |
| 669. | H | 2-methyl-2-(methylsulfonylmethyl)propyl | 4'-Br |
| 670. | H | 4-(N,N-dimethylamino)butyl | 4'-Br |
| 671. | H | cycloheptyl | 4'-Br |
| 672. | H | 2,3-dihydrobenzofuran-7-yl | 4'-Br |
| 673. | H | 4-Br-benzyl | 3'-OH |
| 674. | H | 3-OCH₃-benzyl | 3'-OH |
| 675. | H | 3-NO₂-benzyl | 3'-OH |
| 676. | H | 3-Cl-benzyl | 3'-OH |
| 677. | H | 3-CH₃-benzyl | 3'-OH |
| 678. | H | 4-CH₃-benzyl | 3'-OH |
| 679. | H | 3-F-benzyl | 3'-OH |
| 680. | H | 4-F-benzyl | 3'-OH |
| 681. | H | benzyl | 3'-OH |
| 682. | H | 2-Cl-5-CF₃-benzyl | 3'-OH |
| 683. | H | 2-F-4-Br-benzyl | 3'-OH |
| 684. | H | 3,4-2F-benzyl | 3'-OH |
| 685. | H | 4-OCF₃-benzyl | 3'-OH |
| 686. | H | 3,5-2F-benzyl | 3'-OH |
| 687. | H | 2-Br-benzyl | 3'-OH |
| 688. | H | 1,5-2Cl-benzyl | 3'-OH |
| 689. | H | 2-F-4-Cl-benzyl | 3'-OH |
| 690. | H | 2-F-benzyl | 3'-OH |
| 691. | H | 2-Cl-benzyl | 3'-OH |
| 692. | H | 2,5-2F-benzyl | 3'-OH |
| 693. | H | 2-CH₃-benzyl | 3'-OH |
| 694. | H | 2,4,5-3F-benzyl | 3'-OH |
| 695. | H | 2,6-2F-benzyl | 3'-OH |
| 696. | H | CH₂CH₂CH(CH₃)₂ | 3'-OH |
| 697. | H | 2-ethylphenyl (attached via α-methyl) | 3'-OH |
| 698. | H | C₂H₄NH₂ | 3'-OH |
| 699. | H | 3-fluorocyclopenta-2,4-dien-1-yl | 3'-OH |
| 700. | H | methoxycarbonylmethyl (methyl ester) | 3'-OH |
| 701. | H | 4-carboxyphenyl | 3'-OH |
| 702. | H | aminomethyl (H₂NCH₂–) | 3'-OH |
| 703. | H | 4-methylphenyl | 3'-OH |
| 704. | H | 3-Cl-phenyl | 3'-OH |
| 705. | H | 2-phenylethyl (attached via α-methyl) | 3'-OH |
| 706. | H | 4-(trifluoromethoxy)phenyl | 3'-OH |
| 707. | H | 4-nitrophenyl | 3'-OH |
| 708. | H | 3-chloro-4-hydroxyphenyl | 3'-OH |

TABLE 1-continued

| | R₁ | R₂ | R₄ |
|---|---|---|---|
| 709. | H | 1,4-phenylene-CH₂- | 3'-OH |
| 710. | H | 3-hydroxyphenyl | 3'-OH |
| 711. | H | 2,3-dihydroxypropyl (methyl-branched) | 3'-OH |
| 712. | H | 4-amino-3-methylphenyl | 3'-OH |
| 713. | H | 2'-carboxy-[1,1'-biphenyl]-4-yl-ethyl | 3'-OH |
| 714. | H | 4-(phenyl)phenacyl | 3'-OH |
| 715. | H | 1-(4-bromophenyl)-2-methyl-1-oxopropyl | 3'-OH |
| 716. | H | 3-bromo-5-methylphenyl | 3'-OH |
| 717. | H | pyridin-3-ylmethyl | 3'-OH |
| 718. | H | 4-benzoylphenyl | 3'-OH |
| 719. | H | 2-(3,4-dichlorophenyl)-2-oxoethyl | 3'-OH |
| 720. | H | 2,4-dinitrophenyl (methyl-branched) | 3'-OH |
| 721. | H | cyclopropylmethyl (methyl-branched) | 3'-OH |
| 722. | H | 4-ethylphenyl | 3'-OH |
| 723. | H | piperazin-1-ylmethyl | 3'-OH |
| 724. | H | 4-acetylphenyl | 3'-OH |
| 725. | H | 5-morpholino-1,3,4-thiadiazol-2-yl | 3'-OH |
| 726. | H | 1H-inden-2-yl | 3'-OH |
| 727. | H | 4-[4-(2-hydroxyacetyl)piperazin-1-yl]-3-fluorophenyl | 3'-OH |
| 728. | H | 2-(4-chlorophenyl)ethyl | 3'-OH |
| 729. | H | 6-(1H-pyrrol-1-yl)pyridin-3-yl | 3'-OH |

TABLE 1-continued
| | R₁ | R₂ | R₄ |
|---|---|---|---|
| 730. | H | | 3'-OH |
| 731. | H | | 3'-OH |
| 732. | H | | 3'-OH |
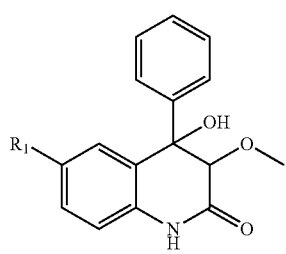
TABLE 2
| No. | R₁ |
|---|---|
| 733 | |
| 734 | |
| 735 | |
| 736 | |
| 737 | |
| 738 | |
| 739 | |
| 740 | |
| 741 | |
| 742 | |
| 743 | |
| 744 | |
| 745 | |
| 746 | |
| 747 | |

TABLE 2-continued

| No. | R₁ |
|---|---|
| 748 | (structure) |
| 749 | (structure) |
| 750 | (structure) |
| 751 | (structure) |
| 752 | (structure) |
| 753 | (structure) |
| 754 | (structure) |
| 755 | (structure) |
| 756 | (structure) |
| 757 | (structure) |
| 758 | (structure) |
| 759 | (structure) |
| 760 | (structure) |
| 761 | (structure) |
| 762 | (structure) |
| 763 | (structure) |
| 764 | (structure) |
| 765 | (structure) |
| 766 | (structure) |
| 767 | (structure) |

TABLE 2-continued
| No. | R₁ |
|---|---|
| 768 | 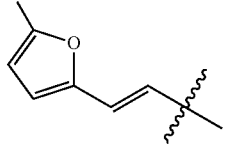 |
| 769 | 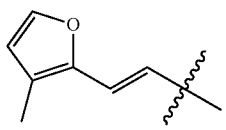 [SMILES: */C=C/c1occc1C] |
| 770 | 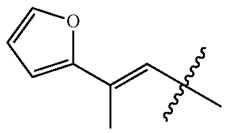 [SMILES: */C=C(\C)c1ccco1] |
| 771 | 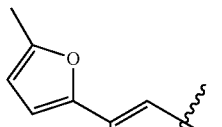 |
| 772 | 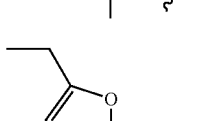 |
| 773 | 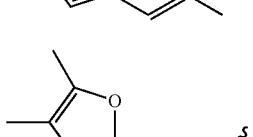 |
| 774 | 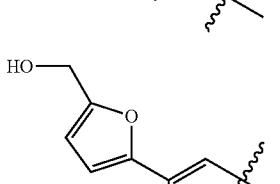 |
| 775 | 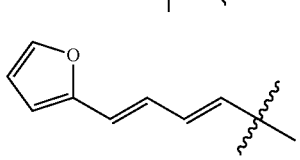 |
| 776 | 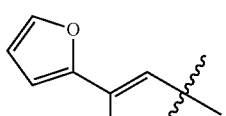 |
| 777 | 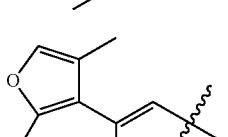 |
| 778 | 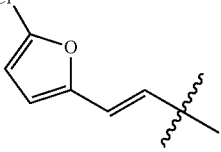 |
| 779 | 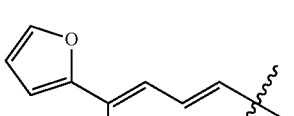 |
| 780 |  |
| 781 | 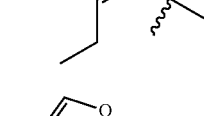 |
| 782 | 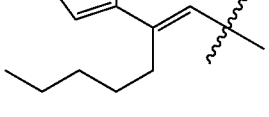 |
| 783 | 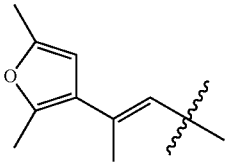 [SMILES: */C=C(\C)c1cc(C)oc1C] |
| 784 | 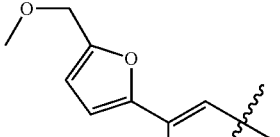 |
| 785 | 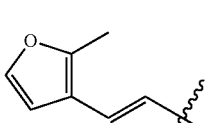 |
| 786 | 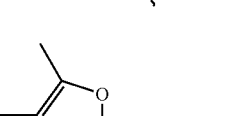 |

TABLE 2-continued
| No. | R₁ |
|---|---|
| 787 | 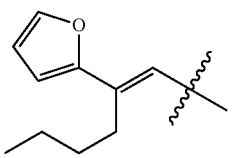 [SMILES: */C=C(\CCCC)c1ccco1] |
| 788 | 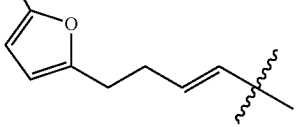 |
| 789 | 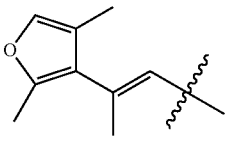 [SMILES: */C=C(\C)c1c(C)coc1C] |
| 790 | 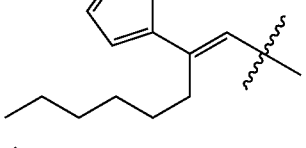 |
| 791 | 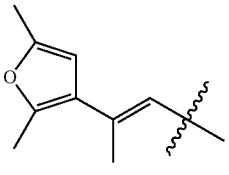 [SMILES: */C=C(\C)c1cc(C)oc1C] |
| 792 | 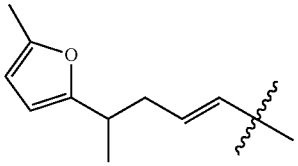 [SMILES: */C=C/CC(C)c1ccc(C)o1] |
| 793 | 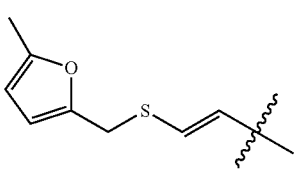 |
| 794 | 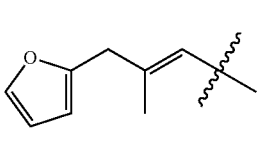 [SMILES: */C=C(\C)Cc1ccco1] |
| 795 | 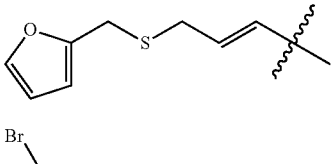 |
| 796 | 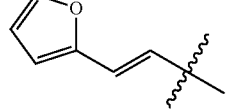 |
| 797 | 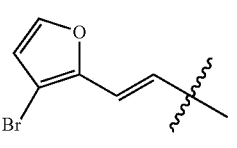 [SMILES: */C=C/c1occc1Br] |
| 798 | 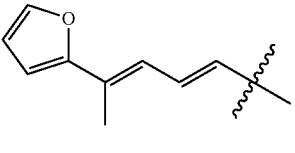 [SMILES: */C=C/C=C(\C)c1ccco1] |
| 799 | 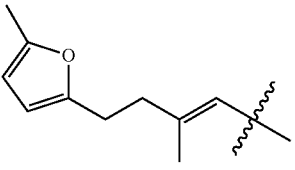 [SMILES: */C=C(\C)CCc1ccc(C)o1] |
| 800 | 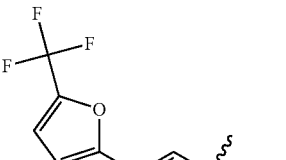 |
| 801 | 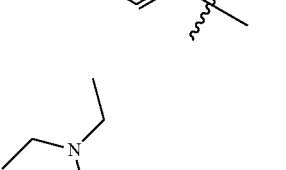 |
| 802 | 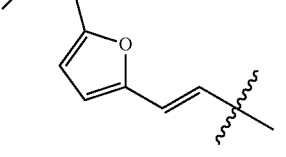 |
| 803 | 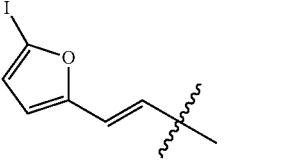 [SMILES: */C=C/c1ccc(I)o1] |
| 804 | 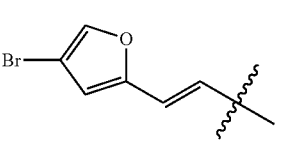 [SMILES: */C=C/c1cc(Br)co1] |
| 805 | 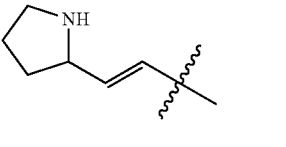 [SMILES: */C=C/C1CCCN1] |

TABLE 2-continued

| No. | R₁ |
|---|---|
| 806 | 3-methylpyrrolidin-2-yl vinyl group (NH pyrrolidine with methyl, attached via CH=CH) |
| 807 | 1-methylpyrrolidin-2-yl vinyl group |
| 808 | pyrrolidin-3-ylidene vinyl group (HN) |
| 809 | hexahydroindolizin-ylidene vinyl group |
| 810 | 4-methylpyrrolidin-2-yl vinyl group (NH) |
| 811 | pyrrolidin-2-ylmethyl-2-methyl-vinyl group (NH) |
| 812 | 1-ethylpyrrolidin-2-yl vinyl group |
| 813 | 1-(cyclopropylmethyl)pyrrolidin-2-yl vinyl group |
| 814 | indolizin-8-yl vinyl group |
| 815 | 4-amino-pyrrolidin-2-yl vinyl group (H₂N, NH) |
| 816 | (1-pyrrolidinyl)-2,2-dimethyl vinyl group |
| 817 | piperidin-2-yl vinyl group (NH) |
| 818 | 4-mercaptopyrrolidin-2-yl vinyl group (HS, NH) |
| 819 | piperidin-2-yl (methyl-substituted) vinyl group (NH) |
| 820 | 4-phenylpyrrolidin-2-yl vinyl group (NH) |
| 821 | octahydrocyclopenta[b]pyrrol-2-yl vinyl group (NH) |
| 822 | N-methyl-azabicyclic ylidene vinyl group |
| 823 | octahydroindol-2-yl vinyl group (NH) |
| 824 | piperidin-3-ylidene vinyl group (HN) |
| 825 | 1-methylpiperidin-3-ylidene vinyl group |
| 826 | octahydrocyclopenta[c]pyrrol-ylidene vinyl group (HN) |

TABLE 2-continued

| No. | R₁ |
|---|---|
| 827 | (azepane-NH with vinyl linker) |
| 828 | (3-azabicyclo[3.1.0]hexane with vinyl linker) |
| 829 | (1-ethylpiperidin-3-ylidene with linker) |
| 830 | (1-isopropylpiperidin-3-ylidene with linker) |
| 831 | (2-azabicyclic NH with vinyl linker) |
| 832 | (1-methylpiperidin-4-yl with allyl linker) |
| 833 | (1H-pyrrol-2-yl with vinyl linker) |
| 834 | (1-methyl-1H-pyrrol-2-yl with vinyl linker) |
| 835 | (5-methyl-1H-pyrrol-2-yl with vinyl linker) |
| 836 | (1,5-dimethyl-1H-pyrrol-2-yl with vinyl linker) |

TABLE 2-continued

| No. | R₁ |
|---|---|
| 837 | (1-tert-butyl-1H-pyrrol-2-yl with vinyl linker) |
| 838 | (3-methyl-1H-pyrrol-2-yl with vinyl linker) |
| 839 | (4-methyl-1H-pyrrol-2-yl with vinyl linker) |
| 840 | (1H-pyrrol-2-yl with 1-methylvinyl linker) |
| 841 | (1-(2-cyanoethyl)-1H-pyrrol-2-yl with 1-methylvinyl linker) |
| 842 | (3,5-dimethyl-1H-pyrrol-2-yl with vinyl linker) |
| 843 | (3,5-dimethyl-1H-pyrrol-2-yl with vinyl linker) |
| 844 | (1-methyl-1H-pyrrol-2-yl with 1-methylvinyl linker) |
| 845 | (1H-pyrrol-2-yl with 1-ethylvinyl linker) |
| 846 | (1-ethyl-1H-pyrrol-2-yl with 1-methylvinyl linker) |

TABLE 2-continued
| No. | R₁ |
|---|---|
| 847 | 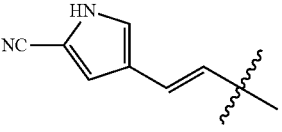 [SMILES: */C=C/c1c[nH]c(C#N)c1] |
| 848 | 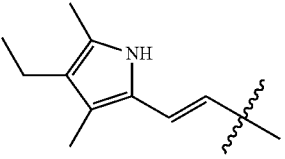 [SMILES: */C=C/c1[nH]c(C)c(CC)c1C] |
| 849 | 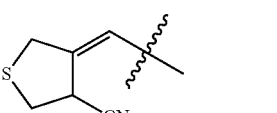 |
| 850 | 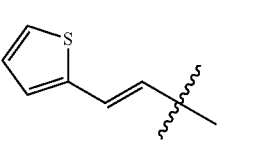 |
| 851 | 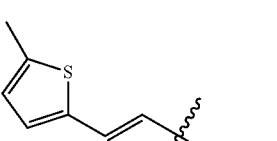 |
| 852 | 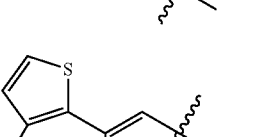 |
| 853 | 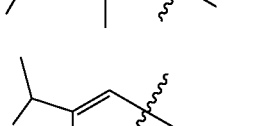 |
| 854 | 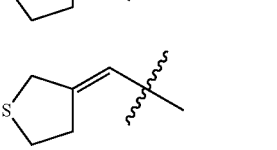 |
| 855 | 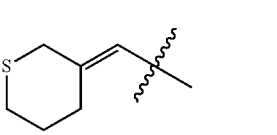 [SMILES: */C=C1\CCCSC1] |
| 856 | 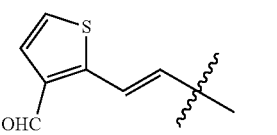 [SMILES: */C=C/c1sccc1C=O] |
| 857 | 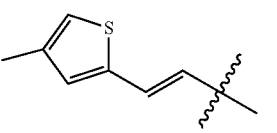 [SMILES: */C=C/c1cc(C)cs1] |
| 858 | 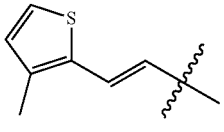 |
| 859 | 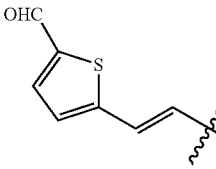 |
| 860 | 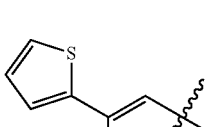 |
| 861 | 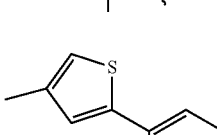 |
| 862 | 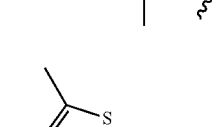 |
| 863 | 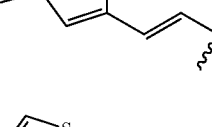 |
| 864 | 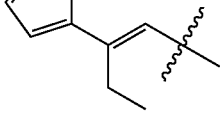 |
| 865 | 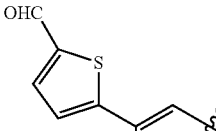 |
| 866 | 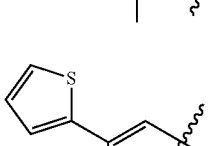 |

TABLE 2-continued
| No. | R₁ |
|---|---|
| 867 | 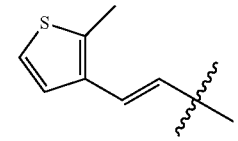 [SMILES: */C=C/c1ccsc1C] |
| 868 | 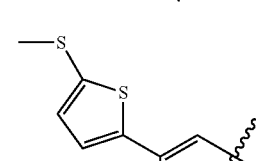 |
| 869 | 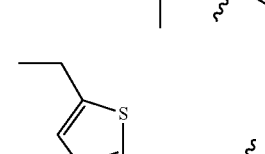 |
| 870 | 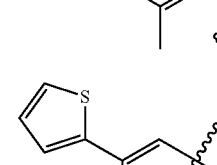 |
| 871 | 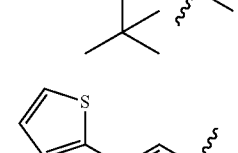 |
| 872 | 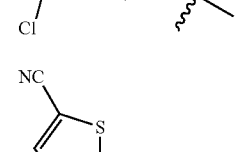 |
| 873 | 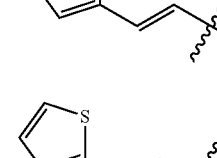 |
| 874 | 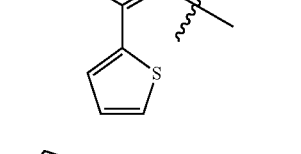 |
| 875 | 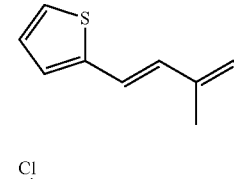 |
| 876 | 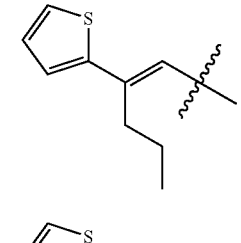 |
| 877 | 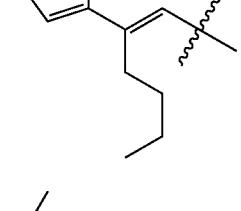 |
| 878 | 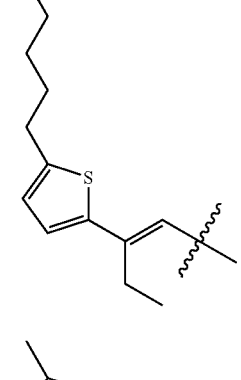 |
| 879 | 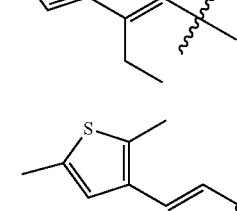 |
| 880 | 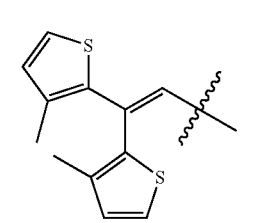 [SMILES: *C=C(c1sccc1C)c1sccc1C] |
| 881 | 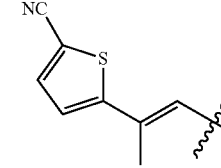 |
| 882 |  |

TABLE 2-continued

| No. | R₁ |
|---|---|
| 883 | (2,4,5-trimethylthiophen-3-yl vinyl group) |
| 884 | (thiophen-2-yl with CN substituent on vinyl) |
| 885 | (thiophen-2-yl vinyl with hexyl chain) |
| 886 | (thiophen-2-yl vinyl with octyl chain) |
| 887 | (thiophen-2-yl vinyl with cyclopropyl) |
| 888 | (3-chlorothiophen-2-yl propenyl) |
| 889 | (2,5-dimethylthiophen-3-yl propenyl) |
| 890 | (5-chlorothiophen-2-yl propenyl) |

TABLE 2-continued

| No. | R₁ |
|---|---|
| 891 | (2,3'-bithiophen-5-yl vinyl) |
| 892 | |
| 893 | (thiophen-2-yl vinyl with CF₃) |
| 894 | (3-bromothiophen-2-yl vinyl) |
| 895 | (4-bromothiophen-2-yl vinyl) |
| 896 | (4-bromo-3-methylthiophen-2-yl vinyl) |
| 897 | |
| 898 | (styryl / phenyl vinyl) |
| 899 | (HOOC-CH₂-CH(OH)-CH₂-CH(OH)-CH=CH–) |
| 900 | (HOOC-CH₂-CH(OH)-CH₂-CH(OH)-CH₂-CH₂–) |

(Structure at bottom: 4-hydroxy-5-hydroxy-3-methoxy-4-phenyl-3,4-dihydroquinolin-2(1H)-one with R₁ substituent)

TABLE 3
| No. | R₁ |
|---|---|
| 899 | 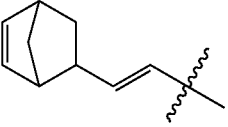 [SMILES: */C=C/C1CC2C=CC1C2] |
| 900 | 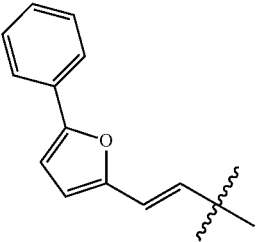 [SMILES: */C=C/c1ccc(-c2ccccc2)o1] |
| 901 | 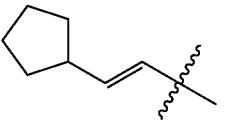 |
| 902 | 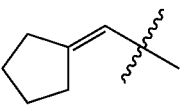 [SMILES: *C=C1CCCC1] |
| 903 | 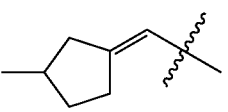 [SMILES: */C=C1\CCC(C)C1] |
| 904 | 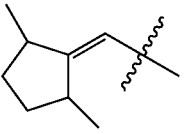 [SMILES: *C=C1C(C)CCC1C] |
| 905 | 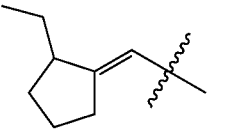 [SMILES: */C=C1\CCCC1CC] |
| 906 | 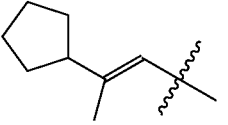 [SMILES: */C=C(\C)C1CCCC1] |
| 907 | 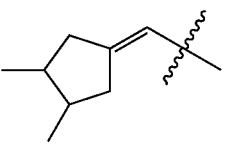 [SMILES: *C=C1CC(C)C(C)C1] |
| 908 | 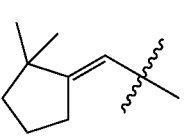 [SMILES: */C=C1\CCCC1(C)C] |
TABLE 3-continued
| No. | R₁ |
|---|---|
| 909 | 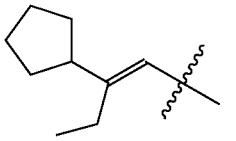 [SMILES: */C=C(\CC)C1CCCC1] |
| 910 | 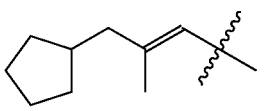 [SMILES: */C=C(\C)CC1CCCC1] |
| 911 | 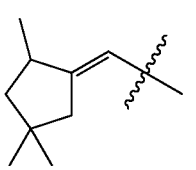 [SMILES: */C=C1\CC(C)(C)CC1C] |
| 912 | 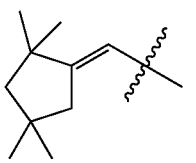 [SMILES: */C=C1\CC(C)(C)CC1(C)C] |
| 913 | 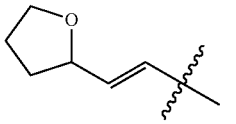 [SMILES: */C=C/C1CCCO1] |
| 914 | 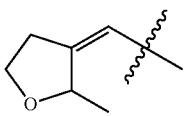 [SMILES: */C=C1/CCOC1C] |
| 915 | 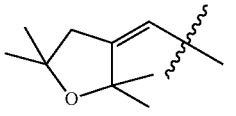 [SMILES: */C=C1/CC(C)(C)OC1(C)C] |
| 916 | 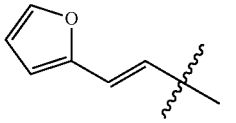 [SMILES: */C=C/c1ccco1] |
| 917 | 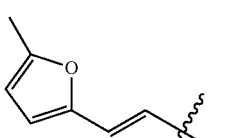 |
| 918 | 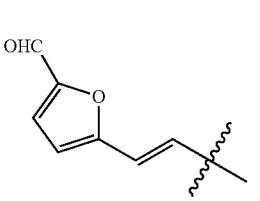 [SMILES: */C=C/c1ccc(C=O)o1] |

TABLE 3-continued
| No. | R₁ |
|---|---|
| 919 | 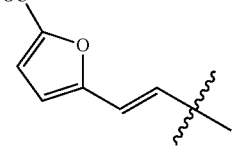 |
| 920 | 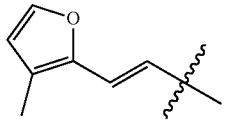 [SMILES: */C=C/c1occc1C] |
| 921 | 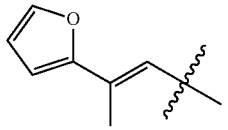 |
| 922 |  |
| 923 | 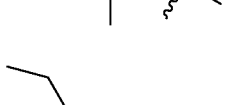 |
| 924 | 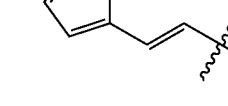 |
| 925 | 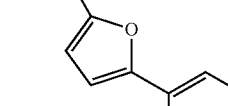 |
| 926 | 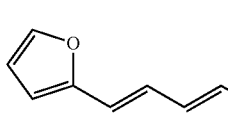 |
| 927 | 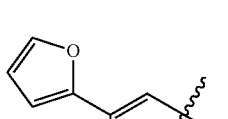 |
| 928 | 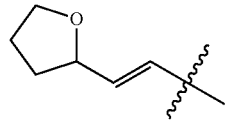 [SMILES: */C=C/C1CCCO1] |
| 929 | 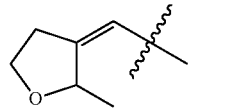 [SMILES: */C=C1/CCOC1C] |
| 930 | 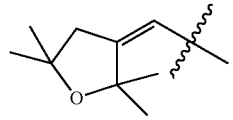 [SMILES: */C=C1/CC(C)(C)OC1(C)C] |
| 931 | 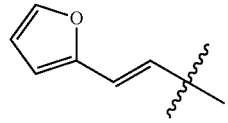 [SMILES: */C=C/c1ccco1] |
| 932 | 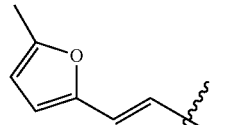 |
| 933 | 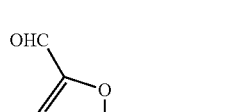 |
| 934 | 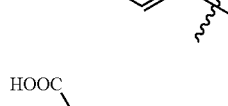 |
| 935 | 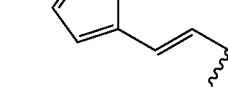 |
| 936 | 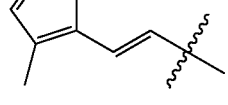 |
| 937 | 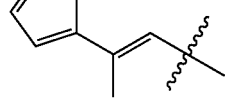 |

TABLE 3-continued
| No. | R₁ |
|---|---|
| 938 | 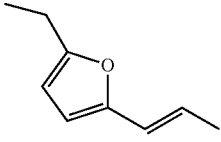 |
| 939 | 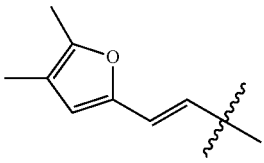 [SMILES: */C=C/c1cc(C)c(C)o1] |
| 940 | 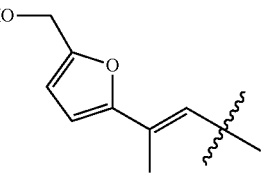 |
| 941 | 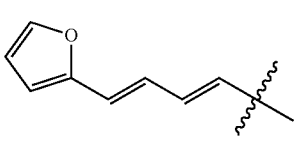 [SMILES: */C=C/C=C/c1ccco1] |
| 942 | 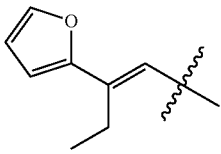 [SMILES: */C=C(\CC)c1ccco1] |
| 943 | 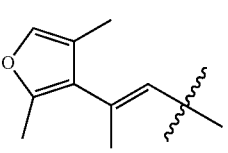 [SMILES: */C=C(\C)c1c(C)coc1C] |
| 944 | 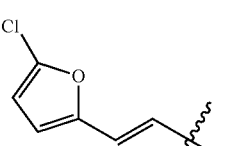 |
| 945 | 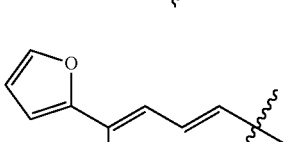 |
| 946 | 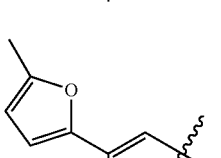 |
| 947 | 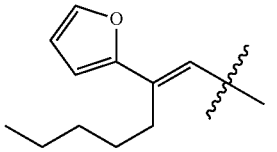 [SMILES: */C=C(\CCCCC)c1ccco1] |
| 948 | 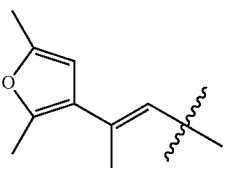 [SMILES: */C=C(\C)c1cc(C)oc1C] |
| 949 | 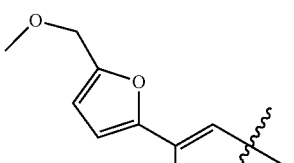 |
| 950 | 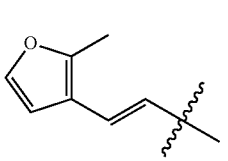 [SMILES: */C=C/c1ccoc1C] |
| 951 | 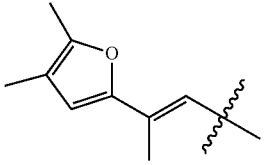 [SMILES: */C=C(\C)c1cc(C)c(C)o1] |
| 952 | 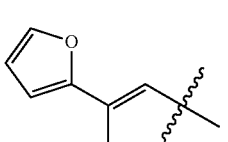 |
| 953 | 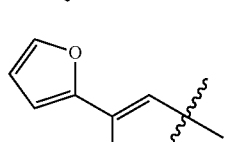 |
| 954 |  |
| 955 | 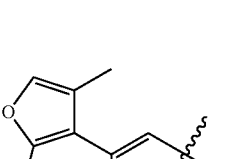 |

TABLE 3-continued
| No. | R₁ |
|---|---|
| 956 | 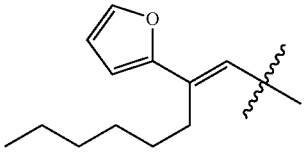 [SMILES: */C=C(\CCCCCC)c1ccco1] |
| 957 | 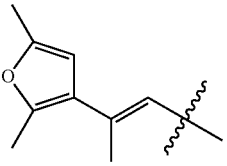 [SMILES: */C=C(\C)c1cc(C)oc1C] |
| 958 | 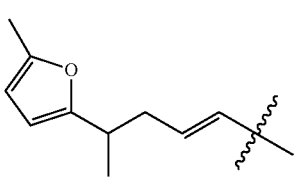 [SMILES: */C=C/CC(C)c1ccc(C)o1] |
| 959 | 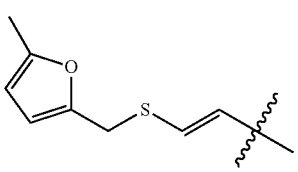 [SMILES: */C=C/SCc1ccc(C)o1] |
| 960 | 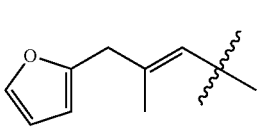 [SMILES: */C=C(\C)Cc1ccco1] |
| 961 | 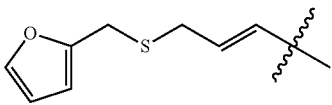 [SMILES: */C=C/CSCc1ccco1] |
| 962 | 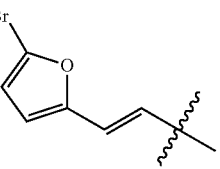 |
| 963 | 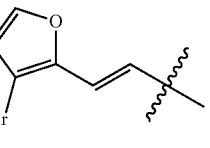 |
| 964 | 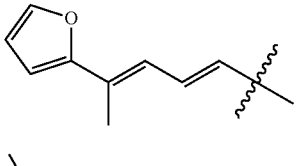 |
| 965 | 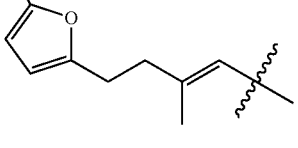 |
| 966 | 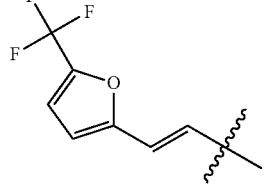 |
| 967 | 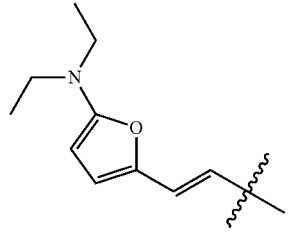 [SMILES: */C=C/c1ccc(N(CC)CC)o1] |
| 968 | 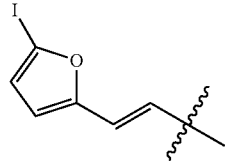 [SMILES: */C=C/c1ccc(I)o1] |
| 969 | 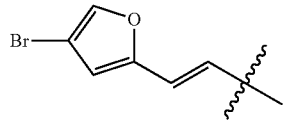 [SMILES: */C=C/c1cc(Br)co1] |
| 970 | 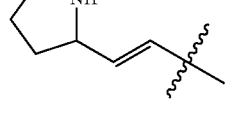 |
| 971 | 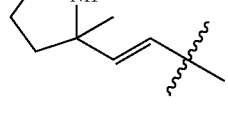 |
| 972 | 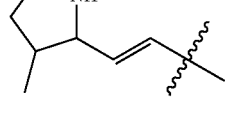 |
| 973 | 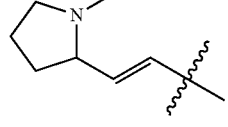 |
| 974 | 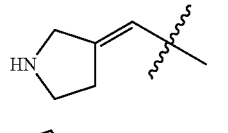 |
| 975 | 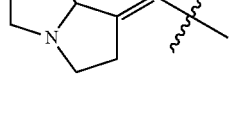 |

TABLE 3-continued

| No. | R₁ |
|---|---|
| 976 | (4-methylpyrrolidin-2-yl, vinyl linker) |
| 977 | (pyrrolidin-2-ylmethyl, 2-methylvinyl linker) |
| 978 | (1-ethylpyrrolidin-2-yl, vinyl linker) |
| 979 | (1-(cyclopropylmethyl)pyrrolidin-2-yl, vinyl linker) |
| 980 | (indolizidinyl, vinyl linker) |
| 981 | (4-aminopyrrolidin-2-yl, vinyl linker) |
| 982 | (1-pyrrolidinyl-neopentyl, vinyl linker) |
| 983 | (piperidin-2-yl, vinyl linker) |
| 984 | (4-mercaptopyrrolidin-2-yl, vinyl linker) |
| 985 | (piperidin-2-yl, 2-methylvinyl linker) |

TABLE 3-continued

| No. | R₁ |
|---|---|
| 986 | (4-phenylpyrrolidin-2-yl, vinyl linker) |
| 987 | (octahydroindol-2-yl, vinyl linker) |
| 988 | (N-methyl-tropane, vinyl linker) |
| 989 | (octahydroindol-2-yl, vinyl linker) |
| 990 | (piperidin-3-ylidene, vinyl linker) |
| 991 | (1-methylpiperidin-3-ylidene, vinyl linker) |
| 992 | (octahydrocyclopenta[c]pyrrol-4-ylidene) |
| 993 | (azepan-2-yl, vinyl linker) |
| 994 | (3-azabicyclo[3.1.0]hexyl, vinyl linker) |
| 995 | (1-ethylpiperidin-3-ylidene, vinyl linker) |
| 996 | (1-isopropylpiperidin-3-ylidene, vinyl linker) |

TABLE 3-continued

| No. | R₁ |
|---|---|
| 997 | (structure) |
| 998 | (structure) |
| 999 | (structure) |
| 1000 | (structure) |
| 1001 | (structure) |
| 1002 | (structure) |
| 1003 | (structure) |
| 1004 | (structure) |
| 1005 | (structure) |
| 1006 | (structure) |
| 1007 | (structure) |
| 1008 | (structure) |
| 1009 | (structure) |
| 1010 | (structure) |
| 1011 | (structure) |
| 1012 | (structure) |
| 1013 | (structure) |
| 1014 | (structure) |
| 1015 | (structure) |
| 1016 | (structure) |

TABLE 3-continued
| No. | R₁ |
|---|---|
| 1017 | 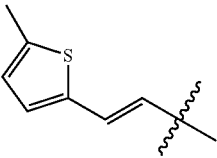 [SMILES: */C=C/c1ccc(C)s1] |
| 1018 | 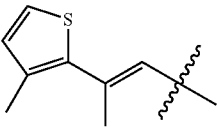 [SMILES: */C=C(\C)c1sccc1C] |
| 1019 | 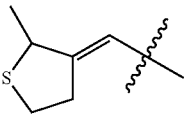 [SMILES: */C=C1\CCSC1C] |
| 1020 | 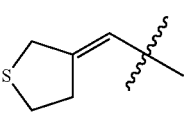 [SMILES: */C=C1\CCSC1] |
| 1021 | 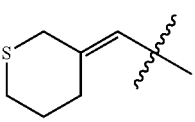 [SMILES: */C=C1\CCCSC1] |
| 1022 | 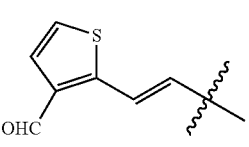 [SMILES: */C=C/c1sccc1C=O] |
| 1023 | 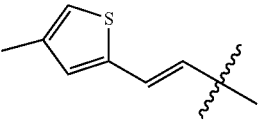 [SMILES: */C=C/c1cc(C)cs1] |
| 1024 | 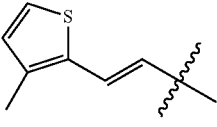 [SMILES: */C=C/c1sccc1C] |
| 1025 | 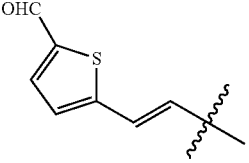 |
| 1026 | 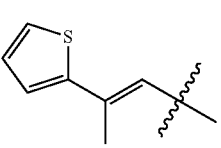 [SMILES: */C=C(\C)c1cccs1] |
| 1027 | 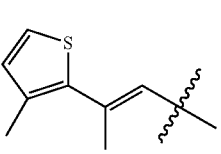 [SMILES: */C=C(\C)c1sccc1C] |
| 1028 | 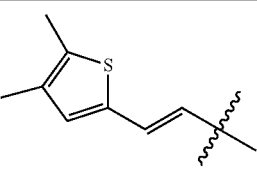 [SMILES: */C=C/c1cc(C)c(C)s1] |
| 1029 | 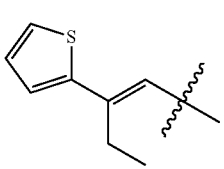 [SMILES: */C=C(\CC)c1cccs1] |
| 1030 | 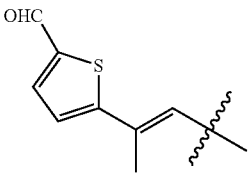 [SMILES: */C=C(\C)c1ccc(C=O)s1] |
| 1031 | 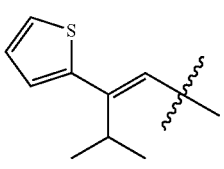 [SMILES: */C=C(/c1cccs1)C(C)C] |
| 1032 | 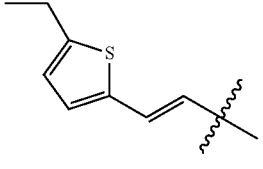 [SMILES: */C=C/c1ccc(CC)s1] |
| 1033 | 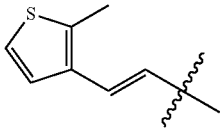 |
| 1034 | 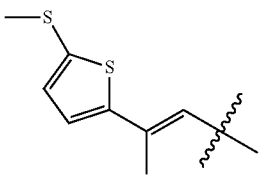 [SMILES: */C=C(\C)c1ccc(SC)s1] |
| 1035 | 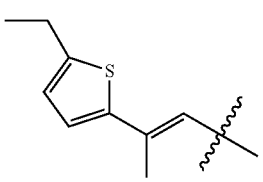 [SMILES: */C=C(\C)c1ccc(CC)s1] |
| 1036 | 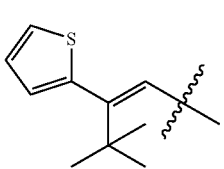 [SMILES: */C=C(/c1cccs1)C(C)(C)C] |

TABLE 3-continued
| No. | R₁ |
|---|---|
| 1037 | 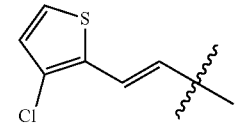 |
| 1038 | 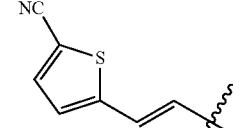 |
| 1039 | 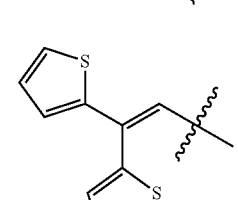 |
| 1040 | 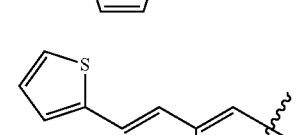 |
| 1041 | 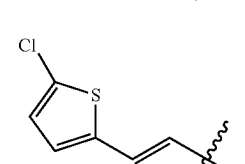 |
| 1042 | 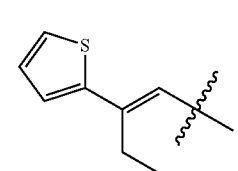 |
| 1043 | 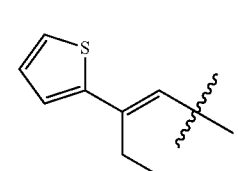 |
| 1044 | 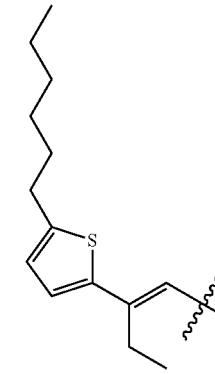 |
| 1045 | 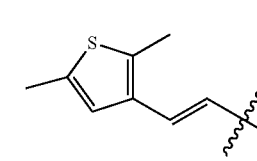 |
| 1046 | 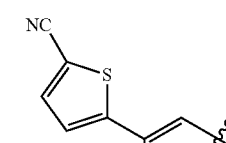 |
| 1047 | 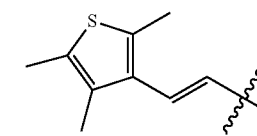 |
| 1048 | |
| 1049 | |
| 1050 | |

TABLE 3-continued

| No. | R₁ |
|-----|-----|
| 1051 | (2-thienyl-substituted alkenyl with hexyl chain) |
| 1052 | (2-thienyl-substituted alkenyl with heptyl chain) |
| 1053 | (2-thienyl-substituted alkenyl with cyclopropyl) |
| 1054 | (3-chloro-2-thienyl-substituted alkenyl with methyl) |
| 1055 | (2,5-dimethyl-3-thienyl substituted alkenyl) |
| 1056 | (5-chloro-2-thienyl substituted alkenyl with methyl) |
| 1057 | (2,3'-bithiophene substituted alkenyl) |
| 1058 | |
| 1059 | (2-thienyl with CF₃ substituted alkenyl) |
| 1060 | (3-bromo-2-thienyl substituted alkenyl) |
| 1061 | (4-bromo-2-thienyl substituted alkenyl) |
| 1062 | (4-bromo-3-methyl-2-thienyl substituted alkenyl) |
| 1063 | |
| 1064 | (phenyl substituted alkenyl) |
| 1065 | (carboxylic acid with two OH groups, alkenyl) |
| 1066 | (carboxylic acid with two OH groups, alkenyl) |
| 1067 | |
| 1068 | |

The invention involves the drug combination, containing compounds of the present invention, or stereoisomer thereof, geometric isomers, tautomer, nitrogen oxide, hydrate, solvate, metabolites, pharmaceutical acceptable salt on or their prodrug, or a pharmaceutical acceptable carrier, excipients, diluent, auxiliary agent, intermediary, or their combination.

The present invention disclose methods of preventing, treating, treating or alleviating various diseases caused by viruses in patients, including administering drugs to patients with effective doses of the pharmaceutical compositions of the present compound that are medically acceptable.

The present also disclose methods of preventing, treating or alleviating various diseases caused by viruses in patients, including administering the patient with an effective dose of the compound medically acceptable In another aspect, the invention relates to the use of the compound of the invention for preparing drugs for the prevention, treatment, treatment or alleviation of various diseases caused by viruses in patients On the other hand, the invention relates to a methodical use of the compound or pharmaceutical composition of the invention for the prevention or treatment of various diseases caused by viruses in animals or humans, which includes the administration of drugs to humans or animals in a medically acceptable effective therapeutic quantity using the compound or pharmaceutical composition of the invention.

In some examples, the invention discloses the a methodical use of treating various diseased like respiratory diseases, pneumonia, gingival stomatitis, corneal conjunctivitis, encephalitis, hepatitis, reproductive system infection, rash, herpes and herpes pharyngitis, hand-foot-mouth disease, immune disease, inflammatory disease, AIDS, etc.

In some examples, the drug disclosed in present are for treatment of diseases caused by respiratory syncytial virus (RSV), herpes simplex virus (HSV), hepatitis b virus (HBV), enterovirus 71 (EV71), influenza virus (H1N1, H3N2, H5N1, H7N9), foot-and-mouth disease virus (FMDV), SARS virus, human immunodeficiency virus (HIV).

The foregoing outlines, but is not limited to, some certain aspects of the invention. Other aspects of the content are described more fully below.

Definitions and General Terms

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, Inc., New York: 2007, all of which are incorporated herein by reference in their entireties.

As described herein, compounds may optionally be substituted with one or more substituents, such as those illustrated above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure may be substituted with more than one substituent selected from a specified group, the substituent may be either the same or different at each position. Wherein the substituents include, but are not limited to, hydroxyl, amino, halo, cyano, aryl, heteroaryl, alkoxy, alkylamino, alkylthio, alkyl, haloalkyl, alkenly, alkynyl, heterocyclyl, thiol, nitro, aryloxy, heteroaryloxy, oxo (O=), carboxy, hydroxyl-substituted alkoxy, hydroxyl-substituted alkyl-C(=O)—, alkyl-C(—O)—, alkyl-S(=O)—, alkyl-S(=O)$_2$—, hydroxy-substituted alkyl-S(=O)—. hydroxy-substituted alkyl-S(=O)$_2$—, carboxyalkoxy, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms. In yet other embodiments, aliphatic groups contain 1-4 carbon atoms and in yet other embodiments, aliphatic groups contain 1-3 carbon atoms. Suitable aliphatic groups include, but are not limited to, linear or branched, substituted or unsubstituted alkyl, alkenyl, or alkynyl groups, such as methyl, ethyl, propyl, isopropyl, butyl, tert-butyl, hexyl, isobutyl, sec-butyl, ethenyl, and the like.

The term "haloaliphatic" refers to an aliphatic group substituted by one or more of the same or different halogen atoms, wherein the aliphatic group is as defined herein, halogen atoms refer to F, Cl, Br or I. Some non-limiting examples include trifluoromethyl, trifluoroethyl, chloromethyl, 2-chloroethylene, and the like.

The term "hydroxyaliphatic" refers to an aliphatic group substituted by one or more hydroxy groups, wherein the aliphatic group is as defined herein. Some non-limiting examples include hydroxyethyl, 2-hydroxypropyl, hydroxymethyl, and the like.

The term "aminoaliphatic" refers to an aliphatic group substituted by one or more amino groups, wherein the aliphatic group is as defined herein. Some non-limiting examples include aminomethyl, 2-aminoethyl, 2-aminoisopropyl, and the like.

The term "alkyl" refers to a saturated linear or branched-chain monovalent hydrocarbon radical of 1-20 carbon atoms, 1-10 carbon atoms, 1-6 carbon atoms, 1-4 carbon atoms, or 1-3 carbon atoms, wherein the alkyl radical may be optionally substituted independently with one or more substituents described below. Further examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$, 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$, 2-methyl-2-butyl (—C(CH$_3$)$_2$CH$_2$CH$_3$), 3-methyl- 2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$(CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$). 2,3-dimety-2-butyl (—C(CH$_3$)$_2$CH(CH$_3$)$_2$), 3,3-dimethyl-2-buty (—CH(CH$_3$)C (CH$_3$)$_3$, 1-heptyl, 1-octyl, and the like. The terms "alkyl" and the prefix "alk-" are inclusive of both straight chain and branched saturated carbon chain.

The term "alkenyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp$^2$ double bond, wherein the alkenyl radical may be optionally substituted independently with one or more substituents described herein, and includes radicals having "cis" and "rans" orientations, or alternatively, "E" and "Z" orientations. Some non-limiting examples include ethenyl or vinyl (—CH═CH$_2$), allyl (—CH$_2$CH═CH$_2$), and the like.

The term "alkynyl" refers to a linear or branched-chain monovalent hydrocarbon radical of 2-12 carbon atoms, 2-8 carbon atoms, 2-6 carbon atoms, or 2-4 carbon atoms, with at least one site of unsaturation, i.e., a carbon-carbon, sp triple bond, wherein the alkynyl radical may be optionally substituted independently with one or more substituents described herein. Some non-limiting examples include ethynyl(—C≡CH), 2-propynyl (—CH$_2$C≡CH), and the like.

The term "hydroxy-substituted alkyl" refers to an alkyl group substituted with one or more hydroxy groups, wherein the alkyl group is as defined herein. Some non-limiting examples include hydroxymethyl, hydroxyethyl, 1,2-dihydroxyethyl, and the like.

The term "carbocycle", "carbocyclyl", "cycloalkyl" refers to a monovalent or multivalent, non-aromatic, saturated or partially unsaturated ring, and not containing heteroatoms, having 3 to 12 carbon atoms as a monocyclic ring or 7 to 12 carbon atoms as a bicyclic ring or a tricyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system. Some non-limiting examples of cycloaliphatic groups include cycloalkyl, cycloalkenyl, and cycloalkynyl. Further examples of cycloaliphatic groups include cyclopropyl, cyclobutyl, cyclopentyl, 1-cyclopent-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamanty, and the like. And "cycloaliphatic", "carbocycle", "carbocyclyl", or "cycloalkyl" may be substituted or unsubstituted, wherein the substituent may be, but is not limited to, hydroxy, amino, halo, cyano, aryl, heteroaryl, alkoxy, alkylamino, alkyl, haloalkyl, alkenyl, alkynyl, heterocyclyl, thiol, nitro, arloxy, hydroxy-substituted alkoxy, hydroxy-substituted —C(═O)—, alkyl-C(═O)—, alkyl-S(═O)—, alkyl-S(═O)$_2$—, hydroxy-substituted alkyl-S(═O)—, hydroxy-substituted alkyl-S(═O)$_2$—, carboxyalkoxy, and the like.

The term "cycloalkyloxy" or "carbocyclyloxy" refers to an optionally substituted cycloalkyl radical or carbocyclyl radical, as defined herein, attached to an oxygen atom, which is connected to the rest of the molecule. Some non-limiting examples include cyclopropyloxy, cyclopentyloxy, cyclohexyloxy, hydroxy-substituted cyclopropyloxy, and the like.

The term "cycloalkylamino" refers to an amino group substituted with one or two cycloalkyl groups, wherein the cycloalkyl group is as defined herein. Some non-limiting examples include cyclopropylamino, cyclopentylamino, cyclohexylamino, hydroxy-substituted cyclopropylamino, dicyclohexylamino, dicyclopropylamino, and the like.

The term "cycloalkyloxyaliphatic" refers to an aliphatic group substituted with one or more cycloalkyloxy groups, wherein the aliphatic group and cycloalkyloxy group are as defined herein. Some non-limiting examples include cyclopropyloxymethyl, cyclopropyloxyethyl, cyclopentyloxymethyl, cyclopentyloxyethyl, cyclohexyloxyethyl, halocyclopropyloxyethyl, and the like.

The term "cycloalkylaminoaliphatic" refers to an aliphatic group substituted with one or more cycloalkylamino groups, wherein the aliphatic group and cycloalkylamino group are as defined herein. Some non-limiting examples include cyclopropylaminomethyl, cyclopropylaminethyl, cyclopentylaminomethyl, cyclopentylaminoethyl, cyclohexylaminoethyl, halocyclopropylaminoethyl, and the like.

The term "cycloalkylaliphatic" or "carbocyclylaliphatic" refers to an aliphatic group substituted with one or more cycloalkyl groups or carbocyclyl groups, wherein the carbocyclyl, cycloalkyl group and aliphatic group are as defined herein. Some non-limiting examples include cyclopropylmethyl, cyclopropylethyl, cyclopropylpropyl, cyclopentylmethyl, cyclohexylethyl, and the like.

The term "heterocycle", "heterocyclyl", "heterocycloaliphatic" or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or SO$_2$, PO or PO$_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or SO$_2$, PO or PO$_2$).

The heterocyclyl may be a carbon radical or heteroatom radical. "Hetetocyclyl" also includes radicals where heterocycle radicals are fused with a saturated, partially unsaturated ring, or heterocyclic ring. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, piperidino, homopiperidinyl, epoxypropyl, azepanyl, oxepanyl, thiepanyl, 4-methoxy-piperidin-1-yl, 1,2,3,6-tetrahydropyridin-1-yl, oxazepinyl, diazepinyl, thiazepinyl, pyrrolin-1-yl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydrothienyl, pyrazolidinylimidazolinyl, imidazolidinyl, 1,2,3,4-tetrahydroisoquinolinyl, 1,2,6-thiadiazane-1-1-dioxo-2-yl, 4-hydroxy-1,4-azaphosphine-4-oxid-1-yl, 2-hydroxy-1-(piperazin-1-yl)ethanon-4-yl, 2-hydroxy-1-(5,6-dihydro-1,2,4-triazin-1(4H)-yl)ethanon-4-yl, 5,6-dihydro-4H-1,2,4-oxadiazin-4-yl, 2-hydroxy-1-(5,6-dihydropyridin-1(2H)-yl) ethanon-4-yl, 3-azabicyco[3.1.0]hexanyl, 3-azabicyclo [4.1.0]heptanyl, azabicyclo[2.2.2]hexanyl, 2-methyl-5,6,7,8-tetrahydro-[1,2,4]triazolo[1,5-c]pyrimidin-6-yl, 4,5,6,7-tetrahydroisoxazol[4,3-c]pyridin-5-yl, 3H-indolyl-2-oxo-5-azabicyclo[2.2.1]heptan-5-yl, 2-oxo-5-azabicyclo[2.2.2] octan-5-yl, quinolizinyl and N-pyridyl urea. Some non-limiting examples of a heterocyclic ring include 1,1-dioxothiomorpholinyl and heterocyclic group wherein 2 carbon atoms on the ring are substituted with oxo (=O) moieties are pyrimidindionyl. The heterocyclic group herein may be substituted or unsubstituted, wherein the substituent may be, but is not limited to, oxo (=O), hydroxy, amino, halo, cyano, heteroaryl, alkoxy, alkylamino, alkyl, haloalkyl, alkenyl, alkynyl, heterocyclyl, thiol, nitro, aryloxy, hydroxyl-substituted alkoxy, hydroxyl-substituted alkyl-C(=O)—, alkyl-C(=O)—, alkyl-S(=O)—, hydroxyl-substituted alkyl-S(=O)—, hydroxyl-substituted alkyl-S(=O)$_2$—, carboxyalkoxy, and the like.

The term "heterocyclylaliphatic" refers to heterocyclic-substituted aliphatic group, wherein the heterocyclic radical and aliphatic group are as defined herein. Some non-limiting examples include pyrrol-2-ylmethyl, piperidin-2-ylethyl, piperazin-2-ylethyl, piperidin-2-ylmethyl, and the like.

The term "heterocyclyloxy" refers to optionally substituted heterocyclyl radical, as defined herein, connected to an oxygen atom, and the oxygen atom serves as the attaching point to the rest of the molecule. Some non-limiting examples include pyrrol-2-yloxy, pyrrol-3-yloxy, piperidin-2-yloxy, piperidin-3-yloxy, piperazin-2-yloxy, piperidin-4-yloxy, and the like.

The term "heterocyclylamino" refers to an amino group substituted with one or two heterocyclyl groups, wherein the heterocyclyl group is as defined herein. Some non-limiting examples include pyrrol-2-ylamino, pyrrol-3-ylamino, piperidin-2-ylamino, piperidin-3-ylamino, piperidin-4-ylamino, piperazin-2-ylamino, dipyrrol-2-ylamino, and the like.

The term "heterocyclyloxyaliphatic" refers to an aliphatic group substituted with one or more heterocyclyloxy groups, wherein the aliphatic group and heterocyclyloxy group are as defined herein. Some non-limiting examples include pyrrol-2-yloxymethyl, piperazin-3-yloxyethyl, piperazin-2-yloxyethyl, morpholin-2-yloxymethyl, piperidin-2-yloxyethyl, and the like. The term "heterocyclylaminoaliphatic" refers to an aliphatic group substituted with one or more heterocyclylamino groups, wherein the aliphatic group and heterocyclylamino group are as defined herein. Some non-limiting examples include pyrrol-2-ylaminomethyl, piperazin-3-lyaminoethyl, piperazin-2-lyaminoethyl, piperidin-2-lyaminoethyl, morpholin-2-lyaminomethyl, and the like.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" refers to a moiety having one or more units of unsaturation.

The term "alkoxy" refers to an alkyl group, as previously defined, attached to the principal carbon chain through an oxygen ("alkoxy") atom. Some non-limiting examples include methoxy, ethoxy, propoxy, butoxy, and the like. And the alkoxy defined above may be substituted or unsubstituted, wherein the substituent may be, but is not limited to, hydroxy, amino, halo, cyano, alkoxy, alkyl, alkenyl, alkynyl, thiol, nitro, and the like.

The term "hydroxy-substituted alkoxy" or "hydroxyalkoxy" refers to an alkoxy group substituted with one or more hydroxy groups, wherein the alkoxy group is as defined above. Some non-limiting examples include hydroxymethoxy, 2-hydroxyethoxy, 2-hydroxypropoxy, 2-hydroxyisopropoxy, and the like.

The term "aminoalkoxy" refers to an alkoxy group substituted with one or more amino groups, wherein the alkoxy group is as defined above. Some non-limiting examples include aminomethoxy, 2-aminoethoxy, 2-aminopropoxy, 2-aminoisopropoxy, and the like.

The term "haloalkyl", "haloalkenyl" or "haloalkoxy" refers to an alkyl group, alkenyl group or alkoxy group substituted with one or more halogen atoms. Some non-limiting examples include trifluoromethyl, 2-chloro-ethenyl, trifluoromethoxy, and the like.

The term "aryl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthracene. And the aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fluoro-substituted phenyl" refers to a phenyl group substituted with one or more fluorine atoms.

The term "arylaliphatic" refers to an aliphatic group substituted with one or more aryl groups, wherein the aliphatic group and the aryl group are as defined herein. Some non-limiting examples include phenylethyl, phenylmethyl, (p-toly)ethyl, styryl, and the like.

The term "aryloxy" refers to optionally substituted aryl radicals, as defined herein, attached to an oxygen atom, wherein the oxygen atom serves as the attaching point to the rest of the molecule. Wherein the aryl radical is as defined herein. Some non limiting examples include phenyloxy, methylphenyloxy, ethylphenyloxy, and the like.

The term "arylamino" refers to an amino group substituted with one or two aryl groups, wherein the aryl group is as defined herein. Some non-limiting examples include phenylamino, (p-fluoropheny)amino, diphenylamino, ditolylamino, (di-p-tolyl)amino, and the like.

The term "aryloxyaliphatic" refers to an aliphatic group substituted with one or more aryloxy groups, wherein the alkoxy group and the aliphatic group are as defined herein. Some no-limiting examples include phenyloxymethoxy, phenyloxyethyl, tolyloxyethyl, phenyloxypropoxy, and the like.

The term "heteroaryloxyaliphatic" refers to an aliphatic group may be substituted with one or more heteroaryloxy groups, wherein the heteroaryloxy group and the aliphatic group are as defined herein. Some non-limiting examples include furanyloxymethyl, pyrimidinyloxyethyl, and the like.

The term "arylaminoaliphatic" refers to an aliphatic group substituted with one or more arylamino groups, wherein the arylamino group and the aliphatic group are as defined herein. Some non-limiting examples include phenylaminomethyl, phenylaminoethyl, tolylaminoethyl, phenylaminopropyl, phenylaminoallyl, and the like.

The term "arylalkoxy" refers to an alkoxy group substituted with one or more aryl groups, wherein the aryl group and the alkoxy group are as defined herein. Some non-limiting examples, include phenylmethoxy, phenylethoxy, (p-tolyl)methoxy, phenylpropoxy, and the like. The aryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkox, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "arylalkylamino" refers to an alkylamino group substituted with one or more aryl groups, wherein the aryl group and the alkylamino group are as defined herein. Some non-limiting examples include phenylmethylamino, phenylethylamino, phenylpropylamino, (p-tolyl)methylamino, and the like.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic". And the heteroaryl defined herein may be substituted or unsubstituted, wherein the substituent may be, but is not limited to, hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O), alkyl-S(=O)—, alkyl-S(==O)$_2$—, hydroxy-substituted alkyl-S(=O)—, hydroxy-substituted alkyl-S(=O)$_2$—, carboxyalkoxy, and the like.

In other embodiments, Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, 1,3,4-thiadiazol-2-yl, pyrazinyl, 2-pyrazinyl, 1,3,5-triazinyl, benzo[d]thiazol-2-yl, imidazo[1,5-a]pyridyl and the following bicycles include: benzimidazolyl, benzofuryl, benzothiophenyl, benzothiazolyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "heteroaryloxy" refers to optionally substituted aryl radicals, as defined herein, attached to an oxygen atom, wherein the oxygen atom serves as the attaching point to the rest of the molecule. Some non-limiting examples include pyrid-2-yloxy, thiazol-2-yloxy, imidazol-2-yloxy, pyrimidin-2-yloxy, and the like.

The term "carboxyalkoxy" refers to an alkoxy group substituted with one or more carboxy groups, wherein the alkoxy group and the carboxy group are as defined herein. Some non-limiting examples include carboxymethoxy, carboxyethoxy, and the like.

The term "alkylthio" refers to radicals containing a linear or branched alkyl radical, of one to ten carbon atoms, attached to a divalent sulfur atom. In other embodiments, alkylthio radicals are lower alkylthio radicals having one to three carbon atoms. Some non-limiting examples of "alkylthio" include methylthio ($CH_3S$—). The term "haloalklthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino" where amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "heteroarylamino" refers to amino groups substituted with one or two heteroaryl radicals, wherein the heteroaryl radical is as defined herein. Some non-limiting examples of heteroarylamino include N-thienylamino, and the like. In other embodiments, the "heteroarylamino" radicals include substituted on the heteroaryl ring portion of the radical.

The term "heteroarylaliphatic" refers to aliphatic groups substituted with one or more heteroaryl radicals, wherein the heteroaryl radical and the aliphatic group are as defined herein. Some non-limiting examples of heteroarylaliphatic include thiophen-2-ylpropenyl, pyridin-4-ylethyl, imidazol-2-methyl, furan-2-ethyl, indole-3-methyl, and the like.

The term "heteroarylalkyl" refers to alkyl groups substituted with one or more heteroaryl radicals, wherein the heteroaryl radical and the alkyl group are as defined herein. Some non-limiting examples of heteroarylalkyl include imidazol-2-methyl, furan-2-ethyl, indole-3-methyl, and the like.

The term "heteroarylalkylamino" refers to nitrogen-containing heteroarylalkyl radicals attached through a nitrogen atom to other radicals, wherein the heteroarylalkyl radicals is as defined herein. Some non-limiting examples of heteroarylalkylamino include pyridin-2-methylamino, thiazol-2-ethylamino, imidazol-2-ethylamino, pyrimidin-2-propylamino, pyrimidin-2-methylamino, and the like.

The term "heteroarylalkoxy" refers to oxy-containing heteroarylalkyl radicals attached through an oxygen atom to other radicals, wherein the heteroarylalkyl radical is as defined herein. Some non-limiting examples of such radicals include pyridin-2-ylmethoxy, thiazol-2-ylethoxy, imidazol-2-ylethoxy, pyrimidin-2-ylpropoxy, pyrimidin-2-ylmethoxy, and the like.

The term "fused bicyclic", "fused cyclic", "fused bicyclyl" or "fused cyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon).

Each cyclic ring in the fused bicyclyl can be either a carbocyclic or a heteroalicyclic. Some non-limiting examples of fused bicyclic ring system include hexahydro-furo[3,2-b]furan, 2,3,3a,4,7,7a-hexahydro-1H-indene, 7-azabicyclo[2.3.0]heptane, fused bicyclo[3.3.0]octane, fused bicyclo[3.1.0]hexane, 1,2,3,4,4a,5,8,8a-octahydro naphthalene, and the like. And the fused bicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted alkyl-S(=O)$_2$—, carboxyalkoxy, and the like.

The term "fused heterobicyclyl" refers to saturated or unsaturated bridged ring system, which refers to a bicyclic ring system that is not aromatic. Such a system may contain isolated or conjugated unsaturation, but not aromatic or heteroaromatic rings in its core structure (but may have aromatic substitution thereon). Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$, Some non-limiting examples of fused heterobicyclic ring system include hexahydro-furo[3,2-b]furan, 7-azabicyclo[2.3.0]heptane, and the like. And the fused heterobicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O)—, alkyl-S(=O)$_2$, hydroxy-substituted alkyl-S(=O)—, hydroxy-substituted alkyl-S(=O)$_2$—, carboxyalkoxy, and the like.

The term "fused bicyclylaliphatic" refers to aliphatic groups substituted with one or more fused bicyclyl groups, wherein the aliphatic group and the fused bicyclyl group are as defined herein. Some non-limiting examples include 1,2,3,4,4a,5,8,8a-octahydro-naphthylethyl, 1,23,4,4a5,8,8a-octahydro-naphthylmethyl, 1,2,3,4,4a,5,8,8a-octahydro-naphthylpropyl, fused bicyclo[3.3.0]octylmethyl, fused bicyclo[3.1.0]hexylethyl, and the like.

The term "fused heterobicyclylaliphatic" refers to aliphatic groups substituted with one or more fused heterobicyclyl groups, wherein the aliphatic group and the fused heterobicyclyl group are as defined herein. Some non-limiting examples include hexahydro-furo[3,2-b]furan-2-ylethyl, hexahydro-furo[3,2-b]furan-2-ylmethyl, 7-azabicyclo[2.3.0]hept-2-ylmethyl, 7-azabicyclo[2.3.0]hept-2-yethyl, 7-azabicyclo[2.3.0]hept-4-ylmethyl, and the like.

The term "fused bicycloxy" refers to optionally substituted fused bicyclyl radicals, as defined herein, oxy-containing fused bicyclyl radicals attached through an oxygen atom to other radicals, wherein the fused bicyclyl radical is as defined herein. Some non-limiting examples include 1,2,3,4,4a,5,8,8a-octahydro-naphthyloxy, fused bicyclo[3.3.0]oct-2-yloxy, fused bicyclo[3.1.0]hex-2-yloxy, and the like.

The term "fused heterobicycloxy" refers to optionally substituted fused heterobicyclyl radicals, as defined herein, oxy-containing fused heterobicyclyl radicals attached through an oxygen atom to other radicals. Some non-limiting examples include hexahydro-furo[3,2-b]furan-2-yloxy, 7-azabicyclo[2.3.0]hept-2-yloxy, 7-azabicyclo[2.3.0]hept-4-yloxy, and the like.

The term "fused bicyclylamino" refers to an amino group substituted with one or two fused bicyclyl groups, wherein the fused bicyclyl group is as defined herein. Some non-limiting examples include 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused bicyclylamino" refers to an amino group substituted with one or two fused bicyclyl groups, wherein the fused bicyclyl group is as defined herein. Some non-limiting examples include 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused bicyclylamino" refers to an amino group substituted with one or two fused bicyclyl groups, wherein the fused bicyclyl group is as defined herein. Some non-limiting examples include 1,2,3,4,4a,5,8,8a-octahydro-naphthylamino, di(1,2,3,4a,5,8,8a-octahydro-naphthyl)amino, fused bicyclo[3.3.0]octylamino, fused bicyclo[3.1.0]hexylamino, and the like.

The term "fused heterobicyclylalkyamino" refers to alkylamino groups substituted with one or more fused heterobicyclyl groups, wherein the fused heterobicyclyl group as defined herein. Some non-limiting examples include hexahydro-furo[3,2-b]furan-2-ylmethylamino, 7-azabicyclo[2.3.0]hept-2-ylmethylamino, 7-azabicyclo[2.3.0]hept-4-ylmethylamino, and the like.

The term "fused bicyclylalkoxy" refers to alkoxy groups substituted with one or more fused bicyclyl groups, wherein the fused bicyclyl group is as defined herein. Some non-limiting examples include 1,2,3,4,4a,5,8,8a-octahydro-naphthylmethoxy, 1,2,3,4,4,5,8,8a-octahydro-naphthylethoxy, fused bicyclo[3.3.0]octylethoxy, fused bicyclo[3.1.0]hexylpropoxy, and the like.

The term "fused heterobicyclylalkoxy" refers to alkoxy groups substituted with one or more fused heterobicyclyl groups, wherein the fused heterobicyclyl group is as defined herein. Some non-limiting examples include hexahydro-furo[3,2-b]furan 2-ylpropoxy, 7-azabicyclo[2.2.1]hept-2-ylethoxy, 7-azabicyclo[2.3.0]hept-4-ylpropoxy, hexahydro-furo[3,2-b]furan-2-ylethoxy, 7-azabicyclo[2.3.0]hept-4-ylpropoxy, 7-azabicyclo[2.3.0]hept-4-ylethoxy, and the like.

The term "fused bicycloxyalkoxy" refers to alkoxy groups substituted with one or more fused bicycloxy groups, wherein the alkoxy group and the fused bicycloxy group are as defined herein. Some non-limiting examples include 1,2,3,4,4a,5,8,8a-octahydro-naphthyloxymethoxy, 1,2,3,4,4a,5,8,8a-octahydro-naphthyloxymethoxy, 1,2,3,4,4a.5,8,8a-octahydro-naphthyloxyethoxy, fused bicyclo[3.3.0]oct-2-yloxyethoxy, fused bicyclo[3.1.0]hex-2-yloxypropoxy, and the like.

The term "fused heterobicycloxyalkoxy" refers to alkoxy groups substituted with one or more fused heterobicycloxy groups, wherein the alkoxy group and the fused heterobicyclyl group are as defined herein. Some non-limiting examples include hexahydro-furo[3,2-b]furan-2-yloxypropoxy, 7-azabicyclo[2.2.1]hept-2-yloxyethoxy, 7-azabicyclo[2.3.0]hept-4-yloxypropoxy, hexahydro-furo[3,2-b]furan-2-yloxyethoxy, 7-azabicyclo[2.3.0]hept-2-yloxypropoxy, 7-azabicyclo[2.3.0]hept-4-yloxyethoxy, and the like.

The term "fused bicyclylaminoalkoxy" refers to alkoxy groups substituted with one or more fused bicyclylamino groups, wherein the alkoxy group and the fused bicyclylamino group are as defined herein. Some non-limiting examples include 1,2,3,4,4a,5,8,8a-octahydro-naphthylaminoethoxy, 1,2,3,4,4a,5,8,8a-octahydro-naphthylaminopropoxy, di(1,2,3,4,4a,5,8,8a-octahydro naphthylaminopropoxy, fused bicyclo[3.3.0]oct-2-ylaminoethoxy, fused bicyclo[3.1.0]hex-2-ylaminopropoxy, and the like.

The term "fused heterobicyclylaminoalkoxy" refers to alkoxy groups substituted with one or more fused heterobicyclylamino groups, wherein the alkoxy group and the fused heterobicyclylamino group are as defined herein. Some non-limiting examples include 7-azabicyclo[2.2.1]hept-2-ylaminoethoxy, 7-azabicyclo[2.3.0]hept-4-ylaminopropoxy, hexahydro-furo[3,2-b]furan-2-ylaminoethoxy, hexahydro-furo[3,2-b]furan-2-ylaminopropoxy, hexahydro-furo[3,2-b]furan-2-ylaminomethoxy, and the like.

The term "spirocyclyl", "spirocyclic", "spiro bicyclyl" or "spiro bicyclic" refers to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in the spirocyclyl or spiro bicyclyl can be either a carbocyclic or a heteroalicyclic. Some non-limiting examples include 2,7-diaza-spiro[4.4]non-2-yl, 7-oxo-2-azaspiro[4.5]dec2-yl, 4-azaspiro[2.4]hept-5-yl, 4-Oxaspiro[2.4]hept-5-yl, 5-azaspiro[2.4]hept5-yl, spiro[2.4]heptyl, spiro[4.4]nonyl, 7-hydroxy-5-azaspiro[2.4]hept-5-yl, and the like. The spirocyclyl or spiro bicyclyl can be optionally substituted, wherein the substituents can be, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxysubstitute alkoxy, hydroxy-substituted alkyl-C(=O), alkyl-C(=O)—, alkyl-S(=O)—, alkyl-S(=O)$_2$—, hydroxy-substituted alkyl-S(=O)—, hydroxy-substituted alkyl-S(=O)$_2$—, carboxy alkoxy, and the like.

The term "spiro heterobicyclyl" refers to a ring originating from a particular annular carbon of another ring. For example, as depicted above, a saturated bridged ring system (ring B and B') is termed as "fused bicyclic", whereas ring A and ring B share an carbon atom between the two saturated ring system, which terms as a "spirocyclyl" or "spiro bicyclyl". Wherein at least one ring in the system contains one or more heteroatoms, wherein each ring in the system contains 3 to 7 ring members and that contains one to six carbon atoms and one to three heteroatoms selected from N, O, P, S, wherein the S or P is optionally substituted with one or more oxo to provide the group SO, SO$_2$, PO or PO$_2$. Some non-limiting examples of spiro heterobicyclic ring system include 4-azaspiro[2.4]hept-5-yl, 4-oxaspiro[2.4]hept-5-yl, 5-azaspiro[2.4]hept-5-yl, 7-hydroxy-5-azaspiro[2.4]hept-5-yl, and the like. And the spiro heterobicyclyl defined herein may be substituted or unsubstituted, wherein the substituents include, but are not limited to, oxo (=O), hydroxy, amino, halogen, cyano, aryl, heteroaryl, alkoxy, alkylamino, alkyl, haloalkyl, alkenyl, alkynyl, heterocyclyl, thiol, nitro, aryloxy, hydroxy-substituted alkoxy, hydroxy-substituted alkyl-C(=O)—, alkyl-C(=O)—, alkyl-S(=O), alkyl-S(=O)$_2$—, hydroxy-substituted alkyl-S(=O)—, hydroxy-substituted alkyl-S(=O)$_2$—, carboxyalkoxy, and the like.

The term "spiro bicyclylaliphatic" refers to aliphatic groups substituted with one or more spiro bicyclyl groups, wherein the aliphatic group and the spiro bicyclyl group are as defined herein. Some non-limiting examples include spiro[2.4]heptylmethyl, spiro[2.4]heptylethyl, spiro[2.4]heptylpropyl, spiro[4.4]nonylmethyl, spiro[4.4]nonylethyl, 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-bydroxy-5-azaspiro[2.4]hept-5-yl-propyl, and the like.

The term "spiro heterobicyclylaliphatic" refers to aliphatic groups substituted with one or more spiro heterobicyclyl groups, wherein the aliphatic group and the fused heterobicyclyl group are as defined herein. Some non-limiting examples include 4-azaspiro[2.4]hept-5-yl-methyl, 4-azaspiro[2.4]hept-5-yl-ethyl, 4-oxaspiro[2.4]hept-5-yl-ethyl, 5-azaspiro[2.4]hept-5-yl-propyl, 7-hydroxy-5-azaspiro[2.4]hept-5-yl-propyl, and the like.

The term "spiro bicycloxy" refers to optionally substituted spiro bicyclyl radicals, as defined herein, oxy-containing spiro bicyclyl radicals attached through an oxygen atom to other radicals, wherein the spiro bicyclyl radical is as defined herein. Some non-limiting examples include spiro[2.4]heptyl-2-oxy, spiro[2.4]heptyl-3-oxy, spiro[2.4]heptyl-4-oxy, spiro[4.4]nonyl-2-oxy, spiro[4.4]nonyl-4-oxy, 4-azaspiro[2,4]hept-5-oxy, and the like.

The term "spiro heterobicycloxy" refers to optionally substituted spiro heterobicyclyl radicals, as defined herein, oxy-containing spiro heterobicyclyl radicals attached through an oxygen atom to other radicals. Some non-limiting examples include 4-azaspiro[2.4]hept-5-yloxy, 4-oxaspiro[2.4]hept-5-yloxy, 5-azaspiro[2.4]hept-5-yloxy, and the like.

The term "spiro bicyclylamino" refers to an amino group substituted with one or two spiro bicyclyl groups, wherein the spiro bicyclyl group is as defined herein. Some non-limiting examples include spiro[2.4]heptyl-2-amino, spiro[2.4]heptyl-3-amino, spiro[2.4]heptyl-4-amino, spiro[4.4]nonyl-2-amino, spiro[4.4]nonyl-4-amino, 4-azaspiro[2.4]hept-5-amino, and the like.

The term "spiro heterobicyclylamino" refers to an amino group substituted with one or two spiro heterobicyclyl groups, wherein the spiro heterobicyclyl group is as defined herein. Some non-limiting examples include 4-azaspiro[2.4]hept-5-ylamino, 4-oxaspiro[2.4]hept-2-ylamino, 4-oxaspiro[2.4]hept-5-ylamino, 5-azaspiro[2.4]hept-5-ylamino, and the like.

The term "spiro bicyclylalkoxy" refers to alkoxy groups substituted with one or more spiro bicyclyl groups, wherein the spiro bicyclyl group is as defined herein. Some non-limiting examples include spiro[2.4]heptyl-2-methoxy, spiro[2.4]heptyl-3-ethoxy, spiro[2.4]heptyl-4-ethoxy, spiro[4.4]nonyl-2-methoxy, spiro[4.4]nonyl-4-propoxy, 4-azaspiro[2.4]hept-5-methoxy, and the like.

The term "spiro heterobicyclylalkoxy" refers to alkoxy groups substituted with one or more spiro heterobicyclyl groups, wherein the spiro heterobicyclyl group is as defined herein. Some non-limiting examples include 4-azaspiro[2.4]hept-5-yl-methoxy, 4-azaspiro[2.4]hept-2-yl-ethoxy, 4-oxaspiro[2.4]hept-5-yl-ethoxy, 5-azaspiro[2.4]hept-5-yl-propoxy, and the like.

The term "spiro bicyclylalkyamino" refers to alkylamino groups substituted with one or more spiro bicyclyl groups, wherein the spiro bicyclyl group is as defined herein. Some non-limiting examples include spiro[2.4]heptyl-2-methylamino, spiro[2.4]heptyl-3-ethylamino, spiro[2.4]heptyl-4-ethylamino, spiro[4.4]nonyl-2-methylamino, spiro[4.4]nonyl-4-propylamino, 4-azaspiro[2.4]hept-5-methylamino, and the like.

The term "spiro heterobicyclylalkyamino" refers to alkylamino groups substituted with one or more spiro heterobicyclyl groups, wherein the spiro heterobicyclyl group is as defined herein. Some non-limiting examples include 4-azaspiro[2.4]hept-5-yl-methylamino, 4-azaspiro[2.4]hept-2-yl-ethylamino, 4-oxaspiro[2.4]hept-5-yl-ethylamino, 5-azaspiro[2.4]hept-5-yl-propylamino, and the like.

The term "spiro bicycloxyalkoxy" refers to alkoxy groups substituted with one or more spiro bicycloxy groups, wherein the alkoxy group and the spiro bicyclyl group are as defined herein. Some non-limiting examples include spiro[2.4]heptyl-2-oxyethoxy, spiro[2.4]heptyl-3-oxypropoxy, spiro[2.4]heptyl-4-oxypropoxy, spiro[4.4]nonyl-2-oxyethoxy, spiro[4.4]nonyl-4-oxypropoxy, 4-azaspiro[2.4]hept-5-oxypropoxy, and the like.

The term "spiro heterobicycloxyalkoxy" refers to alkoxy groups substituted with one or more spiro heterobicycloxy groups, wherein the alkoxy group and the spiro heterobicyclyl group are as defined herein. Some non-limiting examples include 4-azaspiro[2.4]hept-5-yloxyethoxy, 4-oxaspiro[2.4]hept-5-yloxyethoxy, 5-azaspiro[2.4]hept-5-yloxyethoxy, 4-azaspiro[2.4]hept-5-yloxypropoxy, 4-oxaspiro[2.4]hept-5-yloxypropoxy, 5-azaspiro[2.4]hept-5-yloxypropoxy, and the like.

The term "spiro bicyclylaminoalkoxy" refers to alkoxy groups substituted with one or more spiro bicyclylamino groups, wherein the alkoxy group and the spiro bicyclylamino group are as defined herein. Some non-limiting examples include spiro[2.4]heptyl-2-aminoethoxy, spiro[2.4]heptyl-3-aminopropoxy, spiro[2.4]heptyl-4-aminoethoxy, spiro[4.4]nonyl-2-aminoethoxy, spiro[4.4]nonyl-4-aminopropoxy, 4-azaspiro[2.4]hept-5-aminopropoxy, and the like.

The term "spiro heterobicyclylaminoalkoxy" refers to alkoxy groups substituted with one or more spiro heterobicyclylamino groups, wherein the alkoxy group and the spiro heterobicyclylamino group are as defined herein. Some non-limiting examples include 4-azaspiro[2.4]hept-5-ylaminoethoxy, 4-oxaspiro[2.4]hept-2-ylaminopropoxy, 4-oxaspiro[2.4]hept-5-ylaminoethoxy, 5-azaspiro[2.4]hept-5-ylaminopropoxy, and the like.

Unless otherwise stated, structures depicted herein are also meant to include all isomeric (e.g, enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" refers to a compound that is transformed in vivo into a compound of Formula I, II. Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic (C1-C24) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al, Prodrugs: Design and Clinical Applications, *Nature Review Drug Discovery*, 2008, 7, 255-270, and S. J. Hecker et al, Prodrugs of Phosphates and Phosphonates, *Journal of Medicinal Chemistry*, 2008, 51, 2328-2345, all of which are incorporated herein by reference. Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e, they have the ability to rotate the plane of plane-polarized light. In describing an optically active compound, the prefixes D and L, or R and S, are used to denote the absolute configuration of the molecule about its chiral center(s). The prefixes D and L or (+) and (−) are employed to designate the sign of rotation of plane polarized light by the compound, with (−) or L meaning that the compound is levorotatory. A compound prefixed with (+) or D is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salts" refers to organic or inorganic salts of a compound disclosed herein. Pharmaceutically acceptable salts are well known in the art. For example: S. M. Berge et al., describe pharmaceutically acceptable salts in detail in J. Pharmaceutical Sciences, 66: 1-19, 1977, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acidor by using other methods used in the art such as ion exchange. Other pharmaceutically acceptable salts include adipate, malic acid salts, 2-hydracrylic acid salt, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C1-C4\ alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, C1-C8 sulfonate or aryl sulfonate.

The salt of the compound in present invention may be described as the following specific compound salt, but there is no limitation on the present invention.

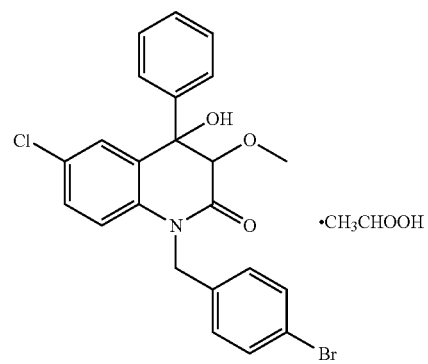

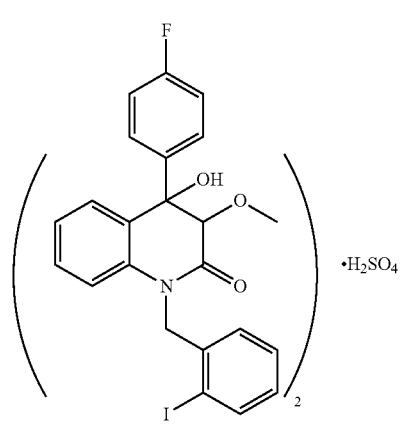

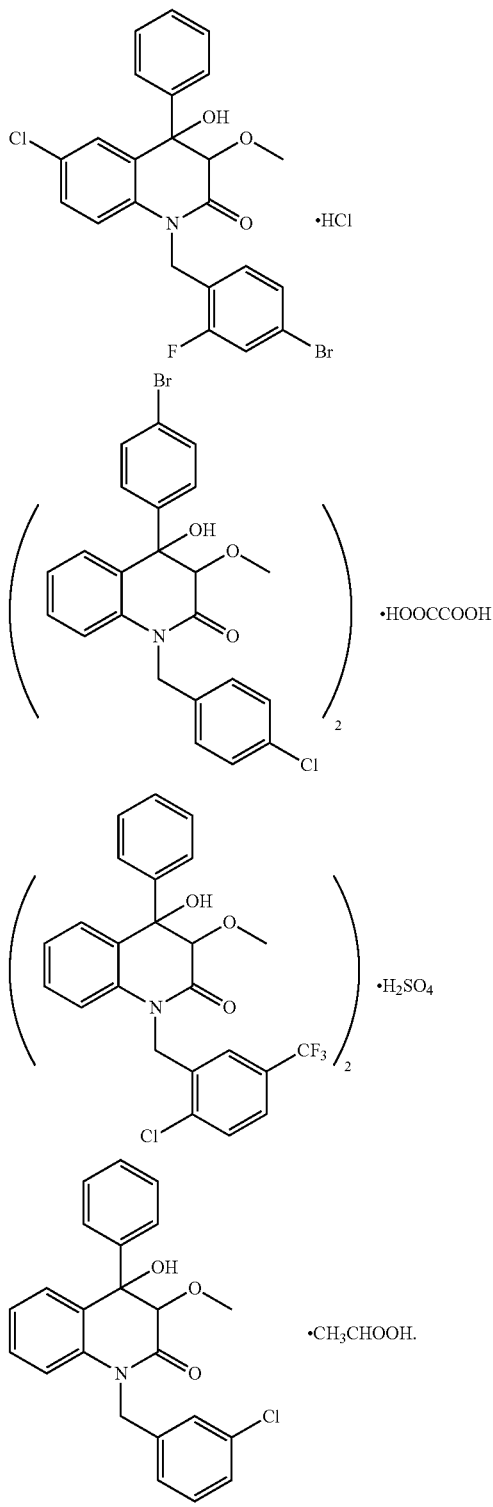

The term "solventate" of the present invention refers to an association of one or more solvent molecules with the compound of the present invention. Solvents forming solvates include, but are not limited to, water, isopropanol, ethanol, methanol, dimethyl sulfoxide, ethyl acetate, acetic acid, amino ethanol. The term "hydrate" refers to the association of solvent molecules with water.

The solventate of the compound in present invention may be described as the following specific compound, but there is no limitation on the present invention.

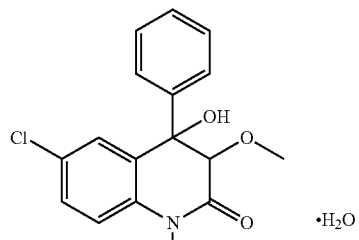

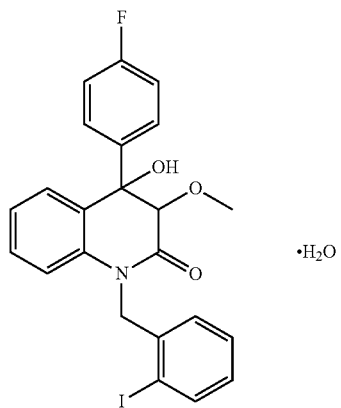

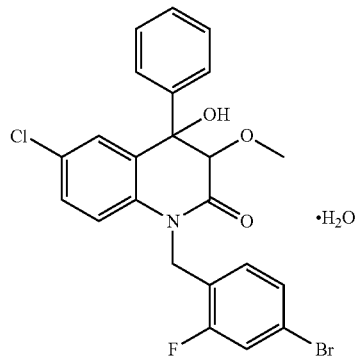

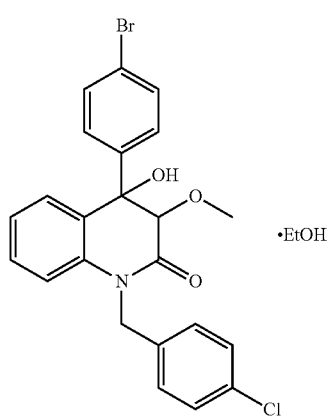

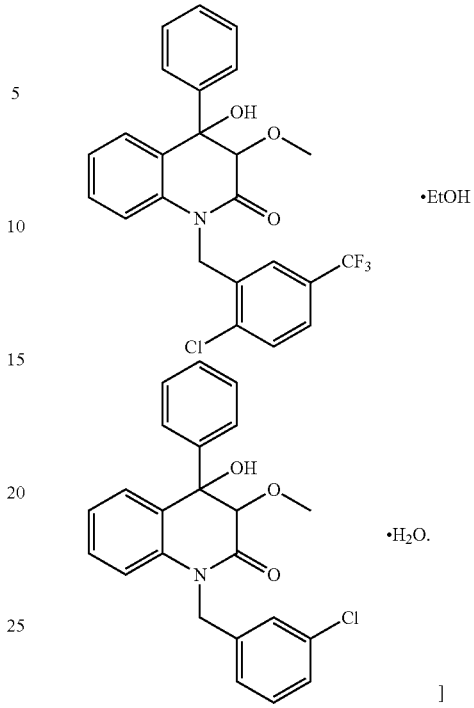

]

Provided herein includes the use of a compound disclosed herein, or a pharmacutically acceptable salt thereof, in the manufacture of a medicament for treating the various diseases caused by virus in a patient, including those described herein. Provided herein is a pharmaceutical composition comprising a therapeutically effective amount of a compound of Formula I-VI in association with at least one pharmacutically acceptable carrier, excipient, diluent, adjuvant or vehicle.

Also provided herein is a method of treating the various diseases caused by virus in a patient or susceptible to such disease, the method comprising treating the subject with a therapeutically effective amount of a compound of Formula I-VI.

Unless otherwise stated, all stereoisomers, geometric isomers, tautomers, nitrogen oxides, hydrates, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" refers to that the substance or composition must be compatible chemically and/or toxiclogically, with the other ingredients comprising a Formulation, and/or the mammal being treated therewith.

The compounds disclosed herein also include salts of such compounds which are not necessarily pharmaceutically acceptable salts, and which may be useful as intermediates for preparing and/or purifying compounds of Formula I-IV and/or for separating enantiomers of compounds of Formula I-IV.

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Some non-limiting examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

According to another aspect, the invention features pharmaceutical compositions that include a compound of Formula I, II, a compound listed herein, or a compound named in Examples 1-83, and a pharmaceutically acceptable carrier, adjuvant, or vehicle. The amount of the compound in the compositions disclosed herein is such that is effective to detectably treat or lessen the various diseases caused by inflammation, immune system disorders in a patient.

It will also be appreciated that the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. As described in the reference below: In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, all of which are herein incorporated by reference in their entireties, are disclosed various carriers used in Formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tisilicate, polyvinyl pyrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, saflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The compositions include orally administered in any orally acceptable dosage form including, but not limited to, capsules, tablets, pills, powders, granules, aqueous suspensions or solutions. The compositions can be orally administered in the following dosage forms: tablets, pellets, capsules, dispensable powders, particles or suspensions, syrup, and elixirs. Alternatively, the compositions disclosed herein can be for external use in the form of ointment, gel, or medicated patch, or they can be administered parenterally in the form of sterile injectable solution or suspension. The compounds disclosed herein may be administered parenterally or intraperitoneally. The compounds disclosed herein (as free bases pharmaceutically acceptable salt) may be formulated into solutions or suspensions in water suitably mixed with surfactant (e.g. hydroxypropyl cellulose, polyvinyl pyrrolidone). Dispersion can also be prepared from a mixture of the active compounds in glycerin, liquid, polyethylene glycol and oil. In the normal condition of storage and usage, these preparations may contain preservatives to prevent the growth of microorganisms.

The pharmaceutical forms suitable for injection include sterile water or dispersion and sterile powder (used for the temporary preparation of sterile injectable solutions or dispersions). In all the cases, these forms must be sterile, and they must be fluid to allow their discharge from the injection syringe. These forms must be stable in the condition of production and storage, and they must prevent from the pollution of microorganisms (such as bacteria and fungi). The carriers may be solvents or dispersion media, including, for example, water, alcohols (such as glycerin, propylene glycol and liquid polyethylene glycol), plant oil and combinations thereof.

The compounds disclosed herein can be administered in a local rather than systemic manner, for example, via injection of the compound directly into organ, often in a depot or sustained release formulation. Furthermore, the pharmaceutical composition comprising a compound disclosed herein can be administered in a targeted drug delivery system, for example, in a liposome coated with organ-specific antibody. The liposomes may be targeted to and taken up selectively by the organ. In addition, the pharmaceutical compositions comprising a compound disclosed herein may be provided in the form of a rapid release formulation, in the form of an extended release formulation, or in the form of an intermediate release formulation For administration by inhalation, the compounds disclosed herein may be in a form as an aerosol, a mist or a powder. The pharmaceutical compound disclosed herein may be conveniently delivered in the form of an aerosol spray presentation from pressurized packs or a nebulizer, with the use of a suitable propellant, e.g., lorodifluoromethane, trichlorofluoromethane, dichlorotetrafluoroethane. carbon dioxide or other suitable gas. In the case of a pressurized aerosol, the dosage unit may be determined by providing a value to deliver a metered amount. Capsules and cartridges, such as, by way of example only, gelatin for use in an inhaler or insufflators maybe formulated containing a powder mix of the compound disclosed herein and a suitable powder base such as lactose or starch.

The compounds disclosed herein may also be formulated in rectal compositions such as enemas, rectal gels, rectal foams, rectal aerosol, suppositories, gel suppositories, or retention enemas, containing conventional suppository bases such as cocoa butter or other glycerides, as well as any synthetic polymers suitable for preparing suppository bases such as polyvinylpyrrolidone, PEG, and the like. In suppository forms of the compositions, a low-melting wax such as, but not limited to, a mixture of fatty acid glycerides, optionally in combination with cocoa butter is first melted.

Additionally, the compound disclosed herein may be used in combination with other agents of treating inflammation, fibrosis, such as, but not limited to, azathioprine, cyclophosphamide, prednisone, prednisolone, aspirin, acetaminophen, indomethacin, naproxen, naproxen, diclofenac, ibuprofen, nimesulide, rofe saxib, celecoxib, levamisole, interleukin, interferon, transfer factor, thymosin, anti-lymphocyte globulin, cyclosporine, mycophenolate mofetil, and the like.

The pharmaceutical compositions disclosed herein may be formulated in conventional manner using one or more physiologically acceptable carriers comprising excipients and auxiliaries which facilitate processing of the active compounds into preparations which may be used pharmaceutically. Proper formulation is dependent upon the route of administration chosen. Any of the well-known techniques, carriers, and excipients may be used as suitable and as understood in the art. The pharmaceutical compositions comprising a compound disclosed herein may be manufactured in a conventional manner. such as, by way of example, by means of conventional mixing, dissolving, granulating, dragee-making, levigating, emulsifying, encapsulating, entrapping, or compression processes.

The pharmaceutical compositions disclosed herein include at least one pharmaceutically acceptable carrier, diluent or excipient and a compound disclosed herein as an active ingredient in free-acid or free-base form, or in a pharmaceutically acceptable salt form. In addition, the pharmaceutical compositions disclosed herein include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions contain other therapeutically valuable substances.

Methods for the preparation of the pharmaceutical compositions disclosed herein include formulating the compounds disclosed herein with one or more inert, pharmaceutically acceptable excipients or carriers to form a solid, semi-solid or liquid. Some non-limiting examples of solid compositions include powders, tablets, dispersible granules, capsules, cachets, and suppositories. Some non-limiting examples of liquid compositions include solutions in which a compound is dissolved, emulsions comprising a compound, or a solution containing liposomes, micelles, or nanoparticles comprising a compound as disclosed herein. Some non-limiting examples of semi-solid compositions include gels, suspensions and creams. The compositions may be in liquid solutions or suspensions, solid forms suitable for solution or suspension in a liquid prior to use, or as emulsions. The pharmaceutical compositions disclosed herein may also contain minor amounts of nontoxic, auxiliary substances, such as wetting or emulsifying agents, pH buffering agents, and so forth.

The compounds disclosed herein are preferably formulated in dosage unit form for ease of administration and uniformity of dosage. The expression "dosage unit form" refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The selective biological properties of the compounds may be enhanced through being modified by additional appropriate functional groups. Such modification is known in the field herein and includes the modification of penetrate to biological cavities (such as blood, lymphatic system, central nervous system), improves oral effectiveness and improves the solubility so that it can be administered by injection, alter metabolism and change the excretion.

DETAILED DESCRIPTION OF EMBODIMENTS

In general, the invention of compounds can be obtained by method described in this invention, unless there is a further instructions, including the definition of substituent such as type I-VI, as shown in the following reaction scheme and implementation example for further example explains the content of the invention, in which $R_1$, $R_2$, $R_3$ and $R_4$, n, k, V, T is defined the same as any of the above place in the invention.

Scheme 1: o-aminophenone or its benzodiazepine substituted derivatives were used as raw materials, adol condensation ring was directly performed after it was reacted with alkoxy acetyl chloride under alkaline conditions to synthesize quinolinones.

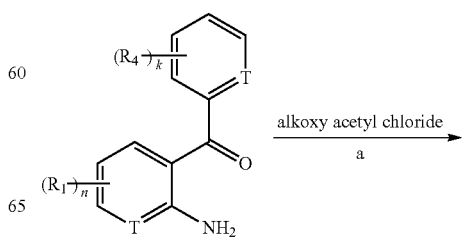

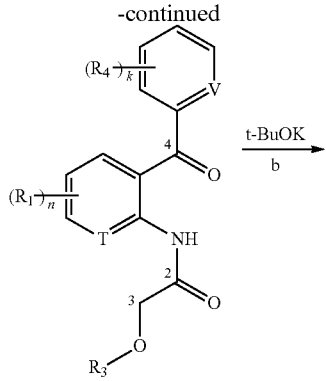

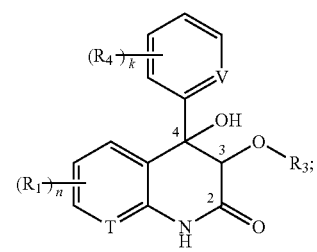

Scheme 2: anthranilic acid or its benzene ring substituted derivatives is used as raw materials, the intermediate 1 was obtained after reacting with benzoyl chloride, and the intermediate 1 reacted with Grignard reagent to produce intermediate 2 of diphenyl ketone, and the intermediate 2 further reacted with alkoxy acetyl chloride under alkaline conditions, and then synthesized quinolinone compound by Adol condensation reaction.

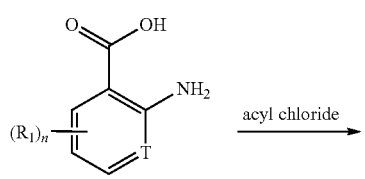

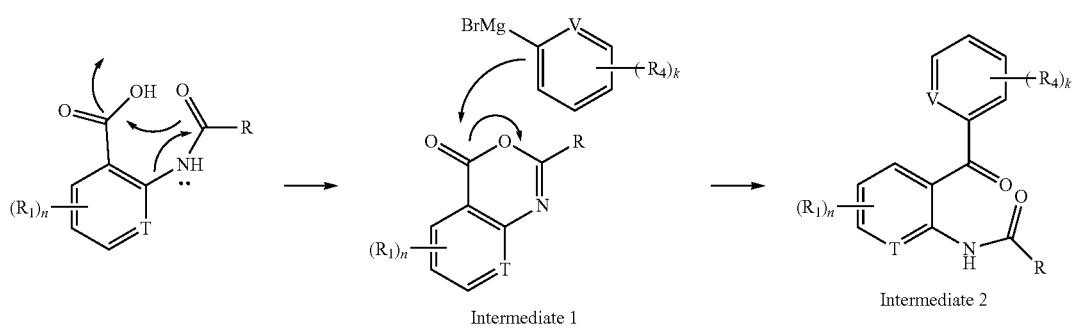

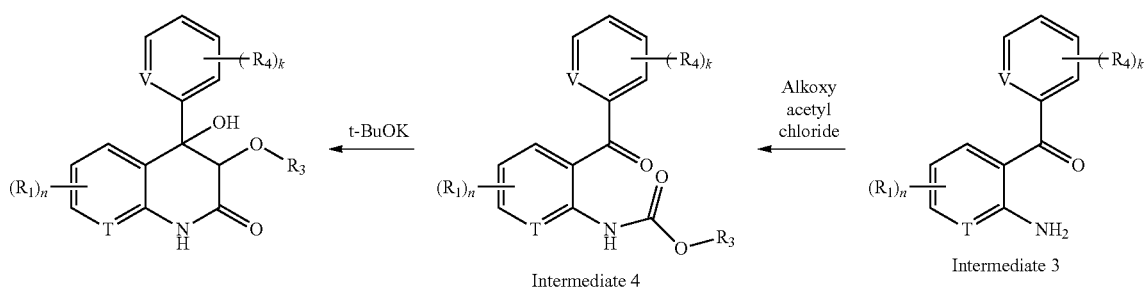

Scheme 3

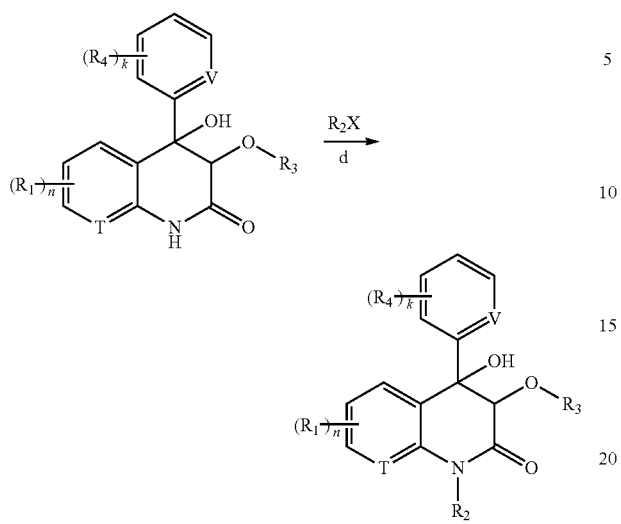

The compound concerned in this invention is obtained by reacting with a halogenated reagent under alkaline conditions with a quinolinone compound synthesized under scheme 1 or scheme 2 as a substrate.

Take the compound 4-hydroxy-3-methoxyl-4-phenyl-3,4-dihydroquinolin-2 (1H)-one as an example, detailed synthetic method is described according to Scheme 1:

Example 1

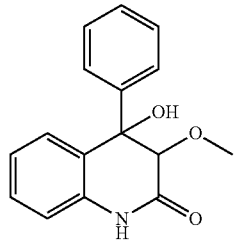 [SMILES: COC1C(=O)Nc2ccccc2C1(O)c1ccccc1]

Under the protection of nitrogen, 2-aminophenone (50 mg, 0.25 mmol) was dissolved in DCM (5 mL). Under the catalyzation of potassium carbonate, methoxyacetyl chloride (45 micron, 0.5 mmol, 2 eq) was added and reacted at room temperature for half an hour before quenching with water. The reaction mixture was extracted by ethyl acetate. The organic phase was removed by reduced pressure distillation. The dry residue was then dissolved in THF (10 mL). t-BuOK (225 mg, 2.5 mmol) was added for reaction at room temperature for 5 hours. The reaction solution was extracted with saturated ammonium chloride solution and ethyl acetate solution. The organic phase was removed by reduced pressure distillation, and the residues were purified by silica gel column chromatography (ethyl acetate/petroleum ether (v/v)=1/2) to obtain the white amorphous powder compound 4-hydroxy-3-methoxyl-4-phenyl-3,4-dihydroquinolin-2 (1H)-ketone (63 mg, 95%). $^1$H NMR (500 MHz, CDCl$_3$): δ ppm 3.54 (s, 3H), 4.00 (s, 1H), 6.85 (d, J=7.8 Hz, 1H), 7.07 (t, J=7.6 Hz, 1H), 7.26-7.34 (m, 7H), 8.4 (s, 1H), $^{13}$C NMR (125 MHz, CDCl$_3$): 59.8, 84.2, 115.4, 124.1, 126.5, 128.1, 128.3, 128.5, 129.5, 135.2, 140.2, 168.1. ESIMS m/z 270.02 [M+H]$^+$, 292.01 [M+Na]$^+$, 92% yield.

Refer to the above synthetic process, 5-chloro-2-aminophenone, 5-iodine-2-aminophenone, 4'-bromo-2-aminophenone, 4'-chloro2-aminophenone, 4'-fluoro-2-aminophenone, phenyl 5-aminophenone, 5-methoxydiphenyl ketone, 5-hydroxydiphenyl ketone were used as raw materials to produce 6-chloro-4-hydroxy-3-methoxy-4-phenyl quinoline-2 (1H)-one, 6-iodine-4-hydroxy-3-methoxy-4-phenyl quinoline-2 (1H)-one, 4-(4-bromine phenyl)-4-hydroxy-3-methoxy quinoline-2 (1H)-one, 4-(4-chlorobenzene)-4-hydroxy-3-methoxy quinoline-2 (1H)-one, 4-(4-phenyl)-4-hydroxy-3-methoxy quinoline-2 (1H)-one, 3-methoxy-4-hydroxy-4-phenyl-1,6-nalidixic-2 (1H) one, 6-methoxy-4-hydroxy-3-methoxy-4-phenylquinolin-2 (1H)-one, 6-hydroxy-4-hydroxy-3-methoxy-4-phenylquinolin-2 (1H)-one.

Example 2

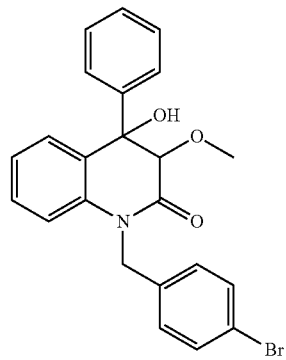 [SMILES: COC1C(=O)N(Cc2ccc(Br)cc2)c2ccccc2C1(O)c1ccccc1]

Under the protection of nitrogen, the compound 4-hydroxy-3-methoxyl-4-phenyl-3,4-dihydroquinolin-2 (1H)-one (100 mg) was dissolved in dry acetonitrile (5 mL). Under the catalyzation of potassium carbonate, the compound was added to benzyl bromide (3-4 eq) and reacted overnight at 60□. After TLC detection, the solvent was removed by reduced pressure distillation. Water and ethyl acetate were added to extract the production. Then the organic phase was condensed under reduced pressure and dried to obtain the target product. $^1$H NMR (500 MHz, acetone-d$_6$): δ ppm 3.48 (s, 3H), 4.29 (s, 1H), 4.84 (s, 1H), 5.12 (d, J=16.0 Hz, 1H), 5.24 (d, J=16.0 Hz, 1H), 7.05 (t, J=7.5 Hz, 1H), 7.08 (d, J=8.2 Hz, 1H), 7.20 (d, J=8.3 Hz, 2H), 7.26 (t, J=8.0 Hz, 1H), 7.33 (overlapped, 6H), 7.46 (d, J=8.3 Hz, 2H), $^{13}$C NMR (125 MHz, acetone-d$_6$): 44.1, 58.7, 76.2, 84.6, 115.2, 120.3, 123.2, 127.0, 127.6, 127.9, 128.1, 128.8, 129.0, 131.0, 131.4, 136.7, 137.9, 141.4, 167.4. ESIMS m/z 438.13/440.13 [M+H]$^+$/[M+2+H]$^+$ (1:1), 460.05/462.05 [M+Na]$^+$/[M+2+Na]$^+$ (1:1); HRESIMS m/z 438.0695 [M+H]$^+$ (calcd for C$_{23}$H$_{21}$O$_3$NBr, 438.0699); 65% yield.

Refer to the above synthetic process, 4-hydroxy-3-methoxyl-1-(3-methoxybenzyl)-4-phenyl-3,4-dihydroquinolin-2 (1H)-one, 4-hydroxy-3-methoxyl-1-(3-nitrobenzyl)-4-phenyl-3,4-dihydroquinolin-2 (1H)-one, 1-(3-chloro benzyl)-4-hydroxy-3-methoxyl-4-phenyl-3,4-dihydroquinolin-2 (1H)-one, 4-hydroxy-3-methoxyl-1-(3-methyl benzyl)-4-phenyl-3,4-dihydroquinolin-2 (1H)-one, 4-hydroxy-3-methoxyl-1-(4-methyl benzyl)-4-phenyl-3,4-dihydroquinolin-2 (1H)-one, 1-(3-fluoro benzyl)-4-hydroxy-3-methoxyl-4-phenyl-3,4-dihydroquinolin-2 (1H)- one, 1-(4-fluoro benzyl)-4-hydroxy-3-methoxyl-4-phenyl-3,4-dihydroquinolin-2 (1H)-one, 1-(4-bromo-2-fluoro benzyl)-4-hydroxy-3-methoxyl-4-phenyl-3,4-dihydroquinolin-2 (1H)-one, 1-(2-chloro-5-(three fluorinated methyl)benzyl)-4-hydroxy-3-methoxy-4-phenyl-3,4-dihydro quinoline-2 (1H)-one, 1-(4-bromo-2-fluoro benzyl)-4-hydroxy-3-methoxyl-4-phenyl-3,4-dihydroquinolin-2 (1H)-one, 1-(3,4-difluoro benzyl)-4-hydroxy-3-methoxyl-4-phenyl-3,4-dihydroquinolin-2 (1H)-one, 4-hydroxy-3-methoxy-4-phenyl-1-(4-(trifluoromethoxyl)benzyl)-3,4-dihydroquinolin-2 (1H)-one, 1-(3,5-difluoro benzyl)-4-hydroxy-3-methoxyl-4-phenyl-3,4-dihydroquinolin-2 (1H)-one, 1-(2-bromobenzyl)-4-hydroxy-3-methoxyl-4-phenyl-3,4-dihydroquinolin-2 (1H)-one, 1-(2,6-dichloro benzyl)-4-hydroxy-3-methoxyl-4-phenyl-3,4-dihydroquinolin-2 (1H)-one, 1-(4-chloro-2-fluoro benzyl)-4-hydroxy-3-methoxyl-4-phenyl-3,4-dihydroquinolin-2 (1H)-one, 1-(2-fluoro benzyl)-4-hydroxy-3-methoxyl-4-phenyl-3,4-dihydroquinolin-2 (1H)-one, 1-(2-chloro benzyl)-4-hydroxy-3-methoxyl-4-phenyl-3,4-dihydroquinolin-2 (1H)-one, 1-(2,5-difluoro benzyl)-4-hydroxy-3-methoxyl-4-phenyl-3,4-dihydroquinolin-2 (1H)-one, 4-hydroxy-3-methoxyl-1-(2-methyl benzyl)-4-phenyl-3,4-dihydroquinolin-2 (1H)-one, 4-hydroxy-3-methoxyl-4-phenyl-1-(2,4,5-trifluoro benzyl)-3,4-dihydroquinolin-2 (1H)-one, 1-(2,6-difluoro benzyl)-4-hydroxy-3-methoxyl-4-phenyl-3,4-dihydroquinolin-2 (1H)-one, 6-chloro-1-(3-chloro benzyl)-4-hydroxyl-3-methoxy-4-phenyl-3,4-dihydroquinoline-2(1H)-one, 6-chloro-1-(3-fluoro benzyl)-4-hydroxyl-3-methoxy-4-phenyl-3,4-dihydroquinoline-2(1H)-one, 6-chloro-1-(4-chloro benzyl)-4-hydroxyl-3-methoxy-4-phenyl-3,4-dihydroquinoline-2 (1H)-one, 6-chloro-1-(4-fluoro benzyl)-4-hydroxyl-3-methoxy-4-phenyl-3,4-dihydroquinoline-2(1H)-one, 1-(4-bromobenzyl)-6-chloro-4-hydroxy-3-methoxyl-4-phenyl-3,4-dihydroquinolin-2 (1H)-one, 1-benzyl-6-chloro-4-hydroxyl-3-methoxy-4-phenyl-3,4-dihydroquinoline-2 (1H)-one, 1-(4-methyl benzyl)-6-chloro-4-hydroxy-3-methoxyl-4-phenyl-3,4-dihydroquinolin-2 (1H)-one, 1-(2,6-dichloro benzyl)-6-chloro-4-hydroxy-3-methoxyl-4-phenyl-3,4-dihydroquinolin-2 (1H)-one, 1-(2-fluoro-4-chloro benzyl)-6-chloro-4-hydroxy-3-methoxyl-4-phenyl-3,4-dihydroquinolin-2 (1H)-one, 1-(2-cyano benzyl)-6-chloro-4-hydroxyl-3-methoxy-4-phenyl-3,4-dihydroquinoline-2 (1H)-one, 1-(3,5-trifluoro methyl benzyl)-6-chloro-4-hydroxy-3-methoxy-4-phenyl-3,4-dihydro quinoline-2 (1H)-one, 1-(3,4-dichloro benzyl)-6-chloro-4-hydroxy-3-methoxyl-4-phenyl-3,4-dihydroquinolin-2 (1H)-one, 4-(4-chlorophenyl)-4-hydroxyl-1-(2-iodobenzyl)-3-methoxyl-3,4-dihydroquinoline-2(1H)-one, 4-(4-chlorophenyl)-4-hydroxyl-1-(2-chloro benzyl)-3-methoxyl-3,4-dihydroquinoline-2(1H)-one, 4-(4-fluorophenyl)-4-hydroxyl-1-(2-bromobenzyl)-3-methoxyl-3,4-dihydroquinolin-2 (1H)-one, 4-(4-fluorophenyl)-4-hydroxyl-1-(2-iodobenzyl)-3-methoxyl-3,4-dihydroquinolin-2 (1H)-one, 4-(4-fluorophenyl)-4-hydroxyl-1-(2-fluoro benzyl)-3-methoxyl-3,4-dihydroquinoline-2(1H)-one, 4-(4-fluorophenyl)-4-hydroxyl-1-(2-chloro benzyl)-3-methoxyl-3,4-dihydroquinoline-2(1H)-one, 4-(4-fluorophenyl)-4-hydroxyl-1-(4-bromobenzyl)-3-methoxyl-3,4-dihydroquinolin-2 (1H)-one, 4-(4-fluorophenyl)-4-hydroxyl-1-(3-chloro benzyl)-3-methoxyl-3,4-dihydroquinolin-2 (1H)-one, 4-(4-bromophenyl)-4-hydroxyl-1-(2-bromobenzyl)-3-methoxyl-3,4-dihydroquinoline-2(1H)-one, 4-(4-bromophenyl)-4-hydroxyl-1-(2-iodobenzyl)-3-methoxyl-3,4-dihydroquinoline-2(1H)-one, 4-(4-bromophenyl)-4-hydroxyl-1-(4-fluoro benzyl)-3-methoxyl-3,4-dihydroquinoline-2(1H)-one, 4-(4-bromophenyl)-4-hydroxyl-1-(4-chloro benzyl)-3-methoxyl-3,4-dihydroquinoline-2(1H)-one, 4-(4-bromophenyl)-4-hydroxyl-1-(3-iodobenzyl)-3-methoxyl-3,4-dihydroquinoline-2(1H)-one, 1-(3-chloro benzyl)-4-hydroxy-6-iodine-3-methoxyl-4-phenyl-3,4-dihydroquinolin-2 (1H)-one, 1-ethyl6-iodine-3-methoxyl-4-phenylquinolin-2 (1H)-one, 1-(4-fluorophenyl)-6-iodine-3-methoxyl-4-phenylquinolin-2 (1H)-one, 5-bromo-1-(3-chloro benzyl)-4-hydroxy-3-methoxyl-4-phenyl-3,4-dihydroquinolin-2 (1H)-one, 1-(3-chloro benzyl)-4,6-dihydroxy-3-methoxyl-4-phenyl-3,4-dihydroquinolin-2 (1H)-one were synthesized.

Example 3

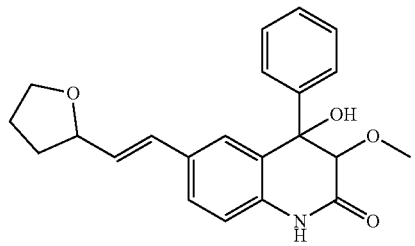 [SMILES: COC1C(=O)Nc2ccc(/C=C/C3CCCO3)cc2C1(O)c1ccccc1]

Step 1) 6-Methyl-2-phenyl-4H-benzo[d][1,3]oxazin-4-one

To a mixture of 2-Amino-5-methylbenzoic acid (0.45 g) and sodium carbonate (0.65 g) in THF being cooled to 0° C. was added benzoyl chloride (2 eq) and allowed to react at room temperature overnight. After the completion of the reaction, the reaction solution was diluted with water, stirred for 10 minutes, and filtered. The filter cake was washed twice with ethyl acetate. The compound was obtained as a white solid.

Step 2) N-(2-benzoyl-4-methylphenyl)benzamide

To a solution of 6-Methyl-2-phenyl-4H-benzo[d][1,3]oxazin-4-one (0.093 g) in dichloromethane at −78° C. was added phenylmagnesium bromide (3-4 eq) dropwise. After being stirred for 2 hour at −78° C., the reaction mixture was quenched by addition of water. and extracted with dichloromethane. The organic phase was concentrated under reduced pressure. The residue was purified by silica gel column chromatography, The compound was obtained as a yellow oil.

Step 3)
(2-Amino-5-methylphenyl)(phenyl)methanone

To a solution of N-(2-Benzoyl-4-methylphenyl)benzamide (1.32 g) in MeOH at room temperature was added NaOH (1.4 g) in water (2 mL) and heated to reflux overnight. The reaction solution was washed with water and extracted with ethyl acetate. The compound was obtained as a yellow oil.

Step 4) (5-Methyl-2-nitrophenyl)(phenyl)methanone

To a solution of (2-Amino-5-methylphenyl) (phenyl) methanone (5.28 g) in toluene (200 mL) at 0° C. was added m-chloroperoxybenzoic acid (5 eq). The resulting mixture was heated to 120° C. and allowed to stir for 6 hours. After the completion of the reaction, the reaction mixture was diluted with water and extracted with ethyl acetate. The organic phase is concentrated under reduced pressure and separated by column chromatography. The compound was obtained as a pale-yellow oil.

Step 5) (5-(Bromomethyl)-2-nitrophenyl) (phenyl)methanone

To a solution of (5-methyl-2-nitrophenyl) (phenyl)methanone (2.41 g) in carbon tetrachloride (100 mL) under nitrogen was added, NBS (2.32 g) and AMBN (90 mg). And the mixture was stirred at 80° C. for 24 hours. After the completion of the reaction, the reaction mixture was diluted with water and extracted with dichloromethane. The organic phase was evaporated under reduced pressure and the residue was purified by silica gel column chromatography (petroleum ether/ethyl acetate (v/v)=8/1), The compound was obtained as pale yellow oil.

Step 6) (5-((diethoxyphosphoryl)methyl)-2-nitrophenyl) (phenyl)methanone

To a solution of 5-(bromomethyl)-2-nitrophenyl) (phenyl) methanone (2.1 g) in 1,4-dioxane (100 mL) at room temperature was added triethyl phosphite (10 eq) dropwise. After being stirred for 2 hour at −78° C., the reaction mixture was quenched by addition of water. and extracted with dichloromethane. The organic phase was concentrated under reduced pressure. The residue was purified by silica gel column chromatography, The compound was obtained as a yellow oil.

Step 7) (E)-(5-(2-(2-methyl-5-(prop-1-en-2-yl)tetrahydrofuran-2-yl)vinyl)-2-nitrophenyl) (Phenyl) ketone To a solution of (5-((diethoxyphosphoryl)methyl)-2-nitrophenyl) (phenyl)methanone (0.8 g) in THF at 0° C. was added NaH (1.2 eq). After being stirred for 30 minutes at 0° C., the reaction mixture was added 2-methyl-5-(prop-1-en-2-yl) tetrahydrofuran-2-carbaldehyde (1.5 eq) and allowed to stir for 2 hours. After the completion of the reaction, the reaction mixture was diluted with water and extracted with ethyl acetate. The organic phase was concentrated under reduced pressure.

The residue was purified by silica gel column chromatography. The compound was obtained as a yellow oil.

Step 8) (E)-(2-Amino-5-(2-(2-methyl-5-(prop-1-en-2-yl)tetrahydrofuran-2-yl)vinyl)phenyl) (Benzene)-one To a solution of (E)-(5-(2-(2-methyl-5-(prop-1-en-2-yl) tetrahydrofuran-2-yl) vinyl)-2-nitrophenyl) (Phenyl)-one (0.1 g) in ethanol (10 mL) and water (5 mL) at room temperature was added Fe (6 eq) and ammonium chloride (6 eq) and heated to 90° C., then allowed to stir for 4 hours. The reaction solution was washed with water and extracted with ethyl acetate. The residue was purified by silica gel column chromatography, The compound was obtained as a yellow oil.

Step 9) (E)-N-(2-benzoyl-4-(2-(2-methyl-5-(prop-1-en-2-yl)tetrahydrofuran-2-yl)vinyl)phenyl)-2-methoxyacetamide To a solution of (E)-(2-Amino-5-(2-(2-methyl-5-(prop-1-en-2-yl)tetrahydrofuran-2-yl)vinyl)phenyl) (Benzene)-one (0.25 g) in dichloromethane at 0° C. was added DIPEA (1.2 eq). After being stirred for 30 minutes at 0° C., the reaction mixture was added 2-methoxyacetyl chloride (1.2 eq) and allowed to stir for 2 hours. After the completion of the reaction, the reaction mixture was diluted with water and extracted with dichloromethane. The organic phase was concentrated under reduced pressure. The residue was purified by silica gel column chromatography. The compound was obtained as a yellow oil.

Step 10) (E)-4-hydroxy-3-methoxy-4-phenyl-6-(2-(tetrahydrofuran-2-yl)vinyl)-3,4-dihydroquinolin-2 (1H)-one To a solution of ((E)-N-(2-benzoyl-4-(2-(2-methyl-5-(prop-1-en-2-yl)tetrahydrofuran-2-yl) vinyl)phenyl)-2-methoxyacetamide (0.12 g) in THF (10 mL) at room temperature was added potassium t-butoxide (10 eq). After being stirred for 1 hour, the reaction mixture was quenched by addition of water. and extracted with ethyl acetate. The organic phase was concentrated under reduced pressure. The residue was purified by silica gel column chromatography, The compound (E)-4-hydroxy-3-methoxy-4-phenyl-6-(2-(tetrahydrofuran-2-yl)vinyl)-3,4-dihydroquinolin-2(1H)-one was obtained as a white solid. ESIMS m/z 366.42.

Example 4

Bicyclo[2.2.1]hept-5-ene-2-carbaldehyde was used as a reagent to react with the (5-((diethoxyphosphoryl)methyl)-2-nitrophenyl) (phenyl)methanone synthesized following Example 3, to give intermediate product (E)-(5-(2-(bicyclo [2.2.1]hept-5-en-2-yl)vinyl)-2-nitrophenyl) (phenyl)methanone, which was then subjected to reaction and post-treatment described in Example 3 to give final product (E)-6-(2-(bicyclo[2.2.1]hept-5-en-2-yl)vinyl)-4-hydroxy-3-methoxy-4-phenyl-3,4-dihydroquinolin-2(1H)-one. ESI-MS m/z 388.48 [M+H]$^+$.

Example 5

5-phenylfuran-2-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(5-phenylfuran-2-yl)vinyl)phenyl)(phenyl)methanone, which was then subjected to reaction and post-treatment described in Example 3 to give final product (E)-4-hydroxy-3-methoxy-4-phenyl-6-(2-(5-phenylfuran-2-yl) vinyl)-3,4-dihydroquinolin-2(1H)-one. ESI-MS m/z 438.50 [M+H]$^+$.

Example 6

Cyclopentanecarbaldehyde was used as a reagent to react with the (5-((diethoxyphosphoryl)methyl)-2-nitrophenyl) (phenyl)methanone synthesized following Example 3, to give intermediate product (E)-(5-(2-cyclopentylvinyl)-2-nitrophenyl)(phenyl)methanone, which was then subjected to reaction and post-treatment described in Example 3 to give final product (E)-6-(2-cyclopentylvinyl)-4-hydroxy-3-methoxy-4-phenyl-3,4-dihydroquinolin-2(1H)-one. ESI-MS m/z 364.46 [M+H]+

Example 7

Cyclopentanone was used as a reagent to react with the (5-((diethoxyphosphoryl)methyl)-2-nitrophenyl) (phenyl)methanone synthesized following Example 3, to give intermediate product (5-(cyclopentylidenemethyl)-2-nitrophenyl)(phenyl)methanone, which was then subjected to reaction and post-treatment described in Example 3 to give final product 6-(cyclopentylidenemethyl)-4-hydroxy-3-methoxy-4-phenyl-3,4-dihydroquinolin-2(1H)-one. ESI-MS m/z 350.43 [M+H]+

Example 8

3-methylcyclopentan-1-one was used as a reagent to react with the (5-((diethoxyphosphoryl)methyl)-2-nitrophenyl)(phenyl)methanone synthesized following Example 3, to give intermediate product (E)-(5-((3-methylcyclopentylidene)methyl)-2-nitrophenyl)(phenyl)methanone, which was then subjected to reaction and post-treatment described in Example 3 to give final product (E)-4-hydroxy-3-methoxy-6-((3-methylcyclopentylidene)methyl)-4-phenyl-3,4-dihydroquinolin-2(1H)-one. ESI-MS m/z 364.46 [M+H]+

Example 9

1-cyclopentylpropan-1-one was used as a reagent to react with the (5-((diethoxyphosphoryl)methyl)-2-nitrophenyl)(phenyl)methanone synthesized following Example 3, to give intermediate product (E)-(5-(2-cyclopentylbut-1-en-1-yl)-2-nitrophenyl)(phenyl)methanone, which was then subjected to reaction and post-treatment described in Example 3 to give final product (E)-6-(2-cyclopentylbut-1-en-1-yl)-4-hydroxy-3-methoxy-4-phenyl-3,4-dihydroquinolin-2(1H)-one.
ESI-MS m/z 392.51 [M+H]+

Example 10

1-cyclopentylpropan-2-one was used as a reagent to react with the (5-((diethoxyphosphoryl)methyl)-2-nitrophenyl)(phenyl)methanone synthesized following Example 3, to give intermediate product (E)-(5-(3-cyclopentyl-2-methylprop-1-en-1-yl)-2-nitrophenyl)(phenyl)methanone, which was then subjected to reaction and post-treatment described in Example 3 to give final product (E)-6-(3-cyclopentyl-2-methylprop-1-en-1-yl)-4-hydroxy-3-methoxy-4-phenyl-3,4-dihydroquinolin-2(1H)-one. ESI-MS m/z 392.51 [M+H]+

Example 11

5-methylhexan-3-one was used as a reagent to react with the (5-((diethoxyphosphoryl)methyl)-2-nitrophenyl)(phenyl)methanone synthesized following Example 3, to give intermediate product (Z)-(5-(2-ethyl-4-methylpent-1-en-1-yl)-2-nitrophenyl)(phenyl)methanone, which was then subjected to reaction and post-treatment described in Example 3 to give final product (Z)-6-(2-ethyl-4-methylpent-1-en-1-yl)-4-hydroxy-3-methoxy-4-phenyl-3,4-dihydroquinolin-2(1H)-one. ESI-MS m/z 380.50 [M+H]+

Example 12

2,2,4-trimethylcyclopentan-1-one was used as a reagent to react with the (5-((diethoxyphosphoryl)methyl)-2-nitrophenyl) (phenyl)methanone synthesized following Example 3, to give intermediate product (E)-(2-nitro-5-((2,2,4-trimethylcyclopentylidene)methyl)phenyl)(phenyl)methanone, which was then subjected to reaction and post-treatment described in Example 3 to give final product (E)-4-hydroxy-3-methoxy-4-phenyl-6-((2,2,4-trimethylcyclopentylidene)methyl)-3,4-dihydroquinolin-2(1H)-one. ESI-MS m/z 392.51 [M+H]+

Example 13

Tetrahydrofuran-2-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(tetrahydrofuran-2-yl)vinyl)phenyl)(phenyl)methanone, which was then subjected to reaction and post-treatment described in Example 3 to give final product (E)-4-hydroxy-3-methoxy-4-phenyl-6-(2-(tetrahydrofuran-2-yl)vinyl)-3,4-dihydroquinolin-2(1H)-one. ESI-MS m/z 366.43 [M+H]+

Example 14

2-methyldihydrofuran-3(2H)-one was used as a reagent to react with the (5-((diethoxyphosphoryl)methyl)-2-nitrophenyl) (phenyl)methanone synthesized following Example 3, to give intermediate product (Z)-(5-((2-methyldihydrofuran-3(2H)-ylidene)methyl)-2-nitrophenyl)(phenyl)methanone, which was then subjected to reaction and post-treatment described in Example 3 to give final product (Z)-4-hydroxy-3-methoxy-6-((2-methyldihydrofuran-3(2H)-ylidene)methyl)-4-phenyl-3,4-dihydroquinolin-2(1H)-one.
ESI-MS m/z 366.43 [M+H]+

Example 15

Furan-2-carbaldehyde was used as a reagent to react with the (5-((diethoxyphosphoryl)methyl)-2-nitrophenyl) (phenyl)methanone synthesized following Example 3, to give intermediate product (E)-(5-(2-(furan-2-yl)vinyl)-2-nitrophenyl)(phenyl)methanone, which was then subjected to reaction and post-treatment described in Example 3 to give final product (E)-6-(2-(furan-2-yl)vinyl)-4-hydroxy-3-methoxy-4-phenyl-3,4-dihydroquinolin-2(1H)-one. ESI-MS m/z 362.40 [M+H]+

Example 16

5-methylfuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(5-methylfuran-2-yl)vinyl)-2-nitrophenyl)(phenyl)methanone, which was then subjected to reaction and post-treatment described in Example 3 to give final product (E)-4-hydroxy-3-methoxy-6-(2-(5-methylfuran-2-yl)vinyl)-4-phenyl-3,4-dihydroquinolin-2(1H)-one. ESI-MS m/z 376.42 [M+H]+

Example 17

Furan-2,5-dicarbaldehyde was used as a reagent to react with the (5-((diethoxyphosphoryl)methyl)-2-nitrophenyl) (phenyl)methanone synthesized following Example 3, to give intermediate product (E)-5-(3-benzoyl-4-nitrostyryl)furan-2-carbaldehyde, which was then subjected to reaction and post-treatment described in Example 3 to give final product (E)-5-(2-(4-hydroxy-3-methoxy-2-oxo-4-phenyl-1-tetrahydroquinolin-6-yl)vinyl) furan-2-carbaldehyde. ESI-MS m/z 390.41 [M+H]$^+$ Example 18

5-formylfuran-2-carboxylic acid was used as a reagent to react with the (5-((diethoxyphosphoryl)methyl)-2-nitrophenyl) (phenyl)methanone synthesized following Example 3, to give intermediate product (E)-5-(3-benzoyl-4-nitrostyryl) furan-2-carboxylic acid, which was then subjected to reaction and post-treatment described in Example 3 to give final product (E)-5-(2-(4-hydroxy-3-methoxy-2-oxo-4-phenyl-1,2,3,4-tetrahydroquinolin-6-yl)vinyl)furan-2-carboxylic acid.
ESI-MS m/z 406.41 [M+H]$^+$ Example 19

3-methylfuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(3-methylfuran-2-yl)vinyl)-2-nitrophenyl)(phenyl)methanone, which was then subjected to reaction and post-treatment described in Example 3 to give final product (E)-4-hydroxy-3-methoxy-6-(2-(3-methylfuran-2-yl)vinyl)-4-phenyl-3,4-dihydroquinolin-2(1H)-one.
ESI-MS m/z 376.42 [M+H]$^+$ Example 20

5-ethylfuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(5-ethylfuran-2-yl)vinyl)-2-nitrophenyl)(phenyl)methanone, which was then subjected to reaction and post-treatment described in Example 3 to give final product (E)-6-(2-(5-ethylfuran-2-yl)vinyl)-4-hydroxy-3-methoxy-4-phenyl-3,4-dihydroquinolin-2(1H)-one.
ESI-MS m/z 390.45 [M+H]$^+$ 1-(5-(hydroxymethyl)furan-2-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(5-(hydroxymethyl)furan-2-yl)prop-1-en-1-yl)-2-nitrophenyl) (phenyl)methanone, which was then subjected to reaction and post-treatment described in Example 3 to give final product (E)-4-hydroxy-6-(2-(5-(hydroxymethyl)furan-2-yl)prop-1-en-1-yl)-3-methoxy-4-phenyl-3,4-dihydroquinolin-2(1H)-one.
ESI-MS m/z 406.45 [M+H]$^+$ Example 22

(E)-3-(furan-2-yl)acrylaldehyde was used as a reagent to react with the (5-((diethoxyphosphoryl)methyl)-2-nitrophenyl) (phenyl)methanone synthesized following Example 3, to give intermediate product (5-((1E,3E)-4-(furan-2-yl)buta-1,3-dien-1-yl)-2-nitrophenyl)(phenyl)methanone, which was then subjected to reaction and post-treatment described in Example 3 to give final product 6-((1E,3E)-4-(furan-2-yl)buta-1,3-dien-1-yl)-4-hydroxy-3-methoxy-4-phenyl-3,4-dihydroquinolin-2(1H)-one.
ESI-MS m/z 388.44 [M+H]$^+$ Example 23

1-(furan-2-yl)propan-1-one was used as a reagent to react with the (5-((diethoxyphosphoryl)methyl)-2-nitrophenyl) (phenyl)methanone synthesized following Example 3, to give intermediate product (E)-(5-(2-(furan-2-yl)but-1-en-1-yl)-2-nitrophenyl)(phenyl)methanone, which was then subjected to reaction and post-treatment described in Example 3 to give final product (E)-6-(2-(furan-2-yl)but-1-en-1-yl)-4-hydroxy-3-methoxy-4-phenyl-3,4-dihydroquinolin-2(1H)-one.
ESI-MS m/z 390.45 [M+H]$^+$ Example 24

2,2,5,5-tetramethyldihydrofuran-3(2H)-one was used as a reagent to react with the (5-((diethoxyphosphoryl)methyl)-2-nitrophenyl) (phenyl)methanone synthesized following Example 3, to give intermediate product 2,2,5,5-tetramethyldihydrofuran-3(2H)-one, which was then subjected to reaction and post-treatment described in Example 3 to give final product (Z)-4-hydroxy-3-methoxy-4-phenyl-6-((2,2,5,5-tetramethyldihydrofuran-3(2H)-ylidene)methyl)-3,4-dihydroquinolin-2(1H)-one. ESI-MS m/z 408.51 [M+H]$^+$ Example 25

4,5-dimethylfuran-2-carbaldehyde was used as a reagent to react with the (5-((diethoxyphosphoryl)methyl)-2-nitrophenyl) (phenyl)methanone synthesized following Example 3, to give intermediate product (E)-(2-amino-5-(2-(4,5-dimethylfuran-2-yl)vinyl)phenyl)(phenyl)methanone, which was then subjected to reaction and post-treatment described in Example 3 to give final product (E)-6-(2-(4,5-dimethylfuran-2-yl)vinyl)-4-hydroxy-3-methoxy-4-phenyl-3,4-dihydroquinolin-2(1H)-one. ESI-MS m/z 390.45 [M+H]$^+$ Example 26

1-(5-(hydroxymethyl)furan-2-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(5-(hydroxymethyl)furan-2-yl)prop-1-en-1-yl)-2-nitrophenyl) (phenyl)methanone, which was then subjected to reaction and post-treatment described in Example 3 to give final product (E)-4-hydroxy-6-(2-(5-(hydroxymethyl)furan-2-yl)prop-1-en-1-yl)-3-methoxy-4-phenyl-3,4-dihydroquinolin-2(1H)-one.
ESI-MS m/z 406.45 [M+H]$^+$ Example 27

(E)-3-(furan-2-yl)acrylaldehyde was used as a reagent to react with the (5-((diethoxyphosphoryl)methyl)-2-nitrophenyl) (phenyl)methanone synthesized following Example 3, to give intermediate product (5-((1E,3E)-4-(furan-2-yl)buta-1,3-dien-1-yl)-2-nitrophenyl)(phenyl)methanone, which was then subjected to reaction and post-treatment described in Example 3 to give final product 6-((1E,3E)-4-(furan-2-yl)buta-1,3-dien-1-yl)-4-hydroxy-3-methoxy-4-phenyl-3,4-dihydroquinolin-2(1H)-one. ESI-MS m/z 388.44 [M+H]$^+$ Example 28

1-(2,4-dimethylfuran-3-yl)ethan-1-one was used as a reagent to react with the (5-((diethoxyphosphoryl)methyl)-

2-nitrophenyl) (phenyl)methanone synthesized following Example 3, to give intermediate product (E)-(5-(2-(2,4-dimethylfuran-3-yl)prop-1-en-1-yl)-2-nitrophenyl)(phenyl) methanone, which was then subjected to reaction and post-treatment described in Example 3 to give final product (E)-6-(2-(2,4-dimethylfuran-3-yl)prop-1-en-1-yl)-4-hydroxy-3-methoxy-4-phenyl-3,4-dihydroquinolin-2(1H)-one. ESI-MS m/z 404.48 [M+H]$^+$ 5-chlorofuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(5-chlorofuran-2-yl)vinyl)-2-nitrophenyl)(phenyl)methanone, which was then subjected to reaction and post-treatment described in Example 3 to give final product (E)-6-(2-(5-chlorofuran-2-yl)vinyl)-4-hydroxy-3-methoxy-4-phenyl-3,4-dihydroquinolin-2(1H)-one. ESI-MS m/z 396.84 [M+H]$^+$

Example 30

1-(furan-2-yl)hexan-1-one was used as a reagent to react with the (5-((diethoxyphosphoryl)methyl)-2-nitrophenyl) (phenyl)methanone synthesized following Example 3, to give intermediate product (E)-(5-(2-(furan-2-yl)hept-1-en-1-yl)-2-nitrophenyl)(phenyl)methanone, which was then subjected to reaction and post-treatment described in Example 3 to give final product (E)-6-(2-(furan-2-yl)hept-1-en-1-yl)-4-hydroxy-3-methoxy-4-phenyl-3,4-dihydroquinolin-2(1H)-one. ESI-MS m/z 432.53 [M+H]$^+$

Example 31

1-(2,5-dimethylfuran-3-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(2,5-dimethylfuran-3-yl)prop-1-en-1-yl)-2-nitrophenyl)(phenyl) methanone, which was then subjected to reaction and post-treatment described in Example 3 to give final product (E)-6-(2-(2,5-dimethylfuran-3-yl)prop-1-en-1-yl)-4-hydroxy-3-methoxy-4-phenyl-3,4-dihydroquinolin-2(1H)-one. ESI-MS m/z 404.48 [M+H]$^+$

Example 32

1-(5-(methoxymethyl)furan-2-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(5-(methoxymethyl)furan-2-yl)prop-1-en-1-yl)-2-nitrophenyl) (phenyl)methanone, which was then subjected to reaction and post-treatment described in Example 3 to give final product (E)-4-hydroxy-3-methoxy-6-(2-(5-(methoxymethyl)furan-2-yl)prop-1-en-1-yl)-4-phenyl-3,4-dihydroquinolin-2(1H)-one.
ESI-MS m/z 420.48 [M+H]$^+$

Example 33

2-methylfuran-3-carbaldehyde was used as a reagent to react with the (5-((diethoxyphosphoryl)methyl)-2-nitrophenyl) (phenyl)methanone synthesized following Example 3, to give intermediate product (E)-(5-(2-(2-methylfuran-3-yl)vinyl)-2-nitrophenyl)(phenyl)methanone, which was then subjected to reaction and post-treatment described in Example 3 to give final product (E)-4-hydroxy-3-methoxy-6-(2-(2-methylfuran-3-yl)vinyl)-4-phenyl-3,4-dihydroquinolin-2(1H)-one. ESI-MS m/z 376.42 [M+H]$^+$

Example 34

1-(4,5-dimethylfuran-2-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(4,5-dimethylfuran-2-yl)prop-1-en-1-yl)-2-nitrophenyl)(phenyl) methanone, which was then subjected to reaction and post-treatment described in Example 3 to give final product (E)-6-(2-(4,5-dimethylfuran-2-yl)prop-1-en-1-yl)-4-hydroxy-3-methoxy-4-phenyl-3,4-dihydroquinolin-2(1H)-one. ESI-MS m/z 404.48 [M+H]$^+$

Example 35

1-(furan-2-yl)butan-1-one was used as a reagent to react with the (5-((diethoxyphosphoryl)methyl)-2-nitrophenyl) (phenyl)methanone synthesized following Example 3, to give intermediate product (E)-(5-(2-(furan-2-yl)pent-1-en-1-yl)-2-nitrophenyl)(phenyl)methanone, which was then subjected to reaction and post-treatment described in Example 3 to give final product (E)-6-(2-(furan-2-yl)pent-1-en-1-yl)-4-hydroxy-3-methoxy-4-phenyl-3,4-dihydroquinolin-2(1H)-one. ESI-MS m/z 404.48 [M+H]$^+$

Example 36

1-(furan-2-yl)pentan-1-one was used as a reagent to react with the (5-((diethoxyphosphoryl)methyl)-2-nitrophenyl) (phenyl)methanone synthesized following Example 3, to give intermediate product (E)-(5-(2-(furan-2-yl)hex-1-en-1-yl)-2-nitrophenyl)(phenyl)methanone, which was then subjected to reaction and post-treatment described in Example 3 to give final product (E)-6-(2-(furan-2-yl)hex-1-en-1-yl)-4-hydroxy-3-methoxy-4-phenyl-3,4-dihydroquinolin-2(1H)-one. ESI-MS m/z 418.51 [M+H]$^+$

Example 37

4-ethoxypent-4-enal was used as a reagent to react with the (5-((diethoxyphosphoryl)methyl)-2-nitrophenyl) (phenyl)methanone synthesized following Example 3, to give intermediate product (E)-(5-(5-ethoxyhexa-1,5-dien-1-yl)-2-nitrophenyl)(phenyl)methanone, which was then subjected to reaction and post-treatment described in Example 3 to give final product (E)-6-(5-ethoxyhexa-1,5-dien-1-yl)-4-hydroxy-3-methoxy-4-phenyl-3,4-dihydroquinolin-2(1H)-one. ESI-MS m/z 394.48 [M+H]$^+$

Example 38

1-(2,4-dimethylfuran-3-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(2,4-dimethylfuran-3-yl)prop-1-en-1-yl)-2-nitrophenyl)(phenyl) methanone, which was then subjected to reaction and post-treatment described in Example 3 to give final product (E)-6-(2-(2,4-dimethylfuran-3-yl)prop-1-en-1-yl)-4-hydroxy-3-methoxy-4-phenyl-3,4-dihydroquinolin-2(1H)-one. ESI-MS m/z 404.48 [M+H]$^+$

Example 39

1-(furan-2-yl)heptan-1-one was used as a reagent to react with the (5-((diethoxyphosphoryl)methyl)-2-nitrophenyl)

(phenyl)methanone synthesized following Example 3, to give intermediate product (E)-2-(1-(4-nitro-3-(1-phenylvinyl)phenyl)oct-1-en-2-yl)furan, which was then subjected to reaction and post-treatment described in Example 3 to give final product (E)-6-(2-(furan-2-yl)oct-1-en-1-yl)-4-hydroxy-3-methoxy-4-phenyl-3,4-dihydroquinolin-2(1H)-one. ESI-MS m/z 446.56 [M+H]$^+$ Example 40

1-(2,5-dimethylfuran-3-yl)ethan-1-one was used as a reagent to react with the (5-((diethoxyphosphoryl)methyl)-2-nitrophenyl) (phenyl)methanone synthesized following Example 3, to give intermediate product (E)-(5-(2-(2,5-dimethylfuran-3-yl)prop-1-yl-en-1-yl)-2-nitrophenyl)(phenyl)methanone, which was then subjected to reaction and post-treatment described in Example 3 to give final product (E)-6-(2-(2,5-dimethylfuran-3-yl)prop-1-en-1-yl)-4-hydroxy-3-methoxy-4-phenyl-3,4-dihydroquinolin-2(1H)-one. ESI-MS m/z 404.48 [M+H]$^+$ Example 41

3-(5-methylfuran-2-yl)butanal was used as a reagent to react with the (5-((diethoxyphosphoryl)methyl)-2-nitrophenyl) (phenyl)methanone synthesized following Example 3, to give intermediate product (E)-(5-(4-(5-methylfuran-2-yl)pent-1-en-1-yl)-2-nitrophenyl)(phenyl)methanone, which was then subjected to reaction and post-treatment described in Example 3 to give final product (E)-4-hydroxy-3-methoxy-6-(4-(5-methylfuran-2-yl)pent-1-en-1-yl)-4-phenyl-3,4-dihydroquinolin-2(1H)-one. ESI-MS m/z 418.51 [M+H]$^+$ Example 42

S-(2-ethoxyallyl) methanethioate was used as a reagent to react with the (5-((diethoxyphosphoryl)methyl)-2-nitrophenyl) (phenyl)methanone synthesized following Example 3, to give intermediate product (E)-(5-(2-((2-ethoxyallyl)thio)vinyl)-2-nitrophenyl)(phenyl)methanone, which was then subjected to reaction and post-treatment described in Example 3 to give final product (E)-6-(2-((2-ethoxyallyl)thio)vinyl)-4-hydroxy-3-methoxy-4-phenyl-3,4-dihydroquinolin-2(1H)-one. ESI-MS m/z 412.52 [M+H]$^+$ Example 43

5-bromofuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(5-bromofuran-2-yl)vinyl)-2-nitrophenyl)(phenyl)methanone, which was then subjected to reaction and post-treatment described in Example 3 to give final product (E)-6-(2-(5-bromofuran-2-yl)vinyl)-4-hydroxy-3-methoxy-4-phenyl-3,4-dihydroquinolin-2(1H)-one. ESI-MS m/z 441.29 [M+H]$^+$ Example 44

5-(trifluoromethyl)furan-2-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(5-(trifluoromethyl)furan-2-yl)vinyl)phenyl)(phenyl)methanone, which was then subjected to reaction and post-treatment described in Example 3 to give final product (E)-4-hydroxy-3-methoxy-4-phenyl-6-(2-(5-(trifluoromethyl)furan-2-yl)vinyl)-3,4-dihydroquinolin-2(1H)-one. ESI-MS m/z 430.40 [M+H]$^+$ Example 45

4-bromofuran-2-carbaldehyde was used as a reagent to react with the (5-((diethoxyphosphoryl)methyl)-2-nitrophenyl) (phenyl)methanone synthesized following Example 3, to give intermediate product (E)-(5-(2-(4-bromofuran-2-yl)vinyl)-2-nitrophenyl)(phenyl)methanone, which was then subjected to reaction and post-treatment described in Example 3 to give final product (E)-6-(2-(4-bromofuran-2-yl)vinyl)-4-hydroxy-3-methoxy-4-phenyl-3,4-dihydroquinolin-2(1H)-one. ESI-MS m/z 441.29 [M+H]$^+$ Example 46

Pyrrolidine-2-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(pyrrolidin-2-yl)vinyl)phenyl)(phenyl)methanone, which was then subjected to reaction and post-treatment described in Example 3 to give final product (E)-4-hydroxy-3-methoxy-4-phenyl-6-(2-(pyrrolidin-2-yl)vinyl)-3,4-dihydroquinolin-2(1H)-one. ESI-MS m/z 365.45 [M+H]$^+$ Example 47

2-methylpyrrolidine-2-carbaldehyde was used as a reagent to react with the (5-((diethoxyphosphoryl)methyl)-2-nitrophenyl) (phenyl)methanone synthesized following Example 3, to give intermediate product (E)-(5-(2-(2-methylpyrrolidin-2-yl)vinyl)-2-nitrophenyl)(phenyl)methanone, which was then subjected to reaction and post-treatment described in Example 3 to give final product (E)-4-hydroxy-3-methoxy-6-(2-(2-methylpyrrolidin-2-yl)vinyl)-4-phenyl-3,4-dihydroquinolin-2(1H)-one. ESI-MS m/z 379.47 [M+H]$^+$ Example 48

1-methylpyrrolidine-2-carbaldehyde was used as a reagent to react with the (5-((diethoxyphosphoryl)methyl)-2-nitrophenyl) (phenyl)methanone synthesized following Example 3, to give intermediate product (E)-(5-(2-(1-methylpyrrolidin-2-yl)vinyl)-2-nitrophenyl)(phenyl)methanone, which was then subjected to reaction and post-treatment described in Example 3 to give final product (E)-4-hydroxy-3-methoxy-6-(2-(1-methylpyrrolidin-2-yl)vinyl)-4-phenyl-3,4-dihydroquinolin-2(1H)-one. ESI-MS m/z 379.47 [M+H]$^+$ Example 49

Hexahydro-1H-pyrrolizin-1-one was used as a reagent to react with the (5-((diethoxyphosphoryl)methyl)-2-nitrophenyl) (phenyl)methanone synthesized following Example 3, to give intermediate product (E)-(5-((hexahydro-1H-pyrrolizin-1-ylidene)methyl)-2-nitrophenyl)(phenyl)methanone, which was then subjected to reaction and post-treatment described in Example 3 to give final product (E)-6-((hexahydro-1H-pyrrolizin-1-ylidene)methyl)-4-hydroxy-3-methoxy-4-phenyl-3,4-dihydroquinolin-2(1H)-one.
ESI-MS m/z 391.48 [M+H]$^+$

Example 50

1-(cyclopropylmethyl)pyrrolidine-2-carbaldehyde was used as a reagent to react with the (5-((diethoxyphosphoryl)methyl)-2-nitrophenyl) (phenyl)methanone synthesized following Example 3, to give intermediate product (E)-(5-(2-(1-(cyclopropylmethyl)pyrrolidin-2-yl)vinyl)-2-nitrophenyl)(phenyl)methanone, which was then subjected to reaction and post-treatment described in Example 3 to give final product (E)-6-(2-(1-(cyclopropylmethyl)pyrrolidin-2-yl)vinyl)-4-hydroxy-3-methoxy-4-phenyl-3,4-dihydroquinolin-2(1H)-one.
ESI-MS m/z 419.54 [M+H]$^+$

Example 51

Octahydroindolizine-8-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(octahydroindolizin-8-yl)vinyl)phenyl)(phenyl)methanone, which was then subjected to reaction and post-treatment described in Example 3 to give final product (E)-4-hydroxy-3-methoxy-6-(2-(octahydroindolizin-8-yl)vinyl)-4-phenyl-3,4-dihydroquinolin-2(1H)-one. ESI-MS m/z 419.54 [M+H]$^+$

Example 52

2,2-dimethyl-3-(pyrrolidin-1-yl)propanal was used as a reagent to react with the (5-((diethoxyphosphoryl)methyl)-2-nitrophenyl) (phenyl)methanone synthesized following Example 3, to give intermediate product (E)-(5-(3,3-dimethyl-4-(pyrrolidin-1-yl)but-1-en-1-yl)-2-nitrophenyl)(phenyl)methanone, which was then subjected to reaction and post-treatment described in Example 3 to give final product (E)-6-(3,3-dimethyl-4-(pyrrolidin-1-yl)but-1-en-1-yl)-4-hydroxy-3-methoxy-4-phenyl-3,4-dihydroquinolin-2(H)-one.
ESI-MS m/z 421.55 [M+H]$^+$

Example 53

Piperidine-2-carbaldehyde was used as a reagent to react with the (5-((diethoxyphosphoryl)methyl)-2-nitrophenyl) (phenyl)methanone synthesized following Example 3, to give intermediate product (E)-(2-nitro-5-(2-(piperidin-2-yl)vinyl)phenyl)(phenyl)methanone, which was then subjected to reaction and post-treatment described in Example 3 to give final product (E)-4-hydroxy-3-methoxy-4-phenyl-6-(2-(piperidin-2-yl)vinyl)-3,4-dihydroquinolin-2(1H)-one. ESI-MS m/z 379.47 [M+H]$^+$

Example 53

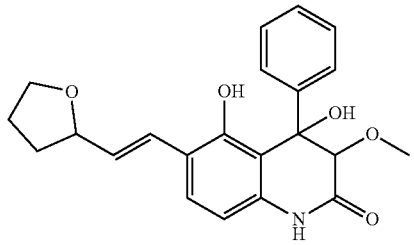 [SMILES: COC1C(=O)Nc2ccc(/C=C/C3CCCO3)c(O)c2C1(O)c1ccccc1]

Step 1) 2-benzoyl-6-methyl-3-nitrophenyl acetate

To a solution of (2-hydroxy-3-methyl-6-nitrophenyl)(phenyl)methanone (3.08 g, 12 mmol) and acetic anhydride (15 mL) in dichloromethane (30 mL) at 0° C. was added concentrated sulfuric acid (0.5 mL, 98%). After being stirred for 3 hours at 0° C., the completion of the reaction, the reaction mixture was diluted with water and extracted with dichloromethane. The organic phase was concentrated under reduced pressure. The residue was purified by silica gel column chromatography. The compound was obtained as a yellow oil.

Step 2) 2-Benzoyl-6-(bromomethyl)-3-nitrophenylacetate

To a solution of 2-benzoyl-6-methyl-3-nitrophenyl acetate (2.41 g) in carbon tetrachloride (100 mL) under nitrogen was added, NBS (2.32 g) and AIBN (90 mg). And the mixture was stirred at 80° C. for 24 hours. After the completion of the reaction, the reaction mixture was diluted with water and extracted with dichloromethane. The organic phase was evaporated under reduced pressure and the residue was purified by silica gel column chromatography (petroleum ether/ethyl acetate (v/v)=8/1) The compound was obtained as pale yellow oil.

Step 3) 2-Benzoyl-6-((diethoxyphosphoryl)methyl)-3-nitrophenylacetate

Under nitrogen, dissolve 2-Benzoyl-6-(bromomethyl)-3-nitrophenylacetate in 1,4-dioxane (100 mL), add triethyl phosphite at room temperature (10 eq). The resulting mixture was heated to 125° C. and allowed to stir for 12 hours. After the completion of the reaction, the reaction mixture was diluted with water and extracted with ethyl acetate. The organic phase was concentrated under reduced pressure. The residue was purified by silica gel column chromatography. The compound was obtained as a yellow oil.

Step 4) (3-Benzoyl-2-hydroxy-4-nitrobenzyl)phosphonic acid diethyl ester

To a solution of 2-Benzoyl-6-((diethoxyphosphoryl)methyl)-3-nitrophenylacetate (1.32 g) in MeOH at room temperature was added Potassium carbonate (0.63, 4.6 mmol). The reaction mixture was stirred at room temperature for 10 mins. The reaction solution was washed with water and extracted with ethyl acetate. The compound was obtained as a yellow oil.

Step 5) (3-Benzoyl-2-(methoxymethoxy)-4-nitrobenzyl)phosphonic acid diethyl ester To a solution of (3-Benzoyl-2-hydroxy-4-nitrobenzyl) phosphonic acid diethyl ester (1.61 g, 4.1 mmol) and diisopropylethylamine (1.06 g, 8.2 mmol) in dichloromethane (30 mL) at 0° C. was added MOMCl (0.50 g, 6.2 mmol).
After being stirred for 12 hours at 0° C., the completion of the reaction, the reaction mixture was diluted with water and extracted with dichloromethane. The organic phase was concentrated under reduced pressure. The residue was purified by silica gel column chromatography. The compound was obtained as a yellow oil.

Step 6) (E)-(3-(2-(furan-2-yl)vinyl)-2-(methoxymethoxy)-6 nitrophenyl) (phenyl)methanone To a solution of (3-Benzoyl-2-(methoxymethoxy)-4-nitrobenzyl)phosphonic acid diethyl ester (0.437 g, 1.0 mmol) in THF at 0° C. was added NaH (1.2 eq). After being stirred for 30 minutes at 0° C., the reaction mixture was added furan-2-carbaldehyde (1.5 eq) and allowed to stir for 2 hours. After the completion of the reaction, the reaction mixture was diluted with water and extracted with ethyl acetate. The organic phase was concentrated under reduced pressure. The residue was purified by silica gel column chromatography. The compound was obtained as a yellow oil.

Step 7) (E)-(6-Amino-3-(2-(furan-2-yl)vinyl)-2-(methoxymethoxy)phenyl)(phenyl) methanone To a solution of (E)-(3-(2-(furan-2-yl)vinyl)-2-(methoxymethoxy)-6 nitrophenyl) (phenyl) methanone (0.219 g, 0.5 mmol) in ethanol (10 mL) and water (5 mL) at room temperature was added Fe (6 eq) and ammonium chloride (6 eq) and heated to 90° C., then allowed to stir for 4 hours. The reaction solution was washed with water and extracted with ethyl acetate. The residue was purified by silica gel column chromatography, The compound was obtained as a yellow oil.

Step 8) (E)-N-(2-benzoyl-4-(2-(furan-2-yl)vinyl)-3-(methoxymethoxy)phenyl)-2-methoxyacetamide To a solution of (E)-(6-Amino-3-(2-(furan-2-yl)vinyl)-2-(methoxymethoxy)phenyl) (phenyl) methanone (0.203 g, 0.50) in dichloromethane at 0° C. was added DIPEA (1.2 eq). After being stirred for 30 minutes at 0° C., the reaction mixture was added 2-methoxyacetyl chloride (1.2 eq) and allowed to stir for 2 hours. After the completion of the reaction, the reaction mixture was diluted with water and extracted with dichloromethane. The organic phase was concentrated under reduced pressure. The residue was purified by silica gel column chromatography. The compound was obtained as a yellow oil.

Step 9) (E)-6-(2-(Furan-2-yl)vinyl)-4-hydroxy-3-methoxy-5-(methoxymethoxy)-4-phenyl-3,4-dihydroquinoline-2(1H)-one To a solution of (E)-N-(2-benzoyl-4-(2-(furan-2-yl)vinyl)(methoxymethoxy)phenyl)-2-methoxyacetamide (0.15 g, 0.314 mmol) in THF (10 mL) at room temperature was added potassium t-butoxide (10 eq). After being stirred for 1 hour, the reaction mixture was quenched by addition of water. and extracted with ethyl acetate. The organic phase was concentrated under reduced pressure. The residue was purified by silica gel column chromatography. The compound was obtained as a white solid.

Step 10) (E)-6-(2-(Furan-2-yl)vinyl)-4,5-dihydroxy-3-methoxy-4-phenyl-3,4-dihydroquinoline-2(1H)-one To a solution of (E)-6-(2-(Furan-2-yl)vinyl)-4-hydroxy-3-methoxy-5-(methoxymethoxy)-4-phenyl-3,4-dihydroquinoline-2(1H)-one (0.11 g, 0.23 mmol) in THF at room temperature was added concentrated hydrochloric acid (0.5 mL, 36%). The reaction mixture was stirred at room temperature for 0.5 h. The reaction solution was washed with water and extracted with ethyl acetate. The compound was obtained as a white solid. ESIMS m/z 382.32.

Example 54

Bicyclo[2.2.1]hept-5-ene-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(3-(2-(bicyclo[2.2.1]hept-5-en-2-yl)vinyl)-2-(methoxymethoxy)-6-nitrophenyl) (phenyl)methanone, which was then subjected to reaction and post-treatment described in example 53 to give final product (E)-6-(2-(bicyclo[2.2.1]hept-5-en-2-yl)vinyl)-4,5-dihydroxy-3-methoxy-4-phenyl-3,4-dihydroquinolin-2(1H)-one. ESI-MS m/z 404.52 [M+H]$^+$.

Example 55

5-phenylfuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-6-nitro-3-(2-(5-phenylfuran-2-yl)vinyl)phenyl)(phenyl)methanone, which was then subjected to reaction and post-treatment described in example 53 to give final product (E)-4,5-dihydroxy-3-methoxy-4-phenyl-6-(2-(5-phenylfuran-2-yl)vinyl)-3,4-dihydroquinolin-2(1H)-one. ESI-MS m/z 454.50 [M+H]$^+$.

Example 56

Cyclopentanecarbaldehyde was used as a reagent to react with the (3-Benzoyl-2-(methoxymethoxy)-4-nitrobenzyl) phosphonic acid diethyl ester synthesized following Example 53, to give intermediate product (E)-(3-(2-cyclopentylvinyl)-2-(methoxymethoxy)-6-nitrophenyl)(phenyl) methanone, which was then subjected to reaction and post-treatment described in example 53 to give final product (E)-6-(2-cyclopentylvinyl)-4,5-dihydroxy-3-methoxy-4-phenyl-3,4-dihydroquinolin-2(1H)-one. ESI-MS m/z 380.46 [M+H]$^+$.

Example 57

Cyclopentanone was used as a reagent to react with the (3-Benzoyl-2-(methoxymethoxy)-4-nitrobenzyl)phosphonic acid diethyl ester synthesized following Example 53, to give intermediate product (3-(cyclopentylidenemethyl)-2-(methoxymethoxy)-6-nitrophenyl)(phenyl)methanone, which was then subjected to reaction and post-treatment described in example 53 to give final product 6-(cyclopentylidenemethyl)-4,5-dihydroxy-3-methoxy-4-phenyl-3,4-dihydroquinolin-2(1H)-one. ESI-MS m/z 366.43 [M+H]$^+$.

Example 58

3-methylcyclopentan-1-one was used as a reagent to react with the (3-Benzoyl-2-(methoxymethoxy)-4-nitrobenzyl) phosphonic acid diethyl ester synthesized following Example 53, to give intermediate product (E)-(2-(methoxymethoxy)-3-((3-methylcyclopentylidene)methyl)-6-nitrophenyl)(phenyl)methanone, which was then subjected to reaction and post-treatment described in example 53 to give final product (E)-4,5-dihydroxy-3-methoxy-6-((3- methylcyclopentylidene)methyl)-4-phenyl-3,4-dihydroquinolin-2(1H)-one. ESI-MS m/z 380.46 [M+H]$^+$.

Example 59

1-cyclopentylpropan-1-one was used as a reagent to react with the (3-Benzoyl-2-(methoxymethoxy)-4-nitrobenzyl) phosphonic acid diethyl ester synthesized following Example 53, to give intermediate product (E)-(3-(2-cyclopentylbut-1-en-1-yl)-2-(methoxymethoxy)-6-nitrophenyl) (phenyl)methanone, which was then subjected to reaction and post-treatment described in example 53 to give final product (E)-6-(2-cyclopentylbut-1-en-1-yl)-4,5-dihydroxy-3-methoxy-4-phenyl-3,4-dihydroquinolin-2(1H)-one. ESI-MS m/z 408.51 [M+H]$^+$.

Example 60

1-cyclopentylpropan-2-one was used as a reagent to react with the (3-Benzoyl-2-(methoxymethoxy)-4-nitrobenzyl) phosphonic acid diethyl ester synthesized following Example 53, to give intermediate product (E)-(3-(3-cyclopentyl-2-methylprop-1-en-1-yl)-2-(methoxymethoxy)-6-nitrophenyl)(phenyl)methanone, which was then subjected to reaction and post-treatment described in example 53 to give final product (E)-6-(3-cyclopentyl-2-methylprop-1-en-1-yl)-4,5-dihydroxy-3-methoxy-4-phenyl-3,4-dihydroquinolin-2(1H)-one. ESI-MS m/z 408.51 [M+H]$^+$.

Example 61

5-methylhexan-3-one was used as a reagent to react with the (3-Benzoyl-2-(methoxymethoxy)-4-nitrobenzyl)phosphonic acid diethyl ester synthesized following Example 53, to give intermediate product (Z)-(3-(2-ethyl-4-methylpent-1-en-1-yl)-2-(methoxymethoxy)-6-nitrophenyl)(phenyl) methanone, which was then subjected to reaction and post-treatment described in example 53 to give final product (Z)-6-(2-ethyl-4-methylpent-1-en-1-yl)-4,5-dihydroxy-3-methoxy-4-phenyl-3,4-dihydroquinolin-2(1H)-one. ESI-MS m/z 396.50 [M+H]$^+$.

Example 62

2,2,4-trimethylcyclopentan-1-one was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-6-nitro-3-((2,2,4-trimethylcyclopentylidene)methyl)phenyl)(phenyl) methanone, which was then subjected to reaction and post-treatment described in example 53 to give final product (E)-4,5-dihydroxy-3-methoxy-4-phenyl-6-((2,2,4-trimethylcyclopentylidene)methyl)-3,4-dihydroquinolin-2(1H)-one.
ESI-MS m/z 408.51 [M+H]$^+$.

Example 63

Tetrahydrofuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(3-(3-methoxybut-1-en-1-yl)-2-(methoxymethoxy)-6-nitrophenyl)(phenyl)methanone, which was then subjected to reaction and post-treatment described in example 53 to give final product (E)-4,5-dihydroxy-3-methoxy-4-phenyl-6-(2-(tetrahydrofuran-2-yl)vinyl)-3,4-dihydroquinolin-2(1H)-one.
ESI-MS m/z 382.43 [M+H]$^+$.

Example 64

2-methyldihydrofuran-3(2H)-one was used as a reagent to react with the (3-Benzoyl-2-(methoxymethoxy)-4-nitrobenzyl)phosphonic acid diethyl ester synthesized following Example 53, to give intermediate product (Z)-(2-(methoxymethoxy)-3-((2-methyldihydrofuran-3 (2H)-ylidene)methyl)-6-nitrophenyl)(phenyl)methanone, which was then subjected to reaction and post-treatment described in example 53 to give final product (Z)-4,5-dihydroxy-3-methoxy-6-((2-methyldihydrofuran-3(2H)-ylidene)methyl)-4-phenyl-3,4-dihydroquinolin-2(1H)-one.
ESI-MS m/z 382.43 [M+H]$^+$.

Example 65

Furan-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(3-(2-(furan-2-yl)vinyl)-2-(methoxymethoxy)-6-nitrophenyl)(phenyl)methanone), which was then subjected to reaction and post-treatment described in example 53 to give final product (E)-6-(2-(furan-2-yl)vinyl)-4,5-dihydroxy-3-methoxy-4-phenyl-3,4-dihydroquinolin-2(1H)-one. ESI-MS m/z 378.40 [M+H]$^+$.

Example 66

5-methylfuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-3-(2-(5-methylfuran-2-yl) vinyl)-6-nitrophenyl)(phenyl)methanone, which was then subjected to reaction and post-treatment described in example 53 to give final product (E)-4,5-dihydroxy-3-methoxy-6-(2-(5-methylfuran-2-yl) vinyl)-4-phenyl-3,4-dihydroquinolin-2(1H)-one.
ESI-MS m/z 392.42 [M+H]$^+$.

Example 67

Furan-2,5-dicarbaldehyde was used as a reagent to react with the (3-Benzoyl-2-(methoxymethoxy)-4-nitrobenzyl) phosphonic acid diethyl ester synthesized following Example 53, to give intermediate product (E)-5-(3-benzoyl-2-(methoxymethoxy)-4-nitrostyryl) furan-2-carbaldehyde, which was then subjected to reaction and post-treatment described in example 53 to give final product (E)-5-(2-(4, 5-dihydroxy-3-methoxy-2-oxo-4-phenyl-1,2,3,4-tetrahydroquinolin-6-yl) vinyl) furan-2-carbaldehyde. ESI-MS m/z 406.41 [M+H]$^+$.

Example 68

5-formylfuran-2-carboxylic acid was used as a reagent to react with the (3-Benzoyl-2-(methoxymethoxy)-4-nitrobenzyl)phosphonic acid diethyl ester synthesized following Example 53, to give intermediate product (E)-5-(3-benzoyl-2-(methoxymethoxy)-4-nitrostyryl) furan-2-carboxylic acid, which was then subjected to reaction and post-treatment described in example 53 to give final product (E)-5-(2-(4, 5-dihydroxy-3-methoxy-2-oxo-4-phenyl-1,2,3,4-tetrahydroquinolin-6-yl)vinyl)furan-2-carboxylic acid. ESI-MS m/z 422.41 [M+H]$^+$.

Example 69

3-methylfuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-3-(2-(3-methylfuran-2-yl) vinyl)-6-nitrophenyl)(phenyl)methanone, which was then subjected to reaction and post-treatment described in example 53 to give final product (E)-4,5-dihydroxy-3-methoxy-6-(2-(3-methylfuran-2-yl) vinyl)-4-phenyl-3,4-dihydroquinolin-2(1H)-one. ESI-MS m/z 392.42 [M+H]$^+$.

Example 70

5-ethylfuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(3-(2-(5-ethylfuran-2-yl)vinyl)-2-(methoxymethoxy)-6-nitrophenyl)(phenyl)methanone, which was then subjected to reaction and post-treatment described in example 53 to give final product (E)-6-(2-(5-ethylfuran-2-yl)vinyl)-4,5-dihydroxy-3-methoxy-4-phenyl-3,4-dihydroquinolin-2(1H)-one. ESI-MS m/z 406.45 [M+H]$^+$.

Example 71

1-(5-(hydroxymethyl)furan-2-yl)ethan-1-one was used as a reagent to react with the (3-Benzoyl-2-(methoxymethoxy)-4-nitrobenzyl)phosphonic acid diethyl ester synthesized following Example 53, to give intermediate product (E)-(3-(2-(5-(hydroxymethyl)furan-2-yl) prop-1-en-1-yl)-2-(methoxymethoxy)-6-nitrophenyl)(phenyl)methanone, which was then subjected to reaction and post-treatment described in example 53 to give final product (E)-4,5-dihydroxy-6-(2-(5-(hydroxymethyl)furan-2-yl)prop-1-en-1-yl)-3-methoxy-4-phenyl-3,4-dihydroquinolin-2(1H)-one. ESI-MS m/z 422.45 [M+H]$^+$.

Example 72

(E)-3-(furan-2-yl)acrylaldehyde was used as a reagent to react with the (3-Benzoyl-2-(methoxymethoxy)-4-nitrobenzyl)phosphonic acid diethyl ester synthesized following Example 53, to give intermediate product (3-((1E,3E)-4-(furan-2-yl)buta-1,3-dien-1-yl)-2-(methoxymethoxy)-6-nitrophenyl)(phenyl)methanone, which was then subjected to reaction and post-treatment described in example 53 to give final product 6-((1E,3E)-4-(furan-2-yl) buta-,3-dien-1-yl)-4,5-dihydroxy-3-methoxy-4-phenyl-3,4-dihydroquinolin-2(1H)-one. ESI-MS m/z 404.44 [M+H]$^+$.

Example 73

1-(furan-2-yl)propan-1-one was used as a reagent to react with the (3-Benzoyl-2-(methoxymethoxy)-4-nitrobenzyl) phosphonic acid diethyl ester synthesized following Example 53, to give intermediate product (E)-(3-(2-(furan-2-yl)but-1-en-1-yl)-2-(methoxymethoxy)-6-nitrophenyl)(phenyl)methanone, which was then subjected to reaction and post-treatment described in example 53 to give final product (E)-6-(2-(furan-2-yl)but-1-en-1-yl)-4,5-dihydroxy-3-methoxy-4-phenyl-3,4-dihydroquinolin-2(1H)-one. ESI-MS m/z 406.45 [M+H]$^+$.

Example 74

2,2,5,5-tetramethyldihydrofuran-3(2H)-one was used as a reagent to react with the (3-Benzoyl-2-(methoxymethoxy)-4-nitrobenzyl)phosphonic acid diethyl ester synthesized following Example 53, to give intermediate product (Z)-(2-(methoxymethoxy)-6-nitro-3-((2,2,5,5-tetramethyldihydrofuran-3(2H)-ylidene)methyl)phenyl)(phenyl)methanone, which was then subjected to reaction and post-treatment described in example 53 to give final product (Z)-4,5-dihydroxy-3-methoxy-4-phenyl-6-((2,2,5,5-tetramethyldihydrofuran-3(2H)-ylidene)methyl)-3,4-dihydroquinolin-2(1H)-one. ESI-MS m/z 424.51 [M+H]$^+$.

Example 75

4,5-dimethylfuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(6-amino-3-(2-(4,5-dimethylfuran-2-yl) vinyl)-2-(methoxymethoxy) phenyl)(phenyl)methanone, which was then subjected to reaction and post-treatment described in example 53 to give final product (E)-6-(2-(4,5-dimethylfuran-2-yl) vinyl)-4,5-dihydroxy-3-methoxy-4-phenyl-3,4-dihydroquinolin-2(1H)-one. ESI-MS m/z 406.45 [M+H]$^+$.

Example 76

1-(5-(hydroxymethyl)furan-2-yl)ethan-1-one was used as a reagent to react with the (3-Benzoyl-2-(methoxymethoxy)-4-nitrobenzyl)phosphonic acid diethyl ester synthesized following Example 53, to give intermediate product (E)-(3-(2-(5-(hydroxymethyl)furan-2-yl) prop-1-en-1-yl)-2-(methoxymethoxy)-6-nitrophenyl)(phenyl)methanone, which was then subjected to reaction and post-treatment described in example 53 to give final product (E)-4,5-dihydroxy-6-(2-(5-(hydroxymethyl)furan-2-yl)prop-1-en-1-yl)-3-methoxy-4-phenyl-3,4-dihydroquinolin-2(1H)-one. ESI-MS m/z 422.45 [M+H]$^+$.

Example 77

(E)-3-(furan-2-yl)acrylaldehyde was used as a reagent to react with the (3-Benzoyl-2-(methoxymethoxy)-4-nitrobenzyl)phosphonic acid diethyl ester synthesized following Example 53, to give intermediate product (3-((1E,3E)-4-(furan-2-yl)buta-1,3-dien-1-yl)-2-(methoxymethoxy)-6-nitrophenyl)(phenyl)methanone, which was then subjected to reaction and post-treatment described in example 53 to give final product 6-((1E,3E)-4-(furan-2-yl)buta-1,3-dien-1-yl)-4,5-dihydroxy-3-methoxy-4-phenyl-3,4-dihydroquinolin-2(1H)-one. ESI-MS m/z 404.44 [M+H]$^+$.

Example 78

1-(2,4-dimethylfuran-3-yl)ethan-1-one was used as a reagent to react with the (3-Benzoyl-2-(methoxymethoxy)-4-nitrobenzyl)phosphonic acid diethyl ester synthesized following Example 53, to give intermediate product (E)-(3-(2-(2,4-dimethylfuran-3-yl) prop-1-en-1-yl)-2-(methoxymethoxy)-6-nitrophenyl)(phenyl)methanone, which was then subjected to reaction and post-treatment described in example 53 to give final product (E)-6-(2-(2,4-dimethylfuran-3-yl)prop-1-en-1-yl)-4,5-hydroxy-3-methoxy-4-phenyl-3,4-dihydroquinolin-2(1H)-one. ESI-MS m/z 420.48 [M+H]$^+$.

Example 79

5-chlorofuran-2-carbaldehyde was used as a reagent to react with the (3-Benzoyl-2-(methoxymethoxy)-4-nitrobenzyl)phosphonic acid diethyl ester synthesized following Example 53, to give intermediate product (E)-(3-(2-(5-chlorofuran-2-yl)vinyl)-2-(methoxymethoxy)-6-nitrophenyl)(phenyl)methanone, which was then subjected to reaction and post-treatment described in example 53 to give final product (E)-6-(2-(5-chlorofuran-2-yl)vinyl)-4,5di-hydroxy-3-methoxy-4-phenyl-3,4-dihydroquinolin-2(1H)-one. ESI-MS m/z 412.84 [M+H]$^+$.

Example 80

1-(furan-2-yl)hexan-1-one was used as a reagent to react with the (3-Benzoyl-2-(methoxymethoxy)-4-nitrobenzyl) phosphonic acid diethyl ester synthesized following Example 53, to give intermediate product (E)-(3-(2-(furan-2-yl)hept-1-en-1-yl)-2-(methoxymethoxy)-6-nitrophenyl)(phenyl)methanone, which was then subjected to reaction and post-treatment described in example 53 to give final product (E)-6-(2-(furan-2-yl)hept-1-en-1-yl)-4,5-dihydroxy-3-methoxy-4-phenyl-3,4-dihydroquinolin-2(1H)-one. ESI-MS m/z 448.53 [M+H]$^+$.

Example 81

1-(2,5-dimethylfuran-3-yl)ethan-1-one was used as a reagent to react with the (3-Benzoyl-2-(methoxymethoxy)-4-nitrobenzyl)phosphonic acid diethyl ester synthesized following Example 53, to give intermediate product (E)-(3-(2-(2,5-dimethylfuran-3-yl)prop-1-en-1-yl)-2-(methoxymethoxy)-6-nitrophenyl) (phenyl)methanone, which was then subjected to reaction and post-treatment described in example 53 to give final product (E)-6-(2-(2, 5-dimethylfuran-3-yl) prop-1-en-1-yl)-4,5-dihydroxy-3-methoxy-4-phenyl-3,4-dihydroquinolin-2(1H)-one.
ESI-MS m/z 420.48 [M+H]$^+$.

Example 82

1-(5-(methoxymethyl)furan-2-yl)ethan-1-one was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-3-(2-(5-(methoxymethyl) furan-2-yl) prop-1-en-1-yl)-6-nitrophenyl)(phenyl)methanone, which was then subjected to reaction and post-treatment described in example 53 to give final product (E)-4,5-dihydroxy-3-methoxy-6-(2-(5-(methoxymethyl)furan-2-yl)prop-1-en-1-yl)-4-phenyl-3,4-dihydroquinolin-2(1H)-one. ESI-MS m/z 436.48 [M+H]$^+$.

Example 83

2-methylfuran-3-carbaldehyde was used as a reagent to react with the (3-Benzoyl-2-(methoxymethoxy)-4-nitrobenzyl)phosphonic acid diethyl ester synthesized following Example 53, to give intermediate product (E)-(2-(methoxymethoxy)-3-(2-(2-methylfuran-3-yl) vinyl)-6-nitrophenyl)(phenyl)methanone, which was then subjected to reaction and post-treatment described in example 53 to give final product (E)-4,5-dihydroxy-3-methoxy-6-(2-(2-methylfuran-3-yl)vinyl)-4-phenyl-3,4-dihydroquinolin-2(1H)-one. ESI-MS m/z 392.42 [M+H]$^+$.

Antiviral Activity Assay

The compound was tested for antiviral activity based on cytopathic effects, with ribavirin as a positive control. The specific experimental scheme is as follows.

Virus Proliferation

The test virus was inoculated on the sensitive cells of the virus, and the cells were placed in a serum-free 1640 medium. The cells were then cultured at the temperature of 5% carbon dioxide and 37° C. until 90% of the cells were infected with the virus. After lesion, the cells were quantitatively divided and stored in the −80° C. refrigerator for later use.

Virus Infectivity Titre

Cell maintenance solution was used to conduct a series of gradient dilution of proliferating virus at 10 times the ratio. The virus was inoculated on hep-2 in 96-well plates and repeated vertically for 3 times as a control test. The cells were then cultured at a temperature of 37° C. with 5% carbon dioxide. After two to three days, the cell support fluid in the pore plate were absorbed and discarded, and 100 μL of 1% neutral red was added to the pore plate again. The staining solution was stained for 2 hours at 37° C., then the staining solution was absorbed and discarded, and the eluent was bleached at 37° C. for 10 minutes. OD value of the tested plate was measured with an enzyme reader at a wavelength of about 540 nm, and the lesion rate and cell specific distance were calculated by specific formula. The dilution index of the lesion rate with the cell specific distance higher than 50% was added together, and the $TCID_{50}$ value of the virus was calculated by Reed-Muench method as $10^{-5.5}$/mL.

Cell survival rate=(OD value of each group−OD value of blank control group)/(OD value of normal cells−OD value of blank control group)

Cytopathic rate=1−cell survival rate

Cell specific distance=(>50% lesion rate−50%)/ (>50% lesion rate−>50% lesion rate)

Virus Inhibition Activity Assay

Preparation of monolayer cells: the cells were degraded by trypsin and placed in 96 microporous plates. The cells could be cultured into monolayer cells for use.

The tested compound were prepared and reserved according to the specification of 100 μL/tube. According to the molecular weight of test compound, dissolve each tube with a suitable solvent of 10 μL. The compound was diluted 10 times in a 2 percent cell culture solution (200 μL), with 10 gradients. They were then inoculated in 96 microporous plates containing monolayer cells. The 11th column was set as blank control group of virus, and the 12th column was set as blank control group of cells. The plate was then cultured at the temperature of 37° C. with 5% carbon dioxide. The cytopathic condition should be observed every day. When the virus control lesion was 90%, the cells in the pore plate were absorbed and discarded, and 100 μL of 1% neutral red was added to the pore plate again. The staining solution was stained for 2 hours at 37° C., then the staining solution was absorbed and discarded, and the eluent was bleached at 37° C. for 10 minutes. OD value of the tested plate was measured with an enzyme reader at a wavelength of about 540 nm. Finally, the cytologic lesion rate and cell survival rate were calculated by formula, and the Reed-Muench method was used to calculate the compound's 50% inhibitory concentration on virus ($EC_{50}$) and 50% toxic concentration on cell ($TC_{50}$).

The data for the inhibitory activity against viruses are shown as follows:

| Compd | RSV (EC50) μM | HSV (EC50) μM | EV71 (EC50) μM | H1N1 (EC50) μM | H7N9 (EC50) μM | CoxB3 (EC50) μM | HIV (EC50) μM | TC50 μM |
|---|---|---|---|---|---|---|---|---|
| 1 | B | C | B | C | B | B | B | ++ |
| 2 | C | D | B | B | A | C | D | ++ |
| 3 | D | D | C | D | C | C | E | ++ |
| 4 | D | C | B | A | B | B | C | +++ |
| 5 | C | B | C | B | C | B | C | +++ |
| 9 | C | C | B | B | C | D | D | ++ |
| 10 | D | C | B | C | D | C | E | ++ |
| 12 | C | B | D | A | B | C | D | +++ |
| 13 | C | B | D | C | B | C | B | +++ |
| 17 | C | B | D | B | D | B | D | ++ |
| 19 | C | C | C | D | B | B | C | ++ |
| 22 | D | C | B | C | C | B | C | +++ |
| 25 | D | C | B | B | A | B | B | +++ |
| 29 | B | D | C | C | B | B | B | ++ |
| 32 | B | C | D | C | B | C | B | ++ |
| 36 | C | D | C | B | B | B | C | +++ |
| 40 | D | B | B | B | C | D | C | ++ |
| 43 | A | C | B | C | B | C | C | ++ |
| 47 | C | D | E | C | C | B | D | +++ |
| 49 | D | C | C | B | C | C | D | +++ |
| 733 | B | C | C | D | D | C | B | ++ |
| 734 | C | C | B | D | C | C | B | +++ |
| 735 | C | D | D | B | C | D | B | ++ |
| 736 | B | D | C | C | B | D | C | ++ |
| 737 | B | C | C | D | E | B | C | ++ |
| 743 | C | D | C | B | E | C | B | + |
| 744 | D | C | D | D | B | E | C | ++ |
| 745 | A | B | C | C | D | A | C | +++ |
| 746 | B | C | B | B | D | E | E | ++ |
| 747 | A | C | D | B | D | C | D | ++ |
| 748 | D | C | B | D | E | B | C | +++ |
| 751 | A | D | B | C | D | B | B | ++ |
| 752 | C | D | C | E | C | C | D | ++ |
| 753 | B | C | D | A | B | D | C | +++ |
| 754 | C | E | C | B | B | D | A | +++ |
| 758 | B | B | D | C | C | C | B | +++ |
| 759 | B | A | E | D | D | B | C | + |
| 760 | C | B | B | D | E | E | D | + |
| 764 | C | B | B | C | A | D | E | +++ |
| 773 | D | C | C | E | D | C | B | ++ |
| 775 | A | D | C | B | E | B | B | ++ |
| 781 | B | D | D | B | C | D | C | +++ |
| 899 | E | E | E | A | B | C | C | +++ |
| 914 | B | B | A | C | D | C | D | ++ |
| 916 | C | E | B | B | E | E | C | + |
| 919 | D | D | C | B | B | A | B | ++ |
| 920 | C | C | D | C | D | B | D | ++ |
| 924 | B | B | D | D | C | E | D | +++ |
| 925 | D | C | B | E | E | C | B | ++ |
| 926 | C | C | B | D | D | D | B | ++ |
| 930 | C | B | E | C | C | B | C | +++ |
| 939 | C | B | A | D | B | B | C | ++ |
| 940 | E | E | C | E | A | D | D | ++ |
| 944 | A | D | D | D | D | C | C | + |
| 947 | B | A | B | D | C | B | B | ++ |
| 948 | B | C | C | D | C | C | D | ++ |

In the table, "A" means the compound concentration is less than 0.05 μM, "B" means the compound concentration is 0.05-5 μM, "C" means the compound concentration is 5-50 μM, and "D" means the compound concentration is 50-120 μM. "E" means more than 120 μM; "++++" means $TC_{50}$ is more than 300 μM, "+++" means $TC_{50}$ is between 100-300 μM, "++" means $TC_{50}$ is between 50-100 μM, "+" means $TC_{50}$ is between 10 to 50 μM.

The activity test shows that the compound has a broad spectrum of antiviral activity, and the activity is stronger than or equal to the positive drug, showing a good application prospect.

The invention claimed is:

1. A method for treating a viral disease, the method comprising administering to a subject a therapeutically effective amount of a pharmaceutical composition, wherein the viral disease is caused by respiratory syncytial virus (RSV), herpes simplex virus (HSV), enterovirus 71 (EV71), Coxsackie B virus, influenza virus (H1N1, H7N9), human immunodeficiency virus (HIV), or combinations thereof, wherein the pharmaceutical composition comprises a compound, or the tautomer, or the stereoisomer, or the racemate, or the nonequal mixture of enantiomers, or the geometric isomer, or the pharmaceutically acceptable salt thereof, wherein the compound has one of the following structures:
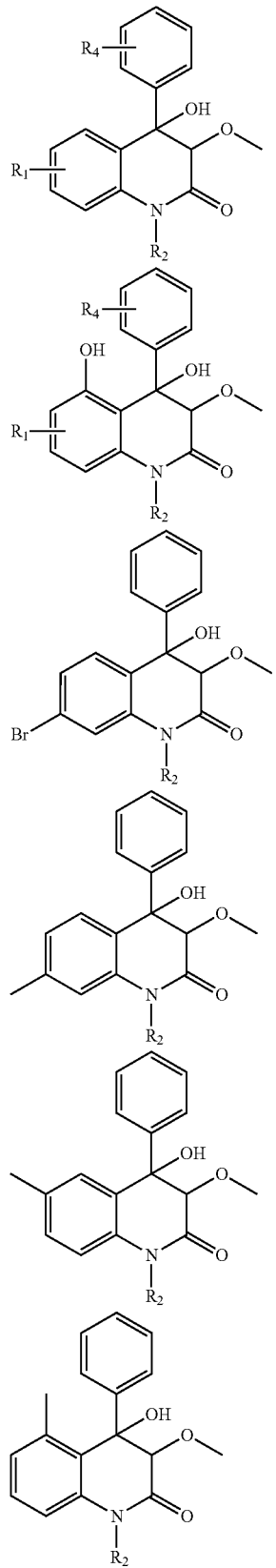
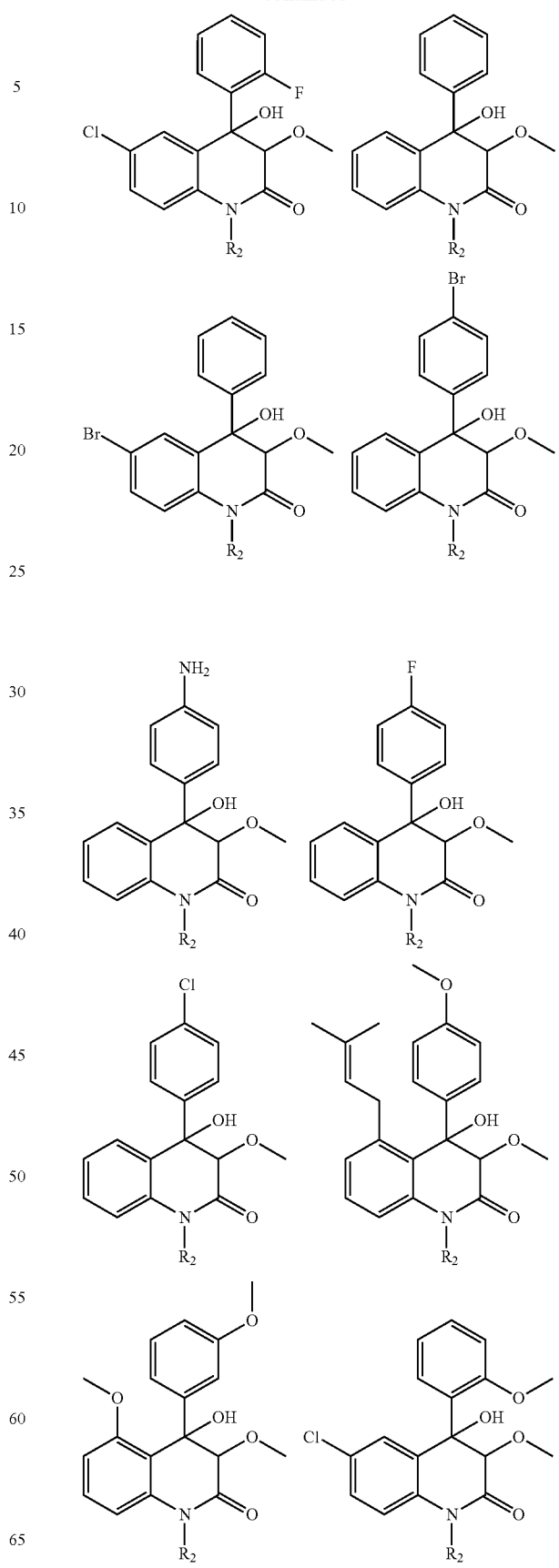
-continued 171
-continued
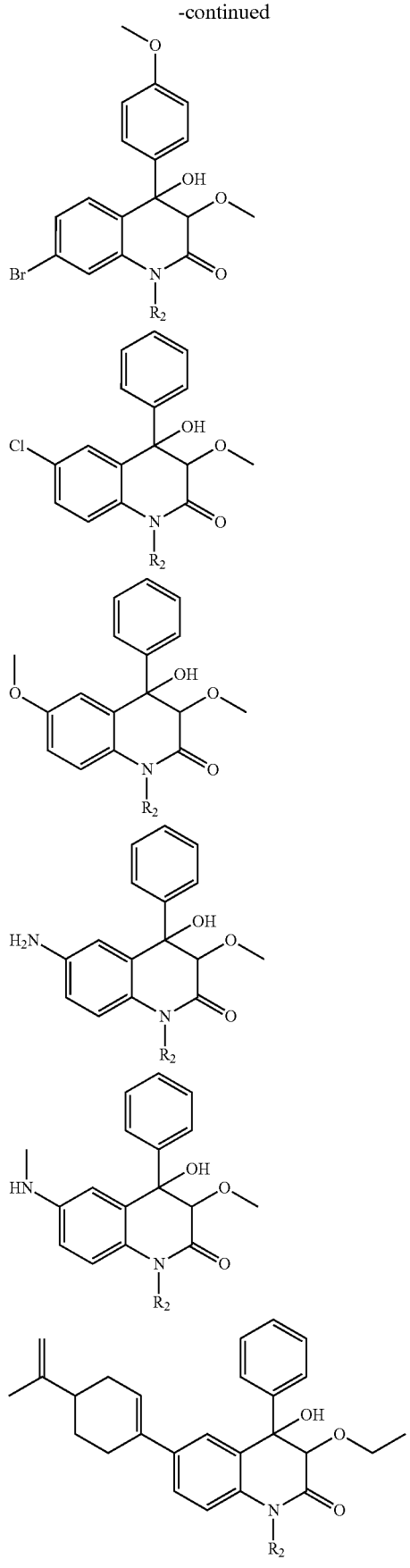
172
-continued
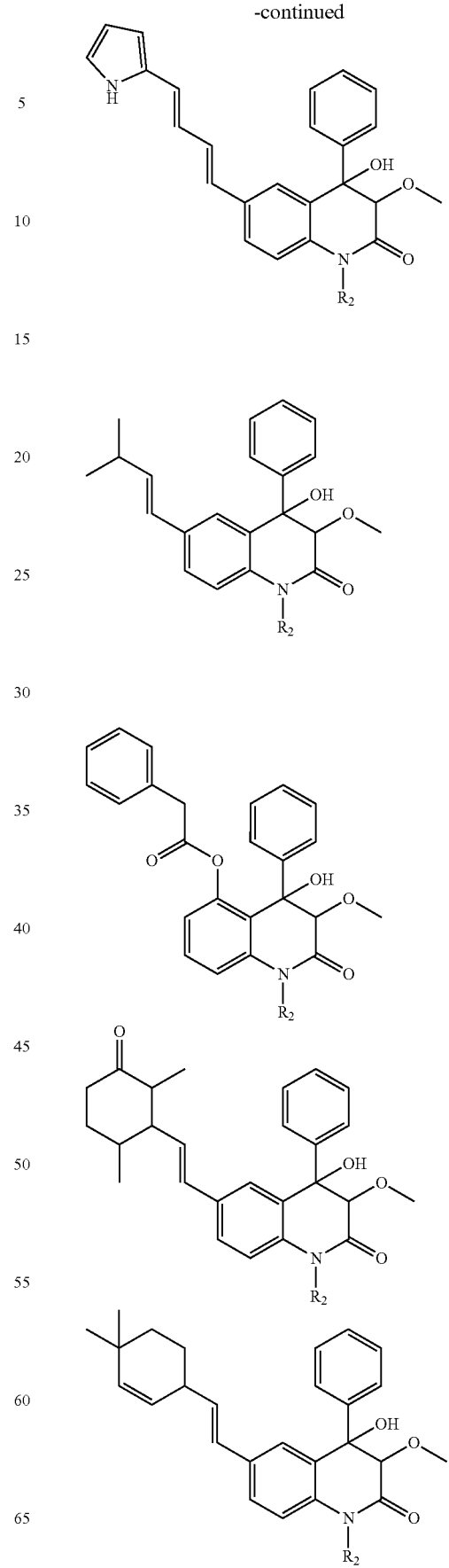

173
-continued
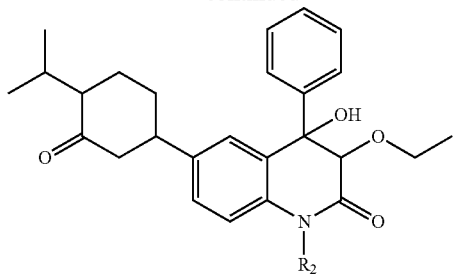
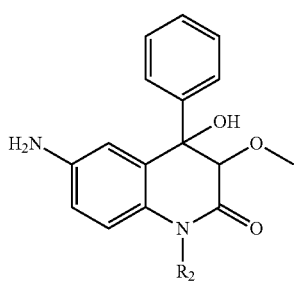
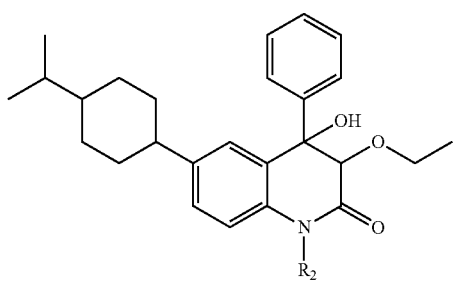
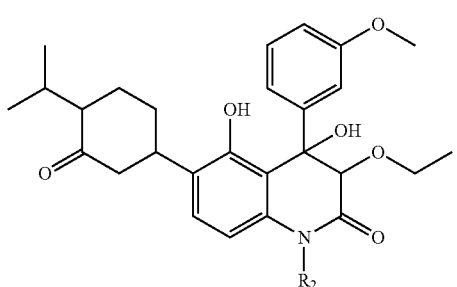
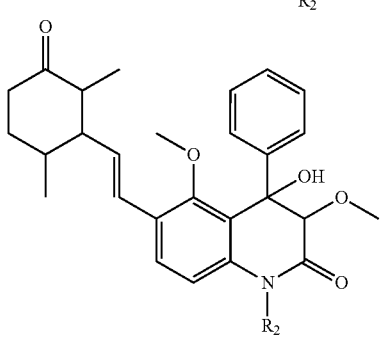
174
-continued
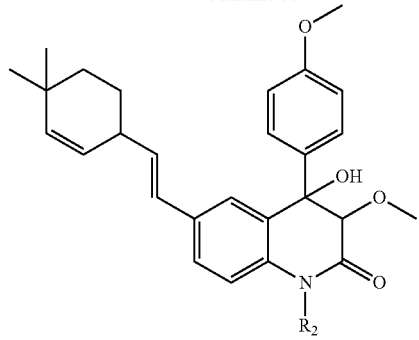
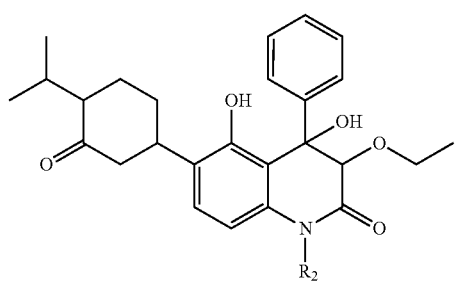
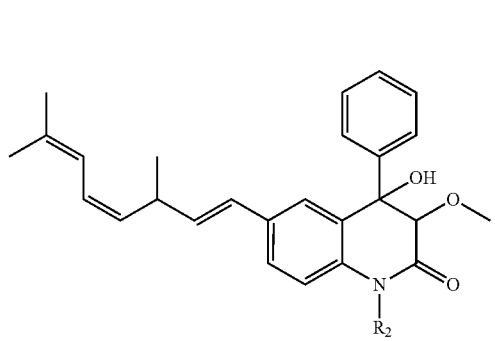
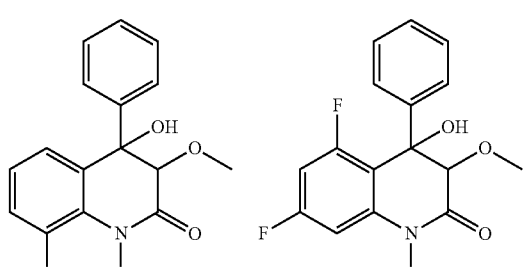
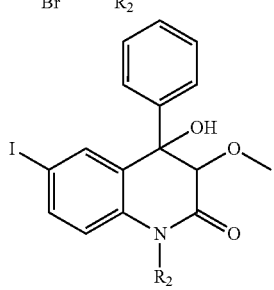

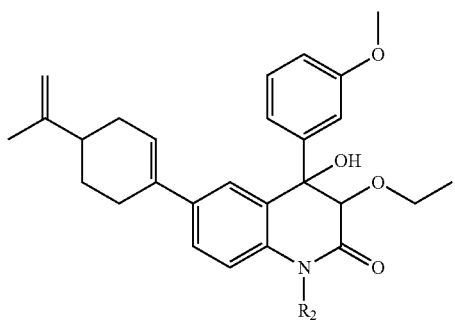
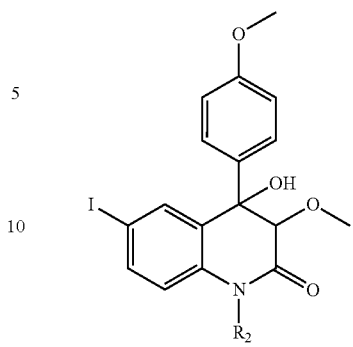
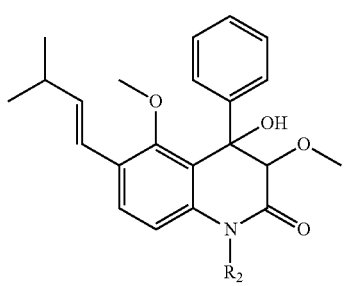
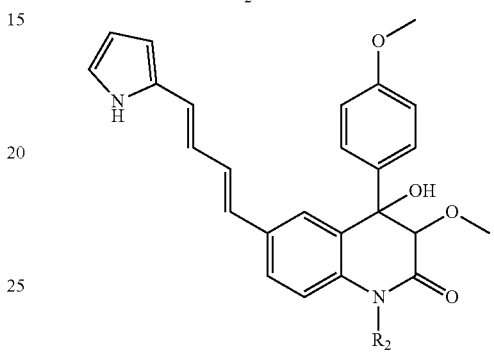
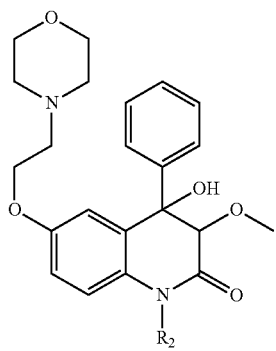
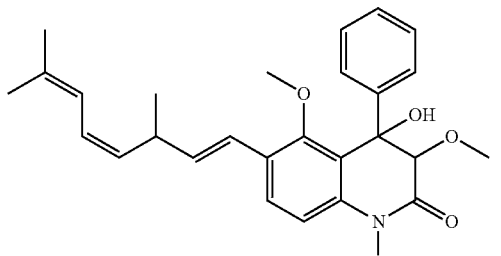
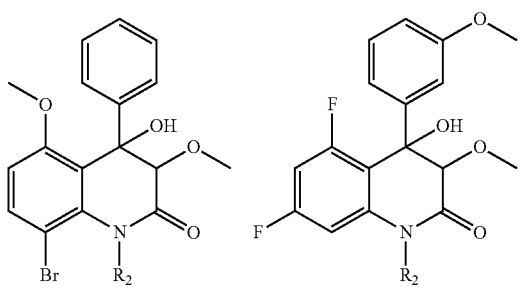
wherein R₂ is selected from following substituents:
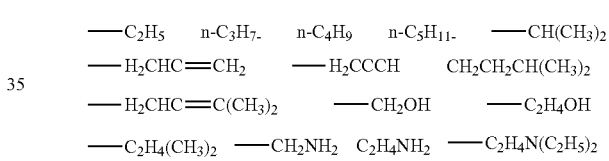
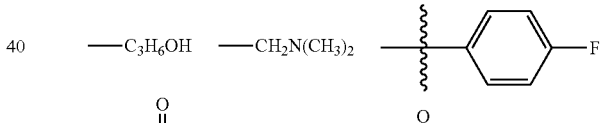
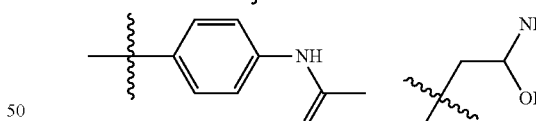
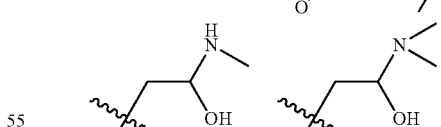
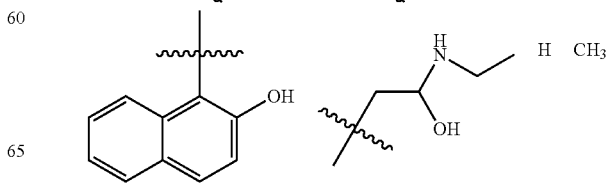

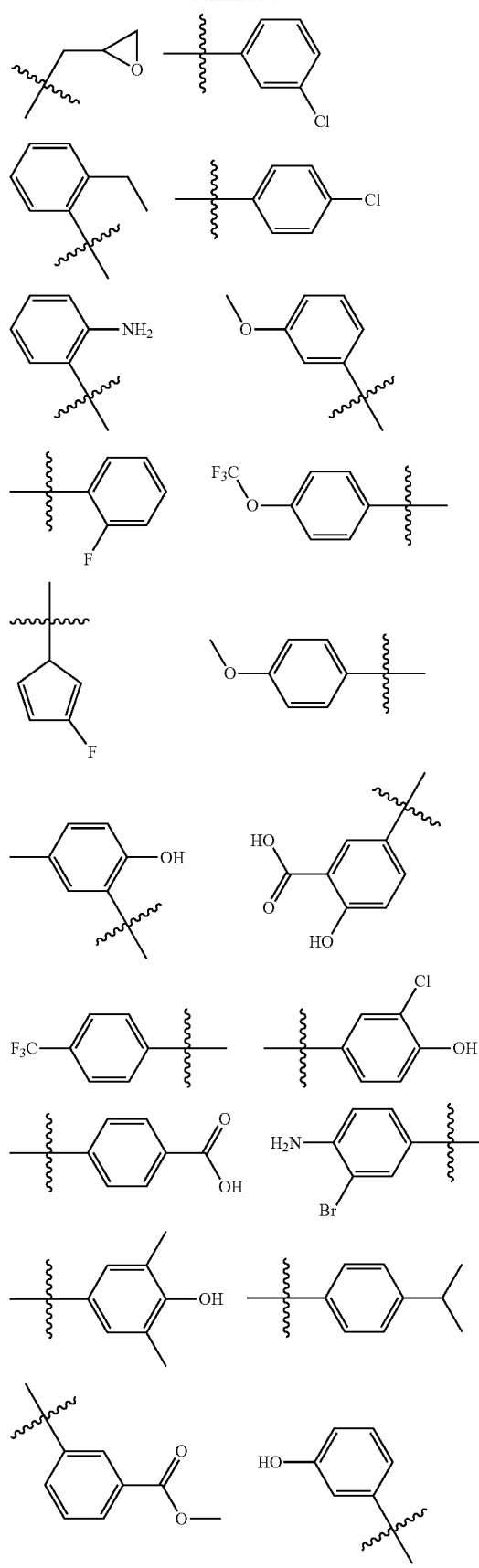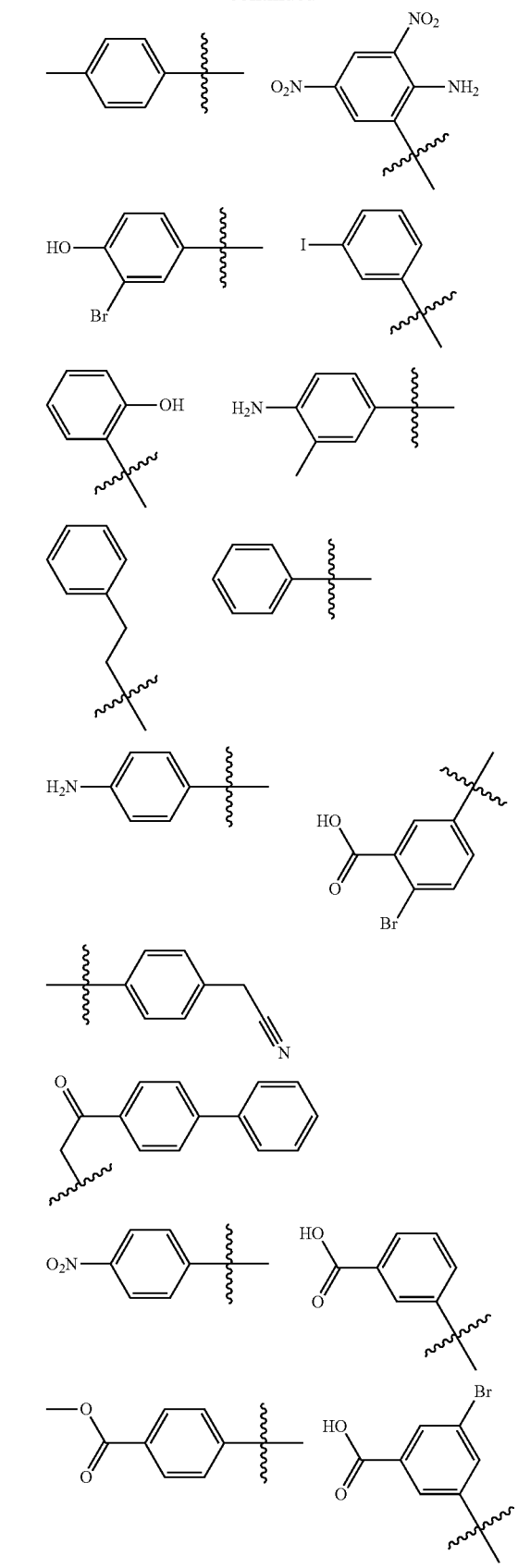

-continued
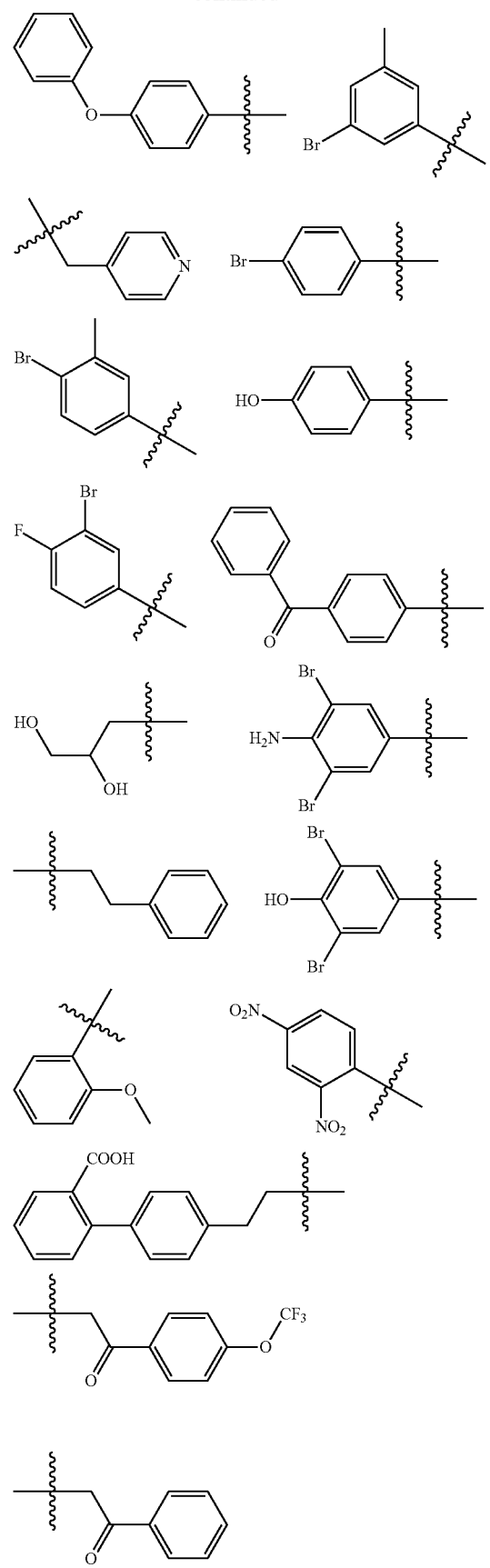
-continued
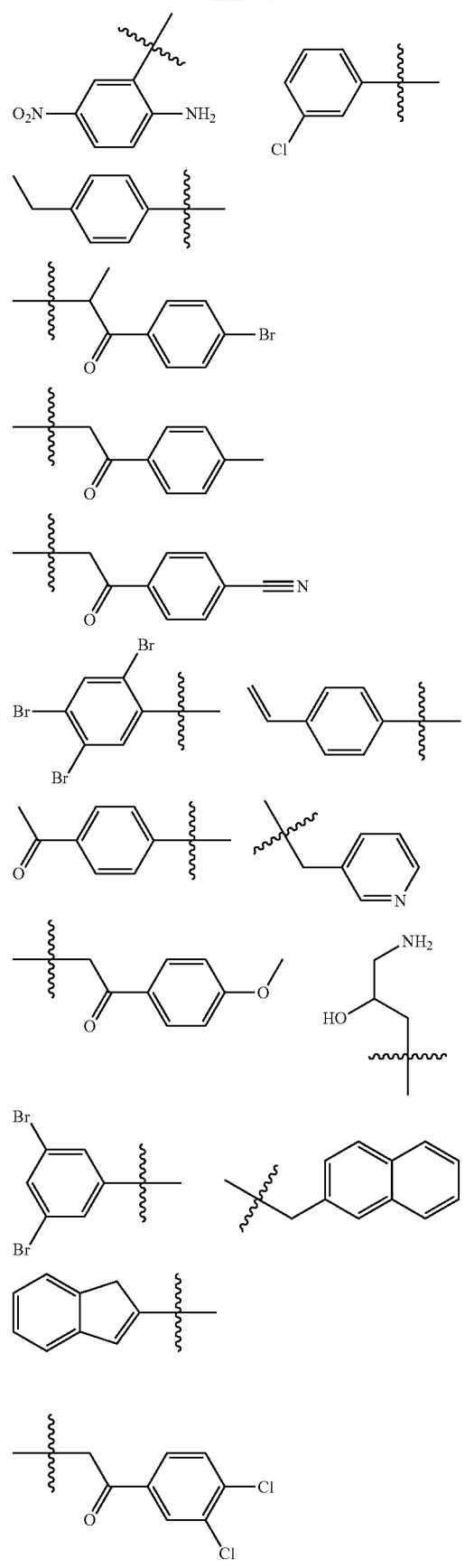

-continued
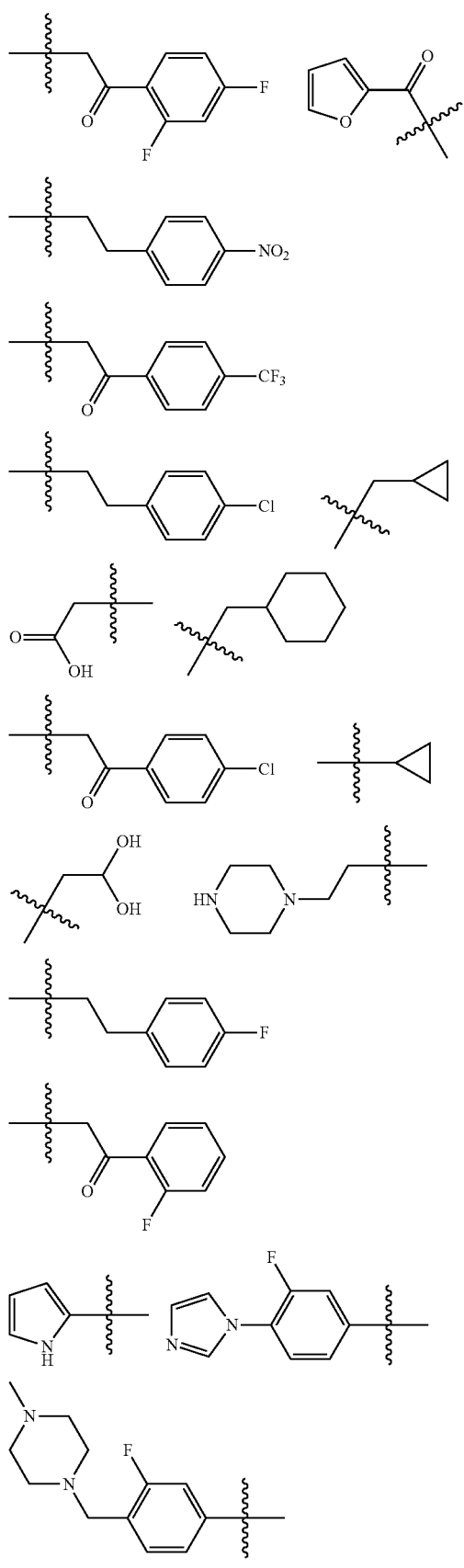
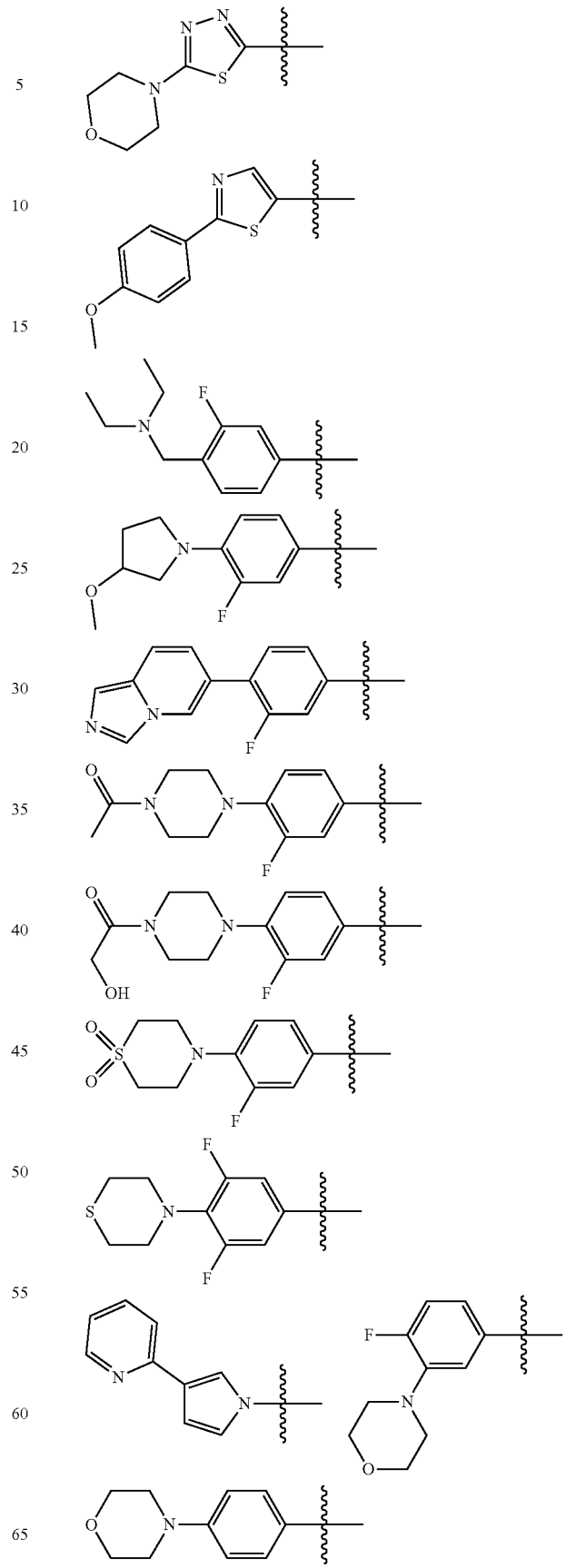

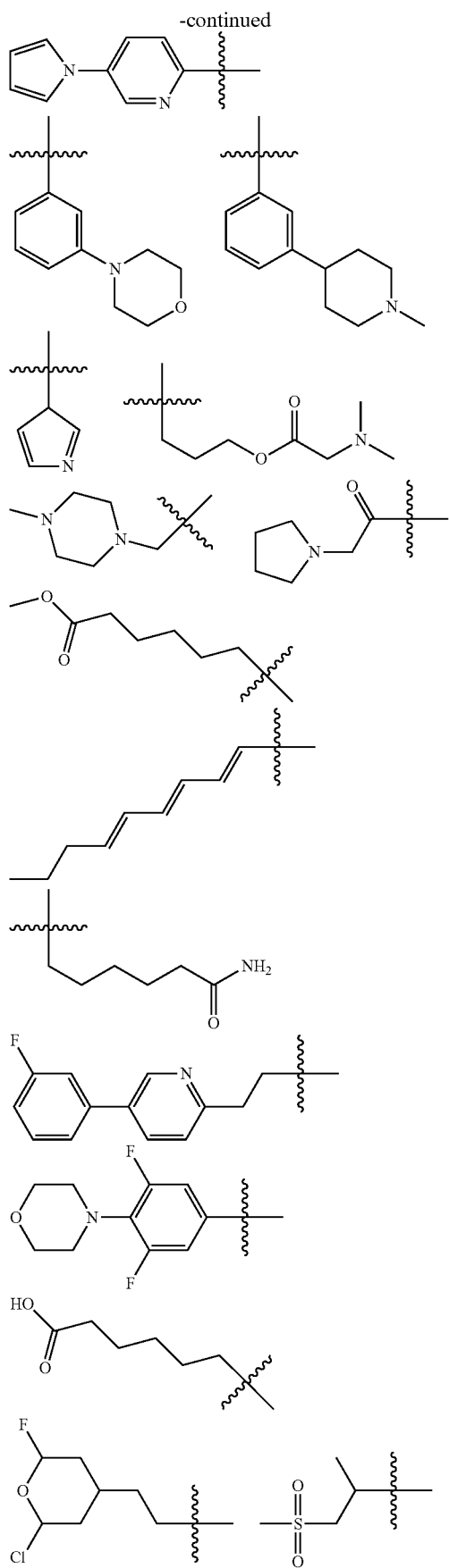
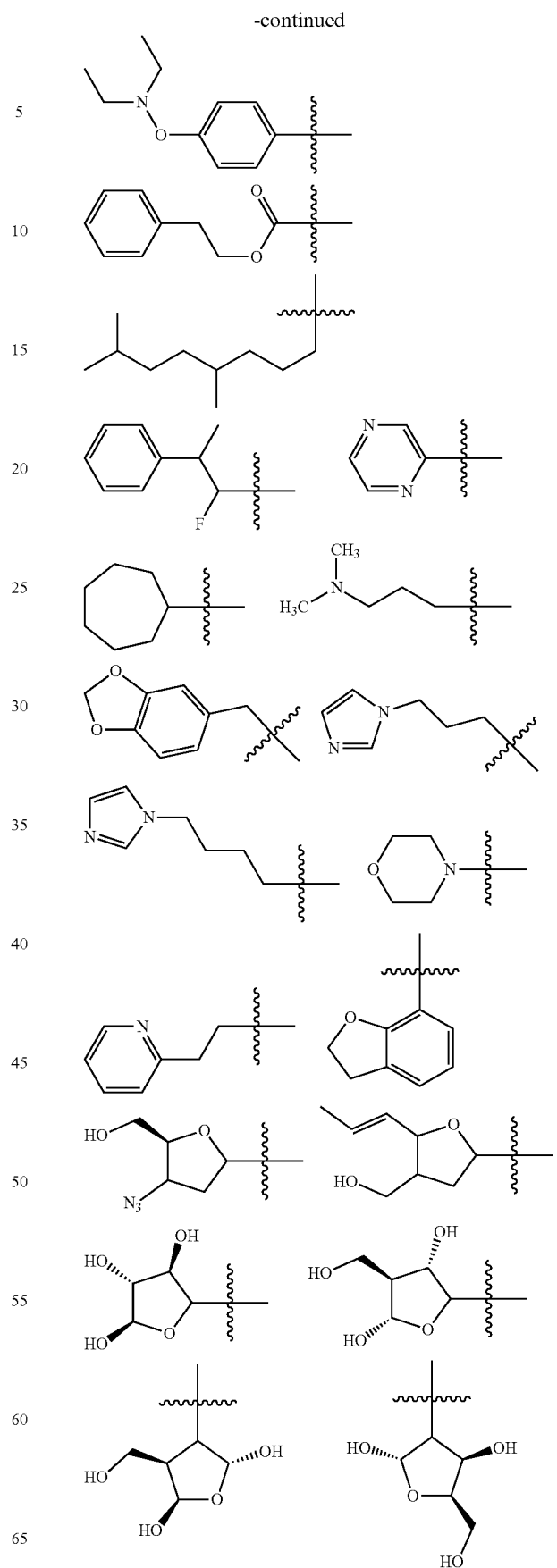

-continued

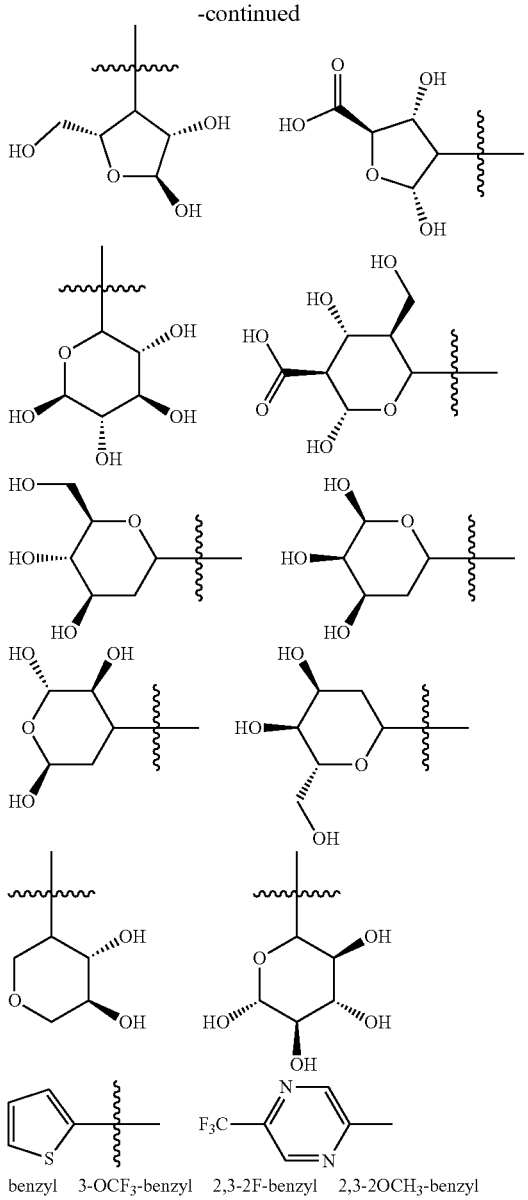

benzyl 3-OCF$_3$-benzyl 2,3-2F-benzyl 2,3-2OCH$_3$-benzyl
2-OCF$_3$-benzyl 3-C(CH$_3$)$_3$-benzyl 2-CH$_3$-benzyl 3-NO$_2$-benzyl
2,4-2F-benzyl 2,4-2OCH$_3$-benzyl 2,3-2F-benzyl
2,5-2OCH$_3$-benzyl 2-F-benzyl 3-COOH-benzyl
2,4-2F-benzyl 2,6-2OCH$_3$-benzyl 3-CH$_3$-benzyl
4-OCF$_3$-benzyl 2-Cl-benzyl 3-COOCH$_3$-benzyl 2,5-2F-benzyl
3,4-2CH$_3$-benzyl 3-OCF$_3$-benzyl 4-NO$_2$-benzyl 2-Br-benzyl
3-COOC$_2$H$_5$-benzyl 2,6-2F-benzyl 3,5-2CH$_3$-benzyl
3-F-benzyl 4-C(CH$_3$)$_3$-benzyl 2-I-benzyl 3-SO$_2$CH$_3$-benzyl
3,4-2F-benzyl 2,3-2Cl-benzyl 3-Cl-benzyl 4-COOH-benzyl
2-CN-benzyl 3-CH$_2$Br-benzyl 3,5-2F-benzyl 2,4-2Cl-benzyl
3-Br-benzyl 4-COOCH$_3$-benzyl 2-CF$_3$-benzyl 4-CH$_3$-benzyl
2,3,4-3F-benzyl 2,5-2Cl-benzyl 3-I-benzyl 4-COOC$_2$H$_5$-benzyl
2-OCF$_3$-benzyl 4-OCF$_3$-benzyl 2,4,5-3F-benzyl 2,6-2Cl-benzyl
3-CN-benzyl 4-SO$_2$CH$_3$-benzyl 2-NO$_2$-benzyl 4-F-benzyl
2,3,5-3F-benzyl 3,4-2Cl-benzyl 3-CF$_3$-benzyl 4-CH$_2$Br-benzyl
2-C(CH$_3$)$_3$-benzyl 4-Cl-benzyl 2,3,6-3F-benzyl 3,5-2Cl-benzyl
2,3,5,6-4F-benzyl 2-F-3-Cl-benzyl 2-COOH-benzyl 4-Br-benzyl
2,4,6-3F-benzyl 2-F-3-Cl-benzyl 2,3,4,5,6-5F-benzyl
2-Cl-4-F-benzyl 2-COOCH$_3$-benzyl 4-I-benzyl
2,3,4,5-4F-benzyl 2-F-3-Br-benzyl 2,3-2CF$_3$-benzyl
3-F-4-OCH$_3$-benzyl 2-COOC$_2$H$_5$-benzyl 4-CN-benzyl
3,4,5-3F-benzyl 3-CF$_3$-5-CF$_3$-benzyl 2,4-2CF$_3$-benzyl
3-Cl-5-F-benzyl 2-SO$_2$CH$_3$-benzyl 4-CF$_3$-benzyl
2,4,5,6-4F-benzyl 3-Cl-4-F-benzyl 2,5-2CF$_3$-benzyl
2-Br-5-F-benzyl 2,6-2CF$_3$-benzyl 2-CN-5-F-benzyl
3,4-2CF$_3$-benzyl 2-Cl-5-CF$_3$-benzyl 3,5-2CF$_3$-benzyl;

wherein R$_1$ and R$_4$ are selected from following substitutions:

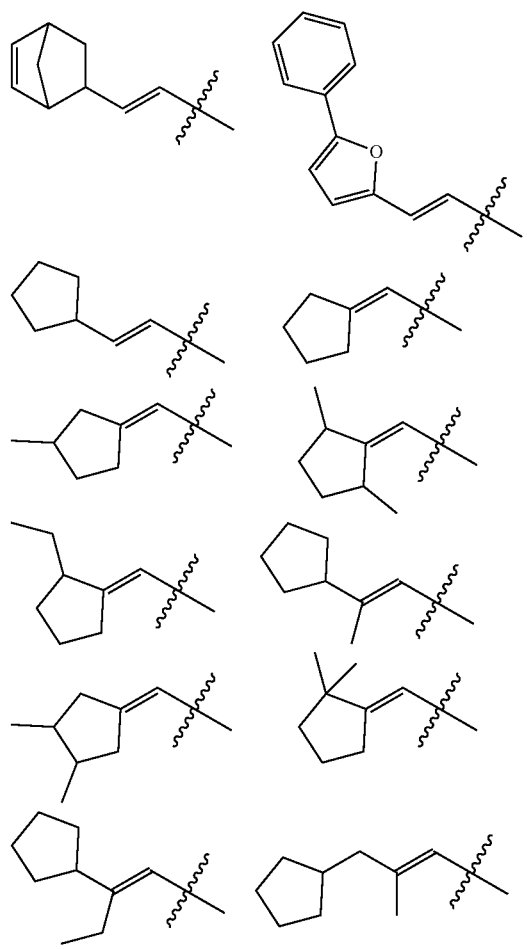

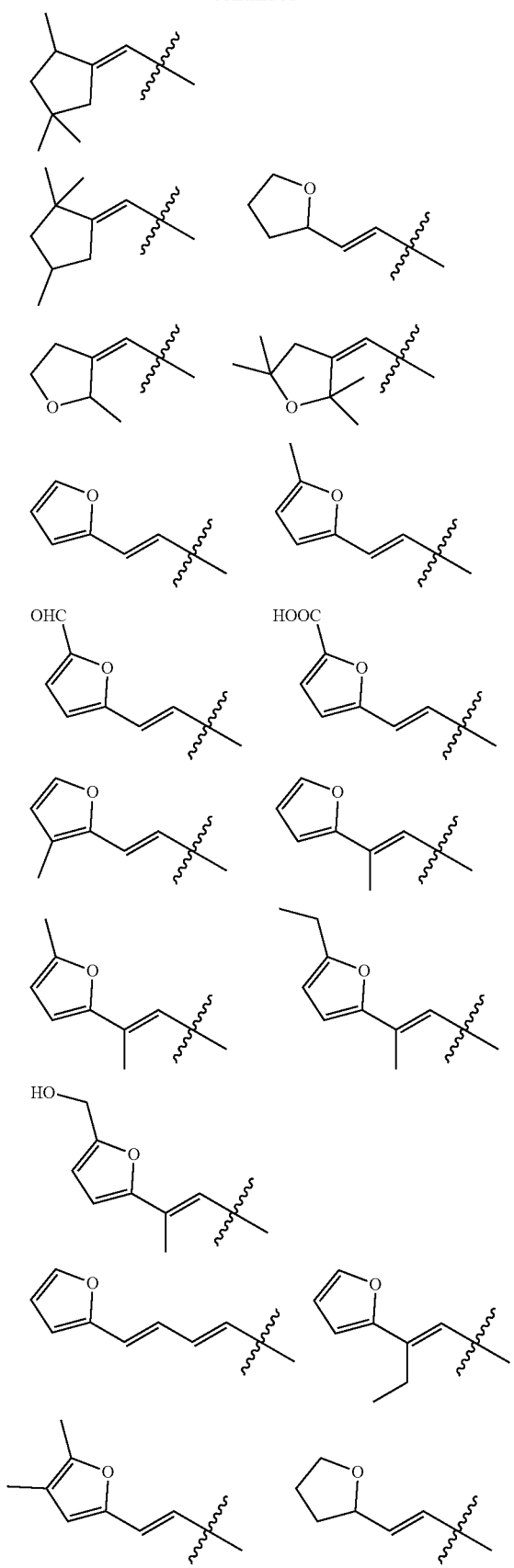
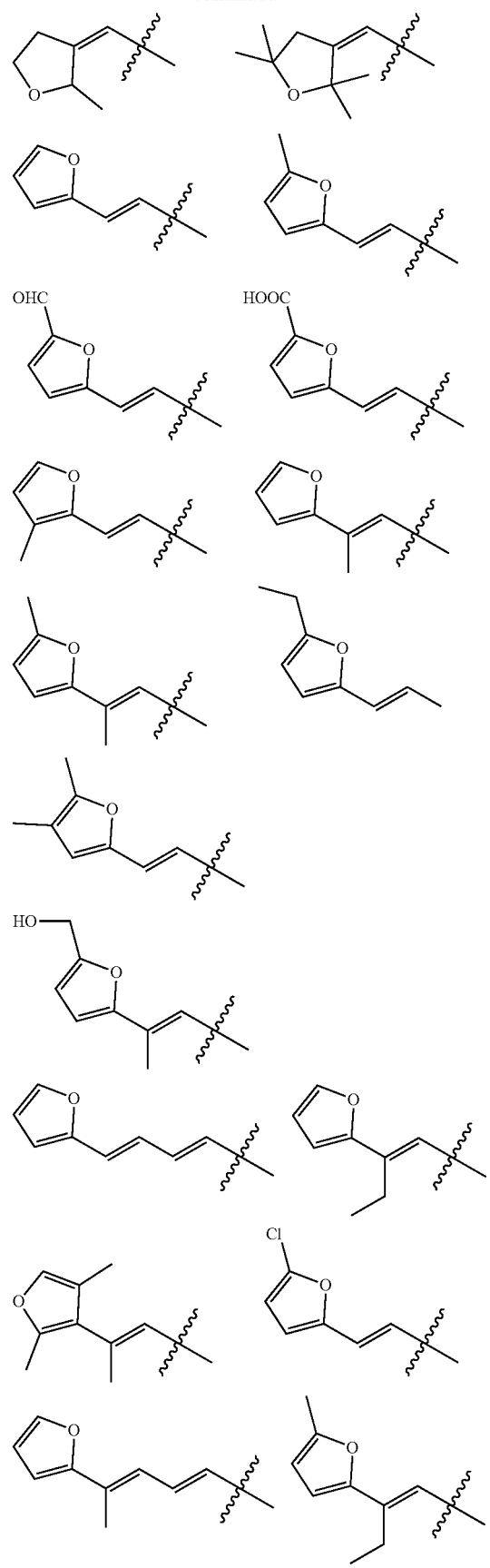

-continued
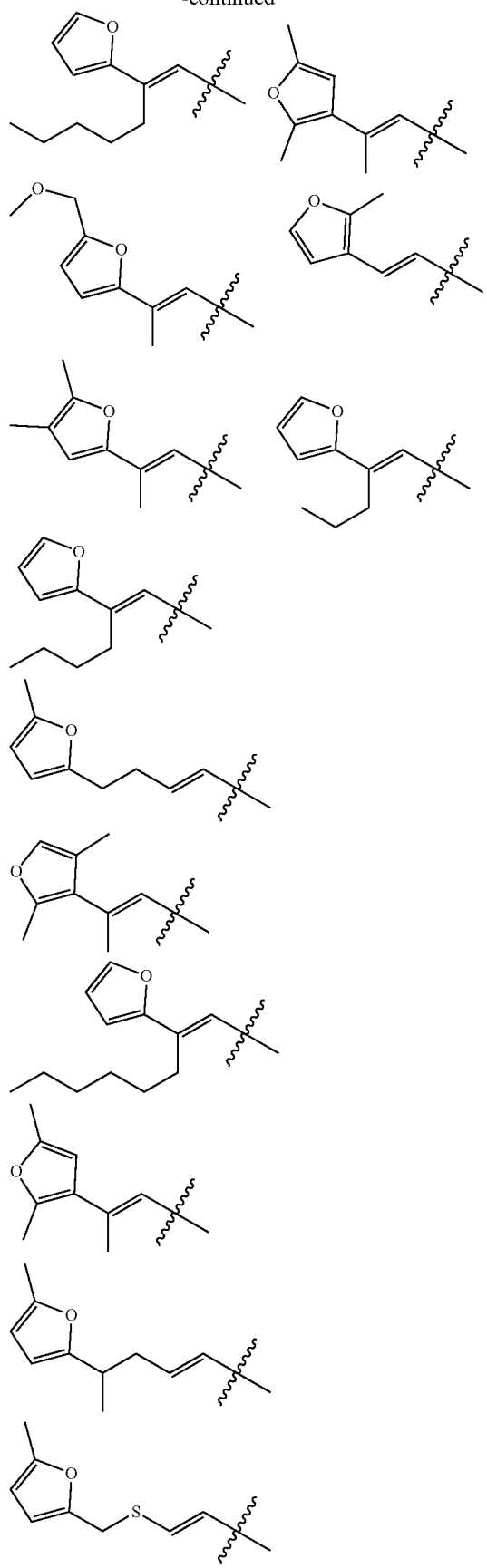
-continued
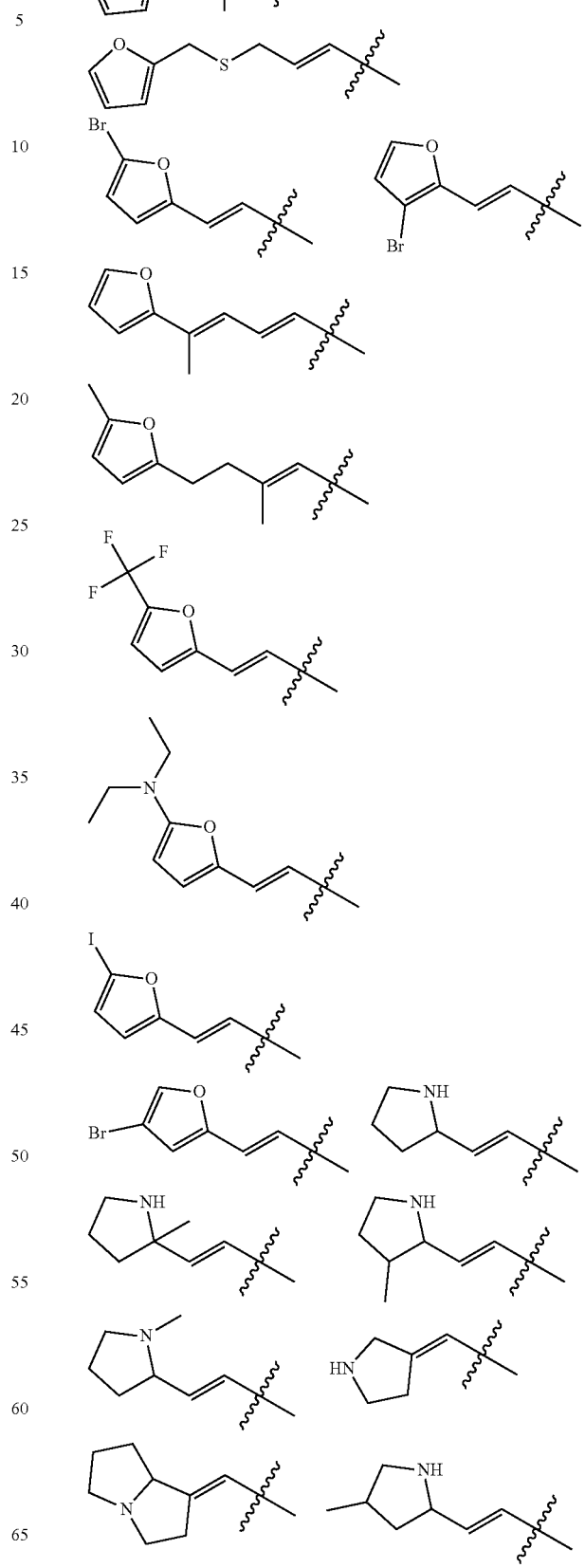

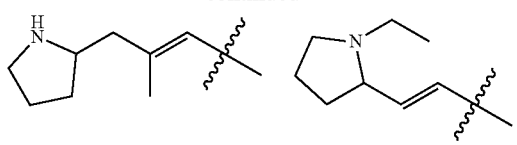
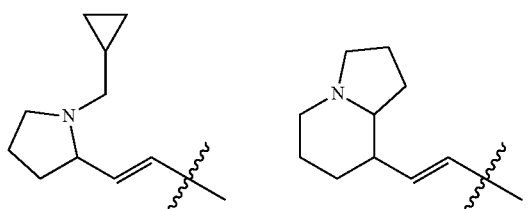
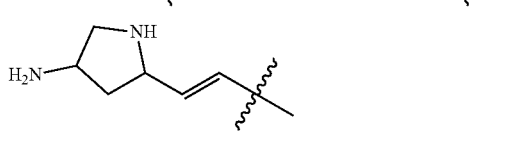
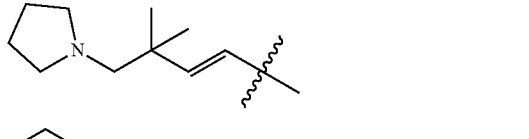
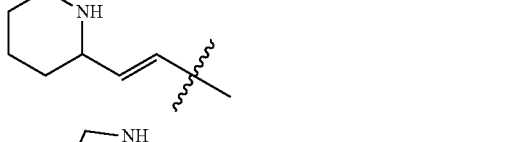
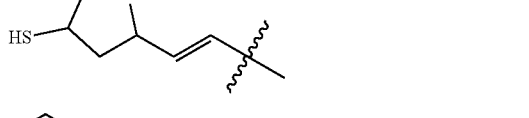
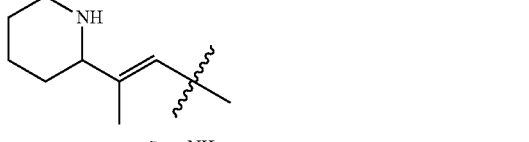
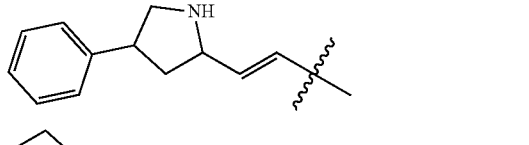
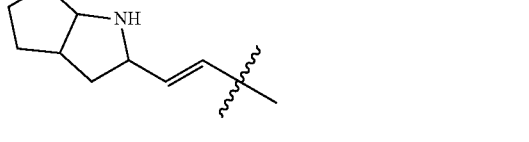
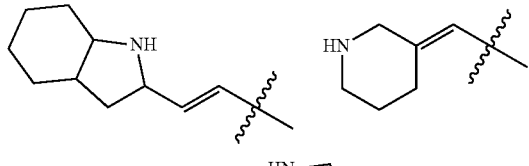
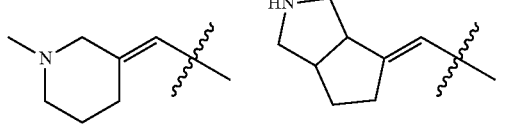
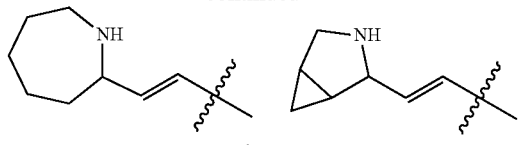
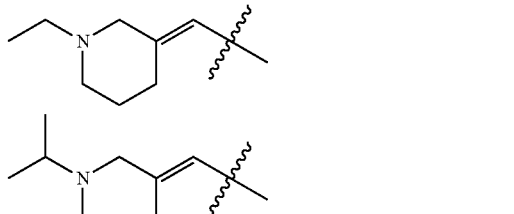
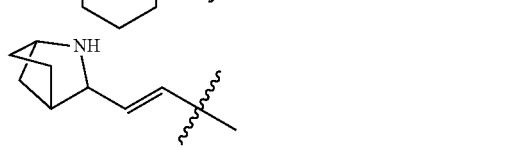
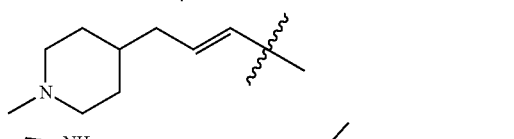
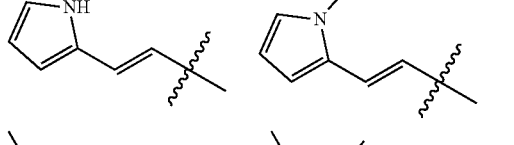
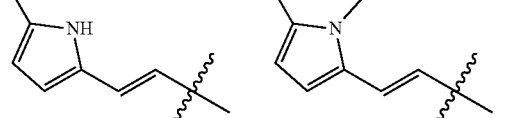
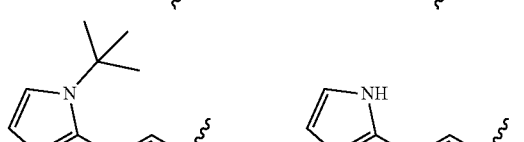
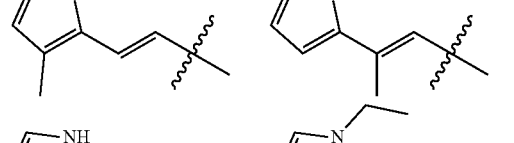
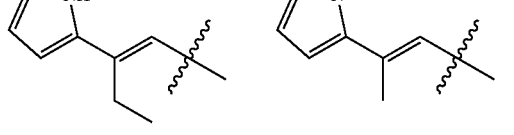

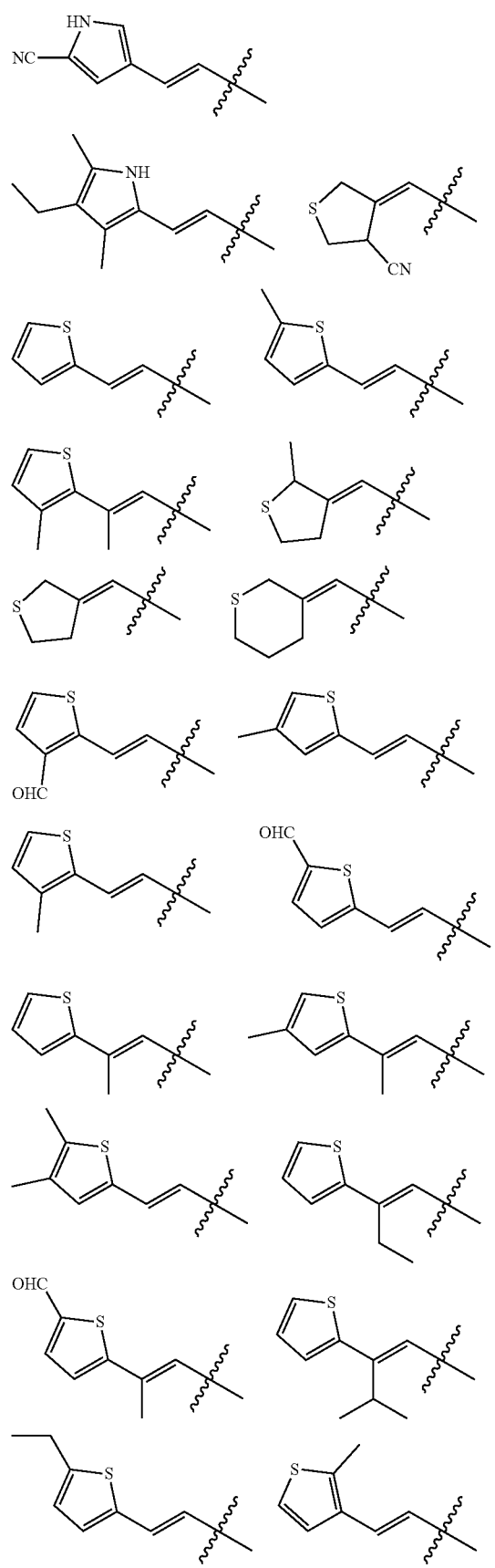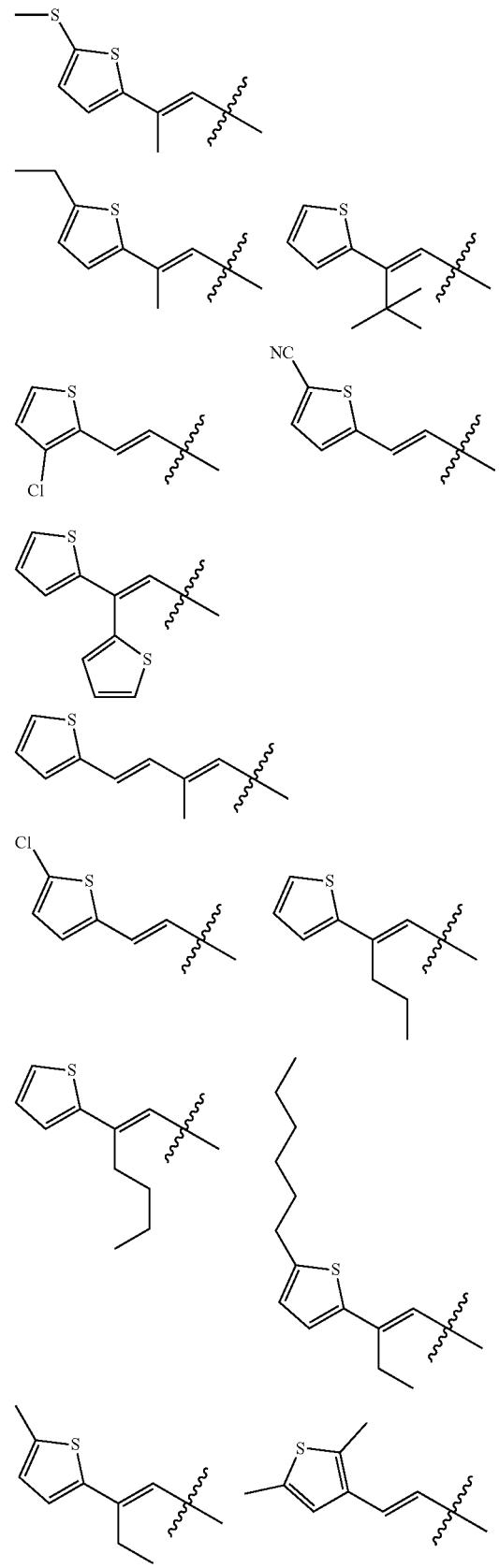

-continued

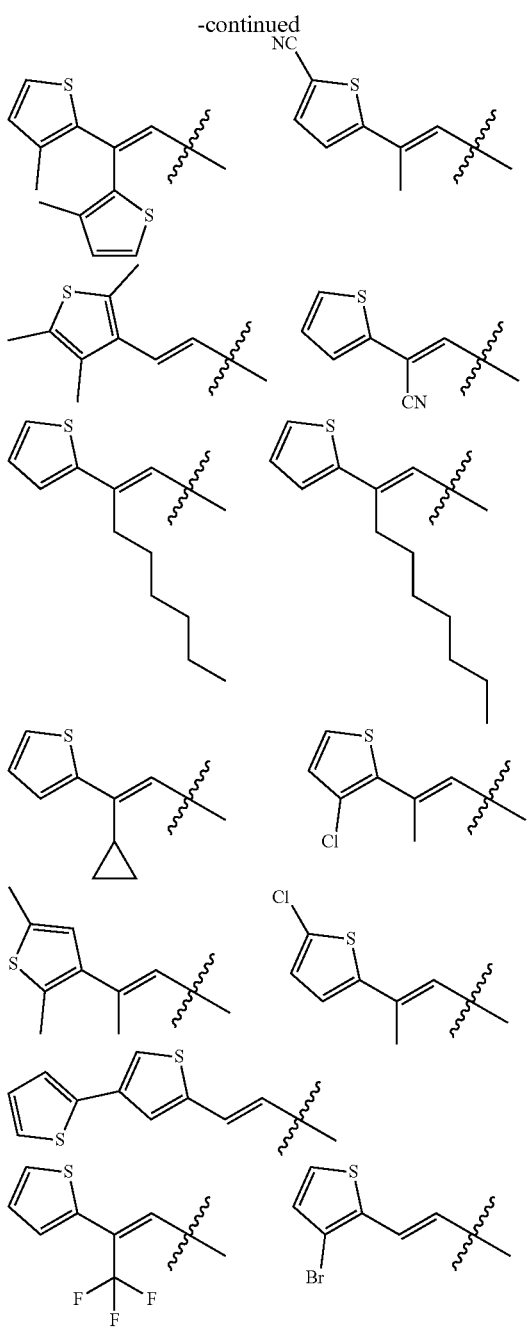

-continued

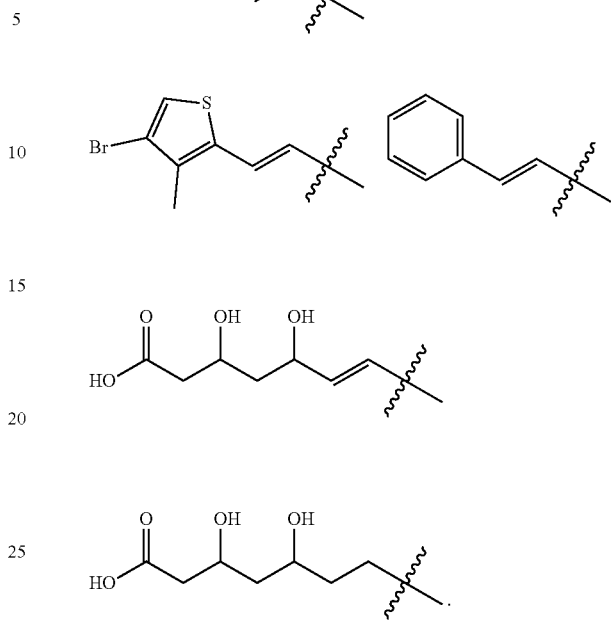

2. The method according to claim 1, wherein the disease is selected from the group consisting of respiratory diseases, pneumonia, gingival stomatitis, encephalitis, herpes and herpes pharyngitis, and enteritis.

3. The method according to claim 1, wherein the pharmaceutically acceptable salt is selected from the group consisting of hydrochloride, sulfate, phosphate, oxalate, maleate, methanesulfonate, succinate, citrate, fumarate, glucuronide, formate, acetate.

4. The method according to claim 1, wherein the compound, the tautomer, the stereoisomer, the racemate, the nonequal mixture of enantiomers, the geometric isomer, or the pharmaceutically acceptable salt thereof, possesses anti-viral activity.

5. The method according to claim 1, wherein the pharmaceutical composition further comprises at least one drug having anti-viral activity, comprising virazole, rimantadine hydrochloride, amantadine hydrochloride, acyclovir, valaciclovir, ganciclovir, interferon, zidovudine, vidarabine, ribavirin, and tibivudine.

* * * * *